(12) United States Patent
Spiegel et al.

(10) Patent No.: US 11,767,301 B2
(45) Date of Patent: Sep. 26, 2023

(54) BI-FUNCTIONAL MOLECULES TO DEGRADE CIRCULATING PROTEINS

(71) Applicant: YALE UNIVERSITY, New Haven, CT (US)

(72) Inventors: David Spiegel, New Haven, CT (US); David Caianiello, Brooklyn, NY (US)

(73) Assignee: YALE UNIVERSITY, New Haven, CT (US)

( * ) Notice: Subject to any disclaimer, the term of this patent is extended or adjusted under 35 U.S.C. 154(b) by 316 days.

(21) Appl. No.: 17/046,192

(22) PCT Filed: Apr. 8, 2019

(86) PCT No.: PCT/US2019/026239
§ 371 (c)(1),
(2) Date: Oct. 8, 2020

(87) PCT Pub. No.: WO2019/199621
PCT Pub. Date: Oct. 17, 2019

(65) Prior Publication Data
US 2021/0139436 A1     May 13, 2021

Related U.S. Application Data

(60) Provisional application No. 62/788,052, filed on Jan. 3, 2019, provisional application No. 62/655,028, filed on Apr. 9, 2018.

(51) Int. Cl.
| | | |
|---|---|---|
| *C07D 249/04* | (2006.01) | |
| *A61K 45/06* | (2006.01) | |
| *C07D 413/14* | (2006.01) | |
| *C07H 15/26* | (2006.01) | |

(52) U.S. Cl.
CPC ............ *C07D 249/04* (2013.01); *A61K 45/06* (2013.01); *C07D 413/14* (2013.01); *C07H 15/26* (2013.01)

(58) Field of Classification Search
None
See application file for complete search history.

(56) References Cited

U.S. PATENT DOCUMENTS

| | | | |
|---|---|---|---|
| 5,958,408 A | 9/1999 | Griffiths et al. | |
| 2004/0009907 A1 | 1/2004 | Alsobrook et al. | |
| 2007/0077197 A1 | 4/2007 | Wedeking et al. | |
| 2007/0249682 A1 | 10/2007 | Zheng et al. | |
| 2016/0082112 A1 | 3/2016 | Spiegel et al. | |
| 2016/0207953 A1 | 7/2016 | Liras et al. | |
| 2016/0362450 A1 | 12/2016 | Schteingart et al. | |

FOREIGN PATENT DOCUMENTS

| | | |
|---|---|---|
| EP | 2191849 A1 | 6/2010 |
| WO | 2006045505 A1 | 5/2006 |
| WO | 2011038234 A2 | 3/2011 |
| WO | 2016040305 A1 | 3/2016 |
| WO | 2019199621 A1 | 10/2019 |
| WO | 2019199634 A1 | 10/2019 |
| WO | 2021072269 A1 | 4/2021 |

OTHER PUBLICATIONS

Supplementary European Search Report for European Patent Application No. 19784404.6 dated Mar. 8, 2022.
Supplementary European Search Report for European Patent Application No. 19785819.4 dated Mar. 5, 2022.
Segers, et al., "Scavenger Receptor-AI-Targeted Iron Oxide Nanoparticles for In Vivo MRI Detection of Atherosclerotic Lesions", Arteriosclerosis, Thrombosis, and Vascular Biology, 32(4), 2012, 971-978.
Stokmaier, "Targeting Hepatocytes via the Asialoglycoprotein-Receptor", Basel, 2010, 3-140, 3-141, 3-142, 3.143, 3-149.
Sugita, et al., "Screening of peptide ligands that bind to the Fc region of IgG using peptide array and its application to affinity purification of antibody", Biochem. Eng. J, 79, 2013, 33-40.
Toldo, et al., "Low-Density Lipoprotein Receptor-Related Protein-1 Is a Therapeutic Target in Acute Myocardial Infarction", JACC: Basic to Translational Science, 2.5, 2017, 561-574.

(Continued)

*Primary Examiner* — Jeffrey S Lundgren
*Assistant Examiner* — Michael J Schmitt
(74) *Attorney, Agent, or Firm* — Saul Ewing LLP; Kathryn Doyle; Domingos J. Silva

(57) ABSTRACT

The present invention is directed to bi-functional compounds which find use as pharmaceutical agents in the treatment of disease states and/or conditions which are mediated through macrophage migration inhibitory factor (MIF) or immunoglubin G (IgG). The present invention is also directed to pharmaceutical compositions which comprise these bi-functional compounds as well as methods for treating disease states and/or conditions which are mediated through MIF/IgG or where MIF/IgG is a contributing factor to the development and perpetuation of diseases and/or conditions, especially including autoimmune diseases and cancer, among others. The purpose of the present invention is to provide a molecular strategy to lower plasma MIF/IgG level in patients with autoimmune diseases or certain types of cancers. The bi-functional molecule construct is comprised of a MIF/IgG-targeting motif, that is derived from small molecule MIF/IgG ligands, and an ASGPr-targeting motif that binds to hepatocyte asialoglycoprotein receptor (ASGPr). The compounds selectively bind MIF or IgG in plasma and subsequently engage the endo-lysosomal pathway of hepatocytes through ASGPr. As a consequence, MIF/IgG is internalized and degraded by hepatocytes, thus resulting in potential attenuation of corresponding disease symptoms which are modulated through MIF/IgG.

18 Claims, 111 Drawing Sheets

Specification includes a Sequence Listing.

(56) References Cited

OTHER PUBLICATIONS

Tsai, et al., "Strategy of Fc-recognizable peptide ligand design for oriented immobilization of antibody", Anal. Chem., 86, 2014, 2931-2938.
Verdoliva, "A new ligand for immunoglobulin G subdomains by screening of a synthetic peptide library", ChemBioChem, 6, 2005, 1242-1253.
Verdoliva, et al., "Affinity purification of polyclonal antibodies using a new all-D synthetic peptide ligand: comparison with protein A and protein G", J. Immunol. Methods, 271, 2002, 77-88.
Wängler, et al., "In Vitro and Initial In Vivo Evaluation of 68Ga-Labeled Transferrin Receptor (TfR) Binding Peptides as Potential Carriers for Enhanced Drug Transport into TfR Expressing Cells", Molecular Imaging and Biology, 13(2), 2011, 332-341.
Watarai, et al., "Posttranslational modification of the glycosylation inhibiting factor (GIF) gene product generates bioactive GIF", Proceedings of the National Academy of Sciences, 97, 2000, 13251-13256.
Willis, et al., "Macrophage migration inhibitory factor mediates late cardiac dysfunction after burn injury", American Journal of Physiology-Heart and Circulatory Physiology, 288, 2005, H795-H804.
Yang, et al., "Hexamer peptide affinity resins that bind the Fc region of human immunoglobulin G", J. Peptide Res, 66, 2005, 120-137.
Yang, et al., "Purification of human immunoglobulin G via Fc-specific small peptide ligand affinity chromatography", J. Chromatogr. A, 1216, 2009, 910-918.
Yoo, et al., "Identification of a peptide ligand for antibody immobilization on biosensor surfaces", Anal. Chem. 86, 2014, 2931-2938.
Zhang, et al., "Identification of a Small Peptide That Inhibits PCSK9 Protein Binding to the Low Density Lipoprotein Receptor", The Journal of Biological Chemistry, 2014, 942-955.
Zhao, et al., "Biomimetic design of affinity peptide ligands for human IgG based on protein A-IgG complex", Biochem. Eng. J, 88, 2014, 1-11.
Zhao, et al., "Dual-ligand affinity systems with octapeptide ligands for affinity chromatography of hIgG and monoclonal antibody", J. Chromatogr. A., 1359, 2014, 64-72.
Zhao, et al., "FYWHCLDE-based affinity chromatography of IgG: effect of ligand density and purifications of human IgG and monoclonal antibody", J. Chromatogr. A, 1355, 2014, 107-114.
Zhao, et al., "Octapeptide-based affinity chromatography of human immunoglobulin G: comparisons of three different ligands", J. Chromatogr. A, 1359, 2014, 100-111.
"International Search Report and Written Opinion issued by the International Searching Authority (RU) dated Aug. 15, 2019 for PCT/US2019/026260."
"International Search Report and Written Opinion issued by the International Searching Authority (RU) dated Aug. 8, 2019 for PCT/US2019/026239."
"International Search Report and Written Opinion issued by the International Searching Authority (US) dated Mar. 22, 2021 for PCT/US2020/055078."
Benedek, et al., "MIF and D-DT are potential disease severity modifiers in male MS subjects", Proceedings of the National Academy of Sciences, 114, 2017, E8421-E8429.
Bonetto, et al., "Identification of cyclic peptides able to mimic the functional epitope of IgG1-Fc for human FcγRI", The FASEB Journal, 23(2), 2009, 575-585.
Braisted, et al., "Discovery of a Potent Small Molecule IL-2 Inhibitor through Fragment Assembly", J. Am. Chem. Soc, 2003, 3714-3715.
Burmester, et al., "Small Molecule Antagonists of the TGF-pl/TGF-p Receptor Binding Interaction", Medical Oncology, 2006, 553-562.
Calandra, et al., "Protection from septic shock by neutralization of macrophage migration inhibitory factor", Nature Medicine, 6, 2000, 164-170.
Camperi, et al., "Monoclonal antibody purification by affinity chromatography with ligands derived from the screening of peptide combinatory libraries", Biotechnol. Lett, 25, 2003, 1545-1548.
Choe, Weonu, et al., "Fc-Binding Ligands of Immunoglobulin G: an Overview of High Affinity Proteins and Peptides", Materials (994), Dec. 8, 2016, 1-17.
Cisneros, "A Fluorescence Polarization Assay for Binding to Macrophage Migration Inhibitory Factor and Crystal Structures for Complexes of Two Potent Inhibitors", J. Am. Chem. Soc. (138), Jun. 14, 2016, 1-27.
Croy, et al., "Two Apolipoprotein E Mimetic Peptides, ApoE(130-149) and ApoE(141-155)2, Bind to LRP1", Biochemistry, 2004, 43(23):, 2004, 7328-7335.
David, et al., "Identification and characterization of highly versatile peptide-vectors that bind non-competitively to the low-density lipoprotein receptor for in vivo targeting and delivery of small molecules and protein cargos", PLOS One, 13(2):e0191052, 2018, 1-30.
Delano, et al., "Convergent Solutions to Binding at a Protein-Protein Interface", Science, 287, 2000, 1279-1283.
Dias, et al., "Protein ligand design: from phage display to synthetic protein epitope mimetics in human antibody Fc-binding peptidomimetics", J. Am. Chem. Soc., 128, 2006, 2726-2732.
Dinon, et al., "Structural refinement of protein A mimetic peptide", J. Mol. Recognit.,24, 2011, 1087-1094.
D'Souza, Aniash A., et al., "Asialoglycoprotein receptor mediated hepatocyte targeting—Strategies and applications", Jrl. of Controlled Release (203), Apr. 10, 2015, 126-139.
Ehrlich, et al., "Identification of model peptides as affinity ligands for the purification of humanized monoclonal antibodies by means of phage display", J. Biochem. Biophys. Method, 49, 2001, 443-454.
Fairbrother, et al., "Novel Peptides Selected to Bind Vascular Endothelial Growth Factor Target the Receptor-Binding Site.", Biochemistry, 1998, 17754-7764.
Fassina, et al., "Protein a mimetic peptide ligand for affinity purification of antibodies", J. Mol. Recognit, 1996, 564-569.
Geuze, et al., "Intracellular site of asialoglycoprotein receptor-ligand uncoupling: double-label immunoelectron microscopy during receptor-mediated endocytosis", Cell, 32, 1983, 277-287.
Gong, et al., "Development of the double cyclic peptide ligand for antibody purification and protein detection", Bioconjug. Chem., 27, 2016, 1569-1573.
Hussain, et al., "Human anti-macrophage migration inhibitory factor antibodies inhibit growth of human prostate cancer cells in vitro and in vivo", Molecular Cancer Therapeutics, 12, 2013, 1223-1234.
Jacquot, et al., ", Guillaume et al., "Optimization and in Vivo Validation of Peptide Vectors Targeting the LDL Receptor", Molecular Pharmaceutics, 3(12), 2016, 4094-4105.
Kang, et al., "Cyclic peptide ligand with high binding capacity for affinity purification of immunoglobulin G", J. Chromatogr. A, 1466, 2016, 105-112.
Kim, et al., "Presumed LRP1-targeting transport peptide delivers B-secretase inhibitor to neurons in vitro with limited efficiency", Scientific Reports, 6, 34297, 2016.
Kim, et al., "Macrophage migration inhibitory factor: a potential therapeutic target for rheumatoid arthritis", The Korean Journal of Internal Medicine, 31, 2016, 634.
Krook, et al., "Novel peptides binding to the Fc-portion of immunoglobulins obtained from a combinatorial phage display peptide library", J. Immunol. Methods, 221, 1998, 51-157.
Landry, et al., "Discovering small molecule ligands of vascular endothelial growth factor that block VEGF-KDR binding using label-free microarray-based assays.", Assay and Drug Development Technologies, 2013, 326-332.
Lee, et al., "Receptor mediated uptake of peptides that bind the human transferrin receptor", European Journal of Biochemistry, 268(7), 2001, 2004-2012.
Lund, et al., "Novel peptide ligand with high binding capacity for antibody purification", J. Chromatogr. A, 1225, 2012, 158-167.

(56) References Cited

OTHER PUBLICATIONS

McEnaney, Patrick J., et al., "Antibody-Recruiting Molecules: an Emerging Paradigm for Engaging Immune Function in Treating Human Disease", ACS Chem. Biol. (7), Jul. 3, 2012, 1139-1151.

Menegatti, et al., "Design of protease-resistant peptide ligands for the purification of antibodies from human plasma", J. Chromatogr. A, 1445, 2016, 93-104.

Menegatti, et al., "mRNA display selection and solid-phase synthesis of Fc-binding cyclic peptide affinity ligands", Biotechnol. Bioeng, 110, 2013, 857-870.

Menegatti, et al., "Reversible cyclic peptide libraries for the discovery of affinity ligands", Anal. Chem., 85, 2013, 9229-9237.

Mezo, et al., "Reduction of IgG in nonhuman primates by a peptide antagonist of the neonatal Fc receptor FcRn", Proceedings of the National Academy of Sciences 105(7), 2008, 2337-2342.

Molino, et al., "Use of LDL receptor-targeting peptide vectors for in vitro and in vivo cargo transport across the blood-brain barrier", The FASEB Journal, 31(5), 2017, 1807-1827.

Mu, et al., "Lipid vesicles containing transferrin receptor binding peptide TfR-T12 and octa-arginine conjugate stearyl-R8 efficiently treat brain glioma along with glioma stem cells", Scientific Reports, 7(1), 2017, 3487.

Nalawansha, Dhanusha A., et al., "Targeted Protein Internalization and Degradation by ENDosome TArgeting Chimeras", ACS Central Science 5(6), May 9, 2019, 1079-1084.

Neven, et al., "Macrophage Scavenger Receptor A Mediates Adhesion to Apolipoproteins A-I and E", Biochemistry 48(50), 2009, 11858-11871.

Parker, et al., "Illuminating HIV gp 120-ligand recognition through computationally-driven optimization of antibody-recruiting molecules", Chem. Sci., 2014, 2311-2317.

Reidy, et al., "Homotrimeric macrophage migration inhibitory factor (MIF) drives inflammatory responses in the corneal epithelium by promoting caveolin-rich platform assembly in response to infection", Journal of Biological Chemistry, 288:, 2013, 8269-8278.

Ribeiro, et al., "he Activation Sequence of Thrombospondin-1 Inter-acts with the Latency-associated Peptide to Regulate Activation of Latent Transforming Growth Factor", The Journal of Biological Chemistry, 1999, 13586-13593.

Roseng, et al., "Uptake, Intracellular Transport, and Degradation of Polyethylene Glycol-modified Asialofetuin in Hepatocytes", The Journal of Biological Chemistry, Jul. 15, 1992, 22987-22930.

Ruan, et al., "A novel peptide ligand RAP12 of LRP1 for glioma targeted drug delivery,", Journal of Controlled Release, 279, 2018, 306-315.

Rullo, et al., "e-engineering the Immune Response to Metastatic Cancer: Antibody-Recruiting Small Molecules Targeting the Urokinase Receptor", Angew. Chem. Int. Ed, 2016, 3642-3646.

Sakamoto, et al., "A novel LRP1-binding peptide L57 that crosses the blood brain barrier", Biochemistry and Biophysics Reports, 12, 2017, 135-139.

Sanhueza, et al., "Efficient Liver Targeting by Polyvalent Display of a Compact Ligand for the Asialoglycoprotein Receptor", Journal of the American Chemical Society, 139, 2017, 3528-3536.

Santi, et al., "Rational design of a transferrin-binding peptide sequence tailored to targeted nanoparticle internalization", Bioconjugate Chemistry, 28(2), 2016, 471-480.

Schwartz, et al., "Characterization of the asialoglycoprotein receptor in a continuous hepatoma line", Journal of Biological Chemistry, 256, 1981, 8878-8881.

FIGURE 1
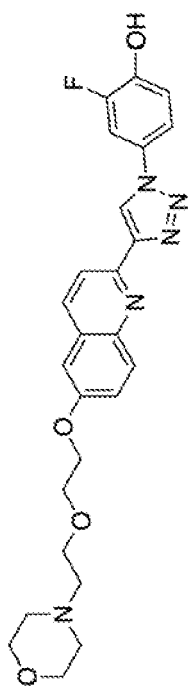
3w (negative control MIF inhibitor)
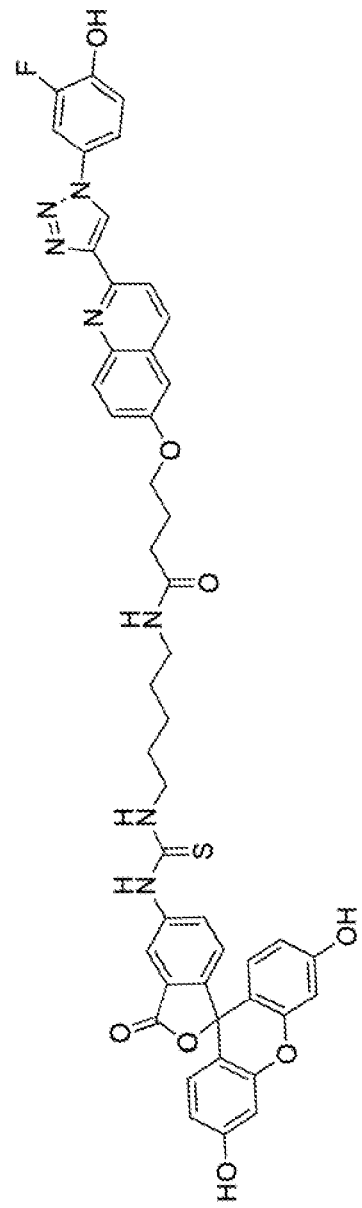
MIF-FITC (fluorescent MIF binder)

MIF-AcF3-2

MIF-AcF3-3

DNP-AcF3-3

FIGURE 65 (Cont'd)
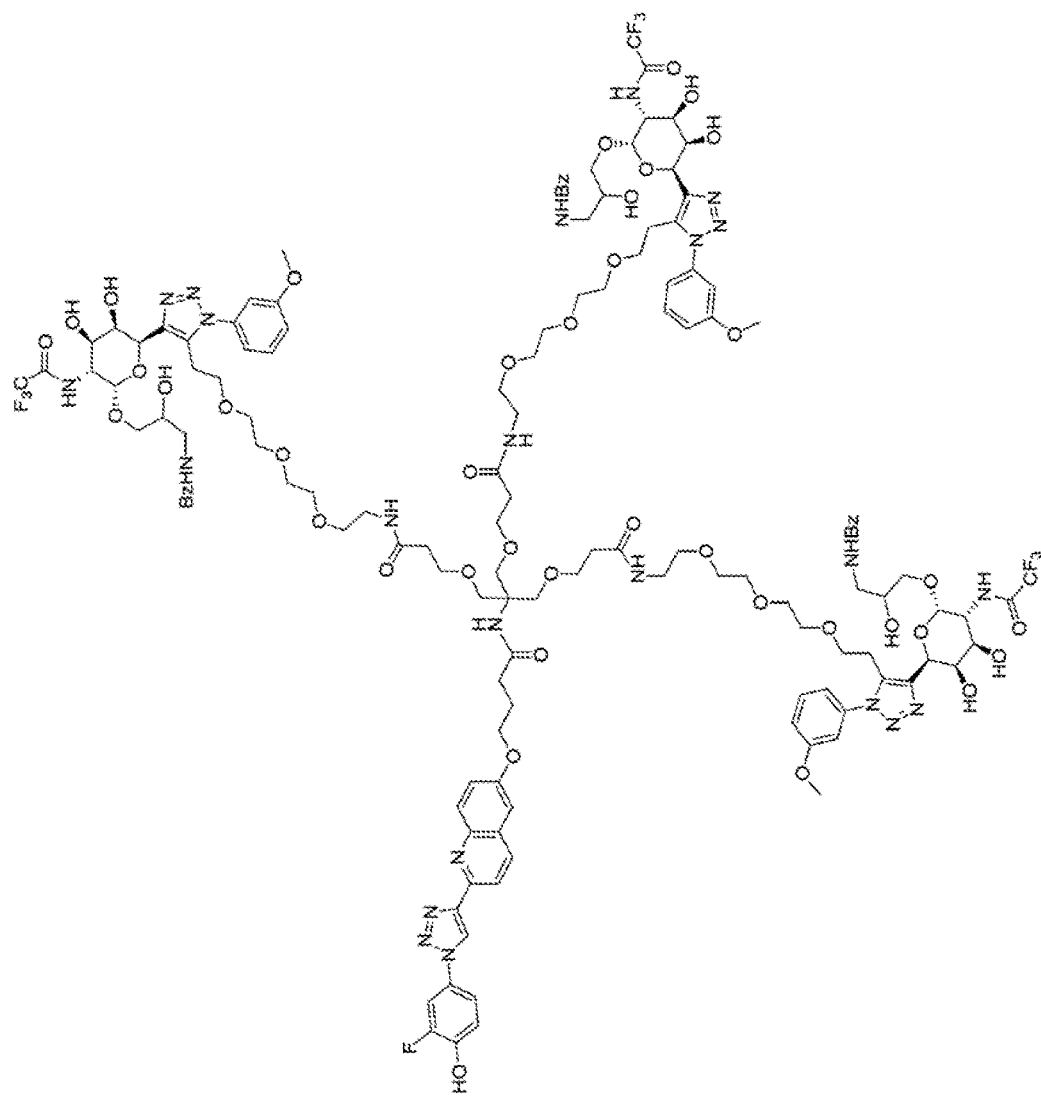
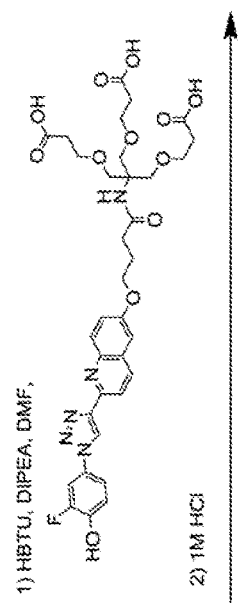

Exemplary $R_1$ and $R_3$ substituents/moieties for the [ASGPRBM] group

Exemplary R₁ and R₃ substituents/moieties for the [ASGPRBM] group

FIGURE 69
Exemplary R₂ substituents/moieties for the [ASGPRBM] group
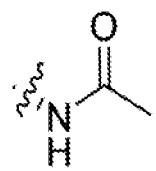 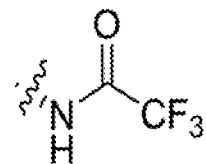 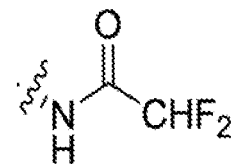
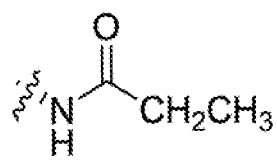 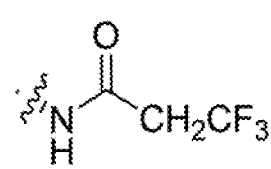 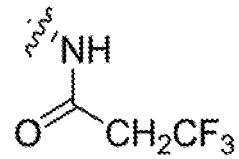
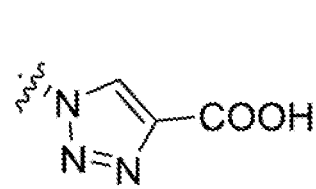 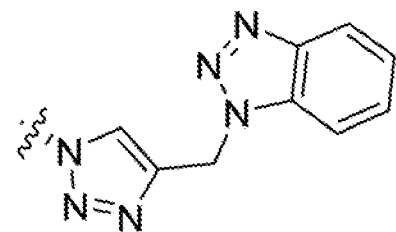
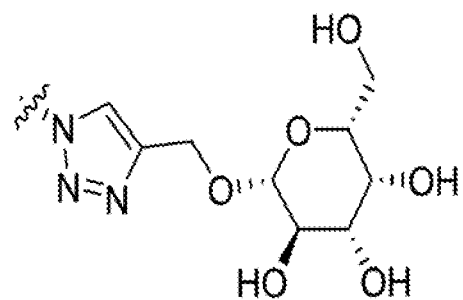 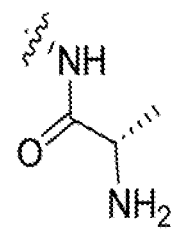

SEQUENCE LISTING

```
<160> NUMBER OF SEQ ID NOS: 20

<210> SEQ ID NO 1
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 1

Thr Trp Lys Thr Ser Arg Ile Ser Ile Phe
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Chemically Synthesized

<400> SEQUENCE: 2

Phe Gly Arg Leu Val Ser Ser Ile Arg Tyr
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 3

Glu Pro Ile His Arg Ser Thr Leu Thr Ala Leu Leu
```

1               5                    10

<210> SEQ ID NO 4
<211> LENGTH: 4
<212> TYPE: PRT
<213> ORGANISM: Artificial Sequence
<220> FEATURE:
<223> OTHER INFORMATION: Chemically Synthesized

<400> SEQUENCE: 4

Ala Pro Ala Arg
1

<210> SEQ ID NO 5
<211> LENGTH: 6
<212> TYPE: PRT
<213> ORGANISM: Artificial Sequence
<220> FEATURE:
<223> OTHER INFORMATION: Chemically Synthesized

<400> SEQUENCE: 5

His Trp Arg Gly Trp Val
1               5

<210> SEQ ID NO 6
<211> LENGTH: 6
<212> TYPE: PRT
<213> ORGANISM: Artificial Sequence
<220> FEATURE:
<223> OTHER INFORMATION: Chemically Synthesized

<400> SEQUENCE: 6

His Tyr Phe Lys Phe Asp
1               5

<210> SEQ ID NO 7
<211> LENGTH: 6
<212> TYPE: PRT
<213> ORGANISM: Artificial Sequence
<220> FEATURE:
<223> OTHER INFORMATION: Chemically Synthesized

<400> SEQUENCE: 7

His Phe Arg Arg His Leu
1               5

<210> SEQ ID NO 8
<211> LENGTH: 6
<212> TYPE: PRT
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (3)..(3)
<223> OTHER INFORMATION: Xaa = citrulline

<400> SEQUENCE: 8

His Trp Xaa Gly Trp Val
1               5

<210> SEQ ID NO 9
<211> LENGTH: 8
<212> TYPE: PRT
<213> ORGANISM: Artificial Sequence
<220> FEATURE:
<223> OTHER INFORMATION: Chemically Synthesized
<220> FEATURE:

```
<221> NAME/KEY: misc_feature
<222> LOCATION: (1)..(8)
<223> OTHER INFORMATION: Ala and Glu of Lys-lactic acid-Glu form a ring
<220> FEATURE:
<221> NAME/KEY: misc_feature
<222> LOCATION: (2)..(2)
<223> OTHER INFORMATION: Ser is N-acetylated
<220> FEATURE:
<221> NAME/KEY: misc_feature
<222> LOCATION: (8)..(8)
<223> OTHER INFORMATION: C(=O)OH of Lys bonds to lactic acid-Glu

<400> SEQUENCE: 9

Ala Ser Arg Trp His Tyr Phe Lys
1               5

<210> SEQ ID NO 10
<211> LENGTH: 8
<212> TYPE: PRT
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (1)..(8)
<223> OTHER INFORMATION: Ala and Glu of Lys-lactic acid-Glu form a ring
<220> FEATURE:
<221> NAME/KEY: misc_feature
<222> LOCATION: (2)..(2)
<223> OTHER INFORMATION: Xaa = N-acetylated 2,3-diaminopropionic acid
<220> FEATURE:
<221> NAME/KEY: misc_feature
<222> LOCATION: (8)..(8)
<223> OTHER INFORMATION: C(=O)OH of Lys bonds to lactic acid-Glu

<400> SEQUENCE: 10

Ala Xaa Arg Trp His Tyr Phe Lys
1               5

<210> SEQ ID NO 11
<211> LENGTH: 7
<212> TYPE: PRT
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (1)..(1)
<223> OTHER INFORMATION: Met terminal NH2 is substituted with glutaric
      acid
<220> FEATURE:
<221> NAME/KEY: misc_feature
<222> LOCATION: (1)..(7)
<223> OTHER INFORMATION: Glutaric acid forms a ring between Lys and Met

<400> SEQUENCE: 11

Met Trp Phe Arg His Tyr Lys
1               5

<210> SEQ ID NO 12
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 12

Asn Lys Phe Arg Gly Lys Tyr Lys
1               5

<210> SEQ ID NO 13
```

```
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 13

Asn Ala Arg Lys Phe Tyr Lys Gly
1               5

<210> SEQ ID NO 14
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 14

Phe Tyr Trp His Cys Leu Asp Glu
1               5

<210> SEQ ID NO 15
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 15

Phe Tyr Cys His Trp Ala Leu Glu
1               5

<210> SEQ ID NO 16
<211> LENGTH: 8
<212> TYPE: PRT
<213> ORGANISM: Artificial Sequence
<220> FEATURE:
<223> OTHER INFORMATION: Chemically Synthesized

<400> SEQUENCE: 16

Phe Tyr Cys His Thr Ile Asp Glu
1               5

<210> SEQ ID NO 17
<211> LENGTH: 4
<212> TYPE: PRT
<213> ORGANISM: Artificial Sequence
<220> FEATURE:
<223> OTHER INFORMATION: Chemically Synthesized

<400> SEQUENCE: 17

Arg Arg Gly Trp
1

<210> SEQ ID NO 18
<211> LENGTH: 7
<212> TYPE: PRT
<213> ORGANISM: Artificial Sequence
<220> FEATURE:
<223> OTHER INFORMATION: Chemically Synthesized

<400> SEQUENCE: 18

Lys His Arg Phe Asn Lys Asp
1               5

<210> SEQ ID NO 19
<211> LENGTH: 13
```

```
<212> TYPE: PRT
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (2)..(12)
<223> OTHER INFORMATION: Cys and Cys form a ring
<220> FEATURE:
<221> NAME/KEY: misc_feature
<222> LOCATION: (13)..(13)
<223> OTHER INFORMATION: terminus is C(=O)NH2

<400> SEQUENCE: 19

Asp Cys Ala Trp His Leu Gly Glu Leu Val Trp Cys Thr
1               5                   10

<210> SEQ ID NO 20
<211> LENGTH: 15
<212> TYPE: PRT
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (1)..(15)
<223> OTHER INFORMATION: Cys and Cys form a ring
<220> FEATURE:
<221> NAME/KEY: misc_feature
<222> LOCATION: (3)..(13)
<223> OTHER INFORMATION: Cys and Cys form a ring
<220> FEATURE:
<221> NAME/KEY: misc_feature
<222> LOCATION: (15)..(15)
<223> OTHER INFORMATION: terminus is C(=O)NH2

<400> SEQUENCE: 20

Cys Asp Cys Ala Trp His Leu Gly Glu Leu Val Trp Cys Thr Cys
1               5                   10                  15
```

BI-FUNCTIONAL MOLECULES TO DEGRADE CIRCULATING PROTEINS

CROSS-REFERENCE TO RELATED APPLICATIONS

This application is a 35 U.S.C. § 371 national phase application from, and claims priority to, International Application No. PCT/US2019/026239, filed Apr. 8, 2019, which claims priority under 35 U.S.C. § 119(e) to U.S. Provisional Patent Application No. 62/655,028, filed Apr. 9, 2018 and U.S. Provisional Patent Application No. 62/788,052, filed Jan. 3, 2019, all of which applications are incorporated herein by reference in their entireties.

STATEMENT REGARDING FEDERALLY SPONSORED RESEARCH

This invention was made with government support under GM067543 awarded by National Institutes of Health and under W81XWH-13-1-0062 awarded by the United States Army Medical Research and Material Command. The government has certain rights in the invention.

SEQUENCE LISTING

The instant application contains a Sequence Listing which has been submitted in ASCII format via EFS-Web and is hereby incorporated by reference in its entirety. Said ASCII copy, created on Jan. 6, 2021, is named 047162-7240US1_replacement_sequence_listing.txt and is 5.31 kilobytes in size.

FIELD OF THE INVENTION

The present invention is directed to bi-functional compounds which find use as pharmaceutical agents in the treatment of disease states and/or conditions which are mediated through macrophage migration inhibitory factor (MIF) or Immunoglobulin G (IgG). The present invention is also directed to pharmaceutical compositions which comprise these bi-functional compounds as well as methods for treating disease states and/or conditions which are mediated through MIF or IgG or where MIF and IgG are contributing factors to the development and perpetuation of diseases and/or conditions, especially including autoimmune diseases and cancer, among others. The purpose of the present invention is to provide a molecular strategy to lower plasma MIF level or IgG levels in patients with autoimmune diseases or certain types of cancers and other diseases. The bi-functional molecule construct is comprised of a MIF-targeting motif that is derived from small molecule MIF ligands or an IgG-binding motif which binds to IgG, and an ASGPr-targeting motif that binds to hepatocyte asialoglycoprotein receptor (ASGPr). The compounds selectively bind MIF or IgG in plasma and subsequently engage the endo-lysosomal pathway of hepatocytes through ASGPr. As a consequence, MIF or IgG is internalized and degraded by hepatocytes, thus resulting in potential attenuation of corresponding disease symptoms which are modulated through MIF and/or IgG.

BACKGROUND AND OVERVIEW OF THE INVENTION

The present invention centers on bi-functional molecules that utilize the endo-lysosomal machinery in the liver to eliminate MIF and/or IgG. MIF is a proinflammatory pluripotent cytokine which contributes to the development and perpetuation of many diseases. These include atherosclerosis, rheumatoid arthritis (RA), systemic lupus erythematosus (SLE), sepsis, inflammatory bowel disease (IBD), among others. In addition, MIF has been shown to participate in the progression of various cancers, including colon cancer, prostate cancer, breast cancer, lung cancer, cervical and adenocarcinoma, among others. In pre-clinical models, inhibition of MIF has been shown to attenuate symptoms and delay disease progression in the above-mentioned diseases.

MIF and IgG significantly contribute to the pathologic process of a number of diseases. MIF neutralizing antibodies and small molecule MIF inhibitors have been developed, where IgG is upregulated in autoimmune and other diseases and causes untoward effects. Because MIF acts through various pathways, a MIF inhibitor may be required to be able to interrupt multiple protein-protein interactions (PPIs), posing a challenge for drug development. In the case of IgG, the removal of IgG molecules which are upregulated and contributing to autoimmune and/or other diseases may be useful to inhibit and/or ameliorate the effects of the disease state. Therefore, a novel approach where MIF or IgG can be degraded as well as inhibited can overcome this difficulty and potentially provide a more robust therapeutic response. Encouraged by preliminary results with bi-functional MIF and IgG degraders, the present inventors decided to further test them in clinical-relevant in vivo models and potentially develop them into therapeutics that target MIF or IgG in diseases. They also intend to use this basic bifunctional molecule strategy to target other circulating proteins of interest to degradation via the ASGPr.

The present invention utilizes bi-functional molecules to target MIF or IgG and is modular and versatile. This offers convenience to apply medicinal chemistry to optimize the molecules. For example, in preliminary experiments, incorporation of more optimized ASGPr binding motifs have been shown to enhance MIF or IgG degradation in vitro. Since the bi-functional molecule is capable of degrading MIF or IgG, it does not require the MIF-binding motif (MIFBM) or the IgG binding moiety (IgGBM) to be an inhibitor, but in practice many of these binders will function as inhibitors of MIF or IgG. The reality of this dual inhibitory action opens up opportunity for the development of potent MIF or IgG binders, which might have been overlooked before for not being able to inhibit various PPIs. Compared to monoclonal antibodies, the small molecule approach of the present invention enables simpler, cheaper and more consistent manufacturing practices and provides for a therapeutic approach with fewer potential immugenic side effects.

BRIEF DESCRIPTION OF THE INVENTION

The present invention is directed to bifunctional small molecules which can be used to inhibit and remove MIF or IgG. The present invention aims to establish a general small molecule strategy to target the selective degradation of MIF or IgG, which contributes to the development and perpetuation of many diseases. The bifunctional molecule construct contains a MIF binding motif derived from known small molecule ligands of MIF of a IgG binding motif which comprises a ligand which binds IgG. These moieties is referred to herein generically as macrophage migration inhibitory factor binding moiety (MIFBM) or alternatively, immunoglobulin G binding moiety (IgGBM). The other end of the bifunctional molecule is a motif that binds to hepatocyte asialoglycoprotein receptor (ASGPr), which is a triantennary N-acetylgalactosamine or other moiety as described herein. We refer to these moieties generically as asialoglycoprotein receptor binding moiety (ASGPRBM). The motifs which are used to provide bifunctional compounds according to the present invention, (MIFBM or IgGBM) and (ASGPRBM), are covalently linked via a linker such as a polyethylene glycol (PEG) or other linker as described herein with adjustable length or other linker as described herein, which optionally contains one or more connector molecule(s) which connects the linker to the MIFBM or IgGBM and/or the ASGPRBM.

The presently claimed bifunctional compounds selectively bind to MIF or IgG in circulation and form a protein complex. When this protein complex passes through the liver, the asialoglycoprotein receptor binding moiety of the molecule (ASGPRBM), preferably a triantennary N-Acetylgalactosamine or other motif as described herein, will engage the endo-lysosomal pathway of hepatocytes through the ASGPr. As a consequence of this mechanism, MIF or IgG is eliminated from circulation by hepatocytes, thus resulting in lowered levels of MIF or IgG with the result being that corresponding disease symptoms are attenuated and/or eliminated from a patient or subject administered the present compounds. In certain instances, the MIF may be substantially reduced or eliminated or the compromising IgG substantially reduced, resulting in substantially reduced symptoms or even a cure or elimination of the disease state or condition.

The approach pursuant to the present invention is inherently advantageous compared to the classical antibody-based strategy to target MIF or IgG of the prior art. The small molecule based approach of the current invention overcomes the limitations of traditional antibody-based strategies, including lack of oral bioavailability, low-temperature storage requirements, immunogenicity, and high-cost.

Furthermore, the present invention is expected to have a more lasting effect compared to the conventional inhibitory approach because MIF or IgG is substantially reduced or eliminated by degradation inside hepatocytes rather than simply inhibited by reversibly blocking the protein-receptor interaction. The bifunctional molecule construct pursuant to the present invention is also versatile in the sense that different disease states and/or conditions can be targeted by inhibiting and degrading MIF or IgG. Thus, previously discovered non-inhibitory protein binders, presently of little value in therapy, can be potentially therapeutically useful in these small molecules.

In one embodiment, the present invention is directed to compounds which are useful for removing circulating proteins which are associated with a disease state or condition in a patient or subject according to the general chemical structure:

[MIFBM/IgGBM]$_{k'}$—[CON]$_h$—[LINKER]$_{i_L}$—[CON]$_{h'}$—[ASGPRBM]$_{j'}$

Wherein [MIFBM/IgGBM] is a MIF or IgG binding moiety which binds respectively to circulating MIF or IgG, which are related to a disease state and/or condition and is to be removed by the action of hepatocytes on circulating protein (the compounds preferably selectively bind to MIF or IgG in plasma);

[ASGPRBM] is a binding moiety which binds to hepatocytes through asialoglycoprotein receptors which are on the surface of hepatocytes, preferably in a patient or subject;

Each [CON] is an optional connector chemical moiety which, when present, connects directly to [MIFBM/IgGBM] or to [ASGPRBM] or connects the [LINKER] to [MIFBM/IgGBM] or to [ASGPRBM] and

[LINKER] is a chemical moiety having a valency from 1 to 15, often 1 to 10, more often 1 to 5 or 1, 2 or 3, which covalently attaches to one or more [ASGPRM] and/or [MIFBM/IgGBM] group, optionally through a [CON], including a [MULTICON] group, wherein said [LINKER] optionally itself contains one or more [CON] or [MULTICON] group(s);

k' is 1 to 15, 1 to 10, 1 to 5, 1 to 3 or 1, 2 or 3;

j' is 1 to 15, 1 to 10, 1 to 5, 1 to 3 or 1, 2 or 3;

h and h' are each independently 0 to 15, 1 to 15, 1 to 10, 1 to 5, 1 to 3 or 1, 2 or 3, preferably h and/or h' is at least 1;

$i_L$ is 0 to 15, often 1 to 15, 1 to 10, 1 to 5, 1 to 3, or 1, 2 or 3, preferably $i_L$ is 1 to 5 or 1, 2 or 3 with the proviso that at least one of h, h' and $i_L$ is preferably at least 1, or a pharmaceutically acceptable salt, stereoisomer, solvate or polymorph thereof.

In an embodiment the present invention is directed to compounds where

[MIFBM] is a moiety according to the chemical structure:

wherein $X_M$ is —(CH$_2$)$_{IM}$, —O—(CH$_2$)$_{IM}$, S—(CH$_2$)$_{IM}$, NR$_M$—(CH$_2$)$_{IM}$, C(O)—(CH$_2$)$_{IM}$—, a PEG group containing from 1 to 8, preferably 1-4 ethylene glycol residues or a —C(O)(CH$_2$)$_{IM}$NR$_M$ group;

$R_M$ is H or a $C_1$-$C_3$ alkyl group which is optionally substituted with one or two hydroxyl groups;
$_{IM}$ is 0-6, preferably 1, 2, 3 or 4, more preferably 1;
[IgGMB] is a group according to the chemical structure:

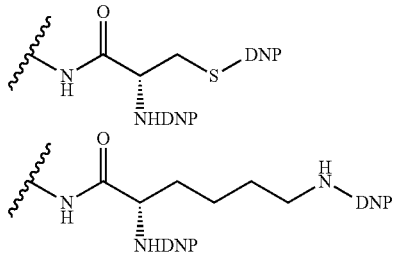

Where DNP is a 2,4-dinitrophenyl group; or
a group according to the chemical structure:

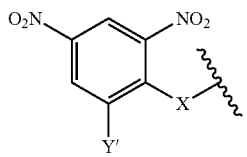

Where Y' is H or $NO_2$ (preferably H);
X is O, $CH_2$, $NR^1$, S(O), $S(O)_2$, —$S(O)_2O$, —$OS(O)_2$, or $OS(O)_2O$; and
$R^1$ is H, a $C_1$-$C_3$ alkyl group, or a —$C(O)(C_1$-$C_3)$ group; or
a group according to the chemical structure:

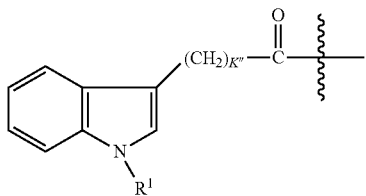

where $R^1$ is the same as above; and
K" is 1-5 (preferably 3-5, most often 4), or
a group represented by the chemical formula:

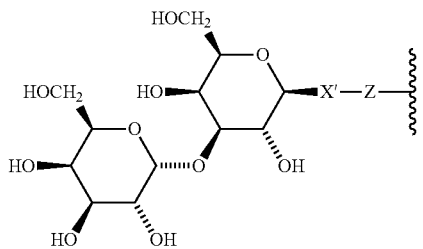

Where X' is $CH_2$, O, N—$R^{1'}$, or S, preferably O;
$R^{1'}$ is H or $C_1$-$C_3$ alkyl; and
Z is a bond, a monosaccharide, disaccharide, oligosaccharide, more preferably a sugar group selected from the monosaccharides, including aldoses and ketoses, and disaccharides, including those disaccharides described herein. Monosaccharide aldoses include monosaccharides such as aldotriose (D-glyceraldehdye, among others), aldotetroses (D-erythrose and D-Threose, among others), aldopentoses, (D-ribose, D-arabinose, D-xylose, D-lyxose, among others), aldohexoses (D-allose, D-altrose, D-Glucose, D-Mannose, D-gulose, D-idose, D-galactose and D-Talose, among others), and the monosaccharide ketoses include monosaccharides such as ketotriose (dihydroxyacetone, among others), ketotetrose (D-erythrulose, among others), ketopentose (D-ribulose and D-xylulose, among others), ketohexoses (D-Psicone, D-Fructose, D-Sorbose, D-Tagatose, among others), aminosugars, including galactoseamine, sialic acid, N-acetylglucosamine, among others and sulfosugars, including sulfoquinovose, among others. Exemplary disaccharides which find use in the present invention include sucrose (which may have the glucose optionally N-acetylated), lactose (which may have the galactose and/or the glucose optionally N-acetylated), maltose (which may have one or both of the glucose residues optionally N-acetylated), trehalose (which may have one or both of the glucose residues optionally N-acetylated), cellobiose (which may have one or both of the glucose residues optionally N-acetylated), kojibiose (which may have one or both of the glucose residues optionally N-acetylated), nigerose (which may have one or both of the glucose residues optionally N-acetylated), isomaltose (which may have one or both of the glucose residues optionally N-acetylated), β,β-trehalose (which may have one or both of the glucose residues optionally N-acetylated), sophorose (which may have one or both of the glucose residues optionally N-acetylated), laminaribiose (which may have one or both of the glucose residues optionally N-acetylated), gentiobiose (which may have one or both of the glucose residues optionally N-acetylated), turanose (which may have the glucose residue optionally N-acetylated), maltulose (which may have the glucose residue optionally N-acetylated), palatinose (which may have the glucose residue optionally N-acetylated), gentiobiluose (which may have the glucose residue optionally N-acetylated), mannobiose, melibiose (which may have the glucose residue and/or the galactose residue optionally N-acetylated), melibiulose (which may have the galactose residue optionally N-acetylated), rutinose, (which may have the glucose residue optionally N-acetylated), rutinulose and xylobiose, among others; or
[IgGBM] is a group according to the chemical structure:

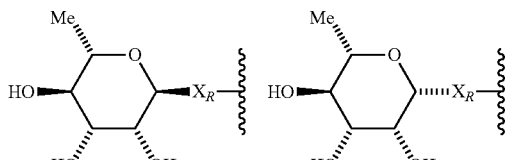

α-L-Rhamnose    β-L-Rhamnose

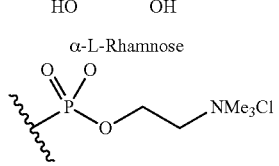

Phosphoryl Choline

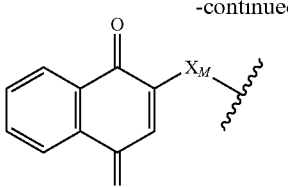

Menadione

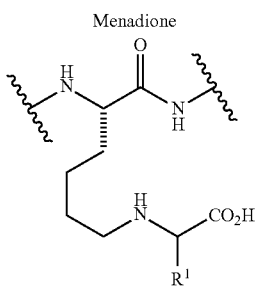

Carboxyethyl Lysine ($R^1$ = Me)

Where $X_R$ is O, S or $NR^1$; and
$X_M$ is O, $NR^1$ or S, and
$R^1$ is H or a $C_1$-$C_3$ alkyl group; or
[IgGBM] is a group according to the chemical structure:

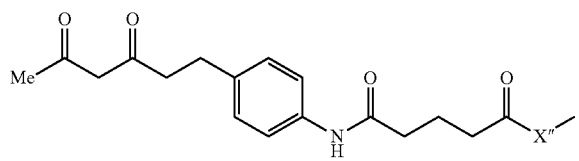

Where X″ is O, $CH_2$, $NR^1$, S; and
$R^1$ is H, a $C_1$-$C_3$ alkyl group or a —C(O)($C_1$-$C_3$) group; or

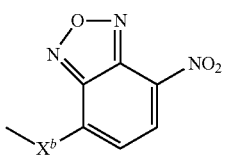

Where $X^b$ is a bond, O, $CH_2$ or $NR^1$ or S; and
$R^1$ is the same as above; or
a group according to the chemical structure:

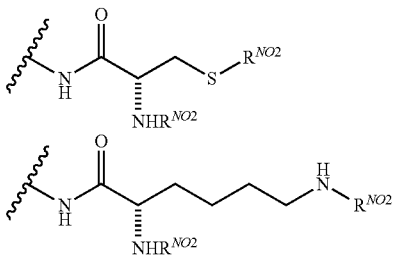

Where $R^{NO2}$ is a dinitrophenyl group optionally linked through $CH_2$, S(O), $S(O)_2$, —$S(O)_2O$, —$OS(O)_2$, or $OS(O)_2O$; or a dinitrophenyl group according to the chemical structure:

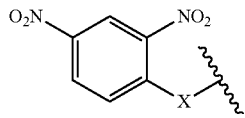

X is O, $CH_2$, $NR^1$, S(O), $S(O)_2$, —$S(O)_2O$, —$OS(O)_2$, or $OS(O)_2O$; and
$R^1$ is H, a $C_1$-$C_3$ alkyl group, or a —C(O)($C_1$-$C_3$) group, or

[IgGBM] is a group according to the chemical structure:

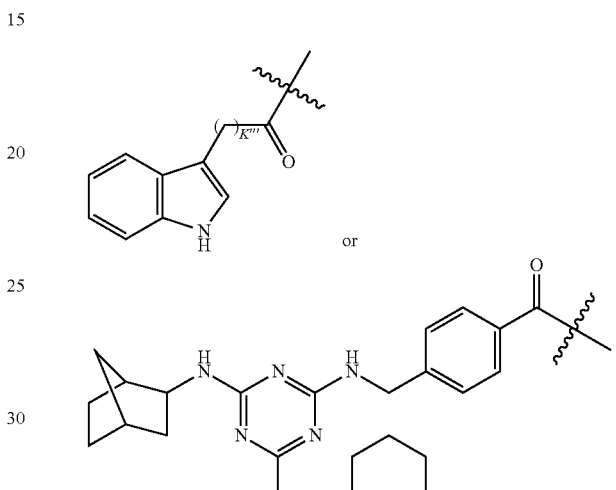

where K‴ is 1-4 (preferably 2-3, most often 3), or a a group according to a chemical structure which is set forth in FIG. 67 hereof which is covalently attached to a [CON] group, a [LINKER] group or a [ASGPRBM] group through an amine group, preferably a primary or secondary alkyl amine group which is optionally substituted on the amine group with a $C_1$-$C_3$ alkyl group; or a

[IgGBM] is a peptide according to the sequence (all references cited are incorporated by reference herein):

PAM (Fassina, et al., *J. Mol. Recognit.* 1996, 9, 564-569);
D-PAM (Verdoliva, et al., *J. Immunol. Methods,* 2002, 271, 77-88);
D-PAM-Φ (Dinon, et al. *J. Mol. Recognit.* 2011, 24, 1087-1094);
TWKTSRISIF (Krook, et al., *J. Immunol. Methods* 1998, 221, 151-157) SEQ ID NO:1;
FGRLVSSIRY (Krook, et al., *J. Immunol. Methods* 1998, 221, 151-157) SEQ ID NO:2;
Fc-III (DeLano, et al., *Science* 2000, 287, 1279-1283);
FcBP-1 (Kang, et al., *J. Chromatogr. A* 2016, 1466, 105-112);
FcBP-2 (Dias, et al., *J. Am. Chem. Soc.* 2006, 128, 2726-2732);
Fc-III-4c (Gong, et al., *Bioconjug. Chem.* 2016, 27, 1569-1573);
EPIHRSTLTALL (Ehrlich, et al., *J. Biochem. Biophys. Method* 2001, 49, 443-454) SEQ ID NO:3;
APAR (Camperi, et al., *Biotechnol. Lett.* 2003, 25, 1545-1548) SEQ ID NO:4;
FcRM (Fc Receptor Mimetic, Verdoliva, et al., *ChemBioChem* 2005, 6, 1242-1253);

HWRGWV (Yang, et al., *J. Peptide Res.* 2006, 66, 110-137) SEQ ID NO:5;

HYFKFD (Yang, et al., *J. Chromatogr. A* 2009, 1216, 910-918) SEQ ID NO:6;

HFRRHL (Menegatti, et al., *J. Chromatogr. A* 2016, 1445, 93-104) SEQ ID NO:7;

HWCitGWV (Menegatti, et al., *J. Chromatogr. A* 2016, 1445, 93-104) SEQ ID NO:8;

D2AAG (Small Synthetic peptide ligand, Lund, et al., *J. Chromatogr. A* 2012, 1225, 158-167);

DAAG (Small Synthetic peptide ligand, Lund, et al., *J. Chromatogr. A* 2012, 1225, 158-167);

cyclo[(N—Ac)S(A)-RWHYFK-Lact-E] (Menegatti, et al., *Anal. Chem.* 2013, 85, 9229-9237) (SEQ ID NO:9-Lact-E);

cyclo[(N—Ac)-Dap(A)-RWHYFK-Lact-E] (Menegatti, et al., *Anal. Chem.* 2013, 85, 9229-9237) (SEQ ID NO:10-Lact-E);

cyclo[Link-M-WFRHYK] (Menegatti, et al., *Biotechnol. Bioeng.* 2013, 110, 857-870) SEQ ID NO:11;

NKFRGKYK (Sugita, et al., *Biochem. Eng. J.* 2013, 79, 33-40) SEQ ID NO:12;

NARKFYKG (Sugita, et al., *Biochem. Eng. J.* 2013, 79, 33-40) SEQ ID NO:13;

FYWHCLDE (Zhao, et al., *Biochem. Eng. J.* 2014, 88, 1-11) SEQ ID NO:14;

FYCHWALE (Zhao, et al., *J. Chromatogr. A* 2014, 1355, 107-114) SEQ ID NO:15;

FYCHTIDE (Zhao, et al., *J. Chromatogr. A* 2014, 1359, 100-111) SEQ ID NO:16;

Dual 1/3 (Zhao, et al., *J. Chromatogr. A* 2014, 1369, 64-72);

RRGW (Tsai, et al., *Anal. Chem.* 2014, 86, 2931-2938) SEQ ID NO:17;

KHRFNKD (Yoo and Choi, *BioChip J.* 2015, 10, 88-94) SEQ ID NO:18;

[ASGPRBM] is a group according to the chemical structure:

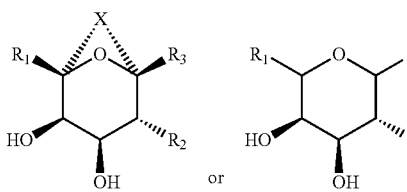

where X is 1-4 atoms in length and comprises O, S, $N(R^{N1})$ or $C(R^{N1})(R^{N1})$ groups such that when X is 1 atom in length, X is O, S, $N(R^{N1})$ or $C(R^{N1})(R^{N1})$, when X is 2 atoms in length, no more than 1 atom of X is O, S or $N(R^{N1})$, when X is 3 or 4 atoms in length, no more than 2 atoms of X are O, S or $N(R^{N1})$;

where $R^{N1}$ is H or a $C_1$-$C_3$ alkyl group optionally substituted with from 1-3 halo groups, preferably F ($R^{N1}$ is preferably H or methyl, more often H);

$R_1$ and $R_3$ are each independently H, —$(CH_2)_K$OH, —$(CH_2)_K$O$C_1$-$C_4$ alkyl, which is optionally substituted with from 1-3 halo (F, Cl, Br, I, preferably F) groups, $C_1$-$C_4$ alkyl, which is optionally substituted with from 1-3 halo (F, Cl, Br, I, preferably F) groups, —$(CH_2)_K$vinyl, O—$(CH_2)_K$vinyl, —$(CH_2)_K$alkynyl, —$(CH_2)_K$COOH, —$(CH_2)_K$C(O)O—$C_1$-$C_4$ alkyl which is optionally substituted with from 1-3 halo, preferably F groups, O—C(O)—$C_1$-$C_4$ alkyl, which is optionally substituted with from 1-3 halo, preferably F groups, —C(O)—$C_1$-$C_4$ alkyl, which is optionally substituted with from 1-3 halo, preferably F groups, or $R_1$ and $R_3$ are each independently a

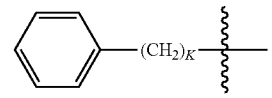

group, which is optionally substituted with up to three (preferably 1) halo groups (preferably F), $C_1$-$C_4$ alkyl groups, each of which is optionally substituted with from one to three halo groups, preferably F, or one or two hydroxyl groups, or O—$C_1$-$C_4$ alkyl groups, each of which alkyl groups is optionally substituted with from one to three halo groups, preferably F, or one or two hydroxyl groups, and K is independently 0-4 (0, 1, 2, 3 or 4), or $R_1$ and $R_3$ are each independently a group according to the chemical structure:

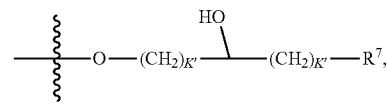

where $R^7$ is O—$C_1$-$C_4$ alkyl, which is optionally substituted with from 1 to 3 halo groups, preferably F and 1 or 2 hydroxy groups, or $R^7$ is a —$NR^{N3}R^{N4}$ group or a

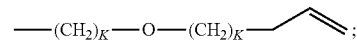

or $R_1$ and $R_3$ are each independently a group according to the structure:

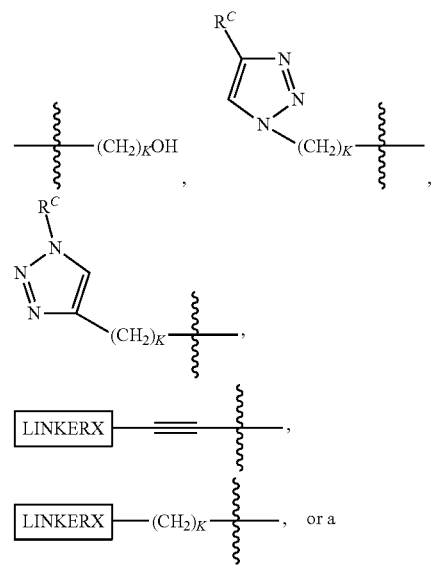

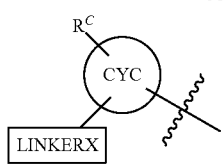
group according to the chemical structure:
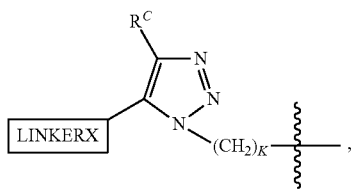
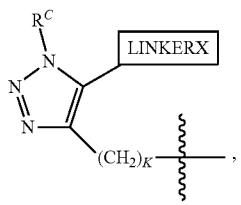
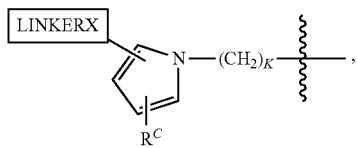
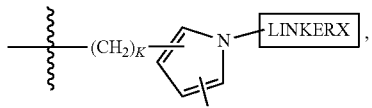
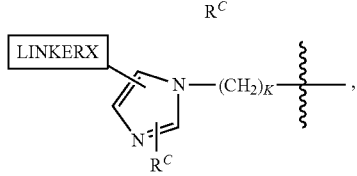
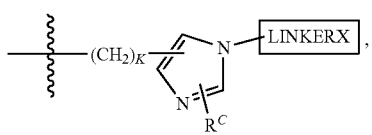
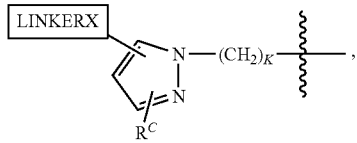
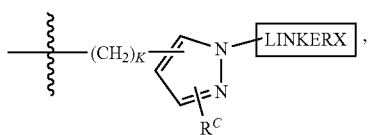
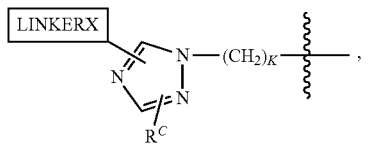
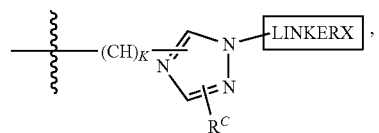
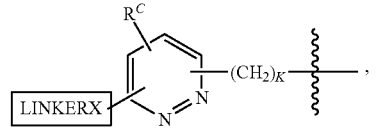
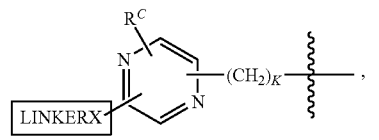
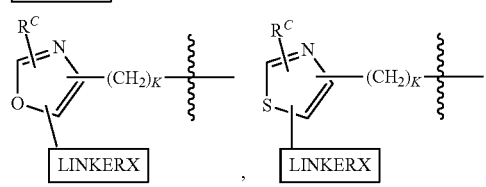
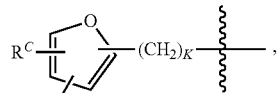
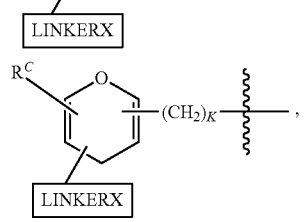
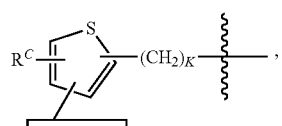
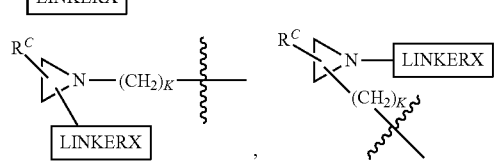
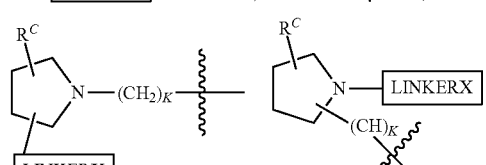
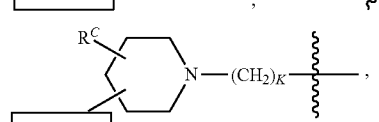
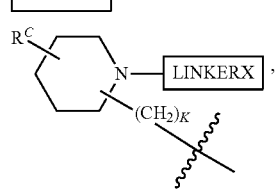

-continued

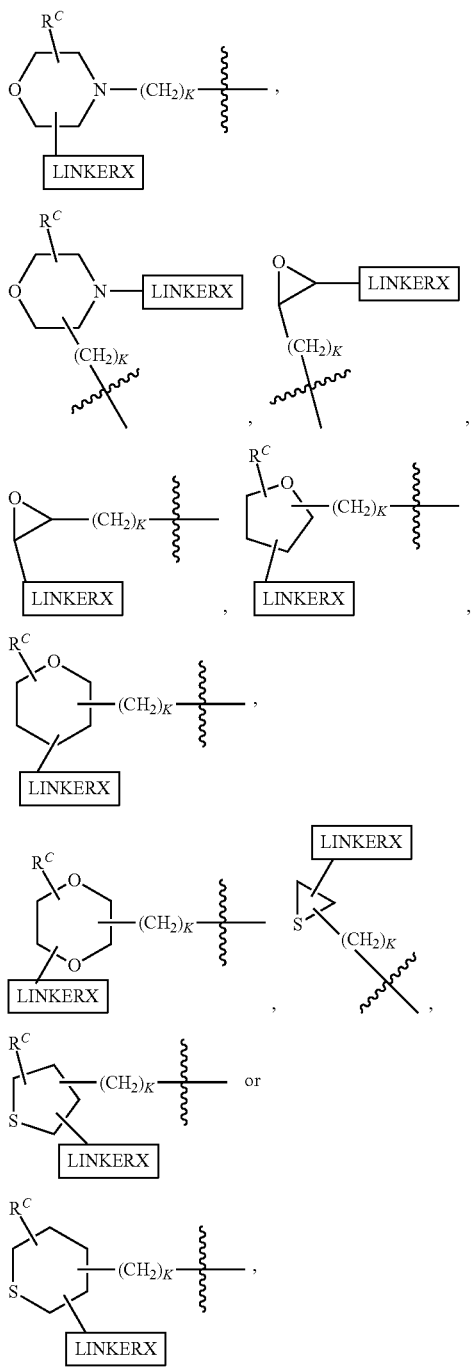

or $R_1$ and $R_3$ are each independently a

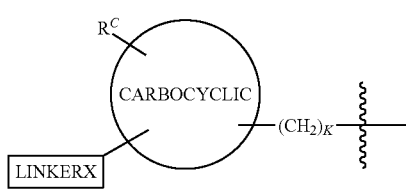

group, where

is a $C_3$-$C_8$ saturated carbocyclic group;
$R^C$ is absent, H, $C_1$-$C_4$ alkyl which is optionally substituted with from 1-3 halo (preferably fluoro) groups or 1-2 hydroxyl groups, or a group according to the structure:

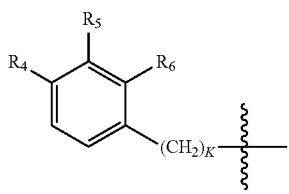

where $R_4$, $R_5$ and $R_6$ are each independently, H, halo (F, Cl, Br, I), CN, $NR^{N1}R^{N2}$, —$(CH_2)_K OH$, —$(CH_2)_K OC_1$-$C_4$ alkyl, which is optionally substituted with from 1-3 halo (F, Cl, Br, I, preferably F) groups, $C_1$-$C_3$ alkyl, which is optionally substituted with from 1-3 halo (F, Cl, Br, I, preferably F) groups, —O—$C_1$-$C_3$-alkyl, which is optionally substituted with from 1-3 halo, preferably F groups, —$(CH_2)_K COOH$, —$(CH_2)_K C(O)O$—$C_1$-$C_4$ alkyl which is optionally substituted with from 1-3 halo, preferably F groups, O—C(O)—$C_1$-$C_4$ alkyl, which is optionally substituted with from 1-3 halo, preferably F groups, —C(O)—$C_1$-$C_4$ alkyl, which is optionally substituted with from 1-3 halo, preferably F groups, or
$R^C$ is a

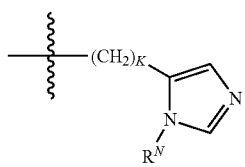

group, a

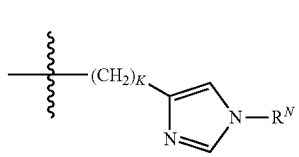

group a

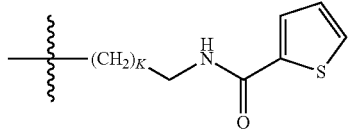

group or a

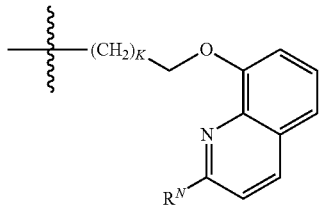

group,
where $R^N$, $R^{N1}$ and $R^{N2}$ are each independently H or a $C_1$-$C_3$ alkyl group which is optionally substituted with from one to three halo groups, preferably F, or one or two hydroxyl groups;

K is independently 0-4 (0, 1, 2, 3 or 4), preferably 0 or 1;

K' is 1-4, preferably 1;

$R^{N3}$ is H, or a $C_1$-$C_3$ alkyl group which is optionally substituted with 1-3 halo groups, preferably F or 1 or 2 hydroxy groups; and $R^{N4}$ is H, a $C_1$-$C_3$ alkyl group which is optionally substituted with 1-3 halo groups, preferably F or 1 or 2 hydroxy groups, or $R^{N4}$ is a

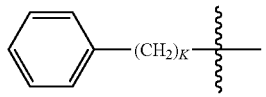

group, where K is preferably 1;

[LINKERX] is a linker group which is comprises to at least one [MFFBM/IgGBM] group and links the [MIFBM/IgGBM] group to the [ASGPRBM] through one or more optional [CON] groups, or

[LINKERX] is a linker group which contains at least one or more functional groups which can be used to covalently bond the linker group to at least one [MIFBM/IgGBM] group or optional [CON] group;

$R_2$ is a

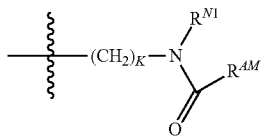

group where $R^{N1}$ and K are the same as above;

$R^{AM}$ is H, a $C_1$-$C_4$ alkyl group optionally substituted with up to 3 halo groups (preferably F) and one or two hydroxyl groups, a —(CH$_2$)$_K$COOH group, a —(CH$_2$)$_K$C(O)O—C$_1$-C$_4$ alkyl group which is optionally substituted with from 1-3 halo, preferably F groups, a O—C(O)—C$_1$-C$_4$ alkyl group, which is optionally substituted with from 1-3 halo, preferably F groups, a —C(O)—C$_1$-C$_4$ alkyl group, which is optionally substituted with from 1-3 halo, preferably F groups, a —(CH$_2$)$_K$—NR$^{N3}$R$^{N4}$ group where R$^{N3}$ is H, or a $C_1$-$C_3$ alkyl group which is optionally substituted with 1-3 halo groups, preferably F or 1 or 2 hydroxy groups; and $R^{N4}$ is H, a $C_1$-$C_3$ alkyl group which is optionally substituted with 1-3 halo groups, preferably F or 1 or 2 hydroxy groups, or $R^{N4}$ is a

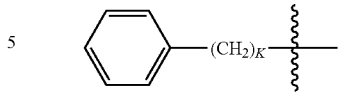

group (K is preferably 1), or $R_2$ is a

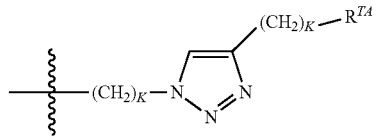

group,
where $R^{TA}$ is H, CN, NR$^{N1}$R$^{N2}$, —(CH$_2$)$_K$OH, —(CH$_2$)$_K$OC$_1$-C$_4$ alkyl, which is optionally substituted with from 1-3 halo (F, Cl, Br, I, preferably F) groups, $C_1$-$C_4$ alkyl, which is optionally substituted with from 1-3 halo (F, Cl, Br, I, preferably F) groups, —(CH$_2$)$_K$COOH, —(CH$_2$)$_K$C(O)O—C$_1$-C$_4$ alkyl which is optionally substituted with from 1-3 halo, preferably F groups, O—C(O)—C$_1$-C$_4$ alkyl, which is optionally substituted with from 1-3 halo, preferably F groups, —C(O)—C$_1$-C$_4$ alkyl, which is optionally substituted with from 1-3 halo, preferably F groups, or $R^{TA}$ is a $C_3$-$C_{10}$ aryl or a three- to ten-membered heteroaryl group containing up to 5 heteroaryl atoms, each of said aryl or heteroaryl groups being optionally substituted with up to three (preferably 1) CN, NR$^{N1}$R$^{N2}$, —(CH$_2$)$_K$OH, —(CH$_2$)$_K$OC$_1$-C$_4$ alkyl, which is optionally substituted with from 1-3 halo (F, Cl, Br, I, preferably F) groups, $C_1$-$C_3$ alkyl, which is optionally substituted with from 1-3 halo (F, Cl, Br, I, preferably F) groups or 1 or 2 hydroxy groups, —O—$C_1$-$C_3$-alkyl, which is optionally substituted with from 1-3 halo, preferably F groups, —(CH$_2$)$_K$COOH, —(CH$_2$)$_K$C(O)O—C$_1$-C$_4$ alkyl which is optionally substituted with from 1-3 halo, preferably F groups, O—C(O)—C$_1$-C$_4$ alkyl, which is optionally substituted with from 1-3 halo, preferably F groups or —(CH$_2$)$_K$C(O)—C$_1$-C$_4$ alkyl which is optionally substituted with from 1-3 halo, preferably F groups, or $R^{TA}$ is a

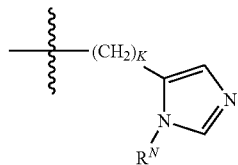

group, a

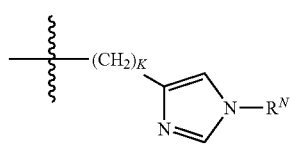

group, a

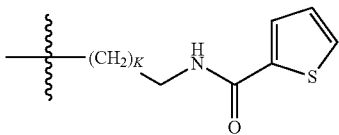

group or a,

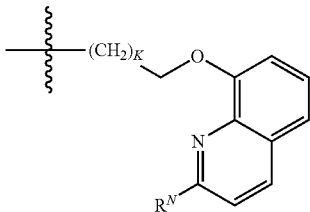

group,
(preferably, $R^{T4}$ is a

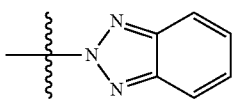 [SMILES: *n1nc2ccccc2n1]

group which is optionally substituted with up to three, preferably 1 $C_1$-$C_3$ alkyl groups which are optionally substituted with up to three halo (preferably F) groups, or $R^{T4}$ is a

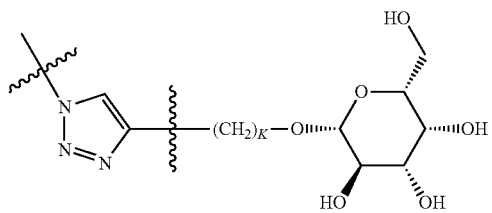

group, wherein $R^N$, $R^{N1}$ and $R^{N2}$ are each independently H or a $C_1$-$C_3$ alkyl group which is optionally substituted with from one to three halo groups, preferably F, or one or two hydroxyl groups and wherein each —$(CH_2)_K$— group is optionally substituted with 1-4, preferably 1 or 2, $C_1$-$C_3$ alkyl groups which are optionally substituted with from 1-3 fluoro groups or 1-2 hydroxyl groups; and K is independently 0-4 (0, 1, 2, 3 or 4), preferably 0 or 1;

[CON] is a connector moiety (including a [MULTICON]) as otherwise described herein; and

[LINKER] is a linking moiety as otherwise described herein which links [MIFBM/IgGBM] to the [ASGPRBM] group and optionally contains one or more connector moieties (which optionally connect(s) more than one chemical moiety to provide said linking moiety or which connects said linking moiety to said [MIFBM/IgGBM] group or said [ASGPRBM] group, or a pharmaceutically acceptable salt, stereoisomer, solvate or polymorph thereof.

In embodiments of the present invention X is often —O—C($R^{N1}$)($R^{N1}$), C($R^{N1}$)($R^{N1}$)—O—, —S—C($R^{N1}$)($R^{N1}$), C($R^{N1}$)($R^{N1}$)—S—, N($R^{N1}$)—C($R^{N1}$)($R^{N1}$), C($R^{N1}$)($R^{N1}$)—N($R^{N1}$) or C($R^{N1}$)($R^{N1}$)—C($R^{N1}$)($R^{N1}$) when X is 2 atoms in length, X is —O—C($R^{N1}$)($R^{N1}$)—C($R^{N1}$)($R^{N1}$), C($R^{N1}$)($R^{N1}$)—O—C($R^{N1}$)($R^{N1}$)—, —O—C($R^{N1}$)($R^{N1}$)—O—, —O—C($R^{N1}$)($R^{N1}$)—S—, —O—C($R^{N1}$)($R^{N1}$)—N($R^{N1}$)—, —S—C($R^{N1}$)($R^{N1}$)—C($R^{N1}$)($R^{N1}$), C($R^{N1}$)($R^{N1}$)—S—C($R^{N1}$)($R^{N1}$)—, C($R^{N1}$)($R^{N1}$)—C($R^{N1}$)($R^{N1}$)—S—, —S—C($R^{N1}$)($R^{N1}$)—S—, —S—C($R^{N1}$)($R^{N1}$)—O—, —S—C($R^{N1}$)($R^{N1}$)—N($R^{N1}$)—, N($R^{N1}$)—C($R^{N1}$)($R^{N1}$)—C($R^{N1}$)($R^{N1}$), C($R^{N1}$)($R^{N1}$)—N($R^{N1}$)—C($R^{N1}$)($R^{N1}$), C($R^{N1}$)($R^{N1}$)—C($R^{N1}$)($R^{N1}$)—N($R^{N1}$), N($R^{N1}$)—C($R^{N1}$)($R^{N1}$)—N($R^{N1}$) or C($R^{N1}$)($R^{N1}$)—C($R^{N1}$)($R^{N1}$)—C($R^{N1}$)($R^{N1}$) when X is 3 atoms in length, and X is —O—C($R^{N1}$)($R^{N1}$)—C($R^{N1}$)($R^{N1}$)—C($R^{N1}$)($R^{N1}$), C($R^{N1}$)($R^{N1}$)—O—C($R^{N1}$)($R^{N1}$)—($R^{N1}$)($R^{N1}$)—, —O—C($R^{N1}$)($R^{N1}$)—O—C($R^{N1}$)($R^{N1}$)—, —S—C($R^{N1}$)($R^{N1}$)—C($R^{N1}$)($R^{N1}$)—C($R^{N1}$)($R^{N1}$)—, C($R^{N1}$)($R^{N1}$)—S—C($R^{N1}$)($R^{N1}$)—C($R^{N1}$)($R^{N1}$)—, C($R^{N1}$)($R^{N1}$)—($R^{N1}$)($R^{N1}$)—S—C($R^{N1}$)($R^{N1}$)—, —S—C($R^{N1}$)($R^{N1}$)—S—C($R^{N1}$)($R^{N1}$)—, N($R^{N1}$)—C($R^{N1}$)($R^{N1}$)—C($R^{N1}$)($R^{N1}$)— C($R^{N1}$)($R^{N1}$)—, C($R^{N1}$)($R^{N1}$)—N($R^{N1}$)—C($R^{N1}$)($R^{N1}$)—C($R^{N1}$)($R^{N1}$), C($R^{N1}$)($R^{N1}$)—C($R^{N1}$)($R^{N1}$)— N($R^{N1}$), N($R^{N1}$)—C($R^{N1}$)($R^{N1}$)—N($R^{N1}$) or C($R^{N1}$)($R^{N1}$)—C($R^{N1}$)($R^{N1}$)— C($R^{N1}$)($R^{N1}$) when X is 4 atoms in length where $R^{N1}$ is the same as above. Most often, $R^{N1}$ is H.

In embodiments of the present invention X is $OCH_2$ or $CH_2O$ and $R^{N1}$ is preferably H.

In embodiments, the [ASGPRBM] group is a group according to the chemical structure:

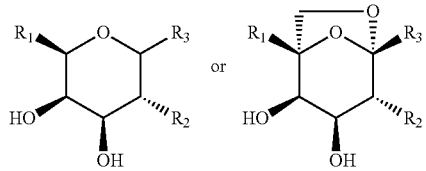

where $R_1$, $R_2$ and $R_3$ are the same as above, or a pharmaceutically acceptable salt, stereoisomer, solvate or polymorph thereof.

In embodiments, the [ASGPRBM] group is a group according to the chemical structure:

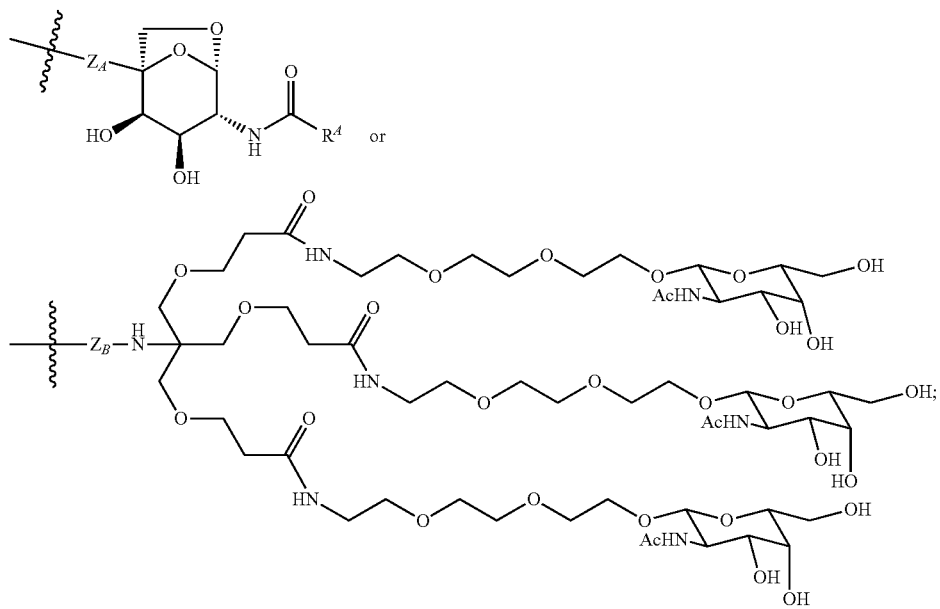

Where $R^A$ is a $C_1$-$C_3$ alkyl group which is optionally (preferably) substituted with 1-5 halo (preferably fluoro) groups (preferably $R^A$ is a methyl or ethyl group which is optionally substituted with from 1-3 fluoro groups);

$Z_A$ is —$(CH_2)_{IM}$, —O—$(CH_2)_{IM}$, S—$(CH_2)_{IM}$, $NR_M$—$(CH_2)_{IM}$, C(O)—$(CH_2)_{IM}$—, a PEG group containing from 1 to 8 preferably 1-4 ethylene glycol residues or a —C(O)$(CH_2)_{IM}NR_M$ group (preferably a PEG containing group comprising from 1 to 8 ethylene glycol, preferably 2-4 ethylene glycol residues) where $_{IM}$ and $R_M$ are the same as above; and $Z_B$ is absent, $(CH_2)_{IM}$, C(O)—$(CH_2)_{IM}$— or C(O)—$(CH_2)_{IM}$—$NR_M$, where $_{IM}$ and $R_M$ are the same as above.

In embodiments according to the present invention, $R_1$ and $R_3$ (preferably $R_1$) are each independently often a group according to the chemical structure:

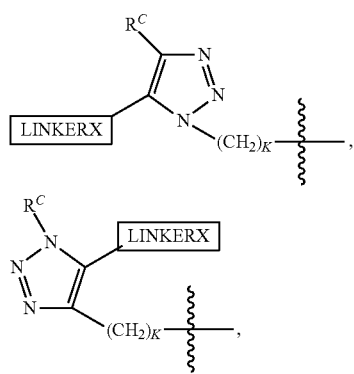

where $R^C$, LINKERX and K are the same as above.

In the above-described compounds,

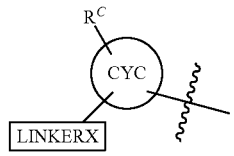

is preferably a group according to the chemical structure:

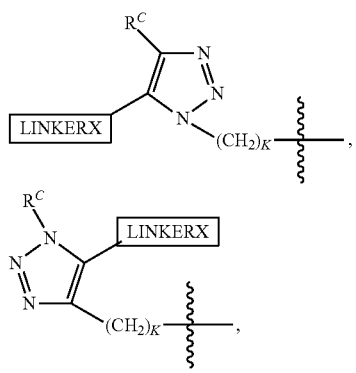

where $R^C$, LINKERX and K are the same as above.

In embodiments, preferred compounds include the compounds which are presented in FIGS. 1, 7 and 13. In embodiments, additional compounds are presented in FIGS. 16-66 and include final compounds set forth therein and intermediates which are used to make final compounds pursuant to the present invention.

In embodiments, $R_1$ and $R_3$ of the [ASGPRBM] group include those moieties which are presented in FIG. 68 hereof. In embodiments, $R_2$ of the [ASGPRBM] group include those moieties which are presented in FIG. 69 hereof.

In embodiments, the IgGBM group is a FCIII group according to the chemical structure

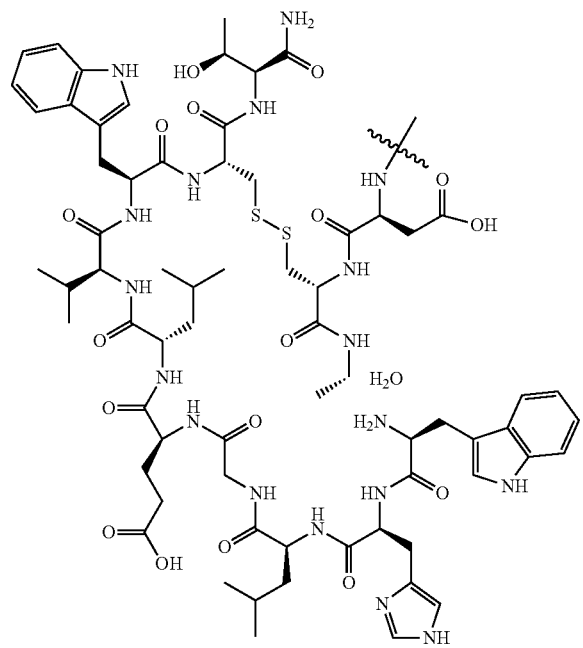

FCIII, which can be represented as (SEQ ID NO: 19)

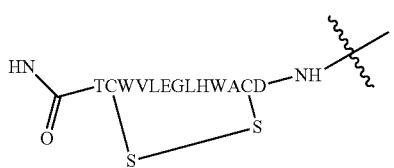

or a FcIII-4c peptide represented as (SEQ ID NO: 20)

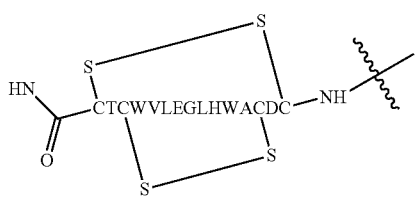

In an additional embodiment, the present invention is directed to a pharmaceutical composition comprising an effective amount of a compound according to the present invention in combination with a pharmaceutically acceptable carrier, additive or excipient, optionally in combination with at least one additional bioactive agent.

In other embodiments, the present invention is directed to a method of treating a disease state or condition where MIF is related to or contributes to a disease state and or condition or the symptomology associated with the disease state or condition. These disease states and/or conditions include, autoimmune diseases and numerous inflammatory diseases for example, rheumatoid arthritis (RA), systemic lupus erythematosus (SLE), Alzheimer's disease, atherosclerosis, heart disease, stroke and cancer (including leukemia), among numerous others. The method of treatment according to the present invention comprises administering to a patient or subject in need of therapy an effective amount of at least one compound according to the present invention, optionally in combination with an additional bioactive agent to reduce the likelihood of, inhibit and/or treat the disease state or condition by removing MIF associated with the disease state and/or condition from the circulation of the patient or subject.

In experiments, bi-functional molecules of the present invention, MIF-GN$_3$ were able to induce the degradation of human MIF injected in mice. Additional work focuses on the evaluation of MIF-GN$_3$ in autoimmune disease models as well as seeking to optimize the bi-functional MIF degrader using different MIF and ASGPr ligands. IgG-targeting molecules were able to recapitulate our results with MIF in cell culture and mediated the removal of IgG from mouse serum. Thus, the present invention provides a useful platform for the development of new therapeutics for these critical diseases.

BRIEF DESCRIPTION OF THE FIGURES

FIG. 69 shows exemplary $R_2$ substituents on ASGPRBM groups as otherwise described herein.

DETAILED DESCRIPTION OF THE INVENTION

Figure 1:
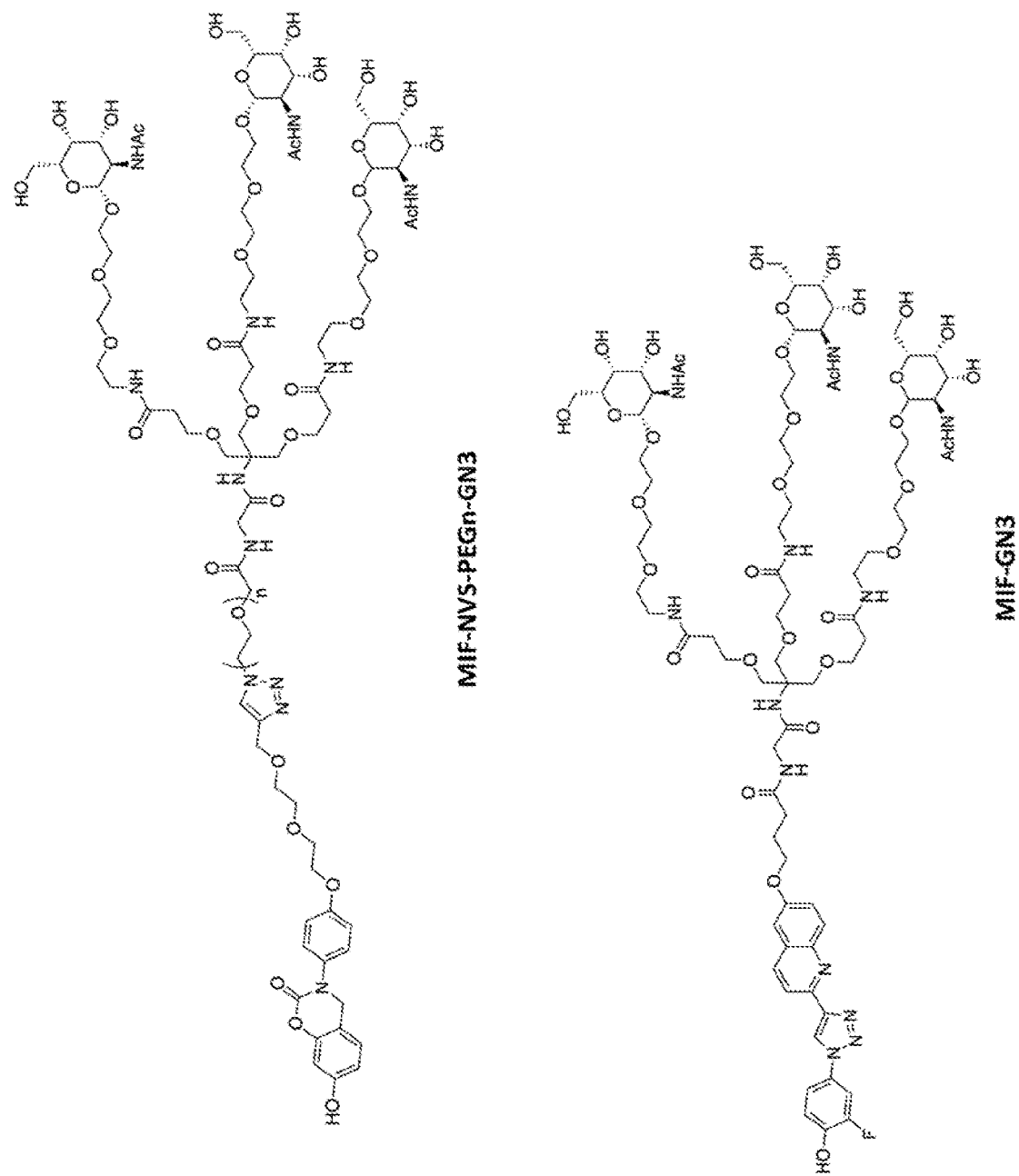
FIG. 1 shows representative compounds according to the present invention. Note that the figure discloses compound 3w (negative control for MIF inhibition), MIF-NVS-PEGnGN3, MIFGN3, MIF-PEGnGN3, MIF-AcF3-1, MIF-AcF3-2 and MIF-AcF3-3. Note that n in the PEG linker preferably ranges from 1-12, 1 to 10, 2 to 8, 2 to 6, 2 to 5 or 1, 2, 3 or 4.
Figure 1:
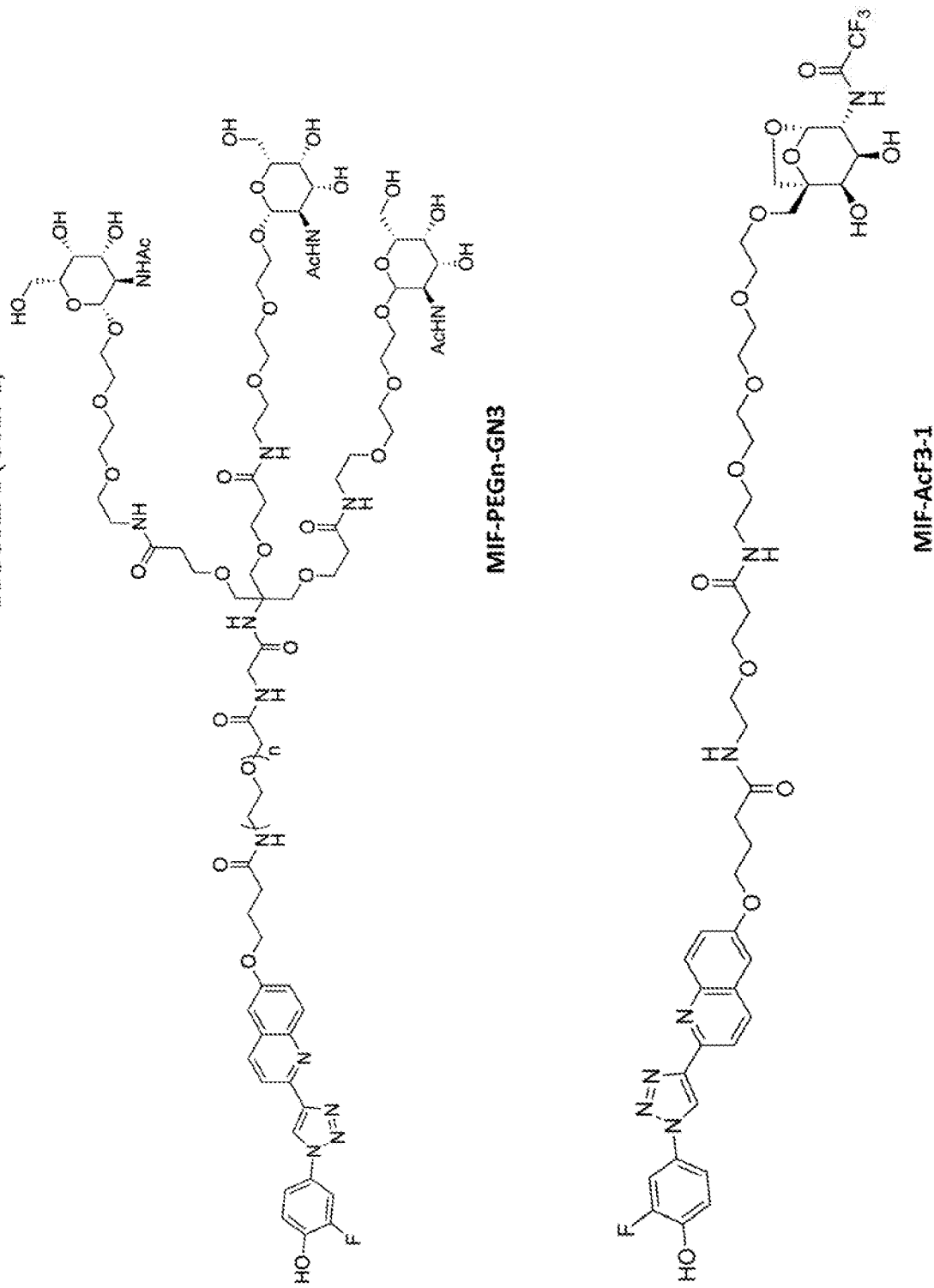
Figure 1:
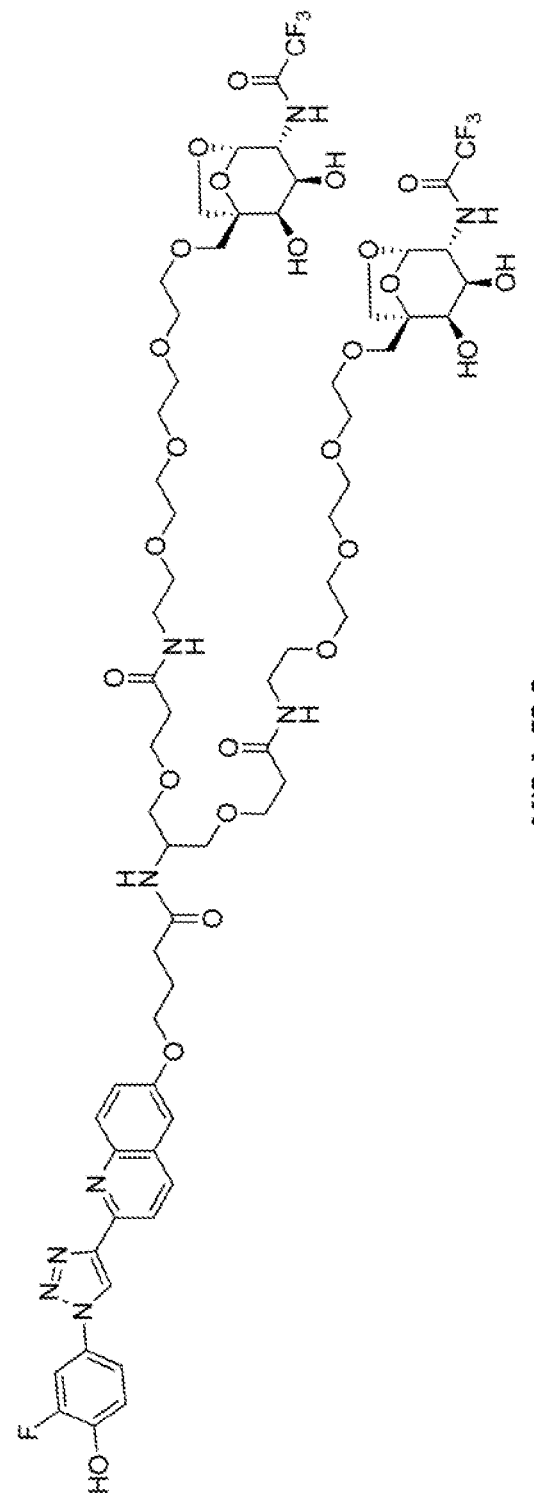
Figure 1:
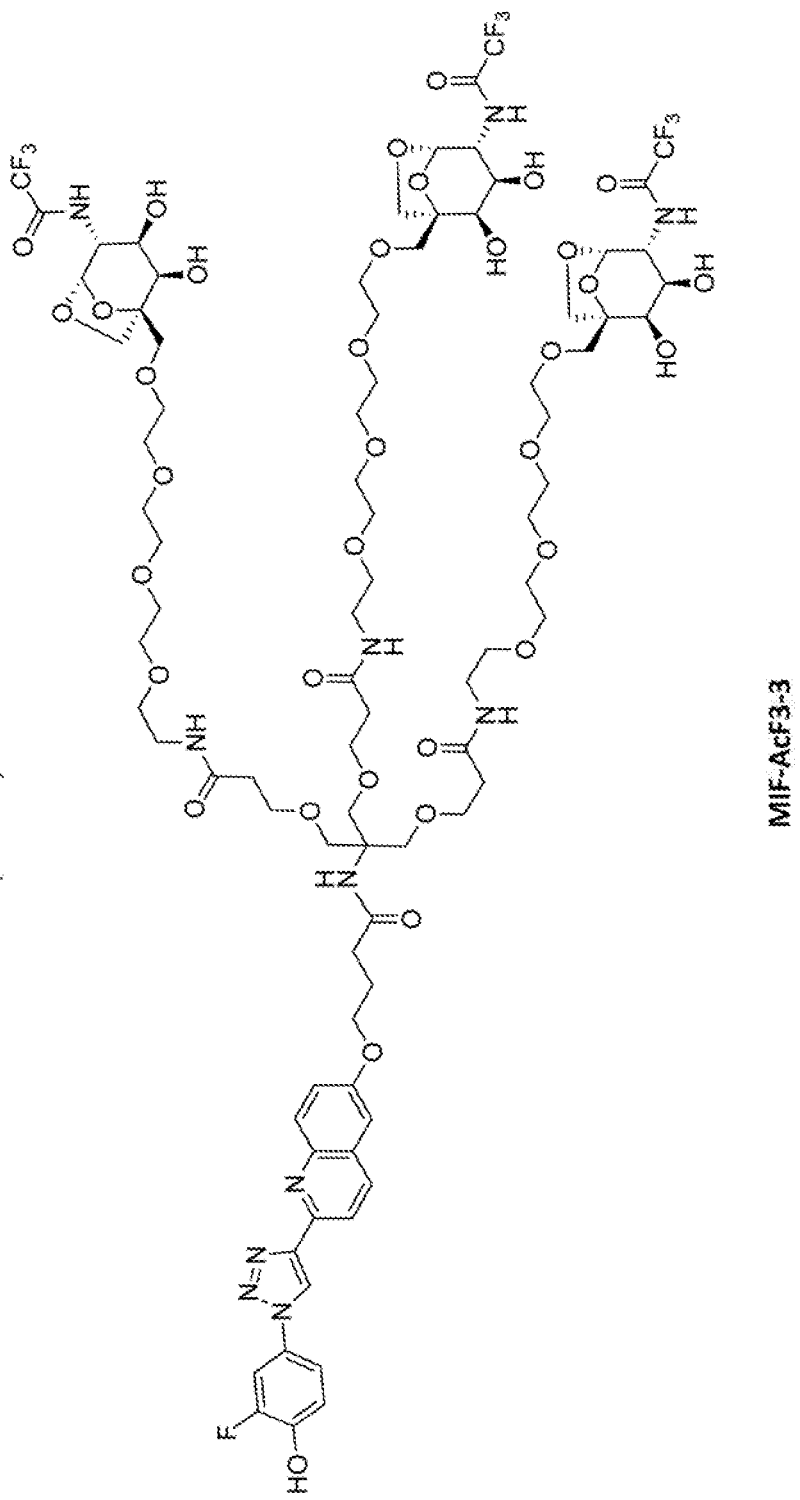

In accordance with the present invention there may be employed conventional chemical synthetic and pharmaceutical formulation methods, as well as pharmacology, molecular biology, microbiology, and recombinant DNA techniques within the skill of the art. Such techniques are well-known and are otherwise explained fully in the literature.

Where a range of values is provided, it is understood that each intervening value, to the tenth of the unit of the lower limit unless the context clearly dictates otherwise (such as in the case of a group containing a number of carbon atoms), between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It is to be noted that as used herein and in the appended claims, the singular forms "a," "an", "and" and "the" include plural references unless the context clearly dictates otherwise.

Furthermore, the following terms shall have the definitions set out below. It is understood that in the event a specific term is not defined hereinbelow, that term shall have a meaning within its typical use within context by those of ordinary skill in the art.

The term "compound", as used herein, unless otherwise indicated, refers to any specific chemical compound disclosed herein and includes tautomers, regioisomers, geometric isomers, stereoisomers and where applicable, optical isomers (enantiomers) thereof, as well as pharmaceutically acceptable salts and derivatives (including prodrug forms) thereof. Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds. The term also refers, within context, to prodrug forms of compounds which have been modified to facilitate the administration and delivery of compounds to a site of activity. It is noted that in describing the present compounds, numerous substituents, linkers and connector molecules and variables associated with same, among others, are described. The use of a bond presented as ----- signifies that a single bond is present or absent, depending on the context of the chemistry described, including the attachment of the bond to another moiety. The use of a bond presented as ======= signifies that a single bond or a double bond is intended depending on the context of the chemistry described. It is understood by those of ordinary skill that molecules which are described herein are stable compounds as generally described hereunder.

The term "patient" or "subject" is used throughout the specification within context to describe an animal, generally a mammal and preferably a human, to whom treatment, including prophylactic treatment (prophylaxis, including especially as that term is used with respect to reducing the likelihood of metastasis of an existing cancer), with the compositions according to the present invention is provided.

For treatment of those infections, conditions or disease states which are specific for a specific animal such as a human patient or a patient of a particular gender, such as a human male or female patient, the term patient refers to that specific animal. Compounds according to the present invention are useful for the treatment of numerous disease states including autoimmune disease states and/or conditions and inflammatory disease states and/or conditions as well as cancer, including especially for use in reducing the likelihood of metastasis or recurrence of a cancer.

The term "effective" is used herein, unless otherwise indicated, to describe an amount of a compound or composition which, in context, is used to produce or effect an intended result, whether that result relates to the inhibition of the effects of a disease state (e.g. an autoimmune disease such as rheumatoid arthritis (RA) or systemic lupus erythematosus (SLE), among others, atherosclerosis, heart disease or stroke, among numerous others or a cancer, including leukemia) on a subject or the treatment or prophylaxis of a subject for secondary conditions, disease states or manifestations of disease states as otherwise described herein. This term subsumes all other effective amount or effective concentration terms (including the term "therapeutically effective") which are otherwise described in the present application.

The terms "treat", "treating", and "treatment", etc., as used herein, refer to any action providing a benefit to a patient at risk for a disease state or condition for which a MIF protein may be removed, such as an autoimmune disease including rheumatoid arthritis (RA) or systemic lupus erythematosus (SLE), among others, atherosclerosis, heart disease, stroke and cancer (including leukemia) including recurrence and/or metastasis of cancer, improvement in the condition through lessening or suppression of at least one symptom of the disease state or condition, inhibition of one or more manifestations of the disease state (e.g., plaque formation, heart disease, cancer growth, reduction in cancer cells or tissue), prevention, reduction in the likelihood or delay in progression of a disease state or condition or manifestation of the disease state or condition, especially including plaque formation in atheroslerosis, deterioration of tissue and inflammation in rheumatoid arthritis, further damage to cardiovascular tissue in heart disease, further damage to central nervous tissue in stroke, cancer, its recurrence or metastasis of the cancer, prevention or delay in the onset of disease states or conditions which occur secondary to the disease state or condition including cancer recurrence or metastasis, among others. Treatment, as used herein, encompasses both prophylactic and therapeutic treatment, depending on the context of the treatment. The term "prophylactic" when used, means to reduce the likelihood of an occurrence or the severity of an occurrence within the context of treatment of disease state or condition, as otherwise described hereinabove.

As used in this application, the terms "about" and "approximately" are used as equivalents. Any numerals used in this application with or without about/approximately are meant to cover any normal fluctuations appreciated by one of ordinary skill in the relevant.

The term "macrophage migration inhibitory factor binding moiety" or "MIFBM" refers to a chemical moiety on one end of the bifunctional compounds according to the present invention which is capable of binding to a circulating MIF protein which is associated with or contributes to a disease state or condition as otherwise described herein. In the present invention, the MIFBM is capable of binding to the circulating MIF protein, forming a complex with the present compounds, and delivering the bound protein to a hepatocyte whereupon the other end of the bifunctional molecule which contains an asialoglycoprotein receptor binding moiety (ASGPRBM) and can bind to the surface of a hepatocyte, respectively. Once attached to the hepatocyte, the bifunctional molecule to which is bound circulating protein is internalized by the hepatocyte through an endocytosis mechanism whereupon the cell will destroy the protein via a lysosomal degradation or other degradation pathway. The term "immunoglobulin G binding moiety" or "IgGBM" is used to describe a moiety which binds to circulating IgG immunoglobulin, forming a complex with bifunctional molecules according to the present invention to be ultimately destroyed in hepatocytes. In certain instances in describing the present invention, the terms MIFBM and IgGBM are used synonymously.

Exemplary MIFBMs for inclusion in bifunctional compounds according to the present invention include moieties found in bifunctional chemical structures which appear in FIG. 1, attached hereto. MIFBMs according to the present invention include moieties according to the chemical structures:

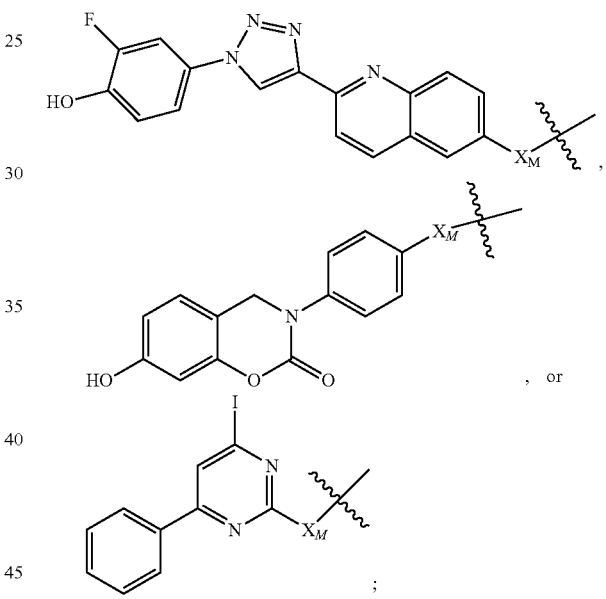

wherein $X_M$ is —$(CH_2)_{IM}$, —O—$(CH_2)_{IM}$, S—$(CH_2)_{IM}$, $NR_M$—$(CH_2)_{IM}$, C(O)—$(CH_2)_{IM}$—, a PEG group containing from 1 to 8, preferably 1-4 ethylene glycol residues or a —C(O)(CH$_2$)$_{IM}$NR$_M$ group;

$R_M$ is H or a $C_1$-$C_3$ alkyl group which is optionally substituted with one or two hydroxyl groups; and $_{IM}$ is 0-6, preferably 1, 2, 3 or 4, more preferably 1.

The term "asialoglycoprotein receptor binding moiety" ("ASGPRBM") refers to a binding moiety which binds to hepatocyte asialoglycoprotein receptor. This binding moiety is also a component of the presently claimed bifunctional compounds bound to the MIHBM moiety through a linker. The ASGPRBM selectively binds to hepatocyte asialoglycoprotein receptor on the surface of hepatocytes. It is through this moiety that bifunctional compounds complexed with circulating protein bind to hepatocytes. Once bound to the hepatocyte, the circulating MIF protein is taken into the hepatocytes via a phagocytosis mechanism wherein the circulating protein is degraded through lysosomal degradation.

Exemplary ASGPRBM groups for use in compounds according to the present invention, among others, include moieties according to the chemical structures:

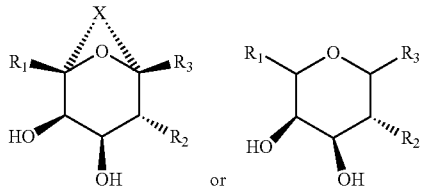

where X is 1-4 atoms in length and comprises O, S, $N(R^{N1})$ or $C(R^{N1})(R^{N1})$ groups such that when X is 1 atom in length, X is O, S, $N(R^{N1})$ or $C(R^{N1})(R^{N1})$, when X is 2 atoms in length, no more than 1 atom of X is O, S or $N(R^{N1})$, when X is 3 or 4 atoms in length, no more than 2 atoms of X are O, S or $N(R^{N1})$;

where $R^{N1}$ is H or a $C_1$-$C_3$ alkyl group optionally substituted with from 1-3 halo groups, preferably F ($R^{N1}$ is preferably H or methyl, more often H);

$R_1$ and $R_3$ are each independently H, $—(CH_2)_K OH$, $—(CH_2)_K OC_1$-$C_4$ alkyl, which is optionally substituted with from 1-3 halo (F, Cl, Br, I, preferably F) groups, $C_1$-$C_4$ alkyl, which is optionally substituted with from 1-3 halo (F, Cl, Br, I, preferably F) groups, $—(CH_2)_K$vinyl, $O—(CH_2)_K$vinyl, $—(CH_2)_K$alkynyl, $—(CH_2)_K COOH$, $—(CH_2)_K C(O)O—C_1$-$C_4$ alkyl which is optionally substituted with from 1-3 halo, preferably F groups, $O—C(O)—C_1$-$C_4$ alkyl, which is optionally substituted with from 1-3 halo, preferably F groups, $—C(O)—C_1$-$C_4$ alkyl, which is optionally substituted with from 1-3 halo, preferably F groups, or $R^1$ and $R_3$ each independently a

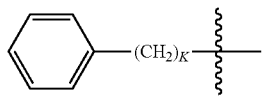

group, which is optionally substituted with up to three (preferably 1) halo groups (preferably F), $C_1$-$C_4$ alkyl groups, each of which is optionally substituted with from one to three halo groups, preferably F, or one or two hydroxyl groups, or $O—C_1$-$C_4$ alkyl groups, each of which alkyl groups is optionally substituted with from one to three halo groups, preferably F, or one or two hydroxyl groups, and K is independently 0-4 (0, 1, 2, 3 or 4), or $R_1$ and $R_3$ are each independently a group according to the chemical structure:

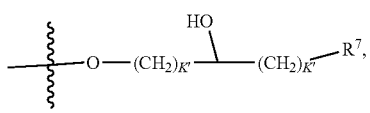

where $R^7$ is $O—C_1$-$C_4$ alkyl, which is optionally substituted with from 1 to 3 halo groups, preferably F and 1 or 2 hydroxy groups, or $R^7$ is a $—NR^{N3}R^{N4}$ group or a

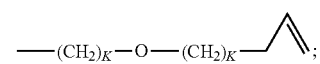

or $R_1$ and $R_3$ are each independently a group according to the structure:

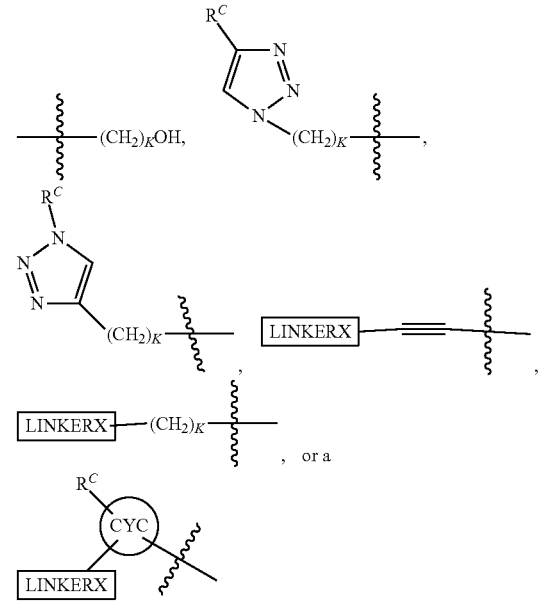

group according to the chemical structure:

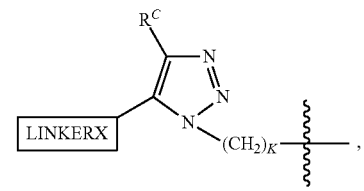

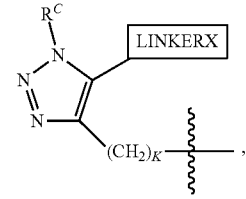

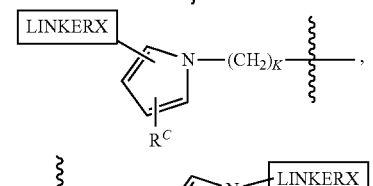

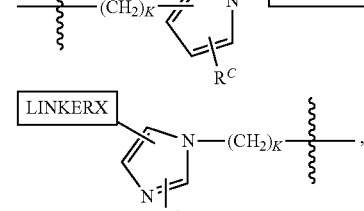

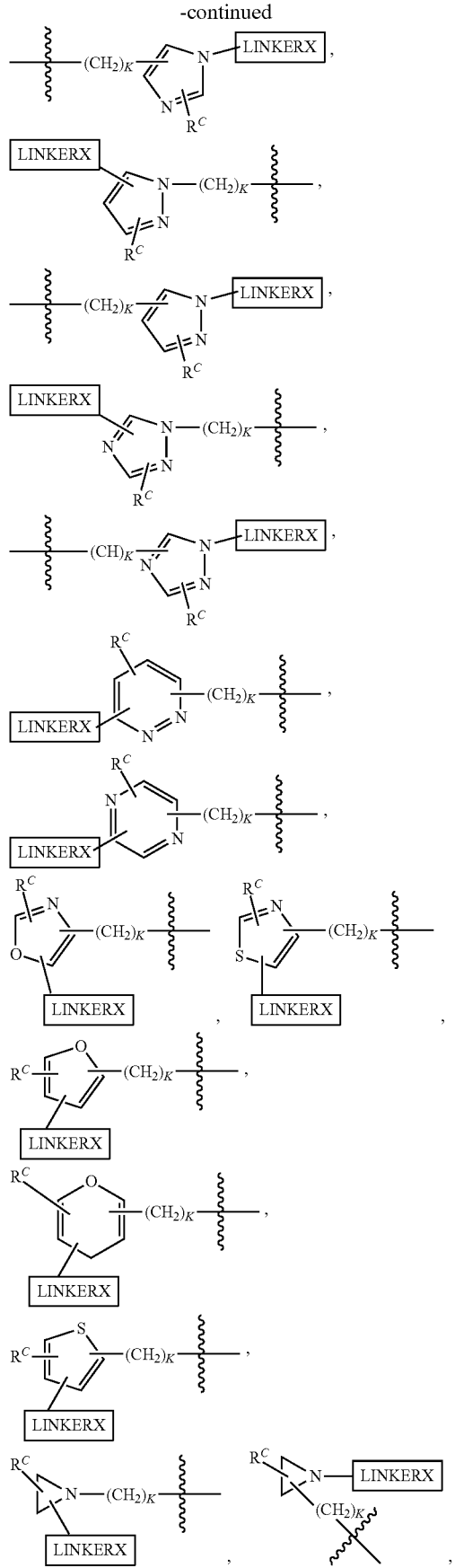
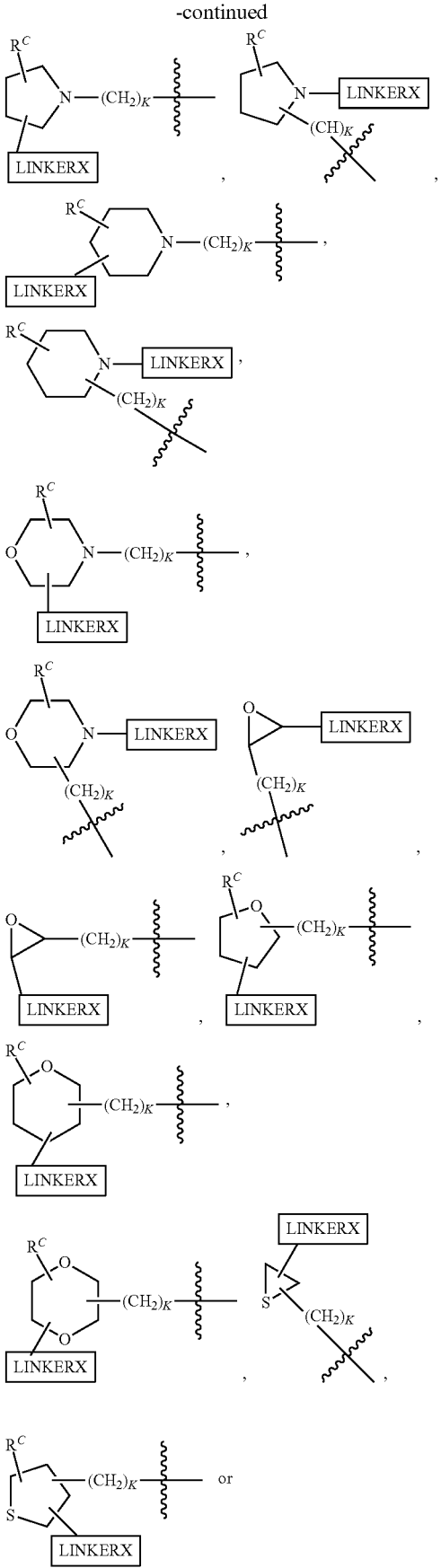

-continued

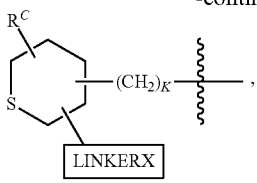

or R¹ is a

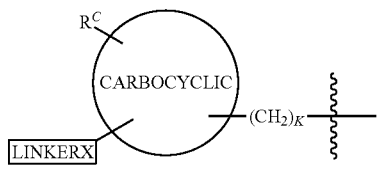

group, where

is a $C_3$-$C_8$ saturated carbocyclic group;

$R^C$ is absent, H, $C_1$-$C_4$ alkyl which is optionally substituted with from 1-3 halo (preferably fluoro) groups or 1-2 hydroxyl groups, or a group according to the structure:

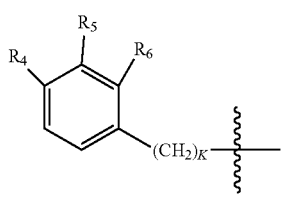

where $R_4$, $R_5$ and $R_6$ are each independently, H, halo (F, Cl, Br, I), CN, $NR^{N1}R^{N2}$, —$(CH_2)_K$OH, —$(CH_2)_K$O$C_1$-$C_4$ alkyl, which is optionally substituted with from 1-3 halo (F, Cl, Br, I, preferably F) groups, $C_1$-$C_3$ alkyl, which is optionally substituted with from 1-3 halo (F, Cl, Br, I, preferably F) groups, —O—$C_1$-$C_3$-alkyl, which is optionally substituted with from 1-3 halo, preferably F groups, —$(CH_2)_K$COOH, —$(CH_2)_K$C(O)O—$C_1$-$C_4$ alkyl which is optionally substituted with from 1-3 halo, preferably F groups, O—C(O)—$C_1$-$C_4$ alkyl, which is optionally substituted with from 1-3 halo, preferably F groups, —C(O)—$C_1$-$C_4$ alkyl, which is optionally substituted with from 1-3 halo, preferably F groups, or $R^C$ is a

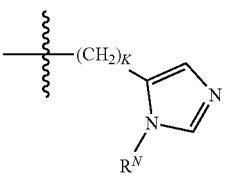

group, a

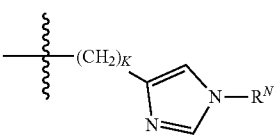

group a

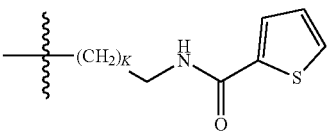

group or a

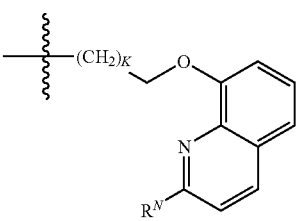

group,
where $R^N$, $R^{N1}$ and $R^{N2}$ are each independently H or a $C_1$-$C_3$ alkyl group which is optionally substituted with from one to three halo groups, preferably F, or one or two hydroxyl groups;
K is independently 0-4 (0, 1, 2, 3 or 4), preferably 0 or 1;
K' is 1-4, preferably 1;
$R^{N3}$ is H, or a $C_1$-$C_3$ alkyl group which is optionally substituted with 1-3 halo groups, preferably F or 1 or 2 hydroxy groups; and
$R^{N4}$ is H, a $C_1$-$C_3$ alkyl group which is optionally substituted with 1-3 halo groups, preferably F or 1 or 2 hydroxy groups, or $R^{N4}$ is a

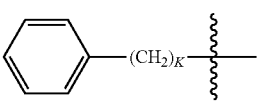

group, where K is preferably 1;
LINKERX is a linker group which is comprises to at least one [MIFBM/IgGBM] group and links the [MIFBM/IgGBM] group to the [ASGPRBM] through one or more optional [CON] groups, or is a linker group which contains at least one or more functional groups which can be used to covalently bond the linker group to at least one [MIFBM/IgGBM] group or optional [CON] group;

$R_2$ is a

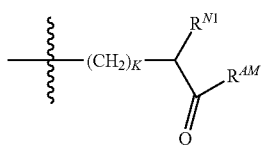

group where $R^{N1}$ and K are the same as above;

$R^{AM}$ is H, a $C_1$-$C_4$ alkyl group optionally substituted with up to 3 halo groups (preferably F) and one or two hydroxyl groups, a —$(CH_2)_K$COOH group, a —$(CH_2)_K$C(O)O—$C_1$-$C_4$ alkyl group which is optionally substituted with from 1-3 halo, preferably F groups, a O—C(O)—$C_1$-$C_4$ alkyl group, which is optionally substituted with from 1-3 halo, preferably F groups, a —C(O)—$C_1$-$C_4$ alkyl group, which is optionally substituted with from 1-3 halo, preferably F groups, a —$(CH_2)_K$—$NR^{N3}R^{N4}$ group where $R^{N3}$ is H, or a $C_1$-$C_3$ alkyl group which is optionally substituted with 1-3 halo groups, preferably F or 1 or 2 hydroxy groups; and $R^{N4}$ is H, a $C_1$-$C_3$ alkyl group which is optionally substituted with 1-3 halo groups, preferably F or 1 or 2 hydroxy groups, or $R^{N4}$ is a

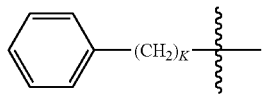

group (K is preferably 1), or $R_2$ is a

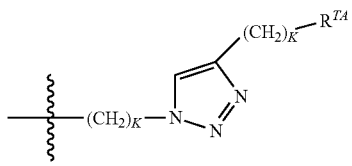

group, where $R^{TA}$ is H, CN, $NR^{N1}R^{N2}$, —$(CH_2)_K$OH, —$(CH_2)_K$O$C_1$-$C_4$ alkyl, which is optionally substituted with from 1-3 halo (F, Cl, Br, I, preferably F) groups, $C_1$-$C_4$ alkyl, which is optionally substituted with from 1-3 halo (F, Cl, Br, I, preferably F) groups, —$(CH_2)_K$COOH, —$(CH_2)_K$C(O)O—$C_1$-$C_4$ alkyl which is optionally substituted with from 1-3 halo, preferably F groups, O—C(O)—$C_1$-$C_4$ alkyl, which is optionally substituted with from 1-3 halo, preferably F groups, —C(O)—$C_1$-$C_4$ alkyl, which is optionally substituted with from 1-3 halo, preferably F groups, or $R^{TA}$ is a $C_3$-$C_{10}$ aryl or a three- to ten-membered heteroaryl group containing up to 5 heteroaryl atoms, each of said aryl or heteroaryl groups being optionally substituted with up to three (preferably 1) CN, $NR^{N1}R^{N2}$, —$(CH_2)_K$OH, —$(CH_2)_K$O$C_1$-$C_4$ alkyl, which is optionally substituted with from 1-3 halo (F, Cl, Br, I, preferably F) groups, $C_1$-$C_3$ alkyl, which is optionally substituted with from 1-3 halo (F, Cl, Br, I, preferably F) groups or 1 or 2 hydroxy groups, —O—$C_1$-$C_3$-alkyl, which is optionally substituted with from 1-3 halo, preferably F groups, —$(CH_2)_K$COOH, —$(CH_2)_K$C(O)O—$C_1$-$C_4$ alkyl which is optionally substituted with from 1-3 halo, preferably F groups, O—C(O)—$C_1$-$C_4$ alkyl, which is optionally substituted with from 1-3 halo, preferably F groups or —$(CH_2)_K$C(O)—$C_1$-$C_4$ alkyl which is optionally substituted with from 1-3 halo, preferably F groups, or $R^{TA}$ is a

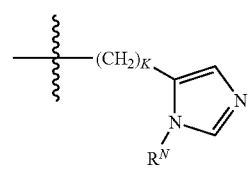

group, a

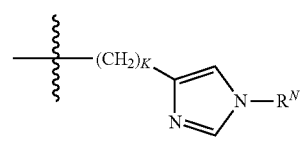

group, a

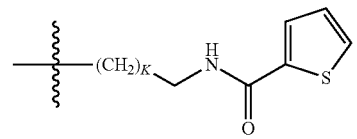

group or a

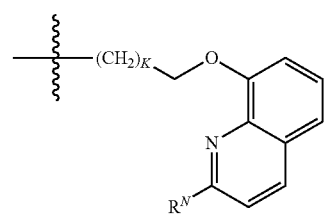

group, (preferably, $R^{TA}$ is a

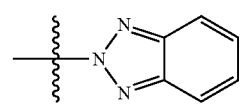 [SMILES: *n1nc2ccccc2n1]

group which is optionally substituted with up to three, preferably 1 $C_1$-$C_3$ alkyl groups which are optionally substituted with up to three halo (preferably F) groups, or $R^{TA}$ is a

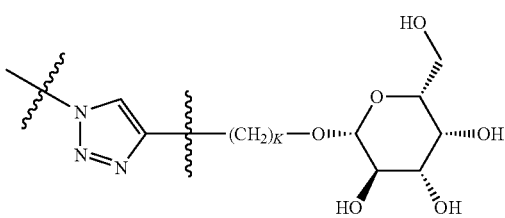

group,
wherein $R^N$, $R^{N1}$ and $R^{N2}$ are each independently H or a $C_1$-$C_3$ alkyl group which is optionally substituted with from one to three halo groups, preferably F, or one or two hydroxyl groups and
wherein each —(CH$_2$)$_K$— group is optionally substituted with 1-4, preferably 1 or 2, $C_1$-$C_3$ alkyl groups which are optionally substituted with from 1-3 fluoro groups or 1-2 hydroxyl groups; and $K$ is independently 0-4 (0, 1, 2, 3 or 4), preferably 0 or 1;
[CON] is a connector moiety (including a [MULTICON]) as otherwise described herein; and
[LINKER] is a linking moiety as otherwise described herein which links [MIFBM/IgGBM] to the [ASGPRBM] group and optionally contains one or more connector moieties (which optionally connect(s) more than one chemical moiety to provide said linking moiety or which connects said linking moiety to said [MIFBM/IgGBM] group or said [ASGPRBM] group, or a pharmaceutically acceptable salt, stereoisomer, solvate or polymorph thereof.

In embodiments of the present invention X is often —O—C($R^{N1}$)($R^{N1}$), C($R^{N1}$)($R^{N1}$)—O—, —S—C($R^{N1}$)($R^{N1}$), C($R^{N1}$)($R^{N1}$)—S—, N($R^{N1}$)—C($R^{N1}$)($R^{N1}$), C($R^{N1}$)($R^{N1}$)—N($R^{N1}$) or C($R^{N1}$)($R^{N1}$)—C($R^{N1}$)($R^{N1}$) when X is 2 atoms in length,
X is —O—C($R^{N1}$)($R^{N1}$)—C($R^{N1}$)($R^{N1}$), C($R^{N1}$)($R^{N1}$)—O—C($R^{N1}$)($R^{N1}$)—, —O—C($R^{N1}$)($R^{N1}$)—O—, —O—C($R^{N1}$)($R^{N1}$)—S—, —O—C($R^{N1}$)($R^{N1}$)—N($R^{N1}$)—, —S—C($R^{N1}$)($R^{N1}$)—C($R^{N1}$)($R^{N1}$), C($R^{N1}$)($R^{N1}$)—S—C($R^{N1}$)($R^{N1}$)—, C($R^{N1}$)($R^{N1}$)—C($R^{N1}$)($R^{N1}$)—S—, —S—C($R^{N1}$)($R^{N1}$)—O—, —S—C($R^{N1}$)($R^{N1}$)—N($R^{N1}$)—, N($R^{N1}$)—C($R^{N1}$)($R^{N1}$)—C($R^{N1}$)($R^{N1}$), C($R^{N1}$)($R^{N1}$)—N($R^{N1}$)—C($R^{N1}$)($R^{N1}$), C($R^{N1}$)($R^{N1}$)—C($R^{N1}$)($R^{N1}$)—N($R^{N1}$), N($R^{N1}$)—C($R^{N1}$)($R^{N1}$)—N($R^{N1}$) or C($R^{N1}$)($R^{N1}$)—C($R^{N1}$)($R^{N1}$)—C($R^{N1}$)($R^{N1}$) when X is 3 atoms in length, and
X is —O—C($R^{N1}$)($R^{N1}$)—C($R^{N1}$)($R^{N1}$)—C($R^{N1}$)($R^{N1}$), C($R^{N1}$)($R^{N1}$)—O—C($R^{N1}$)($R^{N1}$)—($R^{N1}$)($R^{N1}$)—, —O—C($R^{N1}$)($R^{N1}$)—O—C($R^{N1}$)($R^{N1}$)—, —S—C($R^{N1}$)($R^{N1}$)—C($R^{N1}$)($R^{N1}$)—C($R^{N1}$)($R^{N1}$)—, C($R^{N1}$)($R^{N1}$)—S—C($R^{N1}$)($R^{N1}$)—C($R^{N1}$)($R^{N1}$)—, C($R^{N1}$)($R^{N1}$)—($R^{N1}$)($R^{N1}$)—S—C($R^{N1}$)($R^{N1}$)—, —S—C($R^{N1}$)($R^{N1}$)—S—C($R^{N1}$)($R^{N1}$)—, N($R^{N1}$)—C($R^{N1}$)($R^{N1}$)—C($R^{N1}$)($R^{N1}$)— C($R^{N1}$)($R^{N1}$)—, C($R^{N1}$)($R^{N1}$)—N($R^{N1}$)—C($R^{N1}$)($R^{N1}$)—C($R^{N1}$)($R^{N1}$), C($R^{N1}$)($R^{N1}$)— N($R^{N1}$), N($R^{N1}$)—C($R^{N1}$)($R^{N1}$)—N($R^{N1}$) or C($R^{N1}$)($R^{N1}$)—C($R^{N1}$)($R^{N1}$)— C($R^{N1}$)($R^{N1}$) when X is 4 atoms in length where $R^{N1}$ is the same as above. Most often, $R^{N1}$ is H.

In embodiments of the present invention X is OCH$_2$ or CH$_2$O and $R^{N1}$ is preferably H.

In embodiments, the [ASGPRBM] group is a group according to the chemical structure:

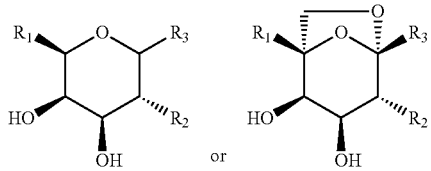

where $R_1$, $R_2$ and $R_3$ are the same as above, or
a pharmaceutically acceptable salt, stereoisomer, solvate or polymorph thereof.

In embodiments, the [ASGPRBM] group is a group according to the chemical structure:

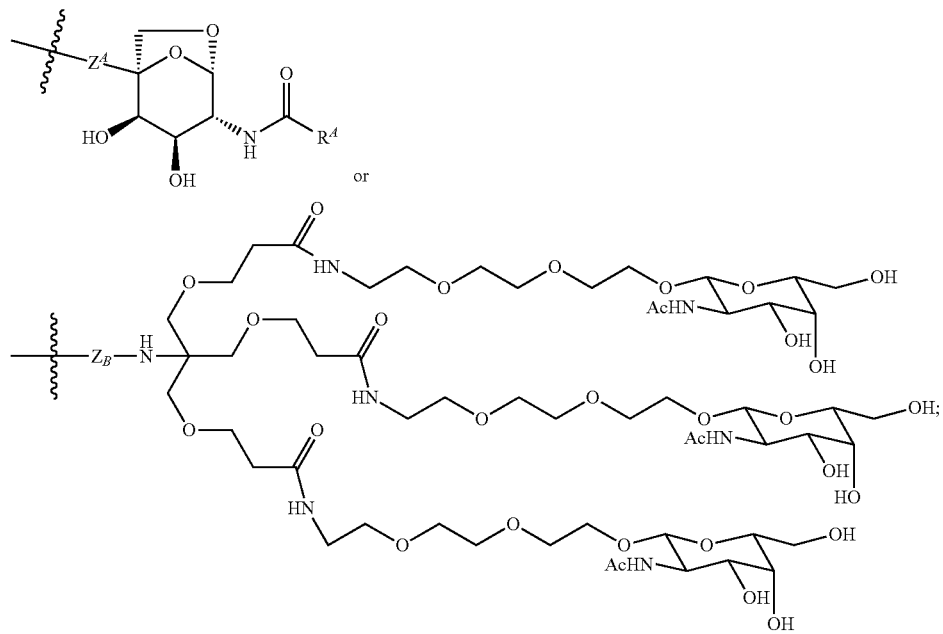

Where $R^A$ is a $C_1$-$C_3$ alkyl group which is optionally (preferably) substituted with 1-5 halo (preferably fluoro) groups (preferably $R^A$ is a methyl or ethyl group which is optionally substituted with from 1-3 fluoro groups);

$Z_A$ is —$(CH_2)_{IM}$, —O—$(CH_2)_{IM}$, S—$(CH_2)_{IM}$, $NR_M$—$(CH_2)_{IM}$, C(O)—$(CH_2)_{IM}$—, a PEG group containing from 1 to 8 preferably 1-4 ethylene glycol residues or a —C(O)$(CH_2)_{IM}NR_M$ group (preferably a PEG containing group comprising from 1 to 8 ethylene glycol, preferably 2-4 ethylene glycol residues) where $_{IM}$ and $R_M$ are the same as above; and $Z_B$ is absent, $(CH_2)_{IM}$, C(O)—$(CH_2)_{IM}$— or C(O)—$(CH_2)_{IM}$—$NR_M$, where $_{IM}$ and $R_M$ are the same as above.

Note that the ASPGRM group set forth above may also be represented as follows:

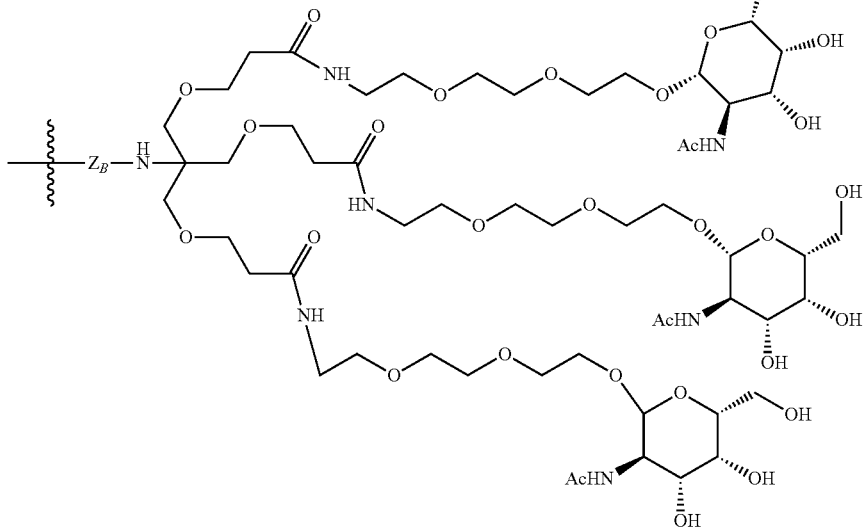

The term "neoplasia" or "cancer" is used throughout the specification to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and most invade surrounding tissues, metastasize to several sites, and are likely to recur after attempted removal and to cause the death of the patient unless adequately treated. As used herein, the term neoplasia is used to describe all cancerous disease states and embraces or encompasses the pathological process associated with malignant hematogenous, ascitic and solid tumors. Neoplasms include, without limitation, morphological irregularities in cells in tissue of a subject or host, as well as pathologic proliferation of cells in tissue of a subject, as compared with normal proliferation in the same type of tissue. Additionally, neoplasms include benign tumors and malignant tumors (e.g., colon tumors) that are either invasive or noninvasive. Malignant neoplasms (cancer) are distinguished from benign neoplasms in that the former show a greater degree of anaplasia, or loss of differentiation and orientation of cells, and have the properties of invasion and metastasis. Examples of neoplasms or neoplasias from which the target cell of the present invention may be derived include, without limitation, carcinomas (e.g., squamous-cell carcinomas, adenocarcinomas, hepatocellular carcinomas, and renal cell carcinomas), particularly those of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, particularly Ewing's sarcoma, hemangiosarcoma, Kaposi's sarcoma, liposarcoma, myosarcomas, peripheral neuroepithelioma, and synovial sarcoma; tumors of the central nervous system (e.g., gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas); germ-line tumors (e.g., bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, and melanoma); mixed types of neoplasias, particularly carcinosarcoma and Hodgkin's disease; and tumors of mixed origin, such as Wilms' tumor and teratocarcinomas (Beers and Berkow (eds.), The Merck Manual of Diagnosis and Therapy, 17.sup.th ed. (Whitehouse Station, N.J.: Merck Research Laboratories, 1999) 973-74, 976, 986, 988, 991). All of these neoplasms may be treated using compounds according to the present invention.

Representative common cancers to be treated with compounds according to the present invention include, for example, prostate cancer, metastatic prostate cancer, stomach, colon, rectal, liver, pancreatic, lung, breast, cervix uteri, corpus uteri, ovary, testis, bladder, renal, brain/CNS, head and neck, throat, Hodgkin's disease, non-Hodgkin's lymphoma, multiple myeloma, leukemia, melanoma, non-melanoma skin cancer, acute lymphocytic leukemia, acute myelogenous leukemia, Ewing's sarcoma, small cell lung cancer, choriocarcinoma, rhabdomyosarcoma, Wilms' tumor, neuroblastoma, hairy cell leukemia, mouth/pharynx, esophagus, larynx, kidney cancer and lymphoma, among others, which may be treated by one or more compounds according to the present invention. Because of the activity of the present compounds, the present invention has general applicability treating virtually any cancer in any tissue, thus the compounds, compositions and methods of the present invention are generally applicable to the treatment of cancer and in reducing the likelihood of development of cancer and/or the metastasis of an existing cancer.

In certain particular aspects of the present invention, the cancer which is treated is metastatic cancer, a recurrent cancer or a drug resistant cancer, especially including a drug resistant cancer. Separately, metastatic cancer may be found in virtually all tissues of a cancer patient in late stages of the disease, typically metastatic cancer is found in lymph system/nodes (lymphoma), in bones, in lungs, in bladder tissue, in kidney tissue, liver tissue and in virtually any tissue, including brain (brain cancer/tumor). Thus, the present invention is generally applicable and may be used to treat any cancer in any tissue, regardless of etiology.

The term "tumor" is used to describe a malignant or benign growth or tumefacent.

The term "autoimmune disease" refers to a disease or illness that occurs when the body tissues are attacked by its own immune system. The immune system is a complex organization within the body that is designed normally to "seek and destroy" invaders of the body, including infectious agents. In diseases which are described as autoimmune diseases, MIF levels are often elevated. The present invention seeks to inhibit or lower elevated MIF levels in patients with autoimmune disease (as well as inflammatory diseases and conditions and cancer) and by decreasing MIF levels, ameliorate many of the symptoms and secondary effects of these disease states and conditions. Examples of autoimmune diseases which often exhibit high expressed levels of MIF including, for example, systemic lupus erythematosus, Sjogren syndrome, Hashimoto thyroiditis, rheumatoid arthritis, juvenile (type 1) diabetes, polymyositis, scleroderma, Addison's disease, vtiligo, pernicious anemia, glomerulonephritis, and pulmonary fibrosis, among numerous others.

A more complete list of autoimmune diseases which may be treated by compounds and pharmaceutical compositions according to the present invention includes Addison's Disease, Autoimmune polyendodrine syndrome (APS) types 1, 2 and 3, autoimmune pancreatitis (AIP), diabetes mellitus type 1, autoimmune thyroiditis, Ord's thyroiditis, Grave's disease, autoimmune oophoritis, endometriosis, autoimmune orchitis, Sjogren's syndrome, autoimmune enteropathy, coeliac disease, Crohns' disease, microscopic colitis, ulcerative colitis, autophospholipid syndrome (APIS), aplastic anemia, autoimmune hemolytica anemia, autoimmune lymphoproliferative syndrome, autoimmune neutropenia, autoimmune thrombocytopenic purpura, cold agglutinin disease, essential mixed cryoglulinemia, Evans syndrome, pernicious anemia, pure red cell aplasia, thrombocytopenia, adiposis dolorosa, adult-onset Still's disease, anklyosing spondylitis, CREST syndrome, drug-induced lupus, enthesitis-related arthritis, esosiniphilic fasciitis, Felty syndrome, AgG4-related disease, juvenile arthritis, Lyme disease (chronic), mixed connective tissue disease (MCTD), palindromic rheumatism, Parry Romberg syndrome, Parsonage-Turner syndrome, psoriatic arthritis, reactive arthritis, relapsing polychondritis, retroperitoneal fibrosis, rheumatic fever, rheumatoid arthritis, sarcoidosis, Schnitzler syndrome, systemic lupus erythematosus, undifferentiated connective tissue disease (UCTD), dematomyositis, fibromyalgia, myositis, inclusion body myositis, myasthenia gravis, neuromyotonia, paraneoplastic cerebellar degeneration, polymysositis, acute disseminated encephalomyelitis (ADEM), acute motor axonic neuropathy, anti-NMDA receptor encephalitis, Balo concentric sclerosis, Bickerstaff s encephalitis, chronic inflammatory demyelinating polyneuropathy, Guillain-Barre syndome, Hashimoto's encephalopathy, idiopathic inflammatory demyelinating diseases, Lambert-Eaton myasthenic syndrome, multiple sclerosis, pattern II, Oshtoran Syndrome, Pendiatric Autoimmune Neuropsychiatric Disorder Associated with *Streptococcus* (PANDAS), progressive inflammatory neuropathy, restless leg syndrome, stiff person syndrome, Syndenham chorea, transverse myelitis, autoimmune retinopathy, autoimmune uveitis, Cogan syndrome, Graves ophthalmopathy, intermediate uveitis, ligneous conjunctivitis, Mooren's ulcer, neuromyelitis optica, opsoclonus myoclonus syndrome, optic neuritis, scleritis, Susac's syndrome, sympathetic ophthalmia, Tolosa-Hunt syndrome, autoimmune inner ear disease (AIED), Meniere's disease, Belief s disease, Eosiniphilic granulomatosis with polyangiitis (EGPA), giant cell arteritis, granulomatosis with polyangiitis (GPA), IgA vasculitis (IgAV), Kawasaki's disease, leukocytoclastic vasculitis, lupus vasculitis, rheumatoid vasculitis, microscopic polyangiitis (MPA), polyarteritis nodosa (PAN), polymyalgia rheumatica, urticarial vasculitis, vasculitis, primary immune deficiency, chronic fatigue syndrome, complex regional pain syndrome, eosiniphilic esopagitis, gastritis, interstitial lung disease, POEMS syndrome, Raynaud's syndrome, primary immunodeficiency and pyoderma gangrenosum, among others.

The term "inflammatory disease" is used to describe a disease or illness with acute, but more often chronic inflammation as a principal manifestation of the disease or illness. Inflammatory diseases include diseases of neurodegeneration (including, for example, Alzheimer's disease, Parkinson's disease, Huntington's disease; other ataxias), diseases of compromised immune response causing inflammation (e.g., dysregulation of T cell maturation, B cell and T cell homeostasis, counters damaging inflammation), chronic inflammatory diseases including, for example, inflammatory bowel disease, including Crohn's disease, rheumatoid arthritis, lupus, multiple sclerosis, chronic obstructive pulmony disease/COPD, pulmonary fibrosis, cystic fibrosis, Sjogren's disease; hyperglycemic disorders, diabetes (I and II), affecting lipid metabolism islet function and/or structure, pancreatic β-cell death and related hyperglycemic disorders, including severe insulin resistance, hyperinsulinemia, insulin-resistant diabetes (e.g. Mendenhall's Syndrome, Werner Syndrome, leprechaunism, and lipoatrophic diabetes) and dyslipidemia (e.g. hyperlipidemia as expressed by obese subjects, elevated low-density lipoprotein (LDL), depressed high-density lipoprotein (HDL), elevated triglycerides and metabolic syndrome, liver disease, renal disease (apoptosis in plaques, glomerular disease), cardiovascular disease (especially including infarction, ischemia, stroke, pressure overload and complications during reperfusion), muscle degeneration and atrophy, low grade inflammation, gout, silicosis, atherosclerosis and associated conditions such as cardiac and neurological (both central and peripheral) manifestations including stroke, age-associated dementia and sporadic form of Alzheimer's disease, and psychiatric conditions including depression), stroke and spinal cord injury, arteriosclerosis, among others. In these diseases, elevated MIF is very often observed, making these disease states and/or conditions response to therapy using compounds and/or pharmaceutical compositions according to the present invention. It is noted that there is some overlap between certain autoimmune diseases and inflammatory diseases as described herein.

The term "linker", refers to a chemical entity including a complex linker connecting a macrophage migration inhibitory factor binding moiety (MIFBM) to the asialoglycoprotein receptor binding moiety (ASGPRBM), optionally through at least one (preferably one or two) connector moiety [CON] through covalent bonds in compounds according to the present invention. The linker between the two active portions of the molecule, that is the MIFBM and the ASGPRBM ranges from about 5 Å to about 50 Å or more in length, about 6 Å to about 45 Å in length, about 7 Å to about 40 Å in length, about 8 Å to about 35 Å in length, about 9 Å to about 30 Å in length, about 10 Å to about 25 Å in length, about 7 Å to about 20 Å in length, about 5 Å to about 16 Å in length, about 5 Å to about 15 Å in length, about 6 Å to about 14 Å in length, about 10 Å to about 20 Å in length, about 11 Å to about 25 Å in length, etc. Linkers which are based upon ethylene glycol units and are between 2 and 15 glycol units, 1 and 8 glycol units, 1, 2, 3, 4, 5, and 6 glycol units in length may be preferred, although the length of certain linkers may be far greater. By having a linker with a length as otherwise disclosed herein, the MIFBM group and the ASGPRBM group may be situated to advantageously take advantage of the biological activity of compounds according to the present invention which bind to asialoglycoprotein receptors on hepatocytes resulting in the selective and targeted degradation of MIF circulating proteins within the lysosomal degradation mechanism or other degradation mechanism of the hepatocytes. The selection of a linker component is based on its documented properties of biocompatibility, solubility in aqueous and organic media, and low immunogenicity/antigenicity. Although numerous linkers may be used as otherwise described herein, a linker based upon polyethyleneglycol (PEG) linkages, polypropylene glycol linkages, or poly ethyleneglycol-co-polypropylene oligomers (up to about 100 units, about 1 to 100, about 1 to 75, about 1 to 60, about 1 to 50, about 1 to 35, about 1 to 25, about 1 to 20, about 1 to 15, 2 to 10, about 4 to 12, about 1 to 8, 1 to 3, 1 to 4, 2 to 6, 1 to 5, etc.) may be favored as a linker because of the chemical and biological characteristics of these molecules. The use of polyethylene (PEG) linkages of between 2 and 15 ethylene glycol units is preferred. When describing linkers according to the present invention, including polyethylene glycol linkers or other linkers, one or more additional groups (e.g., methylene groups, amide groups, keto groups, amine groups, etc., with methylene groups or amide groups being preferred) may be covalently attached at either end of the linker group to attach to a ASGPRBM group, a [CON] group, another linker group or a CPBM group.

Alternative linkers may include, for example, polyamino acid linkers of up to 100 amino acids (of any type, preferably D- or L-amino acids, preferably naturally occurring L-amino acids) in length (about 1 to 75, about 1 to 60, about 1 to 50, about 1 to 45, about 1 to 35, about 1 to 25, about 1 to 20, about 1 to 15, 2 to 10, about 4 to 12, about 5 to 10, about 4 to 6, about 1 to 8, about 1 to 6, about 1 to 5, about 1 to 4, about 1 to 3, etc. in length), optionally including one or more connecting groups (preferably 1 or 2 connecting groups at one or both ends of the polyamino acid linker).

Preferred linkers include those according to the chemical structures:

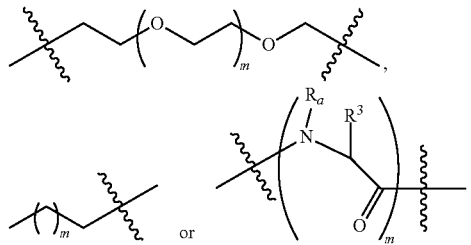

Or a polypropylene glycol or polypropylene-co-polyethylene glycol linker having between 1 and 100 alkylene glycol units, preferably about 1 to 75, about 1 to 60, about 1 to 50, about 1 to 45, about 1 to 35, about 1 to 25, about 1 to 20, about 1 to 15, 2 to 10, about 4 to 12, about 5 to 10, about 4 to 6, about 1 to 8, about 1 to 6, about 1 to 5, about 1 to 4, about 1 to 3;

Where $R_a$ is H, $C_1$-$C_3$ alkyl or alkanol or forms a cyclic ring with $R^3$ (proline) and $R^3$ is a side chain derived from a D- or L amino acid (preferably a naturally occurring L-amino acid) preferably selected from the group consisting of alanine (methyl), arginine (propyleneguanidine), asparagine (methylenecarboxyamide), aspartic acid (ethanoic acid), cysteine (thiol, reduced or oxidized di-thiol), glutamine (ethylcarboxyamide), glutamic acid (propanoic acid), glycine (H), histidine (methyleneimidazole), isoleucine (1-methylpropane), leucine (2-methylpropane), lysine (butyleneamine), methionine (ethylmethylthioether), phenylalanine (benzyl), proline hydroxyproline ($R^3$ forms a cyclic ring with $R_a$ and the adjacent nitrogen group to form a pyrrolidine or hydroxypyrrolidine group), serine (methanol), threonine (ethanol, 1-hydroxyethane), tryptophan (methyleneindole), tyrosine (methylene phenol) or valine (isopropyl);

m (within the context of this use) is an integer from 1 to 100, 1 to 75, 1 to 60, 1 to 55, 1 to 50, 1 to 45, 1 to 40, 2 to 35, 3 to 30, 1 to 15, 1 to 12, 1 to 10, 1 to 8, 1 to 6, 1, 2, 3, 4 or 5.

Another linker according to the present invention comprises a polyethylene glycol linker containing from 1 to 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5 ethylene glycol units, to which is bonded a lysine group or other amino acid moiety at one or both ends of the linker (which can consist of between 1 and 10 amino acids which can bind the MIFBM and/or the ASGPRBM group. Still other linkers comprise amino acid residues (D or L) which are bonded to MIFBM and/or ASGPRBM moieties as otherwise described herein. In another embodiment, as otherwise described herein, the amino acid has anywhere from 1-15 methylene groups separating the amino group from the acid (acyl) group in providing a linker to the MIFBM and/or the ASGPRBM group, wherein the linker contains from 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5 amino acid groups linked together through peptide linkages to form the linker. This linker is represented by the chemical structure:

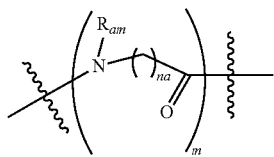

where $R_{am}$ is H or a $C_1$-$C_3$ alkyl optionally substituted with one or two hydroxyl groups;

na is 1-15, 1-12, 1-10, 1-8, 1, 2, 3, 4, 5, 6, 7, 8, 9, 10 or 11;

m is an integer from 1 to 100, 1 to 75, 1 to 60, 1 to 55, 1 to 50, 1 to 45, 1 to 40, 2 to 35, 3 to 30, 1 to 15, 1 to 12, 1 to 10, 1 to 8, 1 to 6, 1, 2, 3, 4 or 51 to 50, 1 to 45, 1 to 40, 2 to 35, 3 to 30, 1 to 15, 1 to 10, 1 to 8, 1 to 6, 1, 2, 3, 4 or 5.

Or another linker is according to the chemical formula:

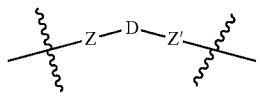

Where Z and Z' are each independently a bond, $-(CH_2)_i-O$, $-(CH_2)_i-S$, $-(CH_2)_i-N-R$,

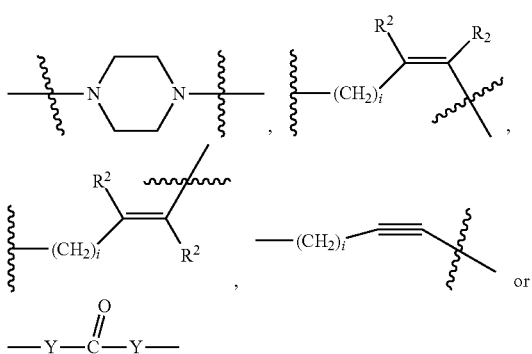

wherein said $-(CH_2)_i$ group, if present in Z or Z', is bonded to a connector (CON), MIFBM or ASGPRBM;

Each R is H, or a $C_1$-$C_3$ alkyl or alkanol group;

Each $R^2$ is independently H or a $C_1$-$C_3$ alkyl group;

Each Y is independently a bond, O, S or N—R;

Each i is independently 0 to 100, 0 to 75, 1 to 60, 1 to 55, 1 to 50, 1 to 45, 1 to 40, 2 to 35, 3 to 30, 1 to 15, 1 to 10, 1 to 8, 1 to 6, 0, 1, 2, 3, 4 or 5;

D is

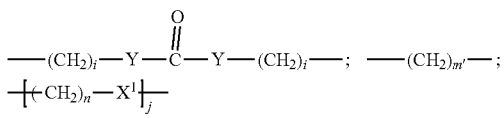

or a bond, with the proviso that Z, Z' and D are not each simultaneously bonds;

j is 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5;

m' is 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5;

n is 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5 (n is preferably 2);

$X^1$ is O, S or N—R; and

R is H, or a $C_1$-$C_3$ alkyl or alkanol group, or a pharmaceutical salt thereof.

Other linkers which are included herein include preferred linkers according to the chemical structure:

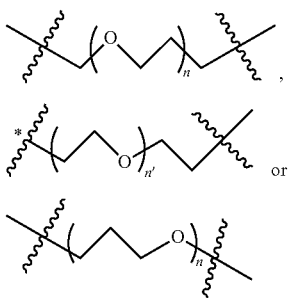

where each n and n' is independently 1 to 25, 1 to 15, 1 to 12, 2 to 11, 2 to 10, 2 to 8, 2 to 6, 2 to 5, 2 to 4 and 2 to 3 or 1, 2, 3, 4, 5, 6, 7, or 8; and each n" is independently 0 to 8, often 1 to 7, or 1, 2, 3, 4, 5 or 6 (preferably 2, 3, 4 or 5).

Linkers also can comprise two or more linker segments (based upon the linkers described above) which are attached directly to each other or through [CON] groups forming a complex linker. Certain linkers which include a [CON] group (especially a diamide [CON] group as otherwise described herein) connecting a first and second (PEG) linker group include the following structures:

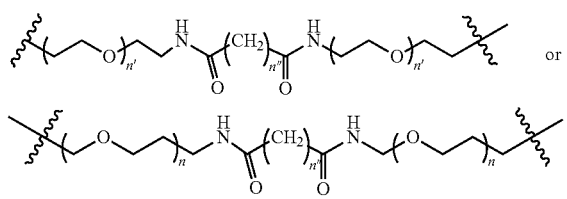

where each n and n' is independently 1 to 25, 1 to 15, 1 to 12, 2 to 11, 2 to 10, 2 to 8, 2 to 6, 2 to 5, 2 to 4 and 2 to 3 or 1, 2, 3, 4, 5, 6, 7, or 8; and each n" is independently 0 to 8, often 1 to 7, or 1, 2, 3, 4, 5 or 6 (preferably 3). Noted is that each of these linkers may also contain alkylene groups containing from 1 to 4 methylene groups at the distal ends of each linker group in order to facilitate connection of the linker group.

Other linkers which include a connector group [CON] include groups which are represented by the chemical formula

PEG-[CON]-PEG

Wherein each PEG is independently a polyethylene glycol group containing from 1-12 ethylene glycol residues and [CON] is a connector group as otherwise set forth herein, preferably a
triazole group

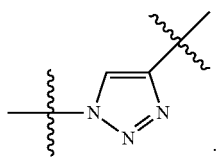 [SMILES: *c1cn(*)nn1]

The term "connector", symbolized in the generic formulas by "CON" or [CON], is used to describe a chemical moiety which is optionally included in bifunctional compounds according to the present invention which forms from the reaction product of an activated linker with a MIFBM moiety (which also is preferably activated for covalently bonding the linker with the moiety) or a ASGPRBM group with an activated linker. The connector group is often the resulting moiety which forms from the facile condensation of two or more separate chemical fragments which contain reactive groups which can provide connector groups as otherwise described to produce bifunctional or multifunctional compounds according to the present invention. It is noted that a connector may be distinguishable from a linker in that the connector is the result of a specific chemistry which is used to provide bifunctional compounds according to the present invention wherein the reaction product of these groups results in an identifiable connector group or part of a connector group which is distinguishable from the linker group, although in certain instances, the connector group is incorporated into and integral with the linker group as otherwise described herein. It is noted also that a connector group may be linked to a number of linkers to provide multifunctionality (i.e., more than one CPBM moiety and/or more than one ASGPRBM/FCRNBM moiety) within the same molecule. It is noted that there may be some overlap between the description of the connector group and the linker group such that the connector group is actually incorporated or forms part of the linker, especially with respect to more common connector groups such as amide groups, oxygen (ether), sulfur (thioether) or amine linkages, urea or carbonate —OC(O)O— groups or as otherwise described herein. It is further noted that a connector (or linker) may be connected to MIFBM, ASGPRBM or a linker at positions which are represented as being linked to another group using the symbol

Where two or more such groups are present in a linker or connector, any of an ASGPRBM, a linker or a MIFBM may be bonded to such a group. Where that symbol is not used, the linker may be at one or more positions of a moiety.

Common connector groups which are used in the present invention include the following chemical groups:

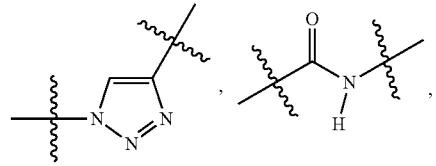

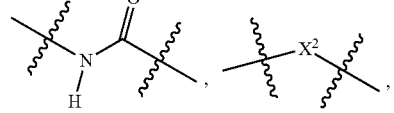

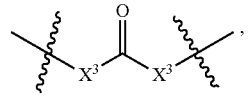

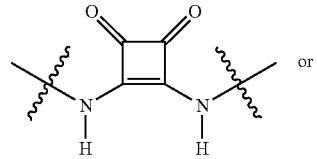

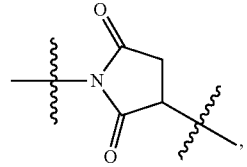

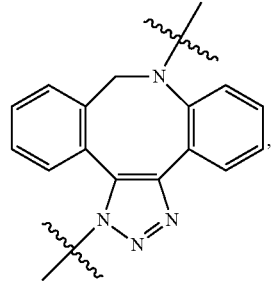

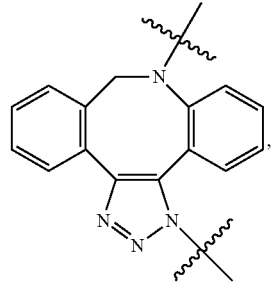

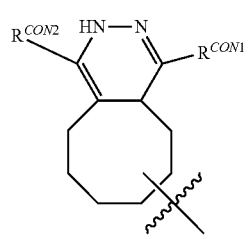

-continued

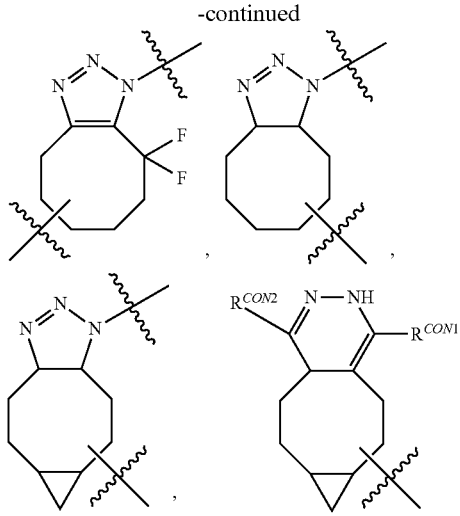

where $R^{CON1}$ and $R^{CON2}$ are each independently H, methyl or a bond (for attachment to another moiety); or a diamide group according to the structure:

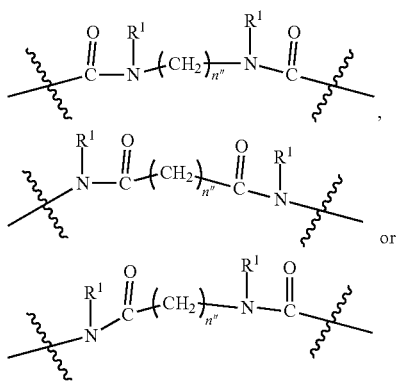

Where $X^2$ is $CH_2$, O, S, $NR^4$, C(O), S(O), $S(O)_2$, —$S(O)_2O$, —$OS(O)_2$, or $OS(O)_2O$;

$X^3$ is O, S, $NR^4$;

$R^4$ is H, a $C_1$-$C_3$ alkyl or alkanol group, or a —C(O)($C_1$-$C_3$) group;

$R^1$ is H or a $C_1$-$C_3$ alkyl group (preferably H); and n" is independently 0 to 8, often 1 to 7, or 1, 2, 3, 4, 5 or 6 (preferably 3);

or the connector group [CON] is a group according to the chemical structure:

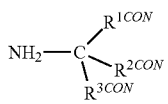

Where $R^{1CON}$, $R^{2CON}$ and $R^{3CON}$ are each independently H, —$(CH_2)_{MC1}$—$(CH_2)_{MC1a}C(O)_{X4}(NR^4)_{X4}$ —$(CH_2)_{MC1a}$, —$(CH_2)_{MC1a}(NR^4)_{X4}C(O)_{X4}$ —$(CH_2)_{MC1a}$ or —$(CH_2)_{MC1a}O$—$(CH_2)_{MC1}$—C(O) $NR^4$—, with the proviso that $R^{1CON}$, $R^{2CON}$ and $R^{3CON}$ are not simultaneously H;

Each MC1 is independently 1-4 (preferably 1 or 2;

Each MC1a is independently 0-4 (preferably 0, 1 or 2); and $R^4$ is H, a $C_1$-$C_3$ alkyl or alkanol group, or a —C(O)($C_1$-$C_3$) group.

The triazole group, indicated above, may be a preferred connector group. An additional preferred connector group is

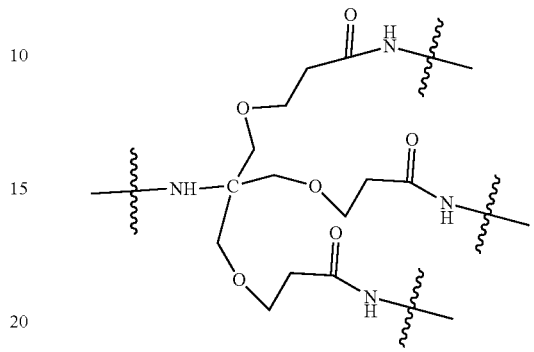

which is linked to at least one MIFBM and/or at least one ASPRGBM (preferably 3 ASPRGBM moieties). This connector group may be used to form GN3.

It is noted that each connector may be extended with one or more methylene groups to facilitate connection to a linker group, another CON group, a MIFBM group or a ASGPRBM. It is noted that in certain instances, within context the diamide group may also function independently as a linker group.

The term "pharmaceutically acceptable salt" or "salt" is used throughout the specification to describe a salt form of one or more of the compositions herein which are presented to increase the solubility of the compound in saline for parenteral delivery or in the gastric juices of the patient's gastrointestinal tract in order to promote dissolution and the bioavailability of the compounds. Pharmaceutically acceptable salts include those derived from pharmaceutically acceptable inorganic or organic bases and acids. Suitable salts include those derived from alkali metals such as potassium and sodium, alkaline earth metals such as calcium, magnesium and ammonium salts, among numerous other acids well known in the pharmaceutical art. Sodium and potassium salts may be preferred as neutralization salts of carboxylic acids and free acid phosphate containing compositions according to the present invention. The term "salt" shall mean any salt consistent with the use of the compounds according to the present invention. In the case where the compounds are used in pharmaceutical indications, including the treatment of prostate cancer, including metastatic prostate cancer, the term "salt" shall mean a pharmaceutically acceptable salt, consistent with the use of the compounds as pharmaceutical agents.

The term "coadministration" shall mean that at least two compounds or compositions are administered to the patient at the same time, such that effective amounts or concentrations of each of the two or more compounds may be found in the patient at a given point in time. Although compounds according to the present invention may be co-administered to a patient at the same time, the term embraces both administration of two or more agents at the same time or at different times, provided that effective concentrations of all coadministered compounds or compositions are found in the subject at a given time. Chimeric antibody-recruiting compounds according to the present invention may be administered with one or more additional anti-cancer agents or other agents which are used to treat or ameliorate the symptoms of cancer, especially prostate cancer, including metastatic prostate cancer.

The term "anticancer agent" or "additional anticancer agent" refers to a compound other than the chimeric compounds according to the present invention which may be used in combination with a compound according to the present invention for the treatment of cancer. Exemplary anticancer agents which may be coadministered in combination with one or more chimeric compounds according to the present invention include, for example, antimetabolites, inhibitors of topoisomerase I and II, alkylating agents and microtubule inhibitors (e.g., taxol), among others. Exemplary anticancer compounds for use in the present invention may include everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an EGFR TK inhibitor, an aurora kinase inhibitor, a PIK-1 modulator, a Bcl-2 inhibitor, an HDAC inhibitor, a c-MET inhibitor, a PARP inhibitor, a Cdk inhibitor, an EGFR TK inhibitor, an IGFR-TK inhibitor, an anti-HGF antibody, a PI3 kinase inhibitors, an AKT inhibitor, a JAK/STAT inhibitor, a checkpoint-1 or 2 inhibitor, a focal adhesion kinase inhibitor, a Map kinase (rack) inhibitor, a VEGF trap antibody, pemetrexed, erlotinib, dasatanib, nilotinib, decatanib, panitumumab, amrubicin, oregovomab, Lep-etu, nolatrexed, azd2171, batabulin, ofatumumab (Arzerra), zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdR$_1$ KRX-0402, lucanthone, LY 317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, irinotecan, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES(diethylstilbestrol), estradiol, estrogen, conjugated estrogen, bevacizumab, IMC-1C11, CHIR-258,); 3-[5-(methylsulfonylpiperadinemethyl)-indolylj-quinolone, vatalanib, AG-013736, AVE-0005, the acetate salt of [D-Ser(Bu t) 6, Azgly 10] (pyro-Glu-His-Trp-Ser-Tyr-D-Ser(Bu t)-Leu-Arg-Pro-Azgly-NH$_2$ acetate [C$_{59}$H$_{84}$N$_{18}$Oi$_4$-(C$_2$H$_4$O$_2$)$_x$ where x=1 to 2.4], goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, Ionafarnib, BMS-214662, tipifarnib; amifostine, NVP-LAQ824, suberoyl analide hydroxamic acid, valproic acid, trichostatin A, FK-228, SU11248, sorafenib, KR$^{N951}$, aminoglutethimide, arnsacrine, anagrelide, L-asparaginase, *Bacillus* Calmette-Guerin (BCG) vaccine, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gemcitabine, gleevac, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, irinotecan, topotecan, doxorubicin, docetaxel, vinorelbine, bevacizumab (monoclonal antibody) and erbitux, cremophor-free paclitaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonists, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa and darbepoetin alfa, vemurafenib among others, including immunotherapy agents such as IDO inhibitors (an inhibitor of indoleamine 2,3-dioxygenase (IDO) pathway) such as Indoximod (NLG-8187), Navoximod (GDC-0919) and NLG802, PDL1 inhibitors (an inhibitor of programmed death-ligand 1) including, for example, nivolumab, durvalumab and atezolizumab, PD1 inhibitors such as pembrolizumab (Merck) and CTLA-4 inhibitors (an inhibitor of cytotoxic T-lymphocyte associated protein 4/cluster of differentiation 152), including ipilimumab and tremelimumab, among others.

In addition to anticancer agents, a number of other agents may be coadministered with chimeric compounds according to the present invention in the treatment of cancer. These include active agents, minerals, vitamins and nutritional supplements which have shown some efficacy in inhibiting cancer tissue or its growth or are otherwise useful in the treatment of cancer. For example, one or more of dietary selenium, vitamin E, lycopene, soy foods, curcumin (turmeric), vitamin D, green tea, omega-3 fatty acids and phytoestrogens, including beta-sitosterol, may be utilized in combination with the present compounds to treat cancer.

Without not being limited by way of theory, compounds according to the present invention which contain a MIF binding moiety (MIFBM) or antibody binding moiety and ASGPR binding moiety selectively bind to liver cells and through that binding, facilitate the introduction of the MIFBM group into hepatocytes which bind the ASGPRBM selectively, where, the MIF protein, inside the hepatocyte is degraded and removed from circulation. Thus, compounds according to the present invention both bind to MIF proteins and remove the MIF proteins from circulation resulting in a dual action which is particularly effective for treating disease states and conditions.

Pharmaceutical compositions comprising combinations of an effective amount of at least one compound disclosed herein, often a bi-functional chimeric compound (containing at least one MIFBM group or antibody binding moiety and at least one ASGPRBM) according to the present invention, and one or more of the compounds as otherwise described herein, all in effective amounts, in combination with a pharmaceutically effective amount of a carrier, additive or excipient, represents a further aspect of the present invention. These may be used in combination with at least one additional, optional anticancer agent as otherwise disclosed herein.

The compositions of the present invention may be formulated in a conventional manner using one or more pharmaceutically acceptable carriers and may also be administered in controlled-release formulations. Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenterally, by inhalation spray, topically, rectally, nasally, buccally, vaginally or via an implanted reservoir, among others. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally (including via intubation through the mouth or nose into the stomach), intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1, 3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions of this invention may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially to treat skin cancers, psoriasis or other diseases which occur in or on the skin. Suitable topical formulations are readily prepared for each of these areas or organs. Topical application for the lower intestinal tract can be effected in a rectal suppository formulation (see above) or in a suitable enema formulation. Topically-acceptable transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water.

Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of compound in a pharmaceutical composition of the instant invention that may be combined with the carrier materials to produce a single dosage form will vary depending upon the host and disease treated, the particular mode of administration. Preferably, the compositions should be formulated to contain between about 0.05 milligram to about 1.5 grams, from 0.1 milligram to 1 gram, 0.5 milligram to 750 milligrams, more often about 1 milligram to about 600 milligrams, and even more often about 10 milligrams to about 500 milligrams of active ingredient, alone or in combination with at least one additional compound which may be used to treat cancer, prostate cancer or metastatic prostate cancer or a secondary effect or condition thereof.

Methods of treating patients or subjects in need for a particular disease state or condition as otherwise described herein, especially cancer, comprise administration of an effective amount of a pharmaceutical composition comprising therapeutic amounts of one or more of the novel compounds described herein and optionally at least one additional bioactive (e.g. anti-cancer, anti-inflammatory) agent according to the present invention. The amount of active ingredient(s) used in the methods of treatment of the instant invention that may be combined with the carrier materials to produce a single dosage form will vary depending upon the host treated, the particular mode of administration. For example, the compositions could be formulated so that a therapeutically effective dose of between about 0.01, 0.1, 1, 5, 10, 15, 20, 25, 30, 35, 40, 45, 50, 55, 60, 65, 70, 75, 80, 85, 90 or 100 mg/kg of patient/day or in some embodiments, greater than 100, 110, 120, 130, 140, 150, 160, 170, 180, 190 or 200 mg/kg of the novel compounds can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease or condition being treated.

A patient or subject (e.g. a human) suffering from an autoimmune disease, an inflammatory disease or cancer can be treated by administering to the patient (subject) an effective amount of a chimeric/bi-functional compound according to the present invention including pharmaceutically acceptable salts, solvates or polymorphs, thereof optionally in a pharmaceutically acceptable carrier or diluent, either alone, or in combination with other known pharmaceutical agents, preferably agents which can assist in treating autoimmune and/or inflammatory diseases or cancer, including metastatic cancer or recurrent cancer or ameliorating the secondary effects and/or symptoms associated with these disease states and/or conditions. This treatment can also be administered in conjunction with other conventional therapies, such as radiation treatment or surgery for cancer.

The present compounds, alone or in combination with other agents as described herein, can be administered by any appropriate route, for example, orally, parenterally, intravenously, intradermally, subcutaneously, or topically, in liquid, cream, gel, or solid form, or by aerosol form.

The active compound is included in the pharmaceutically acceptable carrier or diluent in an amount sufficient to deliver to a patient a therapeutically effective amount for the desired indication, without causing serious toxic effects in the patient treated. A preferred dose of the active compound for all of the herein-mentioned conditions is in the range from about 10 ng/kg to 300 mg/kg, preferably 0.1 to 100 mg/kg per day, more generally 0.5 to about 25 mg per kilogram body weight of the recipient/patient per day. A typical topical dosage will range from about 0.01-3% wt/wt in a suitable carrier.

The compound is conveniently administered in any suitable unit dosage form, including but not limited to one containing less than 1 mg, 1 mg to 3000 mg, preferably 5 to 500 mg of active ingredient per unit dosage form. An oral dosage of about 25-500 mg is often convenient.

The active ingredient is preferably administered to achieve peak plasma concentrations of the active compound of about 0.00001-30 mM, preferably about 0.1-30 μM. This may be achieved, for example, by the intravenous injection of a solution or formulation of the active ingredient, optionally in saline, or an aqueous medium or administered as a bolus of the active ingredient. Oral administration is also appropriate to generate effective plasma concentrations of active agent.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

Oral compositions will generally include an inert diluent or an edible carrier. They may be enclosed in gelatin capsules or compressed into tablets. For the purpose of oral therapeutic administration, the active compound or its prodrug derivative can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or enteric agents.

The active compound or pharmaceutically acceptable salt thereof can be administered as a component of an elixir, suspension, syrup, wafer, chewing gum or the like. A syrup may contain, in addition to the active compounds, sucrose as a sweetening agent and certain preservatives, dyes and colorings and flavors.

The active compound or pharmaceutically acceptable salts thereof can also be mixed with other active materials that do not impair the desired action, or with materials that supplement the desired action, such as other anticancer agents, anti-inflammatory agents, immunosuppressants, antibiotics, antifungals, or antiviral compounds. In certain preferred aspects of the invention, one or more chimeric/bi-functional MIF binding compound according to the present invention is coadministered with another anticancer agent and/or another bioactive agent, as otherwise described herein.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In one embodiment, the active compounds are prepared with carriers that will protect the compound against rapid elimination from the body, such as a controlled and/or sustained release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

Liposomal suspensions or cholestosomes may also be pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound are then introduced into the container. The container is then swirled by hand to free lipid material from the sides of the container and to disperse lipid aggregates, thereby forming the liposomal suspension.

Chemical Synthesis

Figure 7:
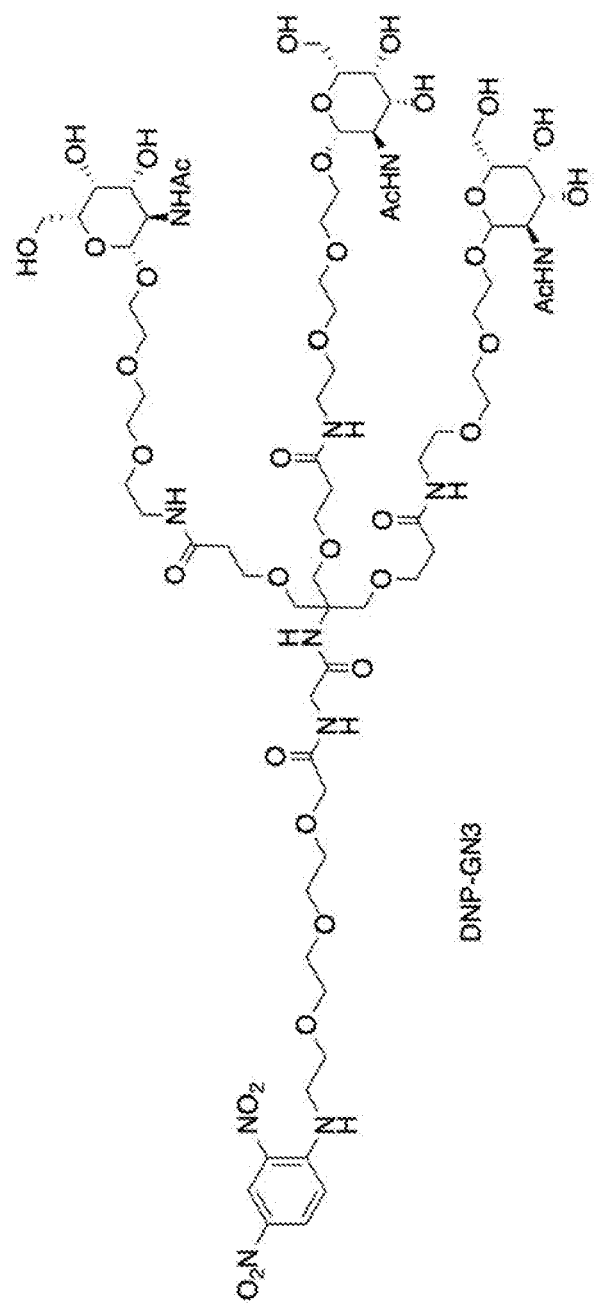
FIG. 7 shows molecules DNP-GN3 and DNP-AcF3-3, which are bifunctional molecules that bind to anti-DNP IgG and ASGPR.
Figure 7:
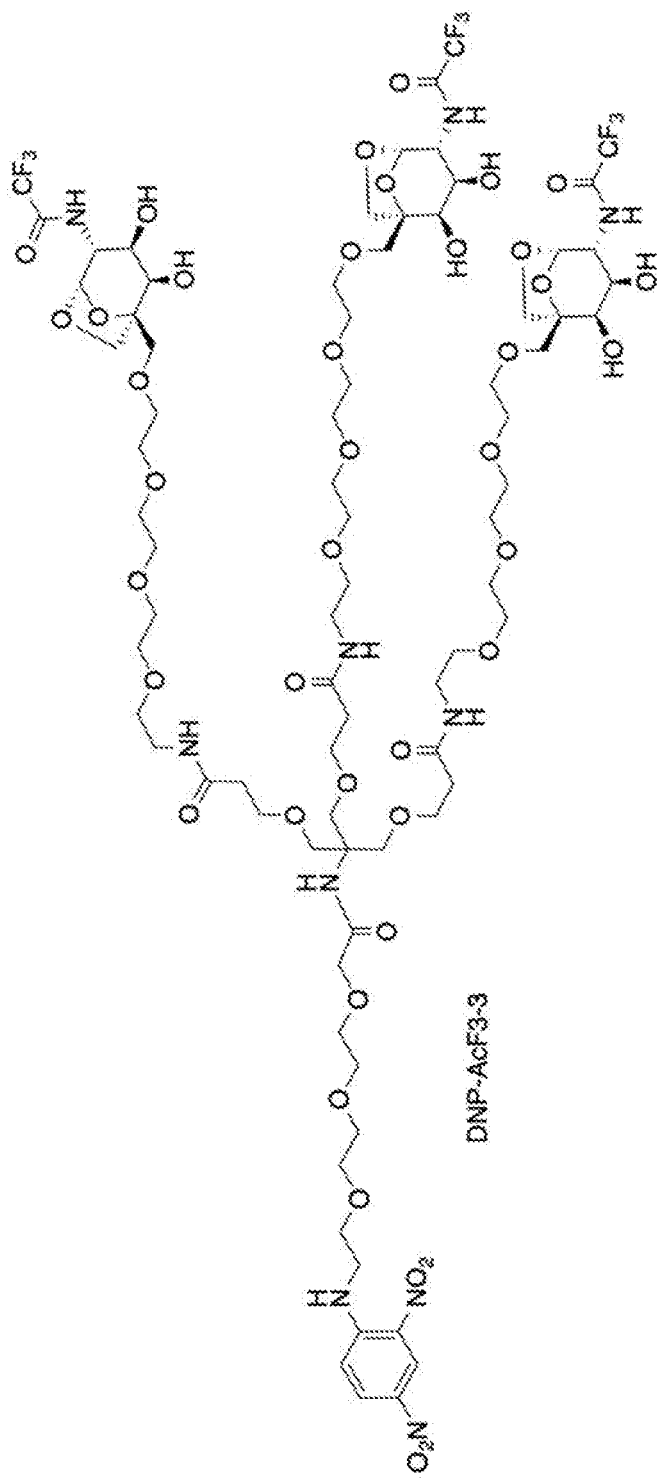
Figure 13:
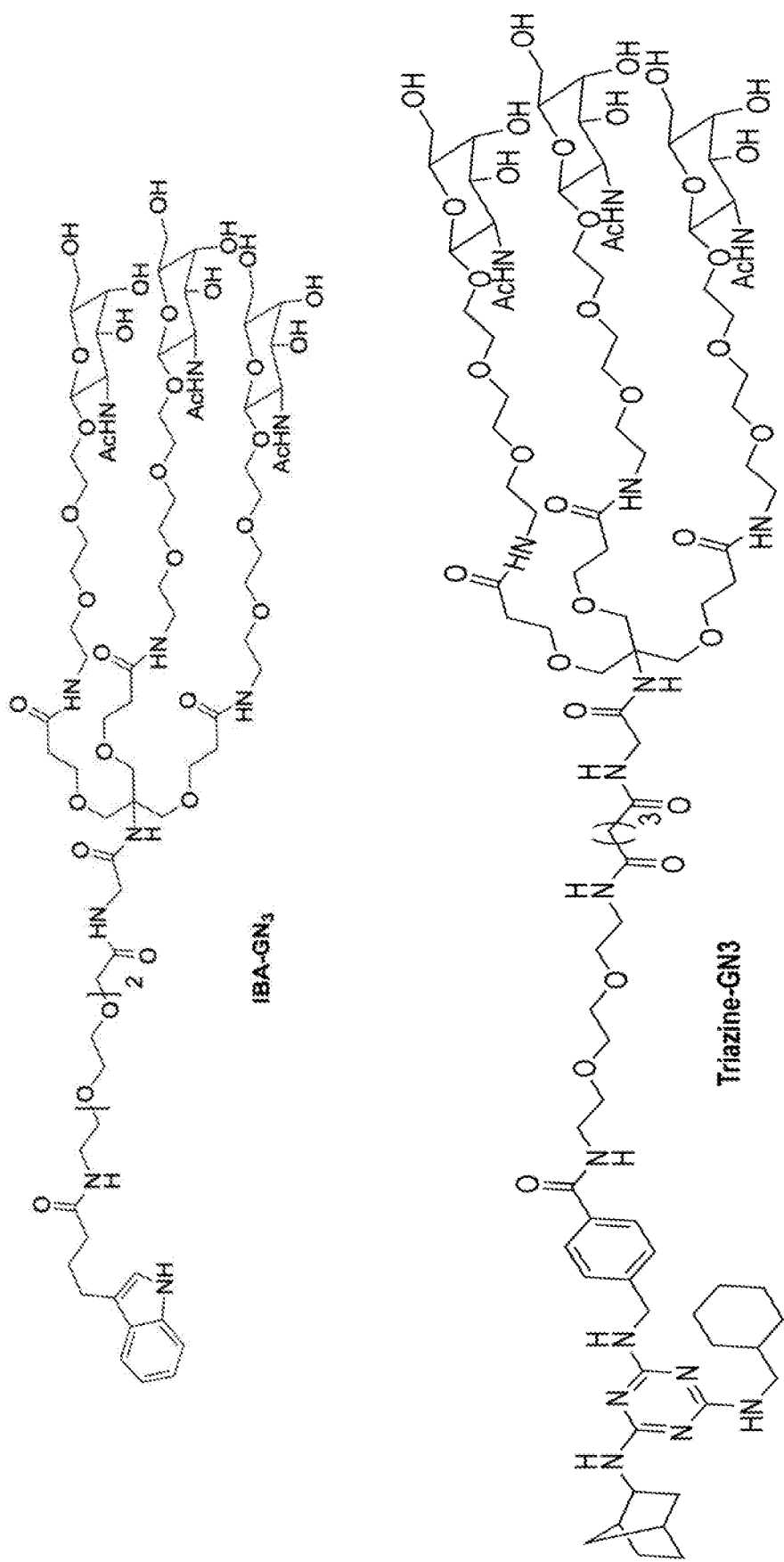
FIG. 13 shows the structures of IgG-degrading molecules IBA-GN3, Triazine-GN3, FcIII-GN3, and FcIII-4c-GN3.
Figure 13:
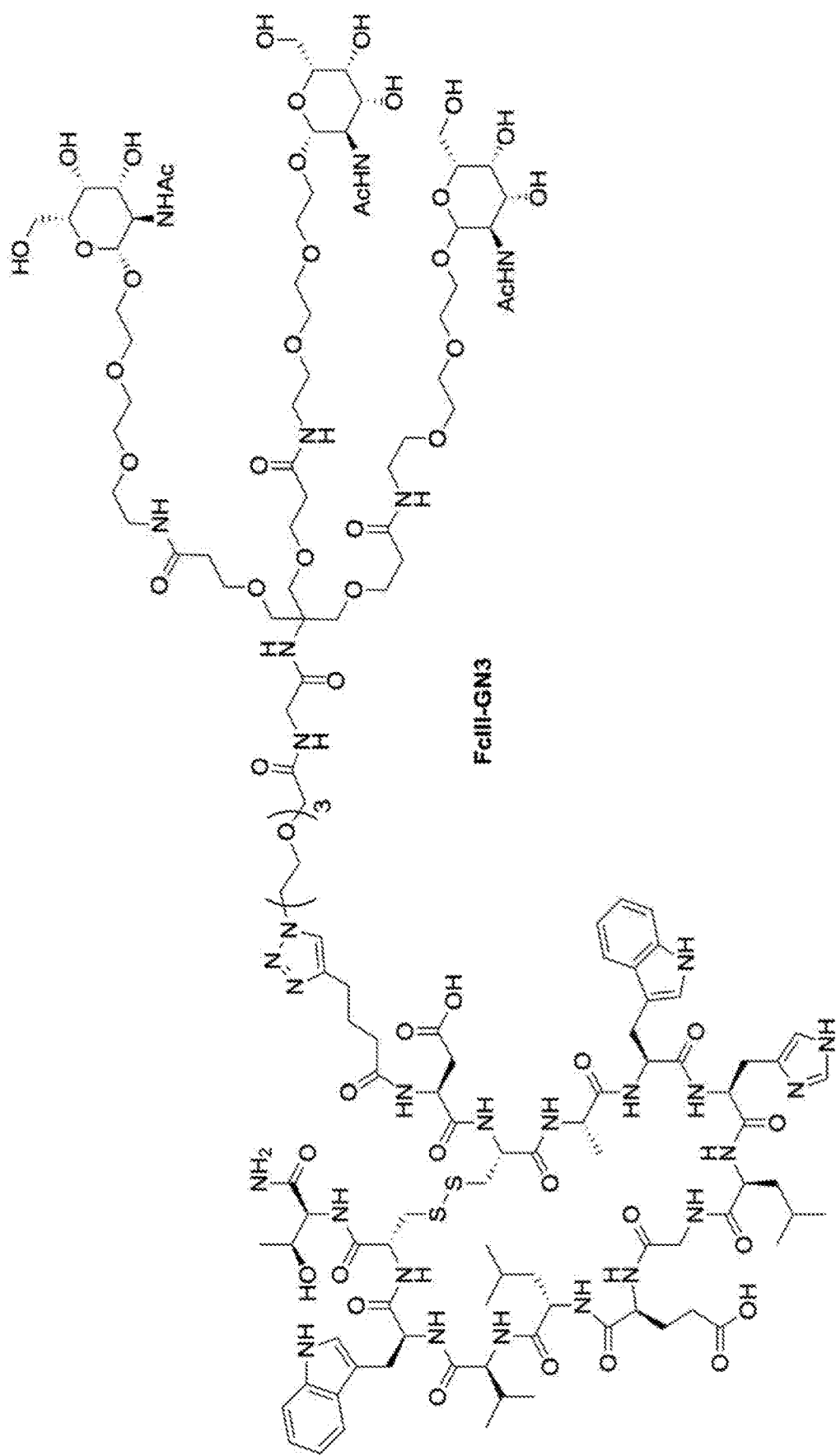
Figure 13:
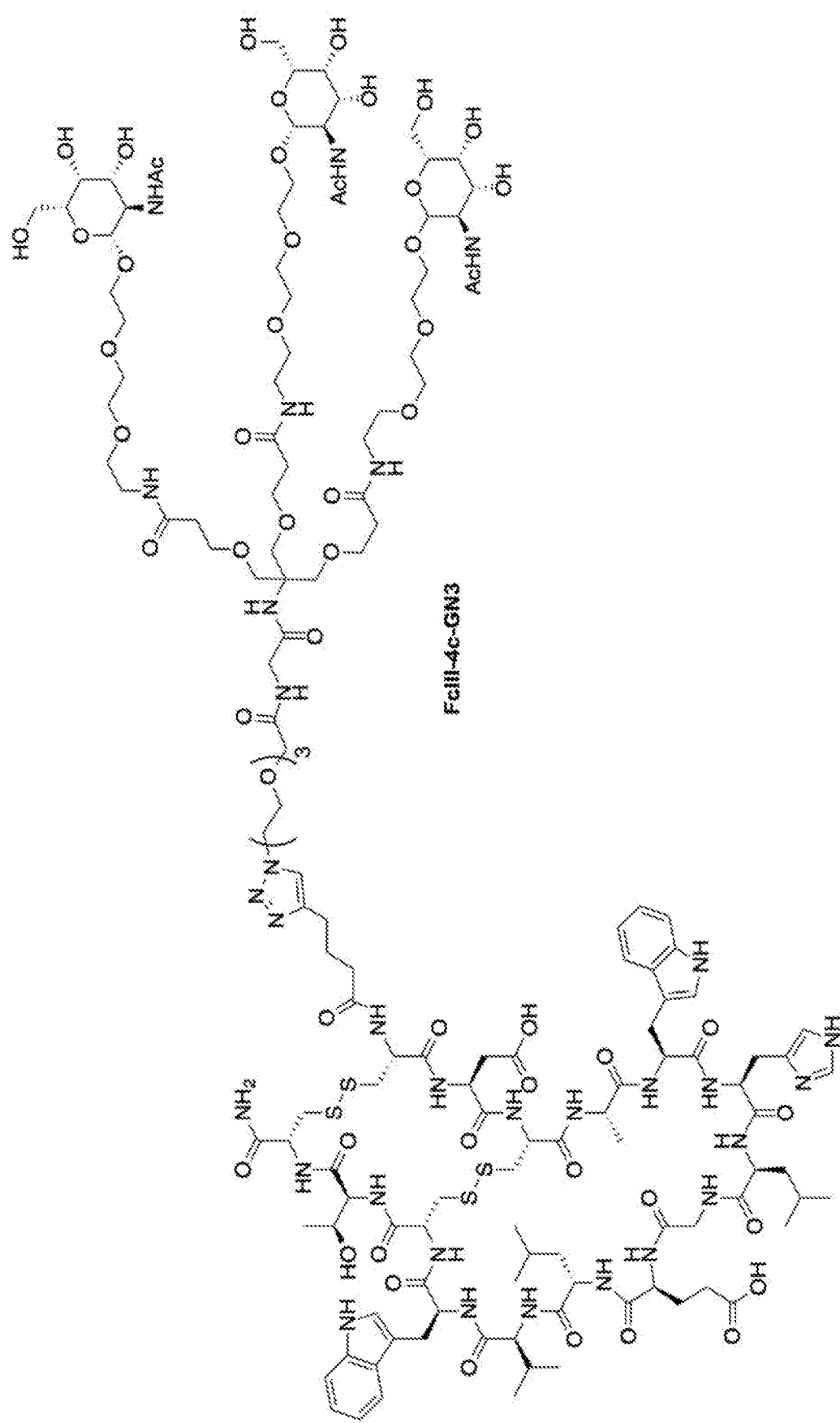

FIGS. 1, 7, and 13 attached hereto identifies particular compounds according to the present invention which exhibit activity in binding to and reducing and/or eliminating unwanted circulating proteins for therapeutic and/or diagnostic purposes. These compounds are based upon an MIF, anti-DNP IgG, or IgG binding moiety to which is covalently attached an ASPGR group such as GN3 or AcF3-3 group through a linker which contains from 1 to 100 ethylene glycol groups, more often from 1 to 15 ethylene glycol groups, from 1 to 10 ethylene glycol groups, often from 2 to 10 ethylene glycol groups which are optionally attached through a [CON] group, such as a 1,2,3-triazole or other [CON] group as described herein.

Figure 16:
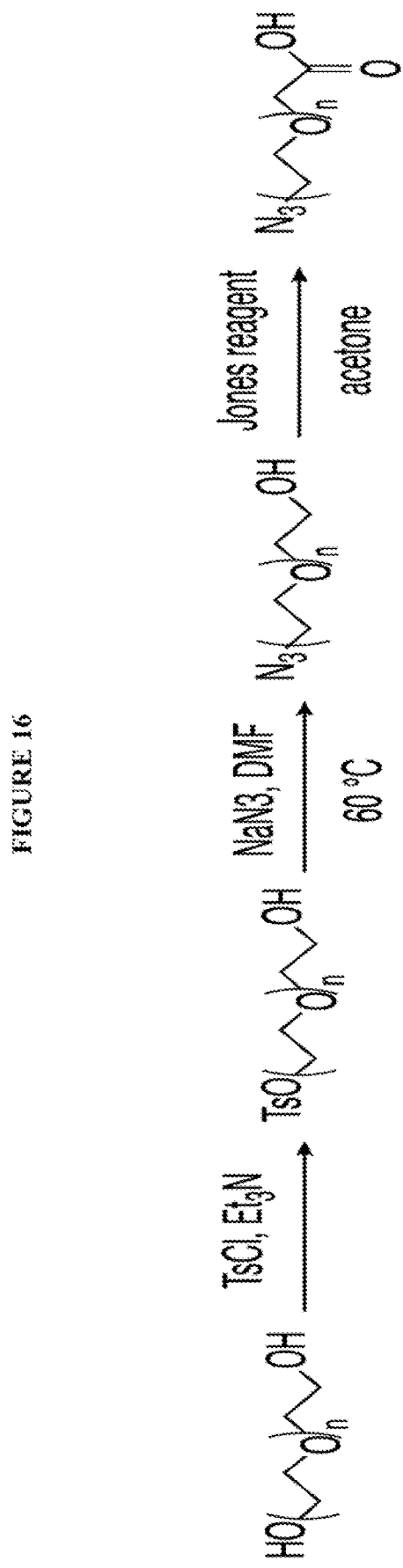
FIGS. 16-18 show the synthesis of PEG linkers used in several molecules outlined in this invention.

FIG. 16 shows the synthesis of azide/amide carboxylic end capped PEG linker intermediates which may be condensed onto an alkynyl precursor (e.g. NVS alkyne precursor of FIG. 5) to provide carboxylic acid capped intermediate which can be used to provide bifunctional molecules.

Figure 17:
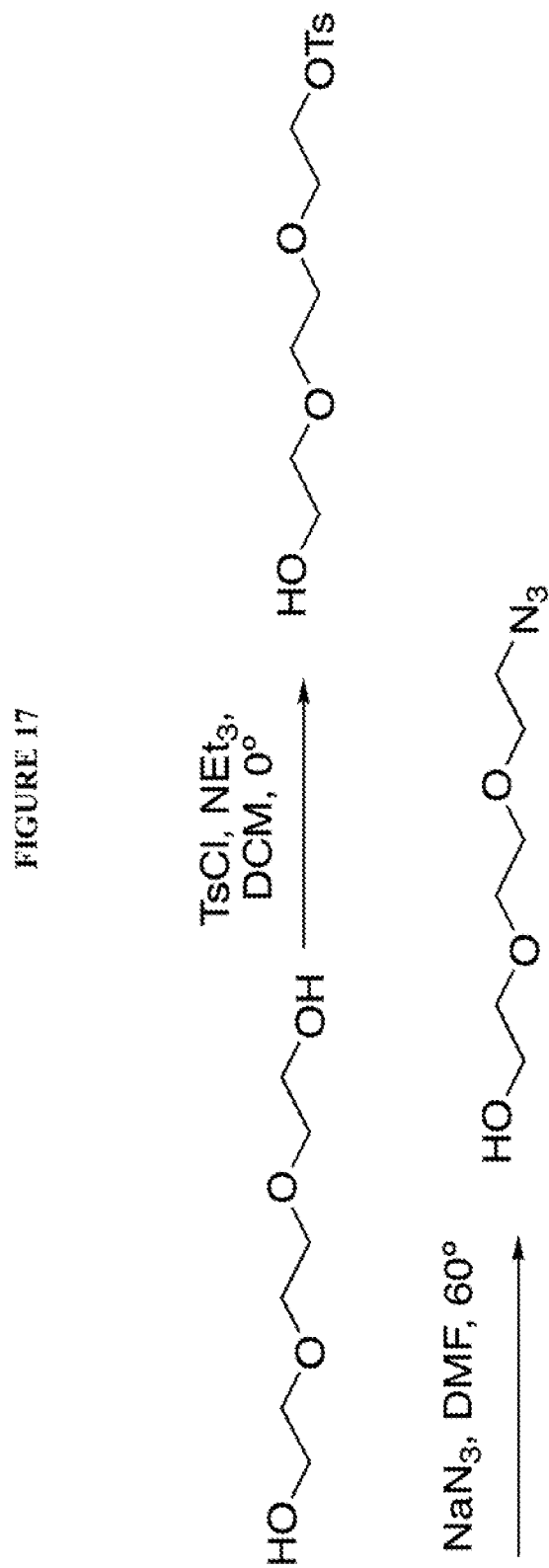

FIG. 17 describes a general method for conversion of PEG molecules into hydroxyl azides. The PEG compound is tosylated (TsCl, DCM, in the presence of base) at reduced temperature and further reacted with sodium azide at elevated temperature in a non-nucleophilic solvent. The final azidoalcohol is used in subsequent figures.

Figure 18:
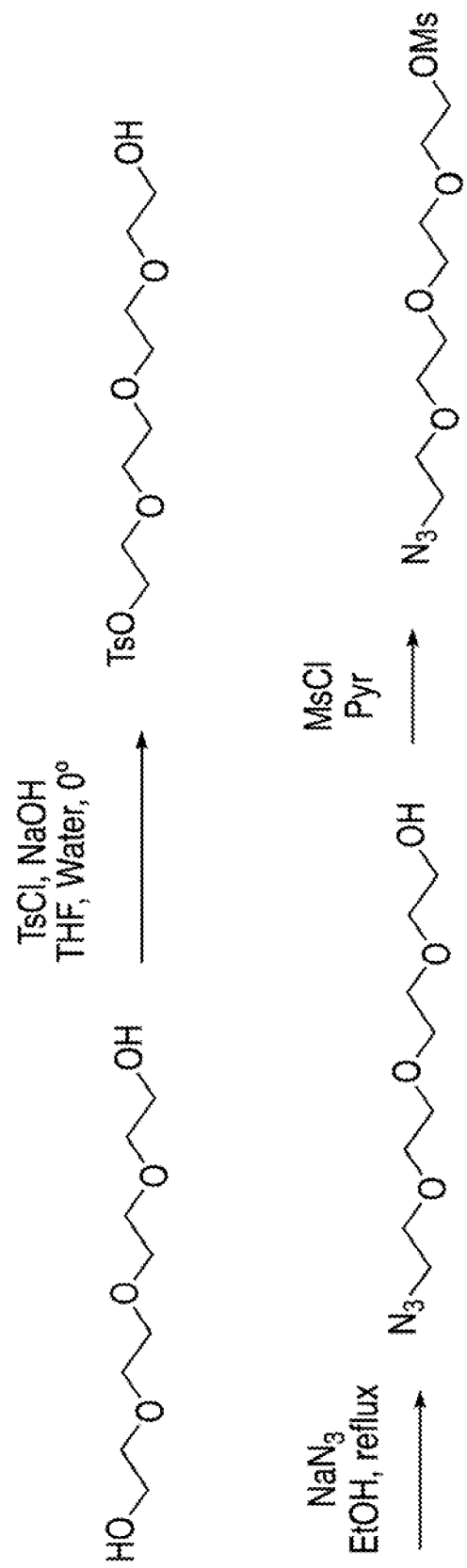

FIG. 18 describes the synthesis of a mesylated azide from a starting PEG molecule employing the same synthetic steps to reach the intermediate azido alcohol. This is then treated with MsCl in pyridine to afford the final compound.

Figure 19:
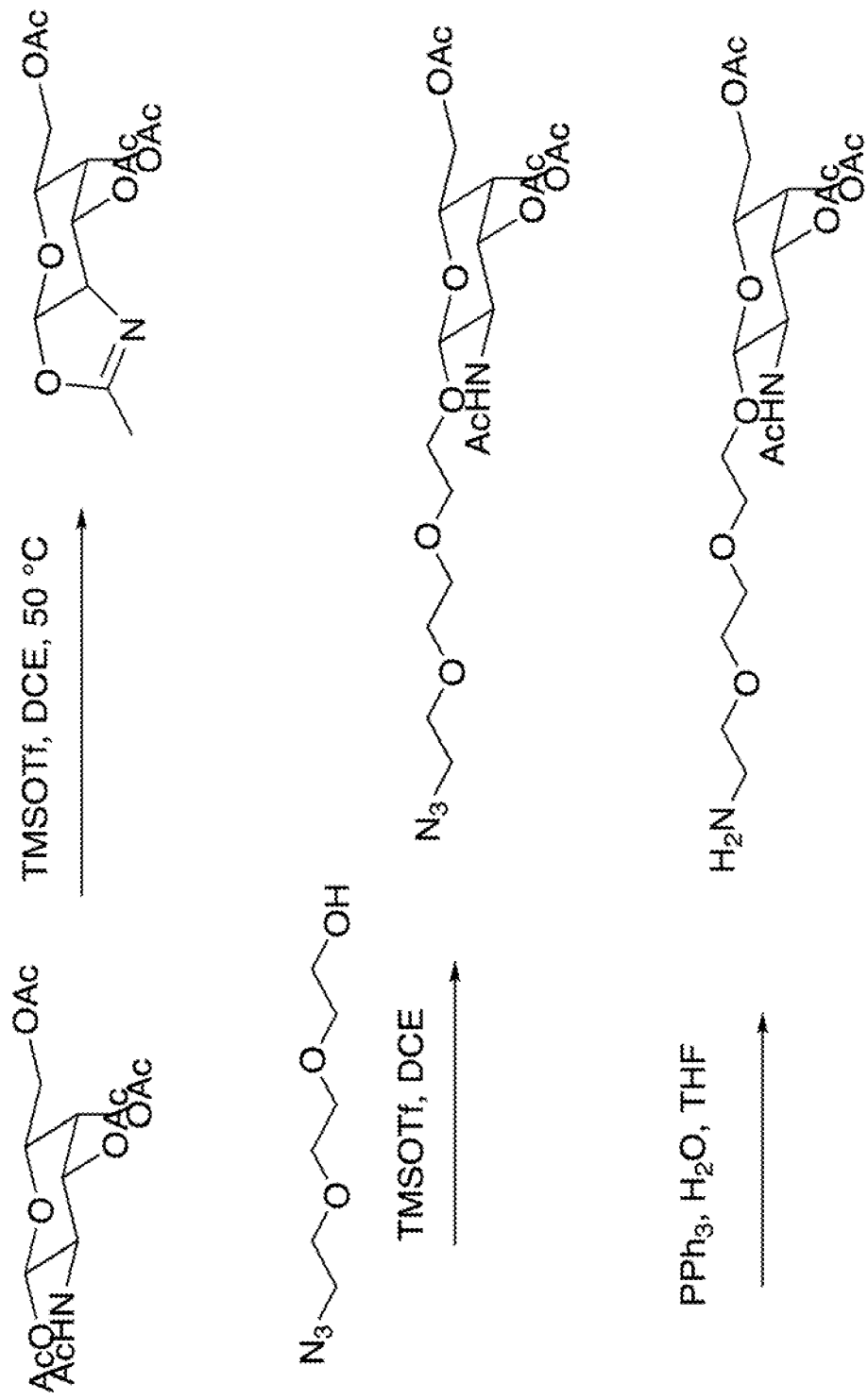
FIGS. 19-21 show the synthesis of ASGPR-binding precursors and ligands used in several molecules in this invention.

FIG. 19 shows the synthesis of the GalNAc ASGPR ligand linked through PEG to a terminating amine. Pentaacetyl galactosamine is reacted with TMSOTf at elevated temperature in DCE to produce a bicyclic intermediate, which is then reacted with an azido alcohol to give an azide intermediate (TMSOTf, DCE). This molecule is then subjected to a Staudinger reduction to give an amine which is used in subsequent figures.

Figure 20:
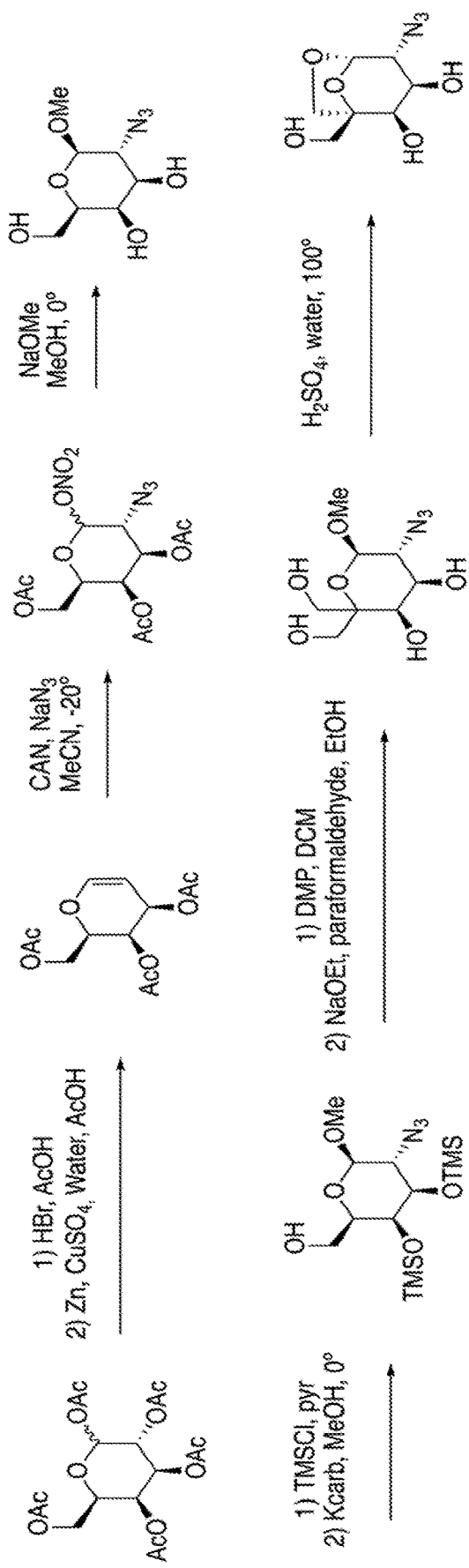

FIG. 20 shows the synthesis of a higher affinity bicyclic ASGPR ligand. Galactose pentaacetate is treated with HBr/AcOH to give the brominated intermediate, which is treated with Zn and CuSO4 (water/AcOH) to give the galactal. This is treated with ammonium cerium nitrate and sodium azide at reduced temperature (MeCN) to give the disubstituted intermediate compound. This is then treated with strong base (NaOMe/MeOH) to give the triol azide intermediate. This compound is silylated completely (TMSCl/pyr) then the primary alcohol is deprotected (potassium carbonate, MeOH, lowered temperature) and oxidized (Dess-Martin Periodinane, DCM). Treatment with strong base (NaOEt/HOEt) and paraformaldehyde gives the tetraol intermediate, which is cyclized in strong acid (H2SO4/water) to give the bicyclic azide ligand.

Figure 21:
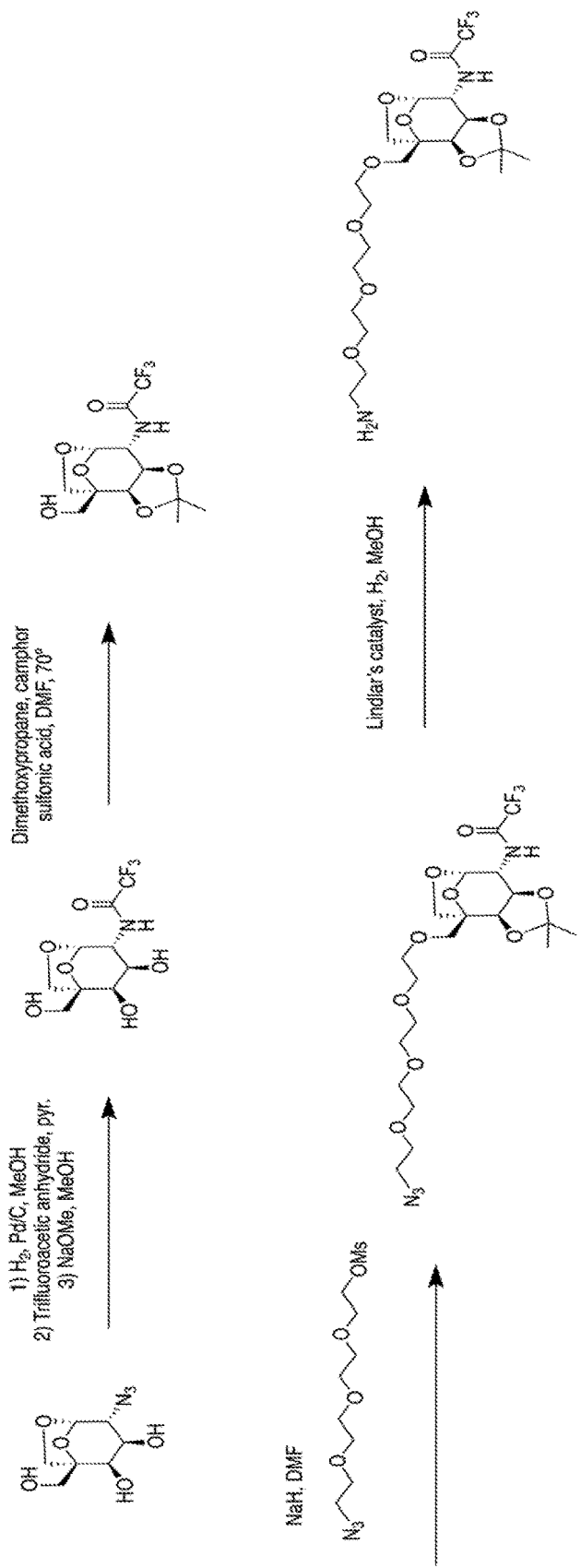

FIG. 21 shows the synthesis of a trifluoro-acetate derivative of the bicyclic ASGPR ligand. The triol azide is reduced (Pd/C, MeOH) to give the intermediate amine, which is then peracylated with trifuloroacetic anhydride. The esters are hydrolyzed with strong base (NaOMe/HOMe) to give the intermediate amide, which is protected using dimethoxypropane in the presence of camphorsulfonic acid in DMF at elevated temperature. This is then reacted a mesylated azido alcohol in the presence of strong base (NaH/DMF) to give an intermediate azide that is reduced (Lindlar's catalyst, MeOH) to give the final amine.

Figure 22:
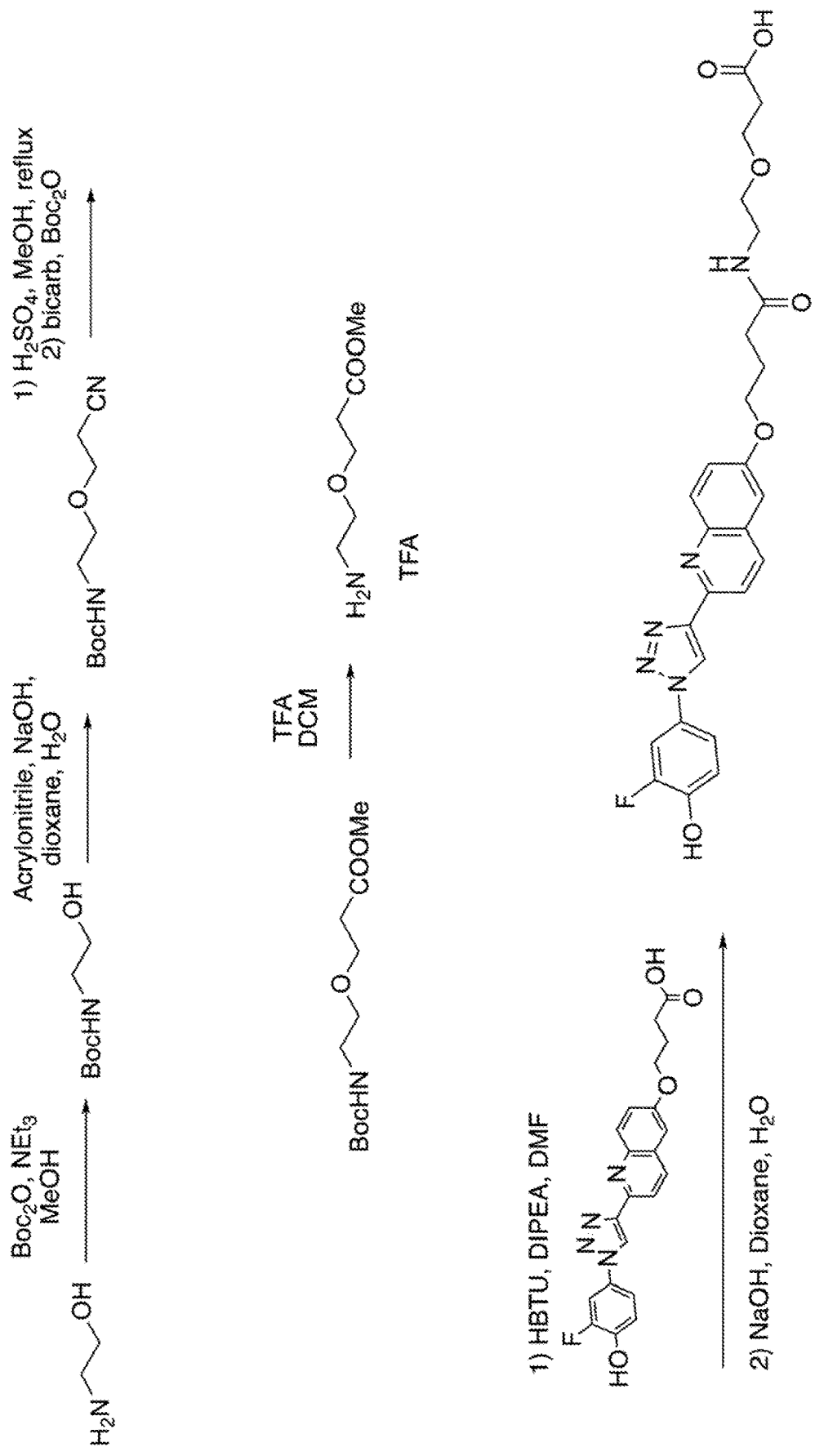
FIGS. 22-26 show the synthesis of valency linkers used in several molecules in this invention.

FIG. 22 shows the synthesis of the MIF-targeting linker to a monovalent linker, which is synthesized through analagous methods as described in a previous figure. The boc-protected methyl ester is deprotected with TFA in DCM, then coupled to the MIF-targeting carboxylic acid (HBTU, DIPEA, DMF). Subsequent hydrolysis with strong base (NaOH/dioxane/H2O) gives the MIF-targeting carboxylic acid.

Figure 23:
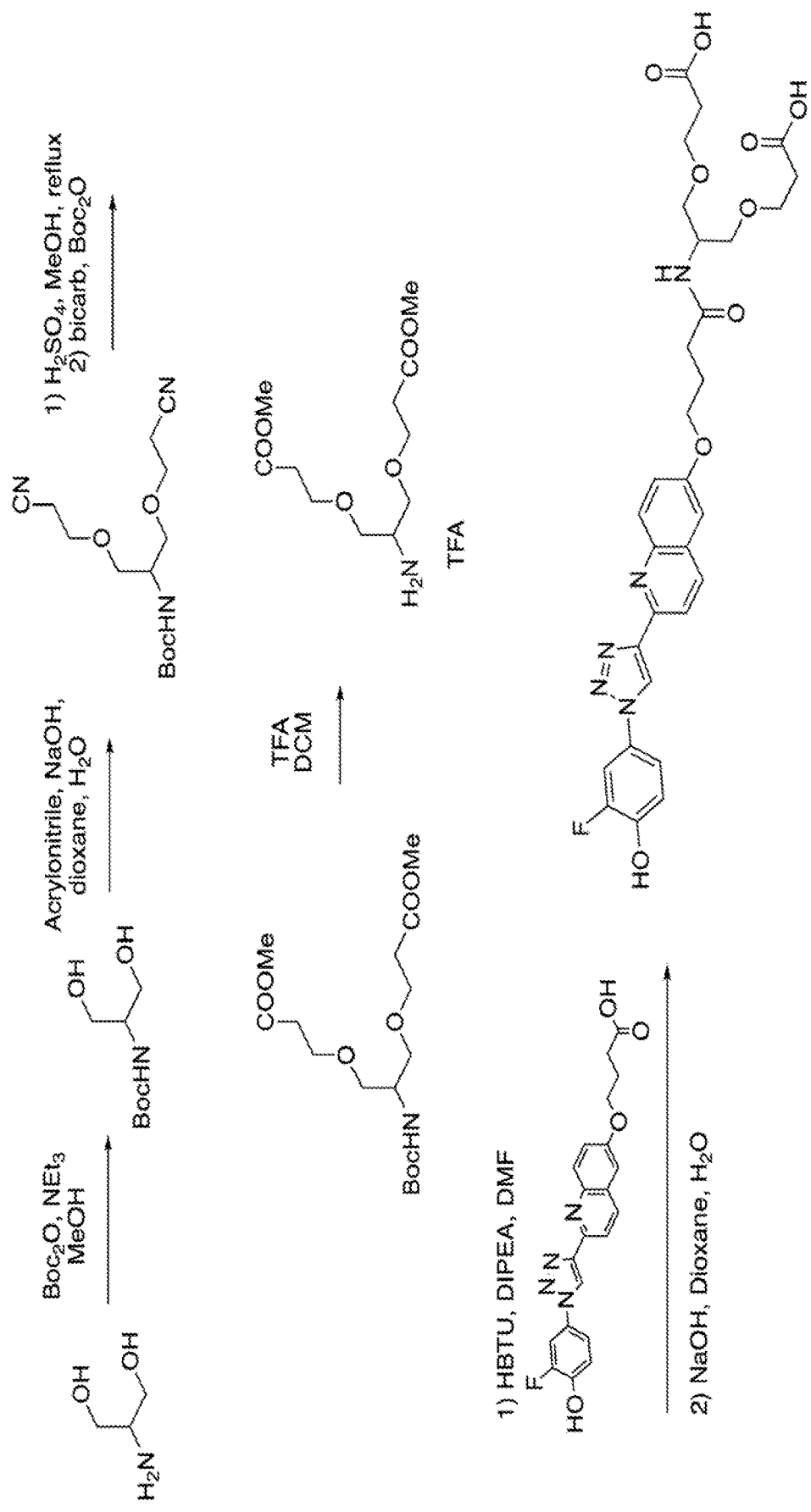

FIG. 23 shows the synthesis of the di-carboxylic acid MIF targeting motif, which is synthesized as described in previous figures.

Figure 24:
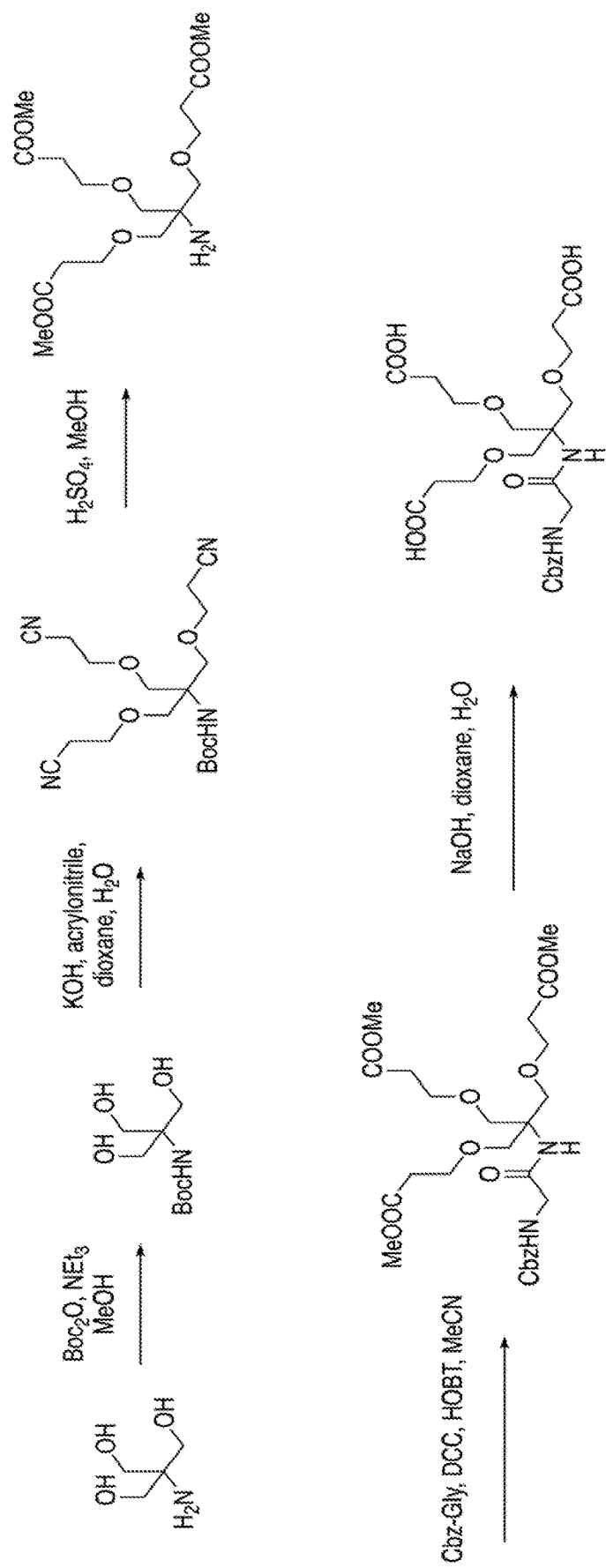

FIG. 24 shows the synthesis of a tris base-derived trivalent linker. Tris base is treated with di-t-butyl dicarbonate in the presence of base to give the hoc protected triol, which is then reacted with acrylonitrile in the presence of base (dioxane/H2O) to give a trinitrile intermediate. This is then converted to the methyl ester through treatment with strong acid in methanol. The amine is then reacted with Cbz-glycine through a DCC-mediated amide formation, and deprotected to give a tricarboxylic acid that is used in subsequent figures.

Figure 25:
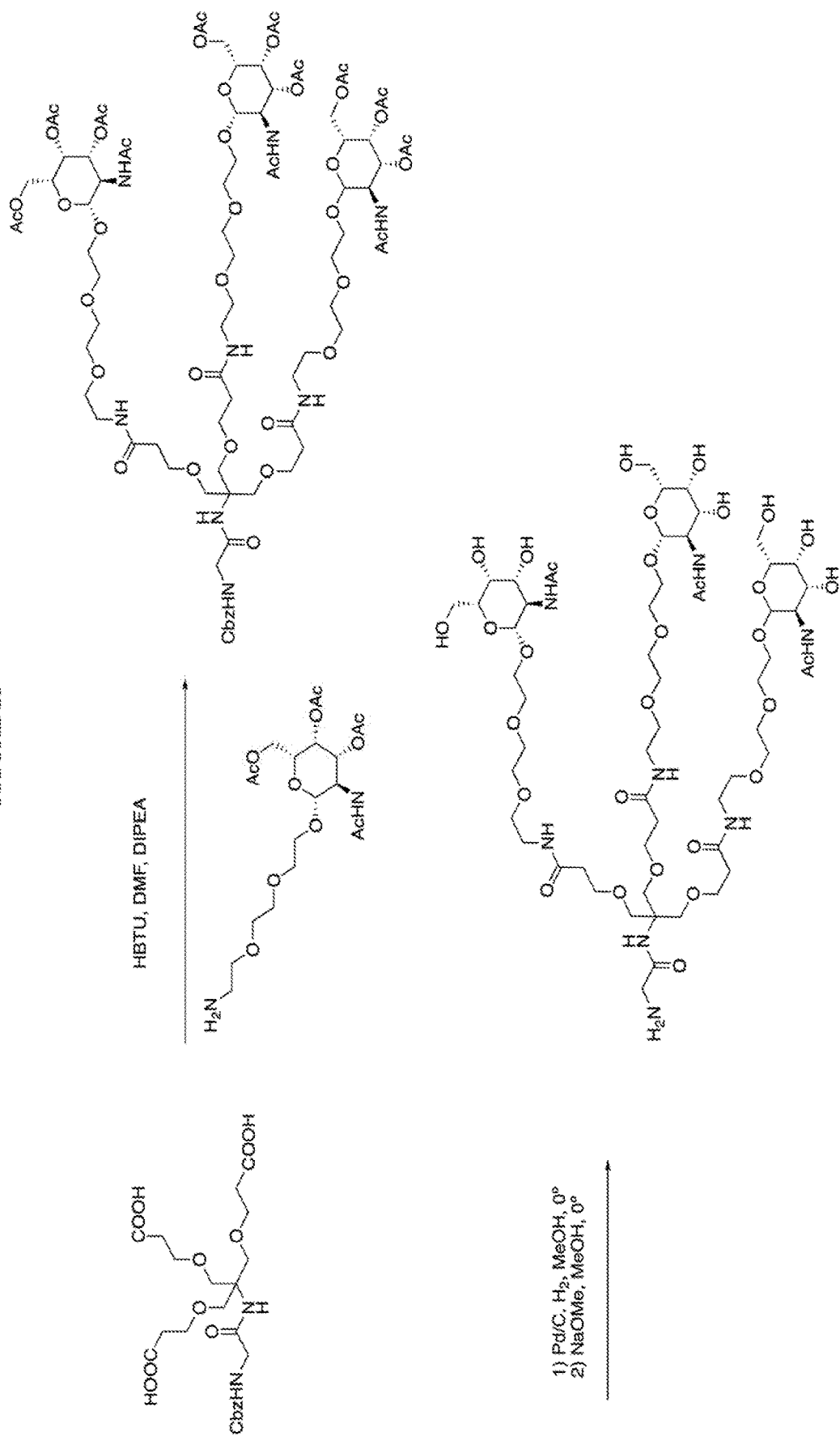

FIG. 25 describes the synthesis of an ASGPR-targeting moiety employing three GalNAc ASGPR ligands. The tricarboxylic acid is reacted with amine-terminated protected GalNAc (amide bond formation in the presence of HBTU and DIPEA), then deprotected by reduction (Pd/C, solvent) and treatment with strong base (NaOMe/MeOH).

Figure 26:
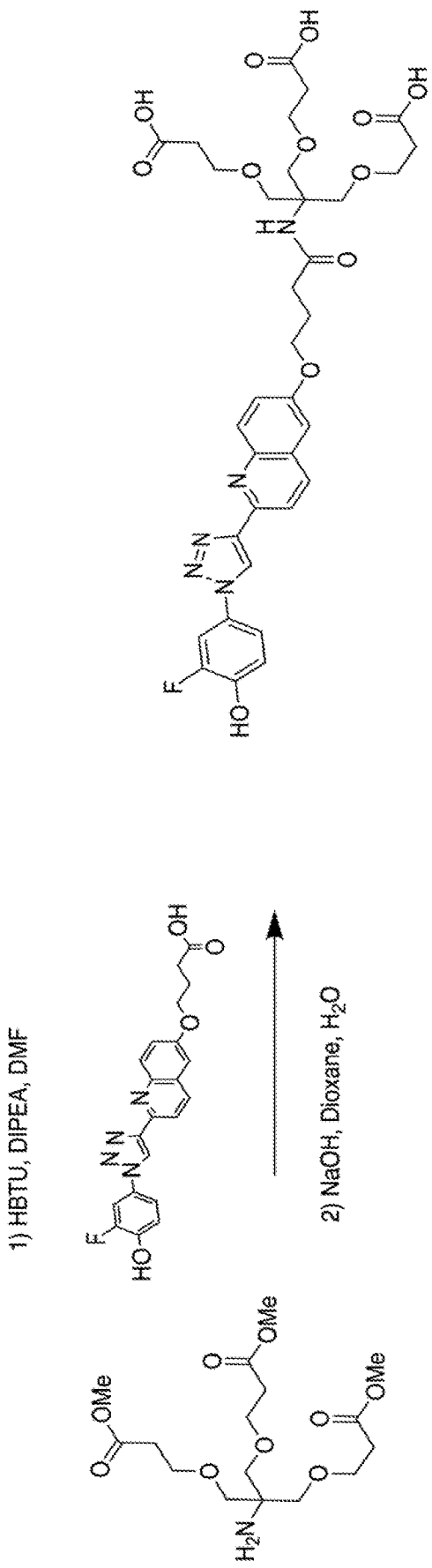

FIG. 26 shows the synthesis of the tri-carboxylic acid MIF targeting motif, which is synthesized as described in previous figures.

Figure 27:
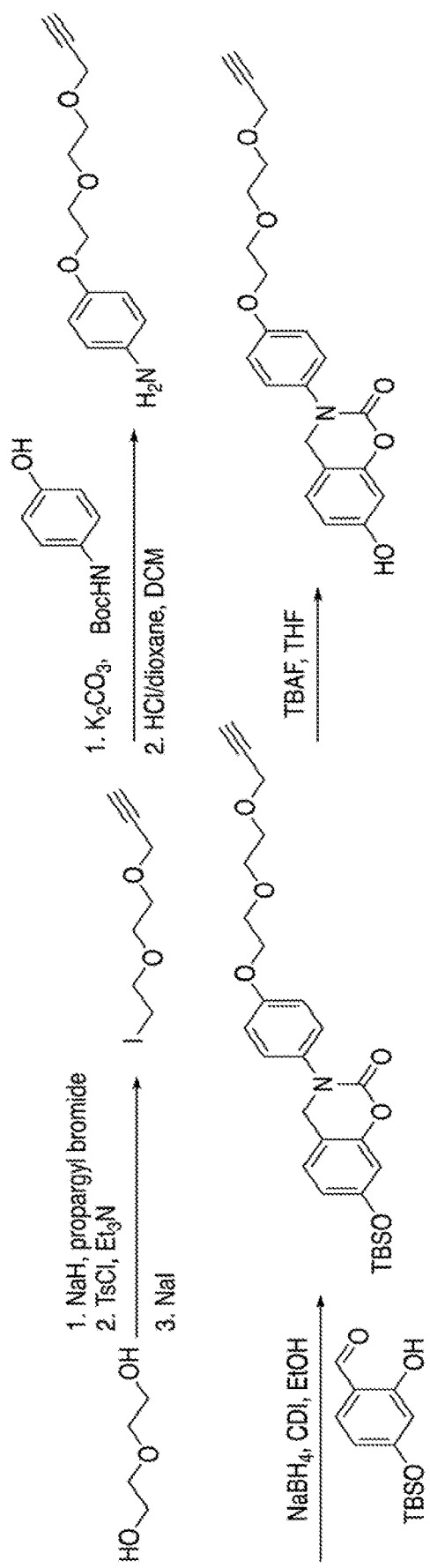
FIGS. 27-28 show the synthesis of MIF ligands used in several bifunctional molecules.

FIG. 27 shows the synthesis of the MIF NVS alkyne precursor which can be reacted with an azido reactant containing a carboxylic acid (as set forth in subsequent figures) to provide MIF-NVS-carboxylic acid capped reactants to produce bifunctional compounds according to the present invention.

Figure 28:
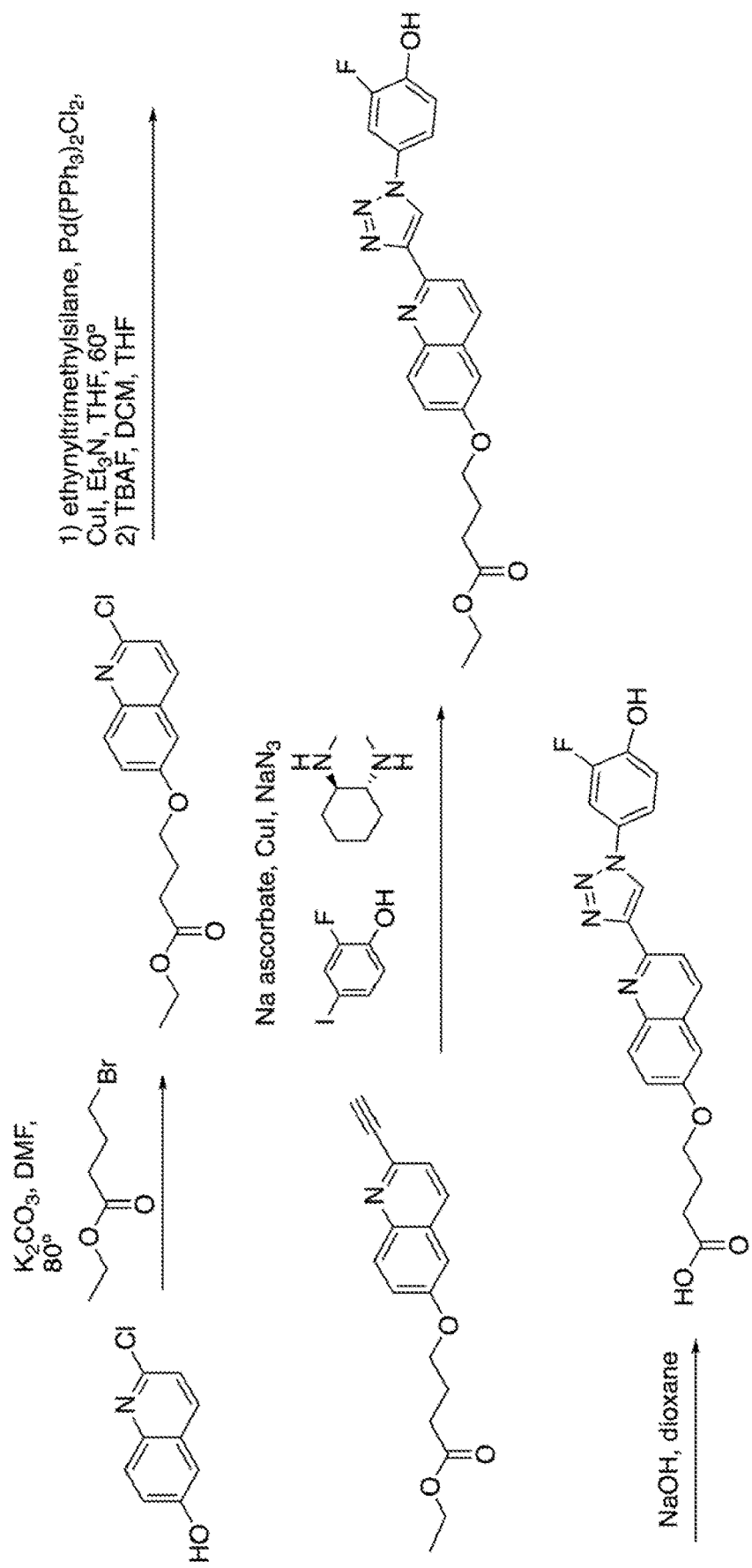

FIG. 28 shows the synthesis of the MIF-targeting moiety terminating in a carboxylic acid. 2-chloroquinolin-6-ol is reacted with ethyl 4-bromobutanoate in the presence of base (DMF, elevated temperature) to give an aryl chloride that then undergoes Sonogashira coupling at evelvated temperature with ethynyltrimethylsilane. The intermediate silylated compound is deprotected with TBAF (DCM/THF). A click reaction then forms a triazole between the alkyne intermediate and in situ synthesized 4-azido-2-fluorophenol to give an ethyl ester intermediate that is hydrolyzed with strong base (NaOH/dioxane) to give the carboxylic acid that is used in subsequent figures.

Figure 29:
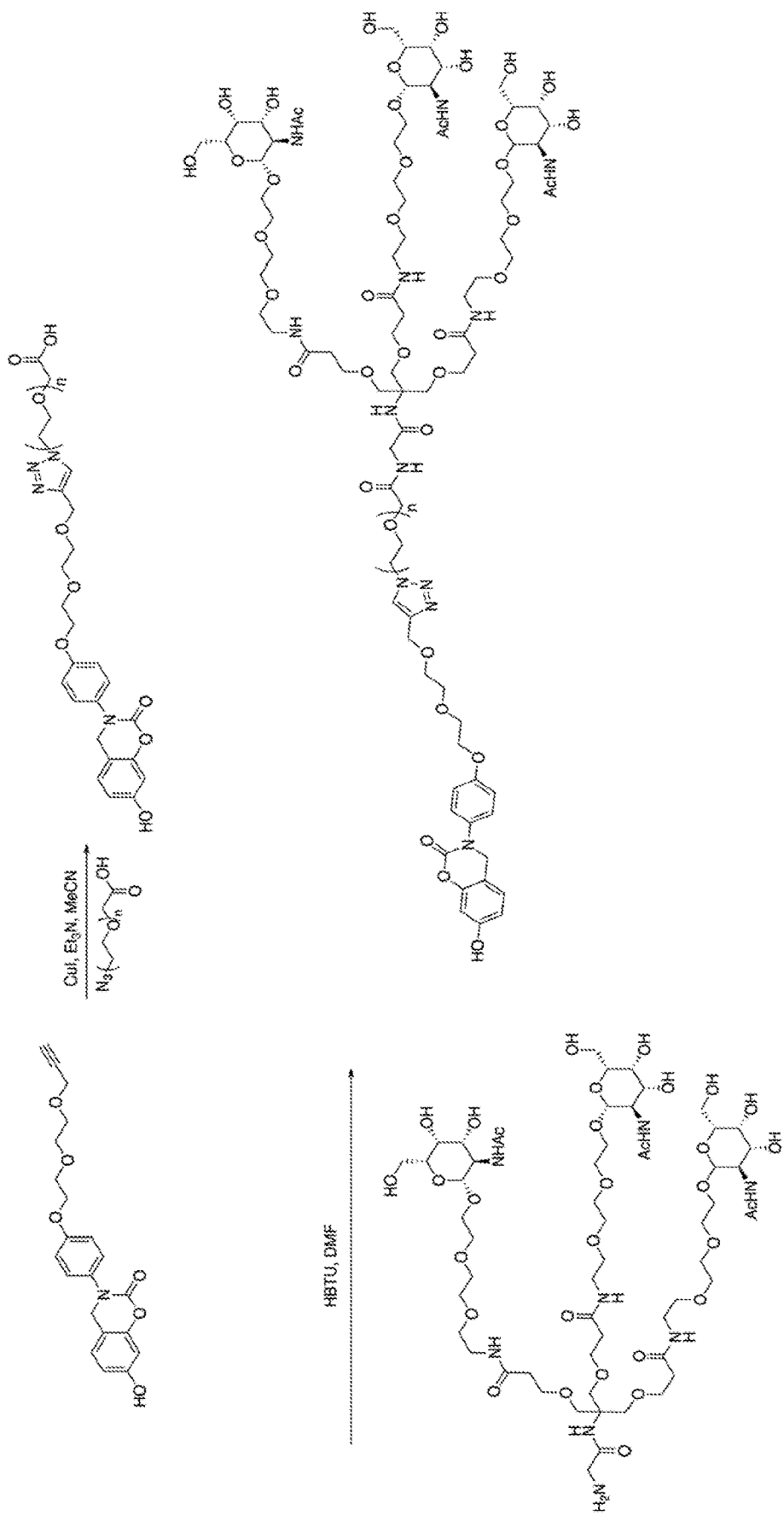
FIG. 29 describes the synthesis of the bifunctional molecule MIF-NVS-PEGn-GN3.

FIG. 29 describes the synthesis of the bifunctional molecule MIF-NVS-PEGn-GN3 through HBTU-mediated coupling in DMF of the ASPGR-targeting amine and the MIF targeting carboxylic acid prepared by first forming the MIF-targeting carboxylic acid by condensing the reactant azido PEG-carboxylic acid onto the MIF moiety containing a alkyne terminated PEG group.

Figure 30:
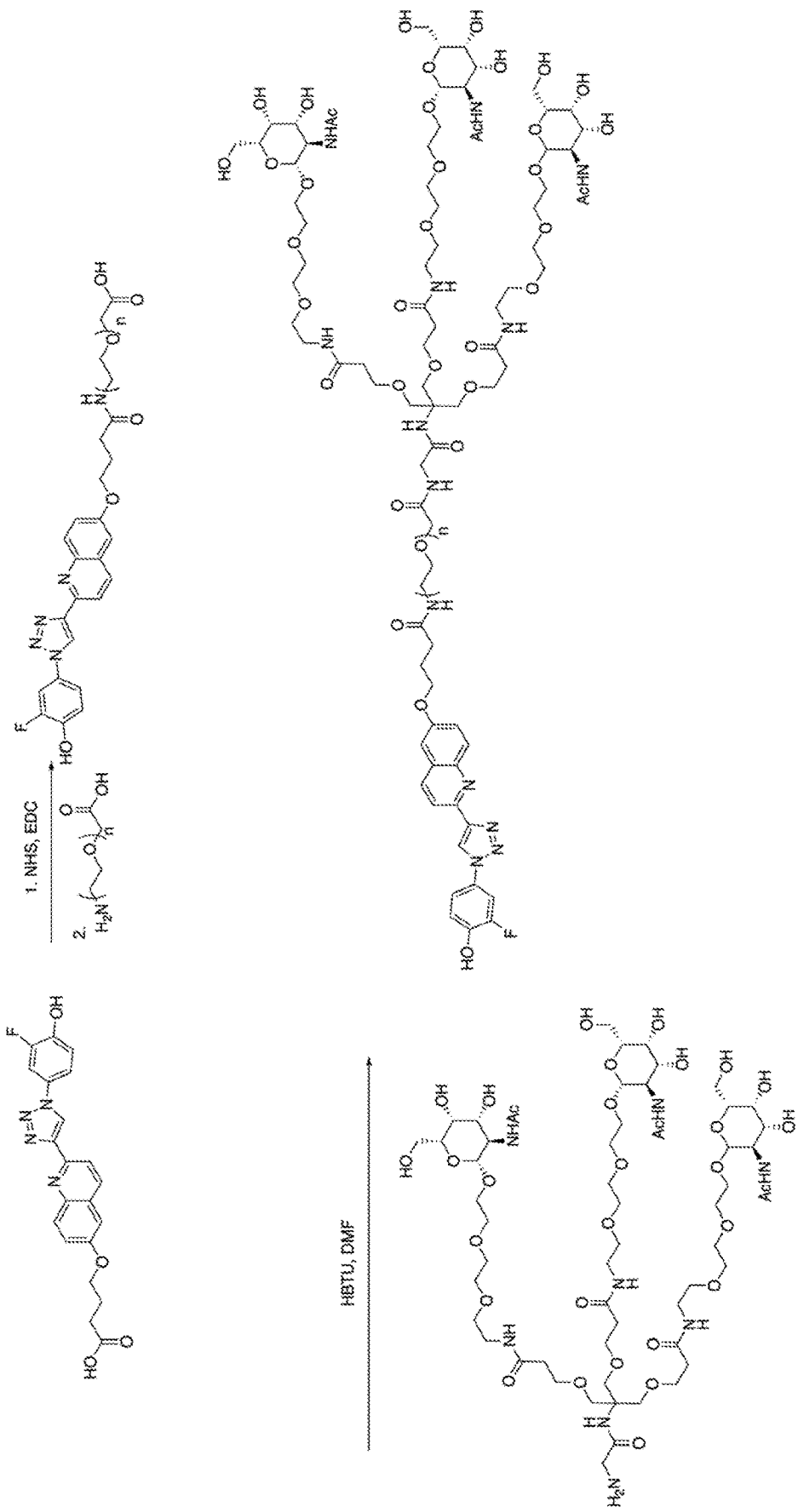
FIG. 30 describes the synthesis of bifunctional molecules MIF-GN3 and MIF-PEGn-GN3.

FIG. 30 describes the synthesis of bifunctional molecules MIF-GN3 and MIF-PEGn-GN3 through HATU-mediated coupling (DMF, DIPEA) of ASGPR-targeting amine and MIF-targeting carboxylic acid.

Figure 31:
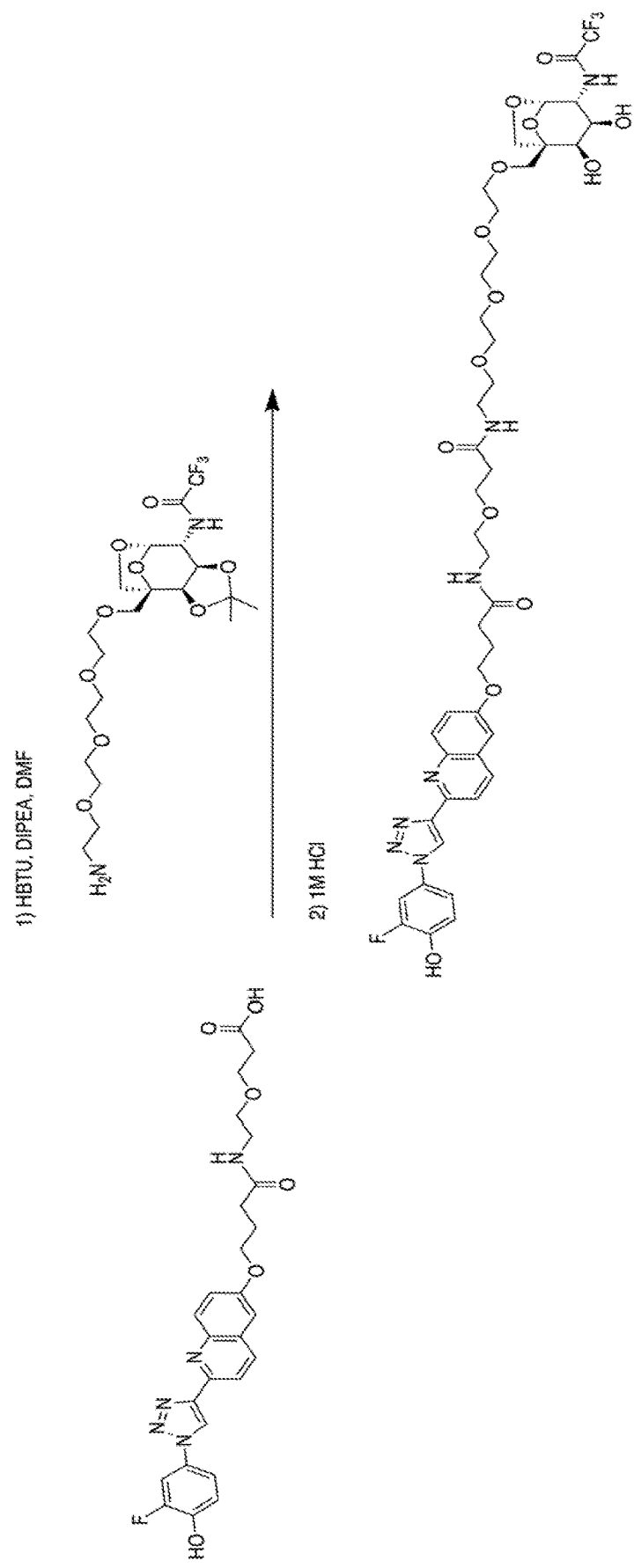
FIG. 31 describes the synthesis of the bifunctional molecule targeting MIF and ASGPR, containing one bicyclic ASGPR AcF3 ligands.

FIG. 31 describes the synthesis of the bifunctional molecule targeting MIF and ASGPR, containing one bicyclic ASGPR AcF3 ligands. MIF-binding mono-carboxylic acid is treated with HBTU, DIPEA, the amine terminated ligand, and DMF to give the amide, which is then deprotected with 1M HCl to give the final compound.

Figure 32:
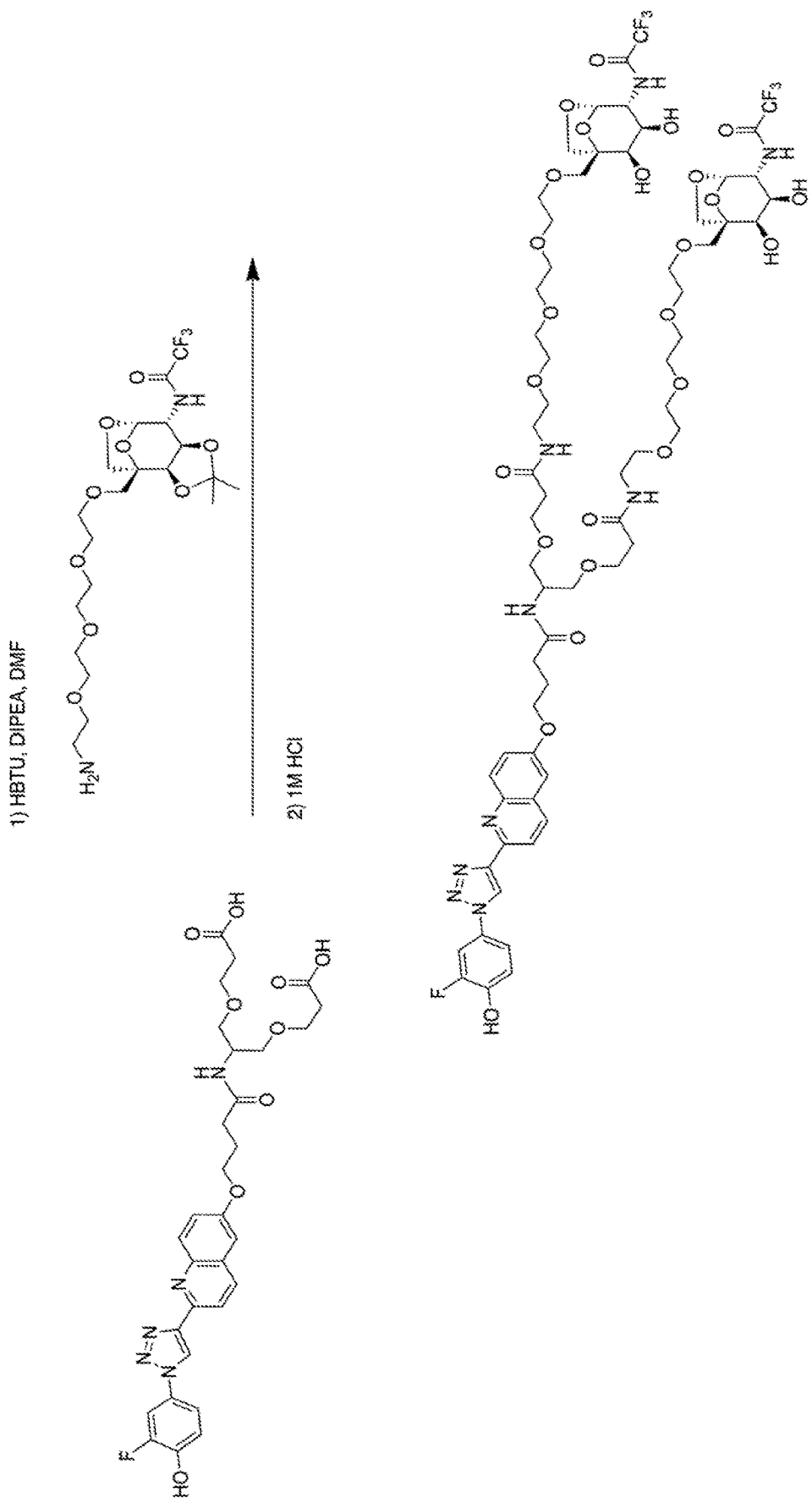
FIG. 32 describes the synthesis of the bifunctional molecule targeting MIF and ASGPR, containing two bicyclic ASGPr AcF3 ligands.

FIG. 32 describes the synthesis of the bifunctional molecule targeting MIF and ASGPR, containing two bicyclic ASGPr ligands. It is synthesized as described above.

Figure 33:
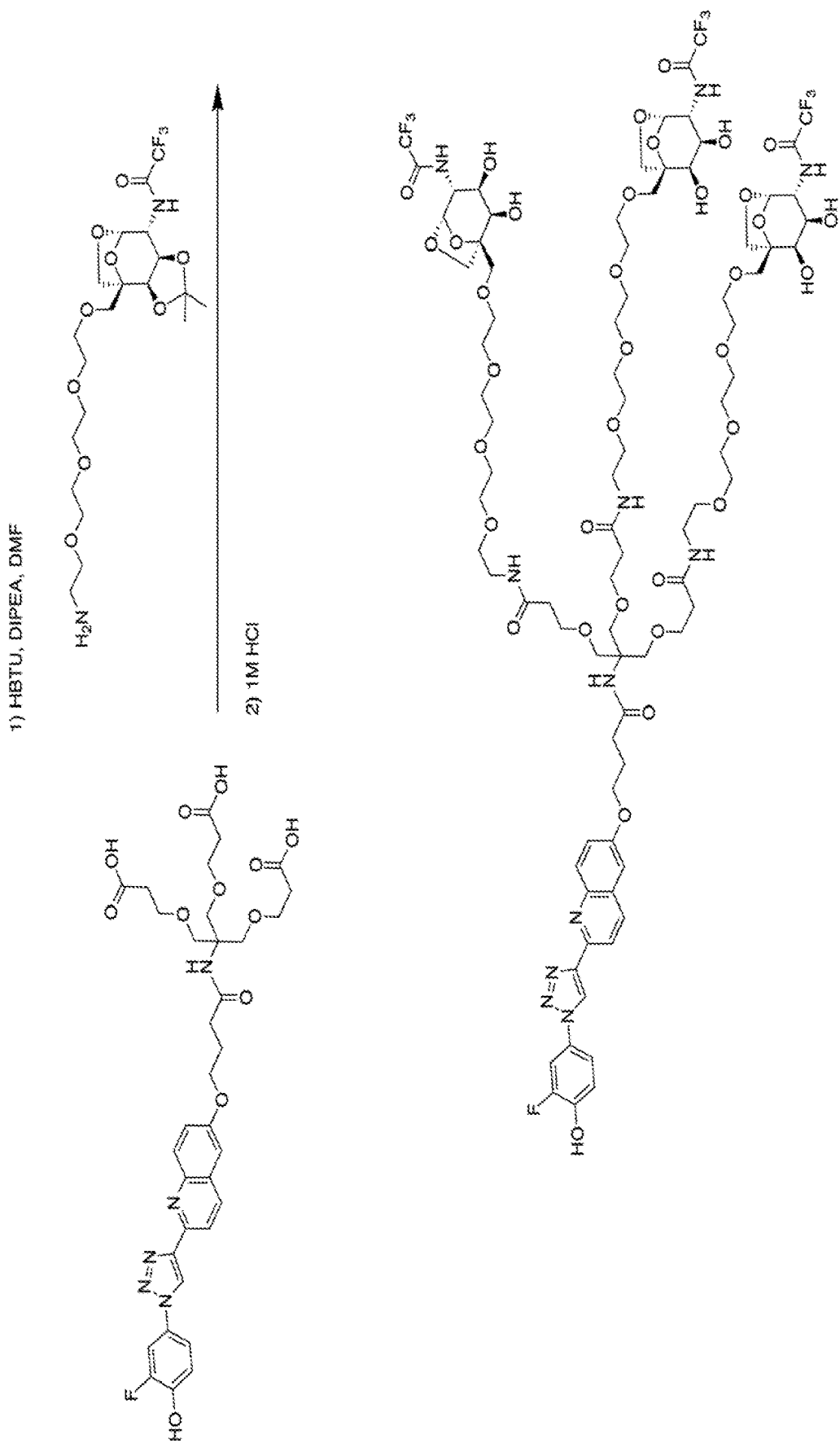
FIG. 33 describes the synthesis of the bifunctional molecule targeting MIF and ASGPR, containing three bicyclic ASGPr ligands.

FIG. 33 describes the synthesis of the bifunctional molecule targeting MIF and ASGPR, containing three bicyclic ASGPr ligands. It is synthesized as described above.

Figure 34:
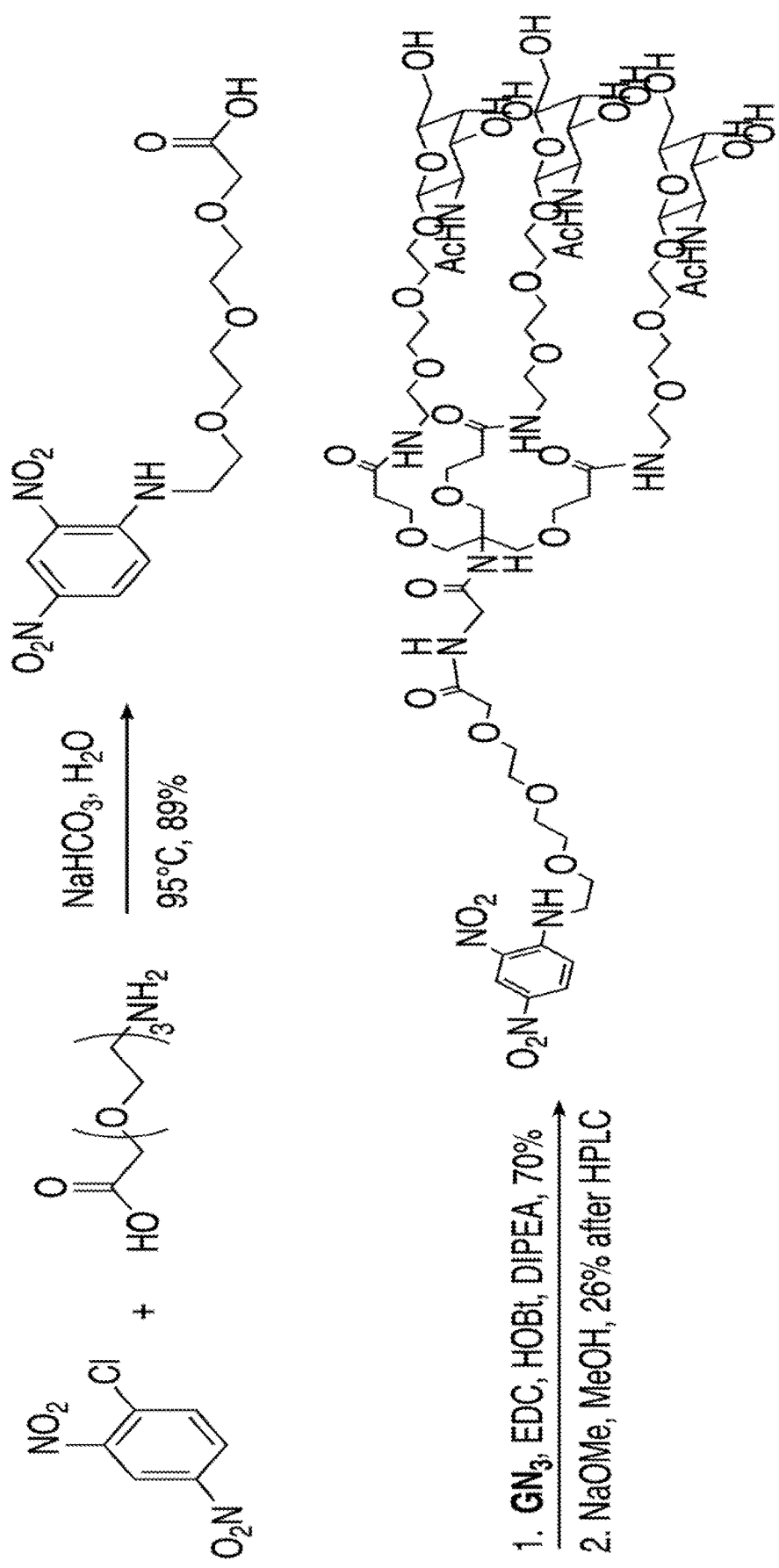
FIG. 34 shows the synthesis of DNP-GN3.

FIG. 34 shows the synthesis of DNP-GN3. 2,4-dinitro chlorobenzene was treated with an amino carboxylic acid in the presence of weak base to give the di-nitro analine carboxylic acid intermediate. Further steps were carried out as described for previous molecules.

Figure 35:
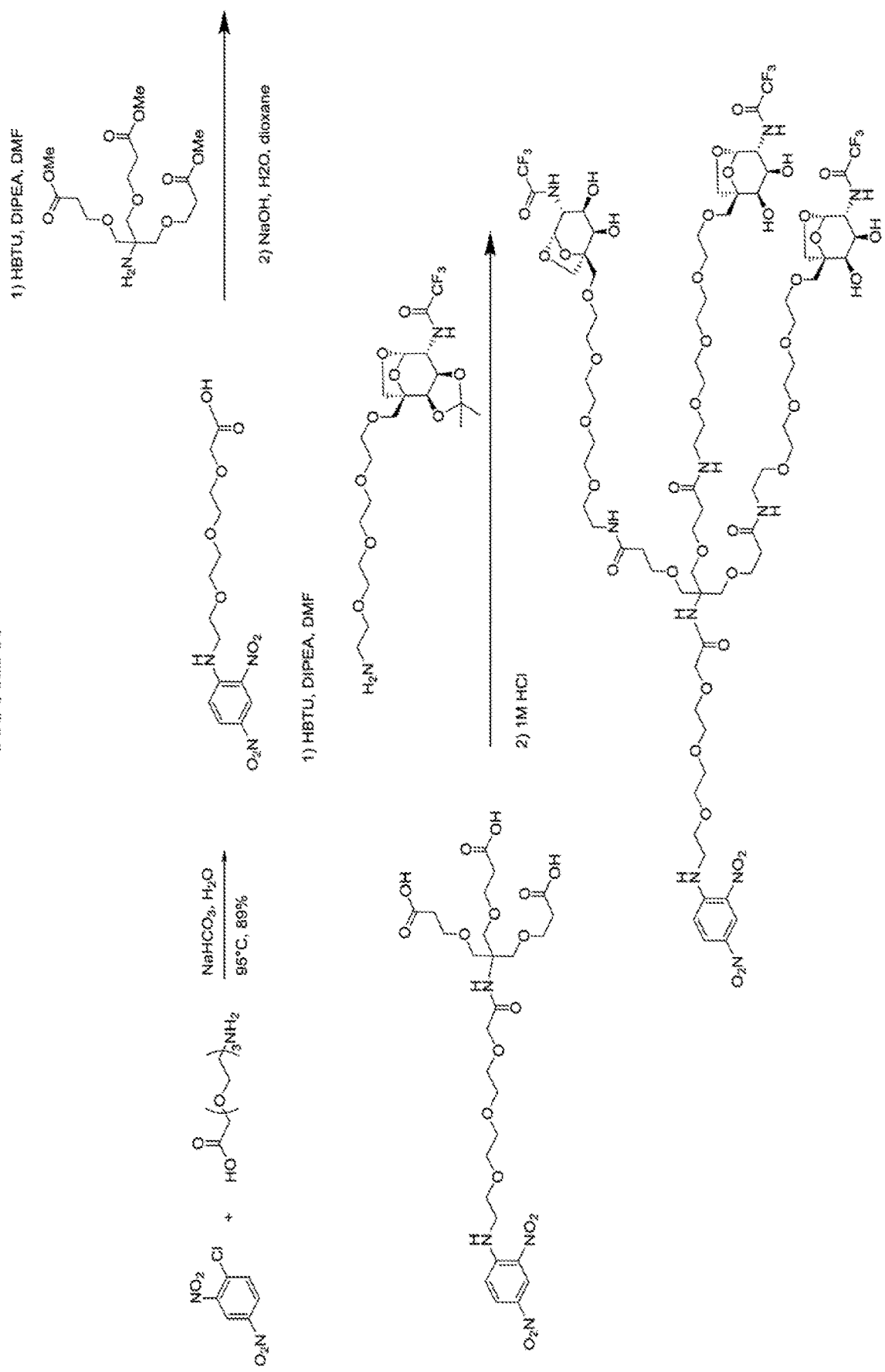
FIG. 35 shows the synthesis of DNP-AcF3-3.

FIG. 35 shows the synthesis of DNP-AcF3-3, which was carried out with methods analogous previous compounds.

Figure 36:
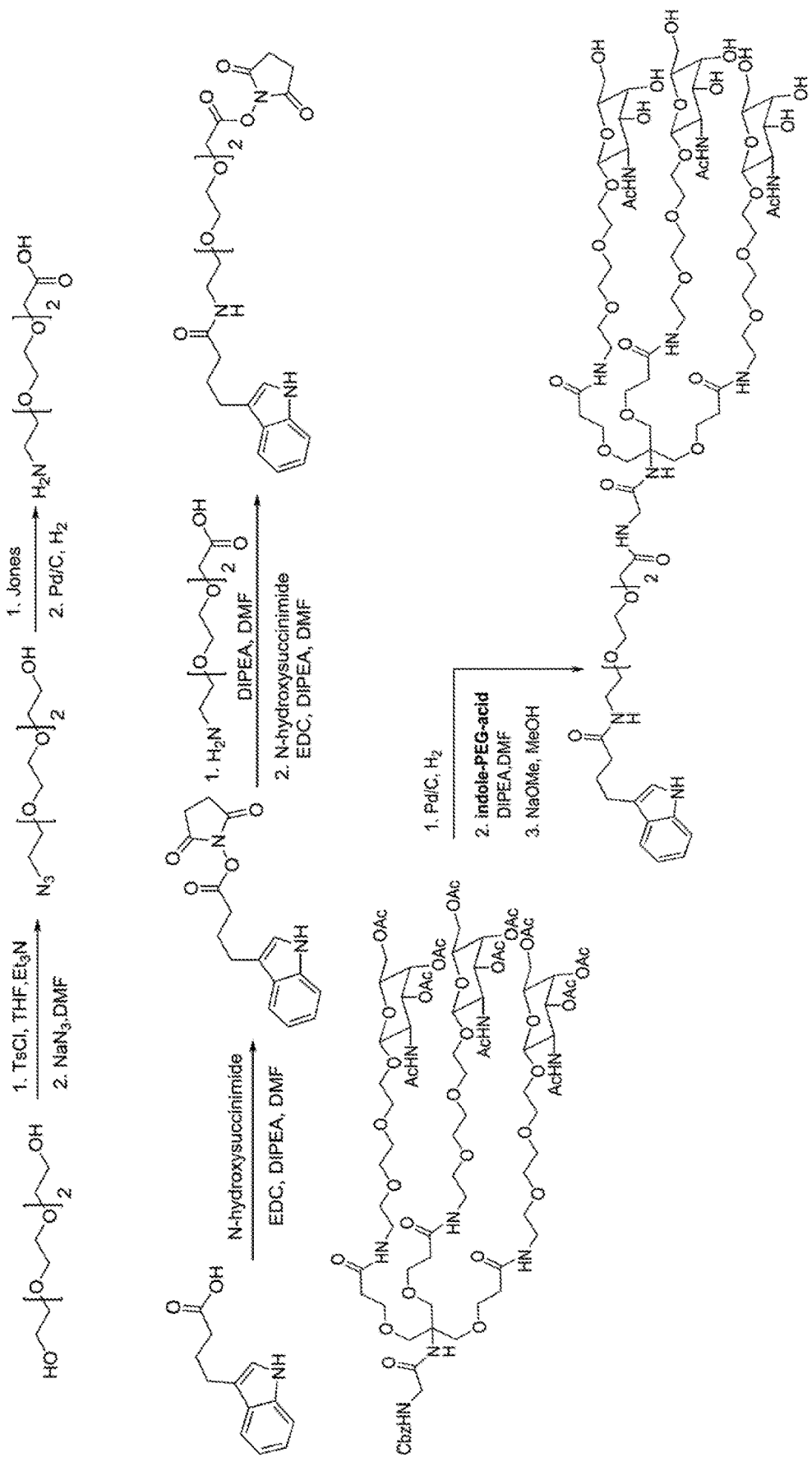
FIG. 36 shows the synthetic scheme used to obtain IBA-GN3.

FIG. 36 shows the synthetic scheme used to obtain IBA-GN3. Pentaethylene glycol was treated with tosyl chloride in the presence of base to give the mono-tosylated alcohol, which was then treated with sodium azide at elevated temperature to give the azidoalcohol. This compound was then oxidized using Jones reagent, then reduced with Palladium on carbon under hydrogen atmosphere to give a carboxylic acid-amine. Separately, indole butyric acid was treated with N-hydroxysuccinimide, EDC, and DIPEA to give the NHS-ester indole, which was then reacted with the above carboxylic acid-amine. The product was again reacted with N-hydroxysuccinimide, EDC, and DIPEA to give a NHS ester. This NHS ester was reacted with NH2-GN3, which was prepared as described previously. The subsequent amide was deprotected with NaOMe in MeOH to give compound IBA-GN3.

Figure 37:
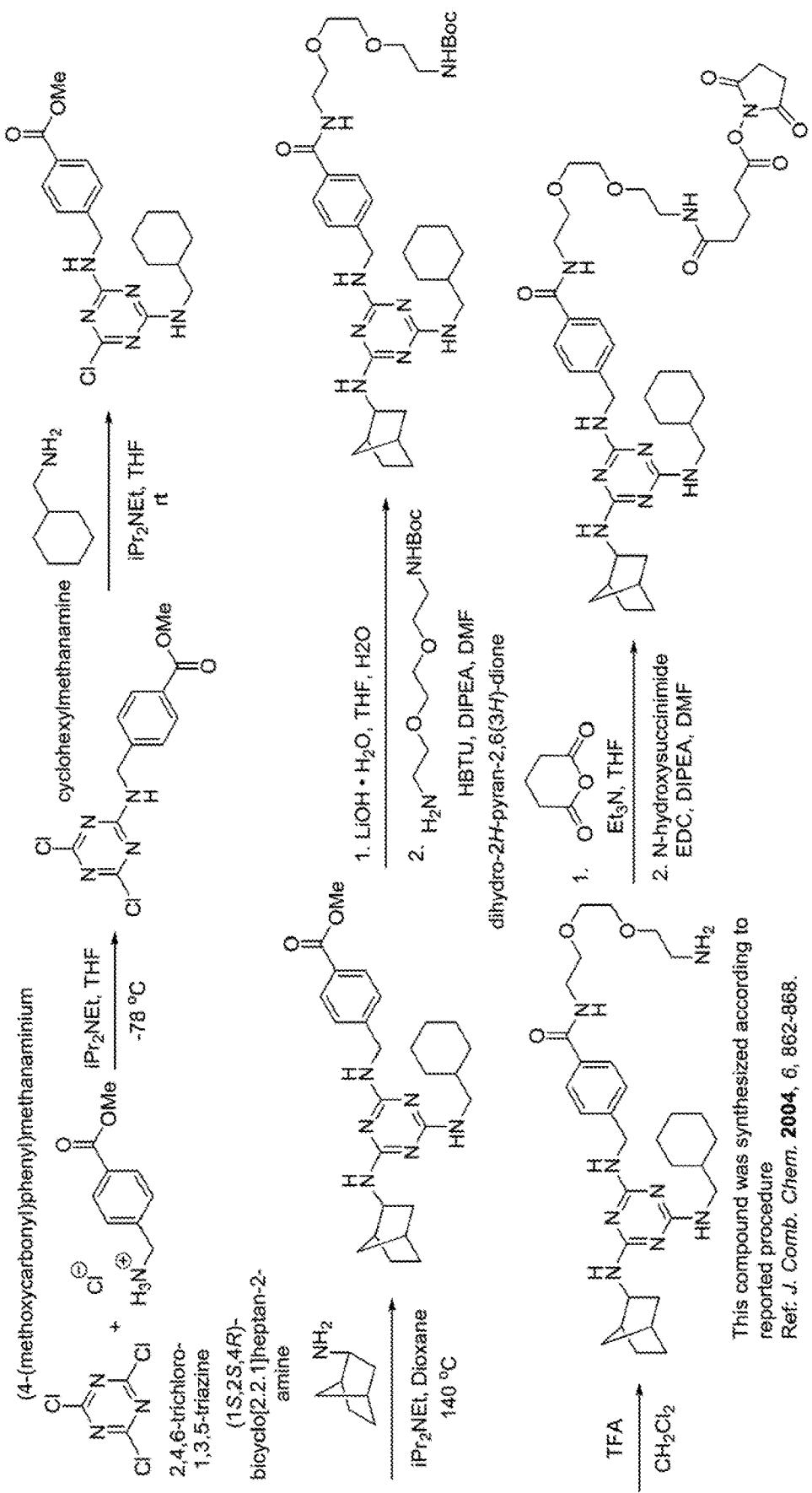
FIG. 37 shows the synthesis of triazine-GN3.
Figure 37:
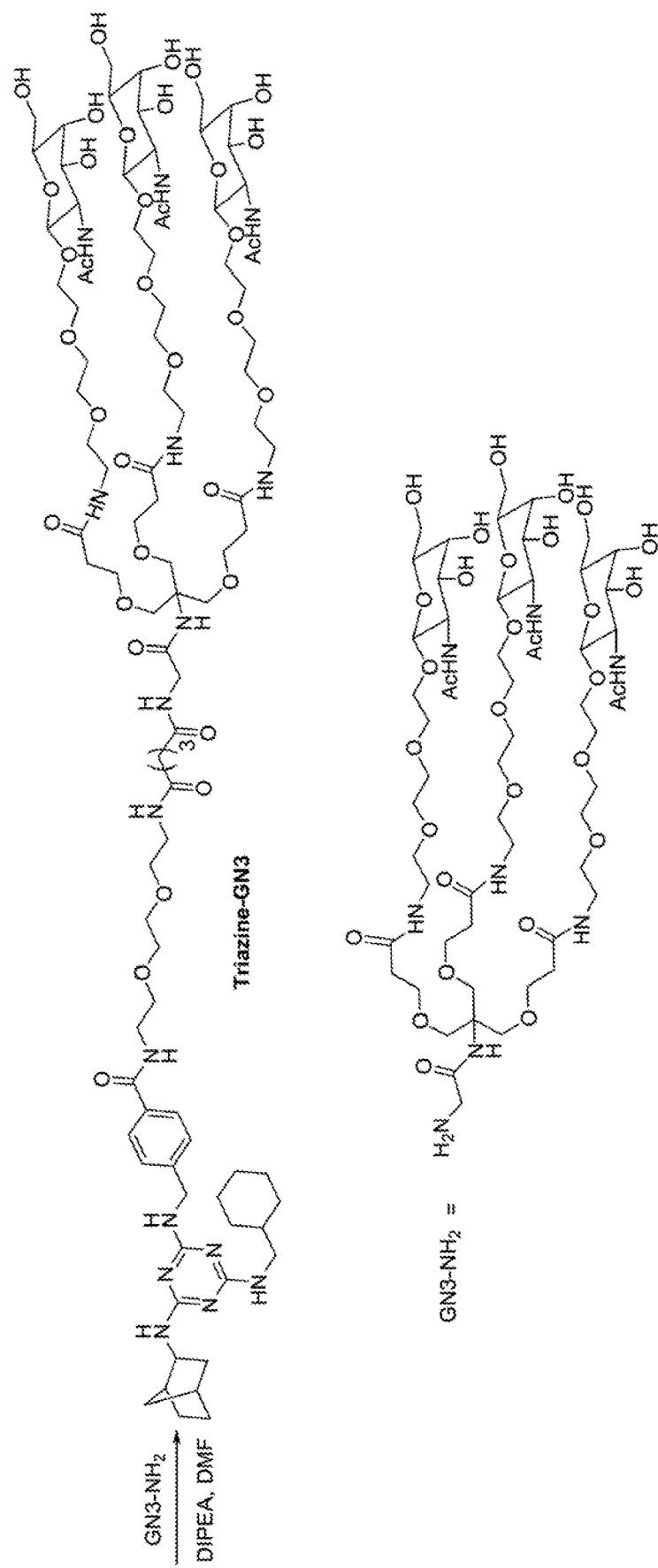

FIG. 37 shows the synthesis of triazine-GN3. Cyanuric chloride was treated with (4-(methoxycarbonyl)phenyl) methanaminium in THF and diisopropylethlamine at −78° C. to give the mono-substituted product. This was then treated with cyclohexylmethanamine at room temperature to afford the second substitution. The final substitution was accomplished under elevated temperature with (1S,2S,4R)-bicyclo[2.2.1]heptan-2-amine to give the trisubstituted triazine. Deprotection with lithium hydroxide followed by amide coupling with a monoprotected diamine gave the Boc-protected derivative, which was deprotected and reacted with glutaric anhydride to give a carboxylic acid that was converted to an NHS ester using standard coupling conditions. This was reacted with NH2-GN3 to give the final product.

Figure 38:
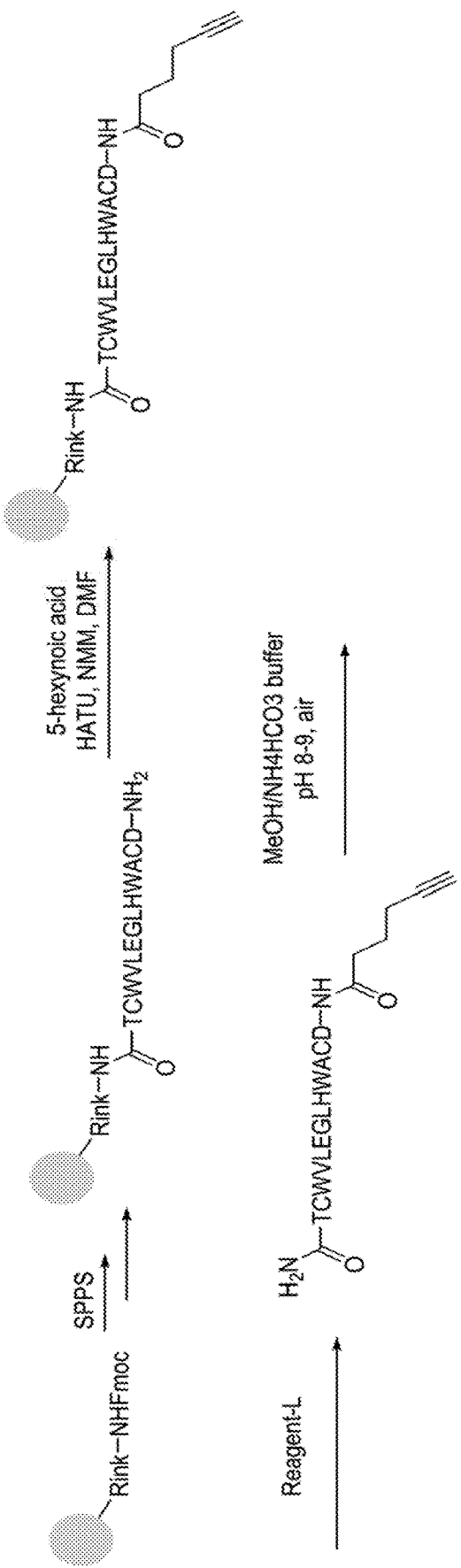
FIG. 38 shows the synthetic scheme used to access FcIII-GN3.
Figure 38:
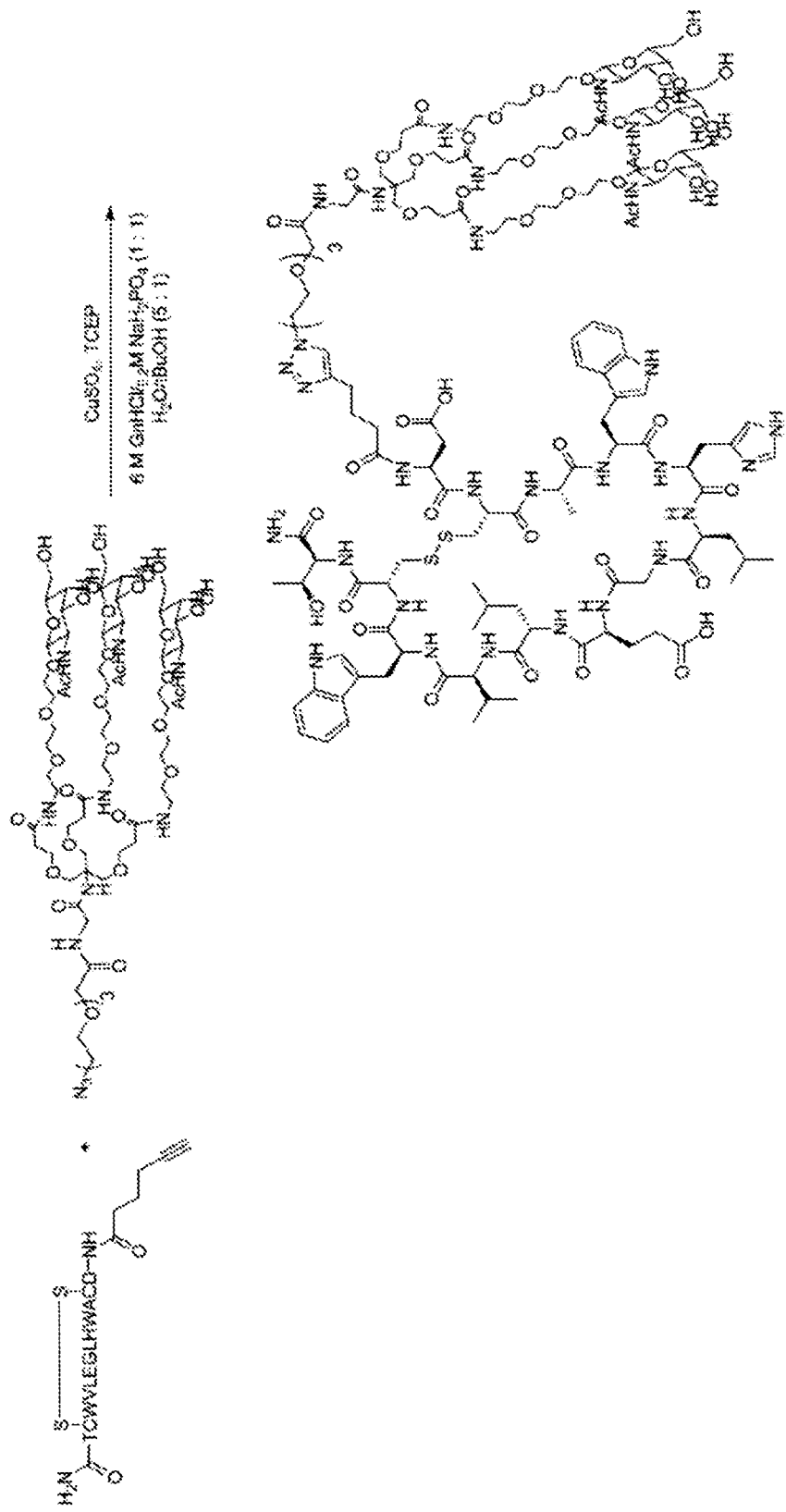

FIG. 38 shows the synthetic scheme used to access FcIII-GN3. The hexynyl peptide was prepared using standard solid phase peptide synthesis techniques. The peptide was removed from Rink resin using Reagent L, then oxidized using ammonium bicarbonate buffer (pH8-9) in MeOH under air to give the cyclic peptide. The peptide was reacted with GN3-azide, which was described previously, to give the product triazole FcIII-GN3.

Figure 39:
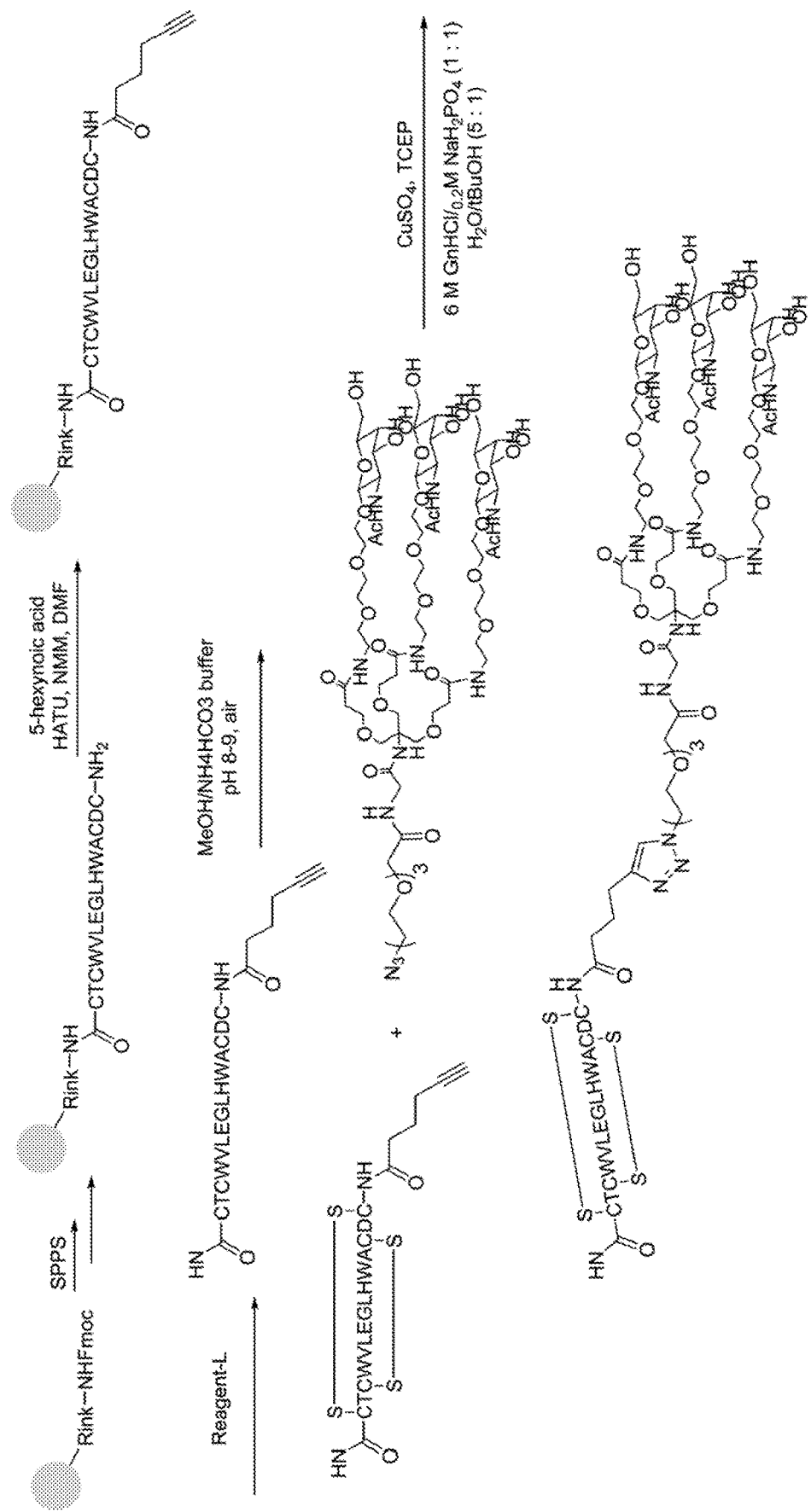
FIG. 39 shows the synthetic scheme used to access FcIII-4c-GN3.
Figure 40:
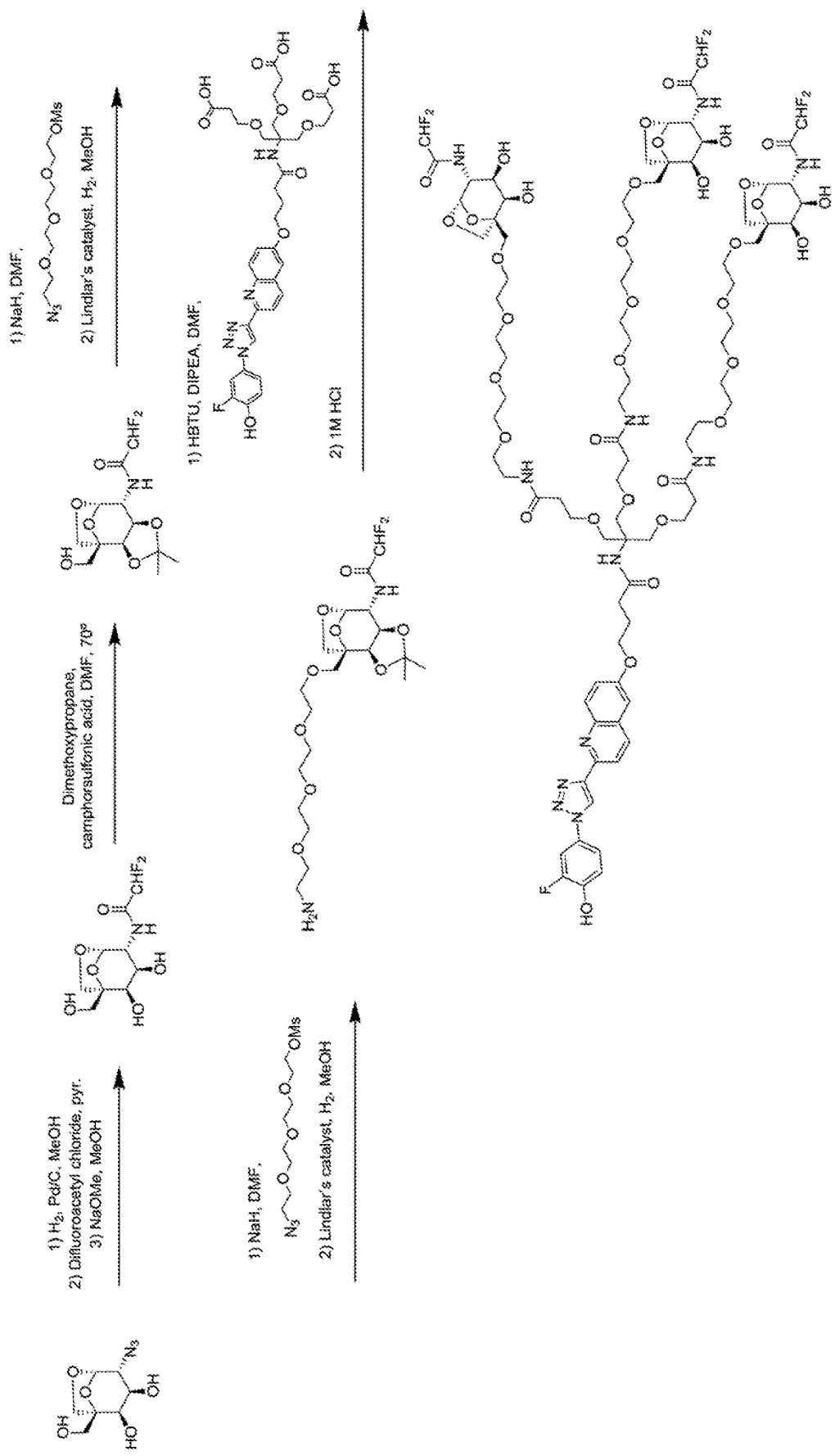
FIGS. 40-43 describe the synthesis of bifunctional molecules targeting MIF and ASGPr, containing three bicyclic ASGPR ligands with different substitutions on the 2-amine of the sugar.
Figure 41:
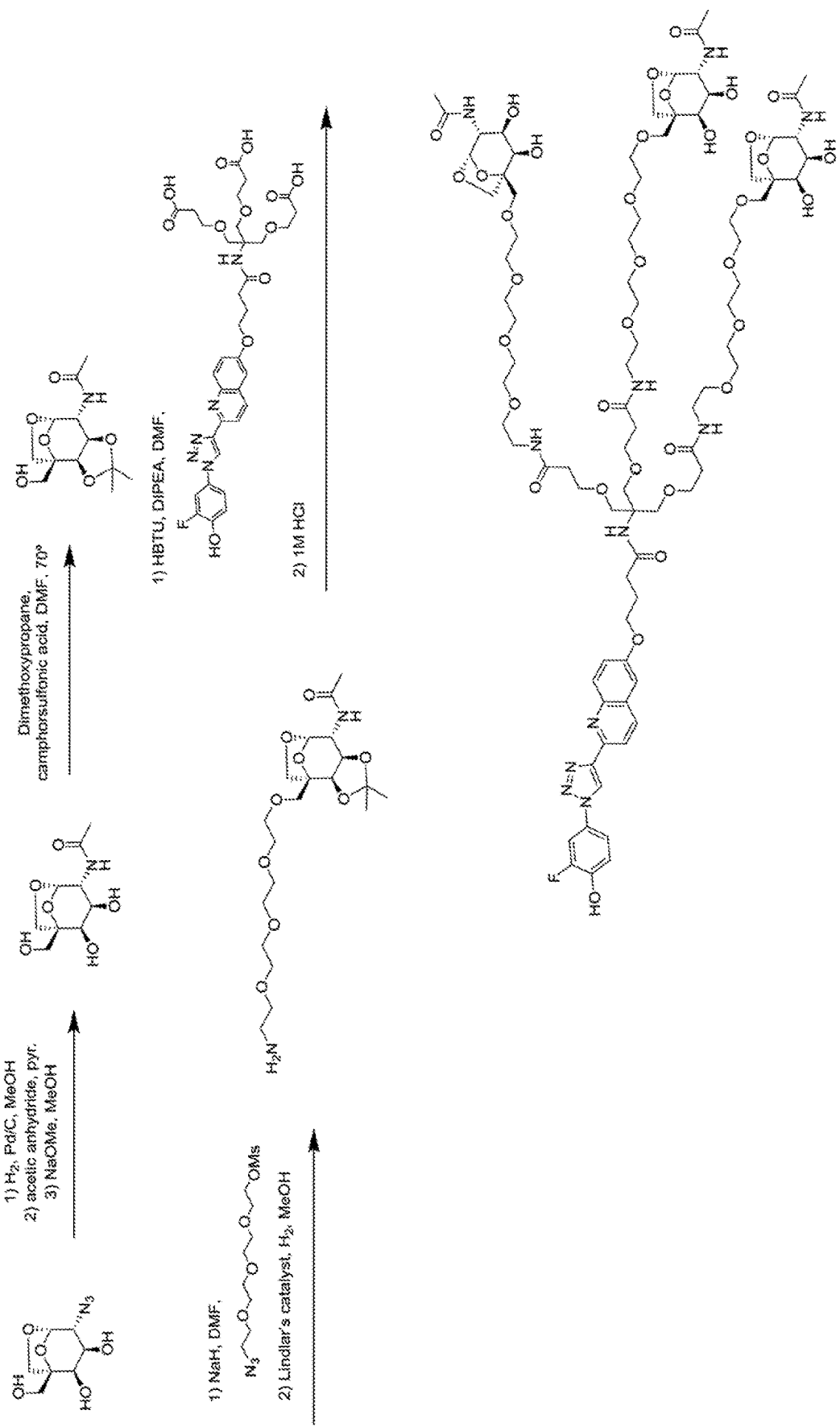
Figure 42:
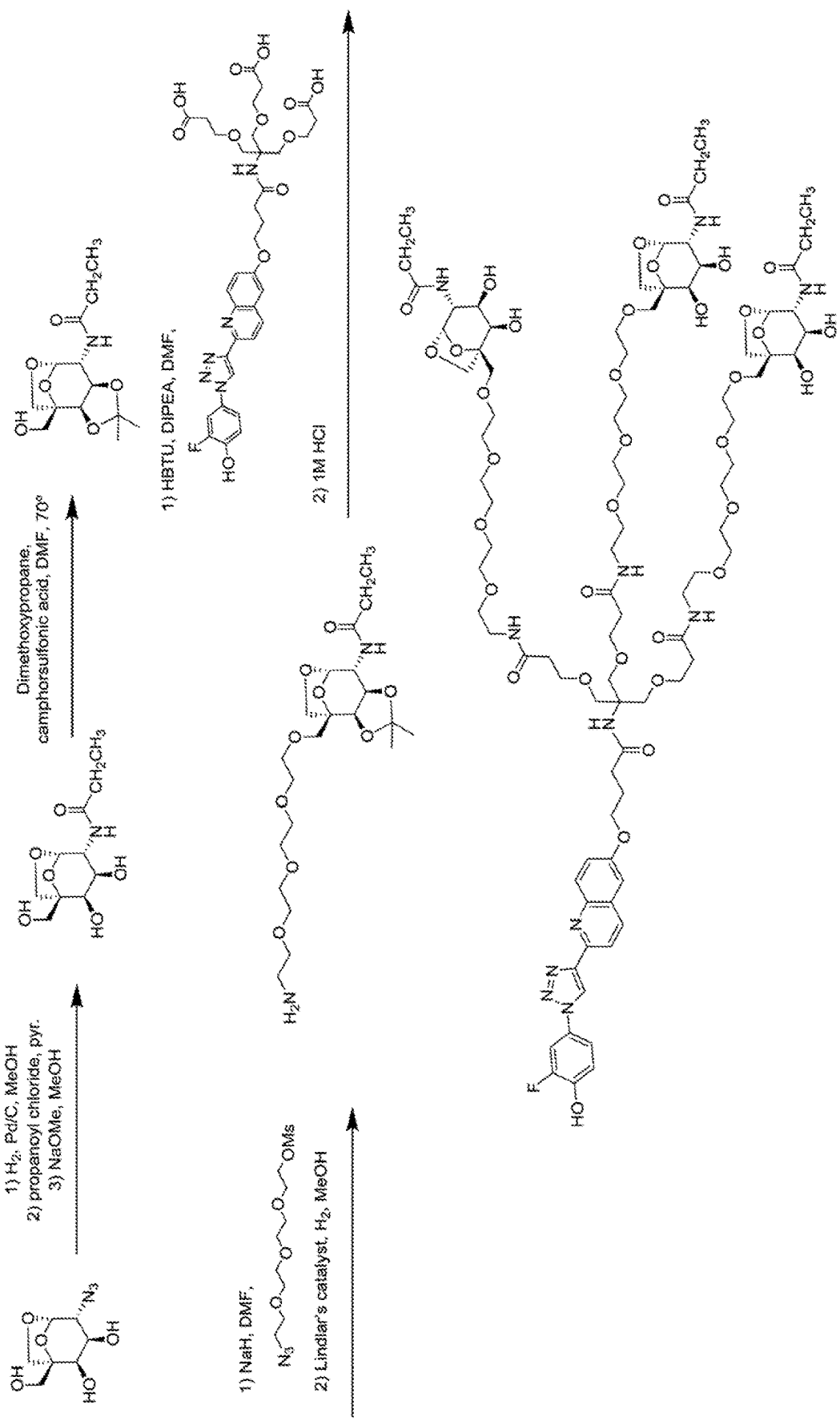
Figure 43:
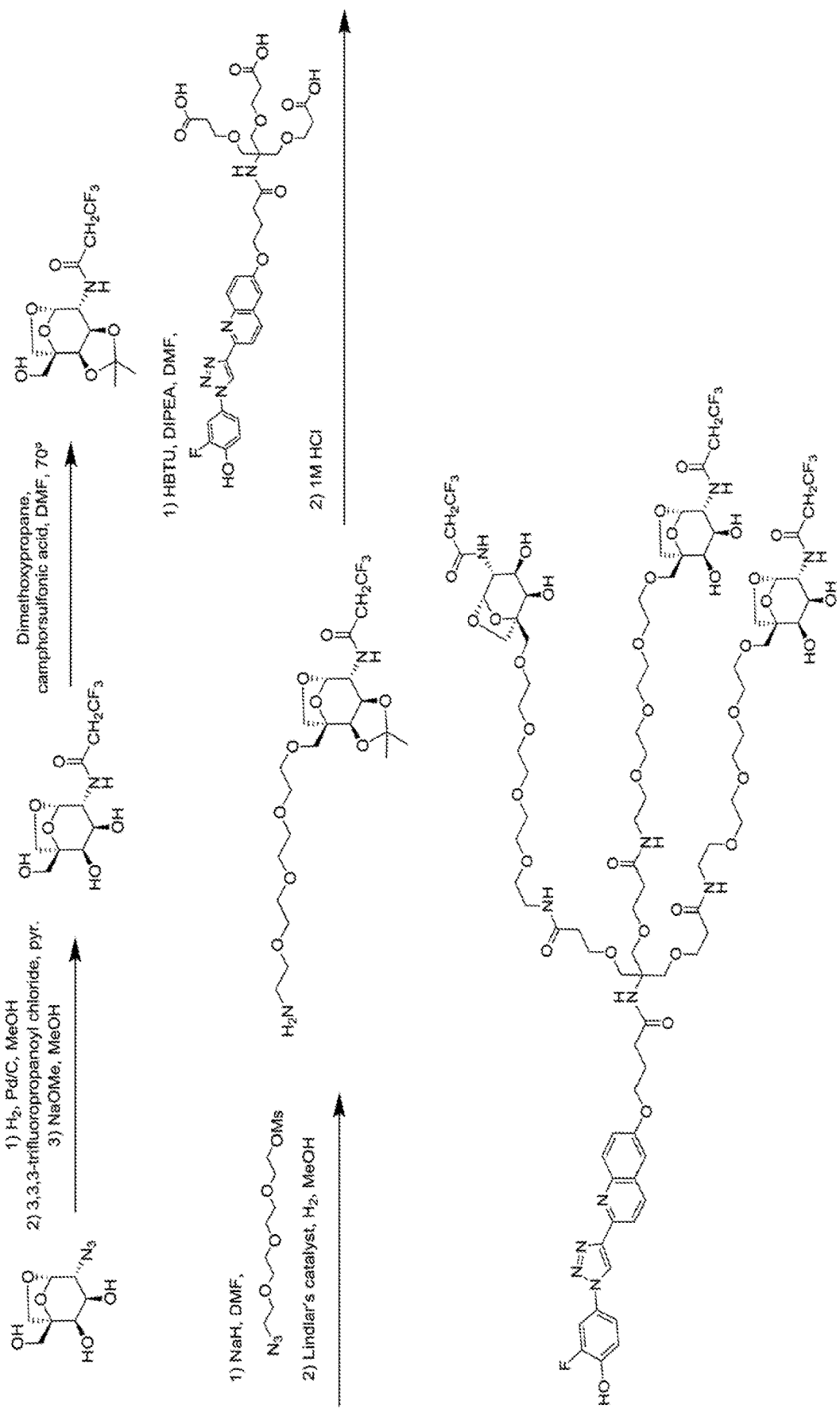

FIG. 39 shows the synthetic scheme used to access FcIII-4c-GN3, which was accomplished using methods described above.

FIGS. 40-43 describe the synthesis of bifunctional molecules targeting MIF and ASGPr, containing three bicyclic ASGPR ligands with different substitutions on the 2-amine of the sugar. They are synthesized through analagous methods described above as set forth in the attached figures.

Figure 44:
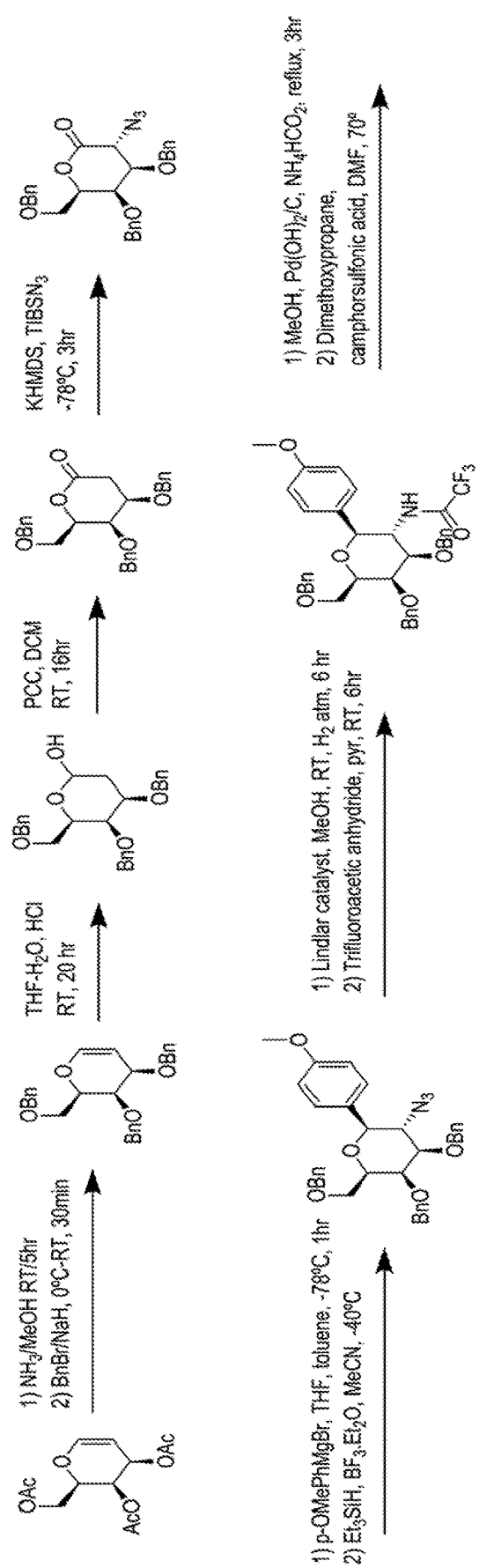
FIG. 44 shows the synthesis of compound MIF-18-3.
Figure 44:
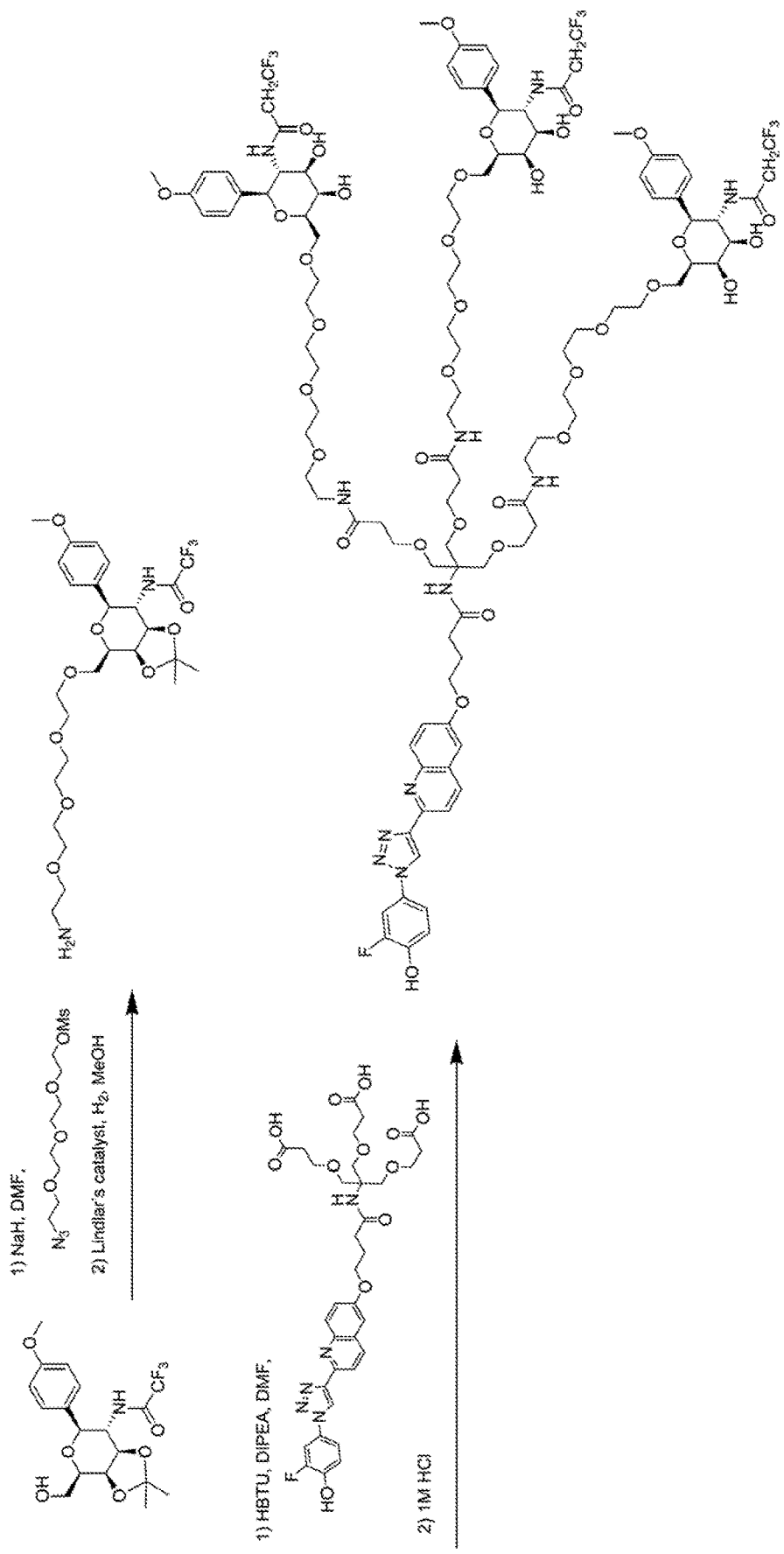

FIG. 44 shows the synthesis of compound MIF-18-3. Tri-acyl galactal was deprotected with ammonia in methanol, then tri-benzyl protected with benzylbromide in the presence of base. The alkene was hydrolyzed overnight with HCl in THF/H2O, then oxidized with PCC to give an aldehyde. Sodium azide was then added alpha to the carbonyl with KHMDS and TIBSN3 at lowered temperature. The intermediated was then treated with p-OMePhMgBr in THF and toluene to give an intermediate alcohol, which was then reduced using Et3SiH in the presence of BF3-Et2O at reduced temperature. The resulting azide was then reduced with Lindlar's catalyst under a hydrogen atmosphere to give the corresponding amine, which was acylated with trifluoroacetic acid in pyridine. The benzyl groups were then removed with Pd(OH2) on carbon in MeOH at reflux, and the resulting tri-ol protected as an acetal with dimethoxypropane and camphorsulfonic acid at elevated temperature. The remainder of the synthesis was carried out as described for previous molecules.

Figure 45:
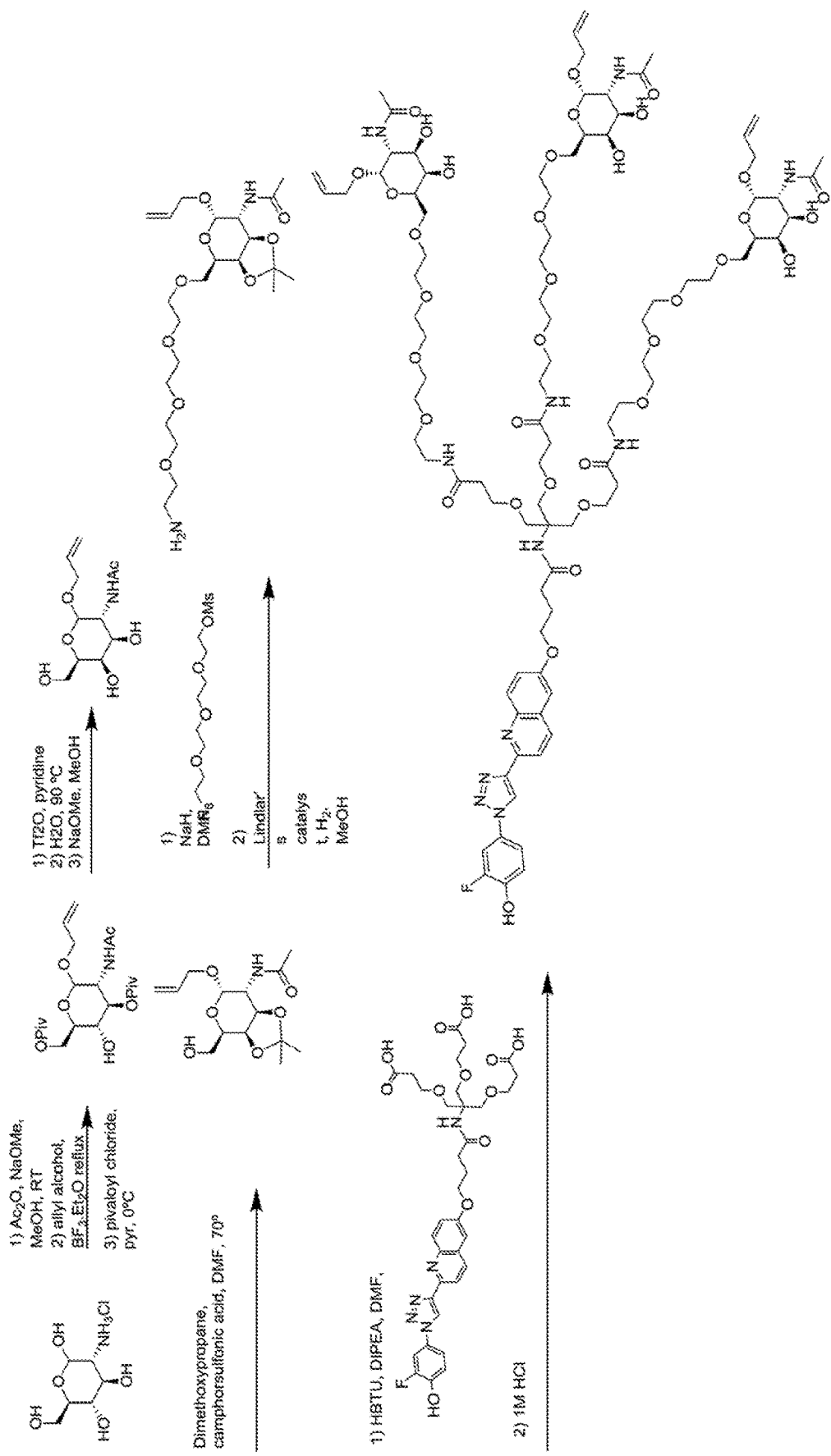
FIG. 45 shows the synthesis of compound MIF-31-3.

FIG. 45 shows the synthesis of compound MIF-31-3. Galactosamine hydrochloride was fully protected with acetic anhydride, then treated with allyl alcohol in the presence of BF3 ehtrate to give the allyl intermediate. Treatment with pivaloyl chloride in pyridine gave a di-Piv protected intermediate, which was treated with triflic anhydride and subsequently subjected to hydrolysis in water at elevated temperature. The pivaloyl groups were removed by treatment with NaOMe in MeOH to give the allyl triol intermediate. Subsequent steps were performed as described for previous molecules.

Figure 46:
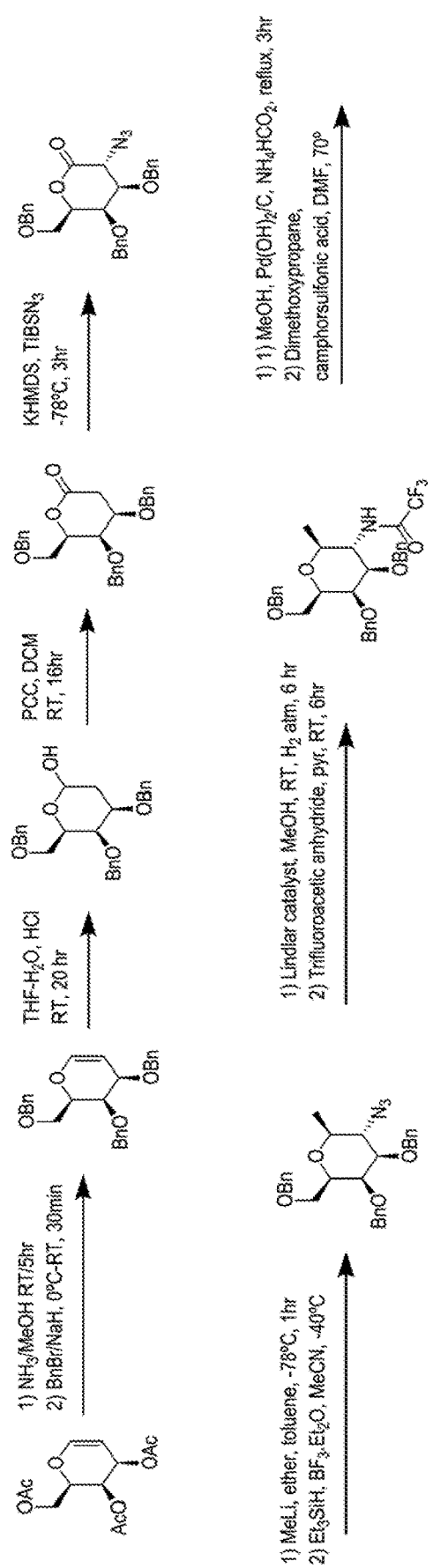
FIG. 46 shows the synthesis of compound MIF-15-3.
Figure 46:
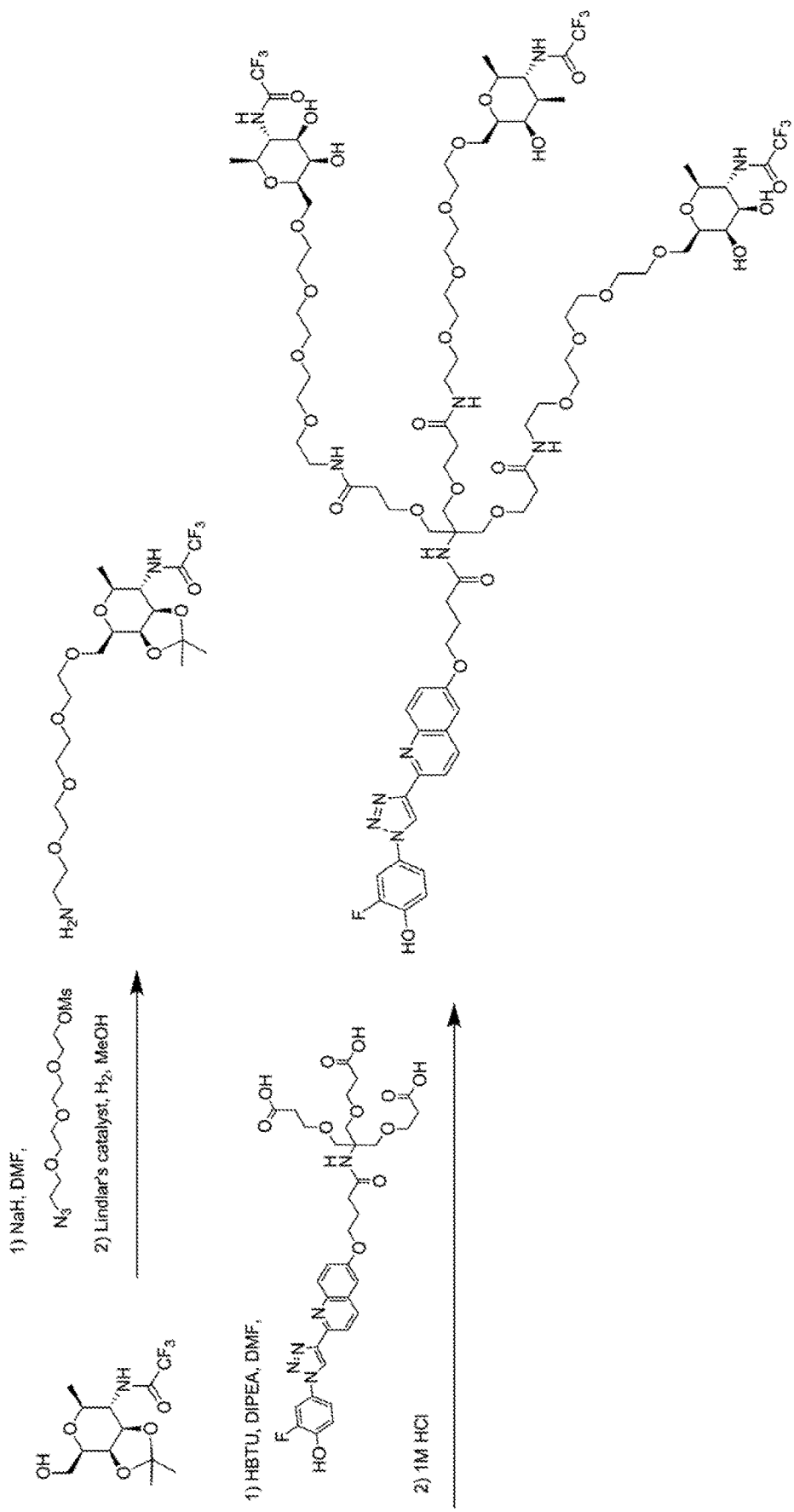

FIG. 46 shows the synthesis of compound MIF-15-3, which was synthesized using procedures analogous to compounds described above.

Figure 47:
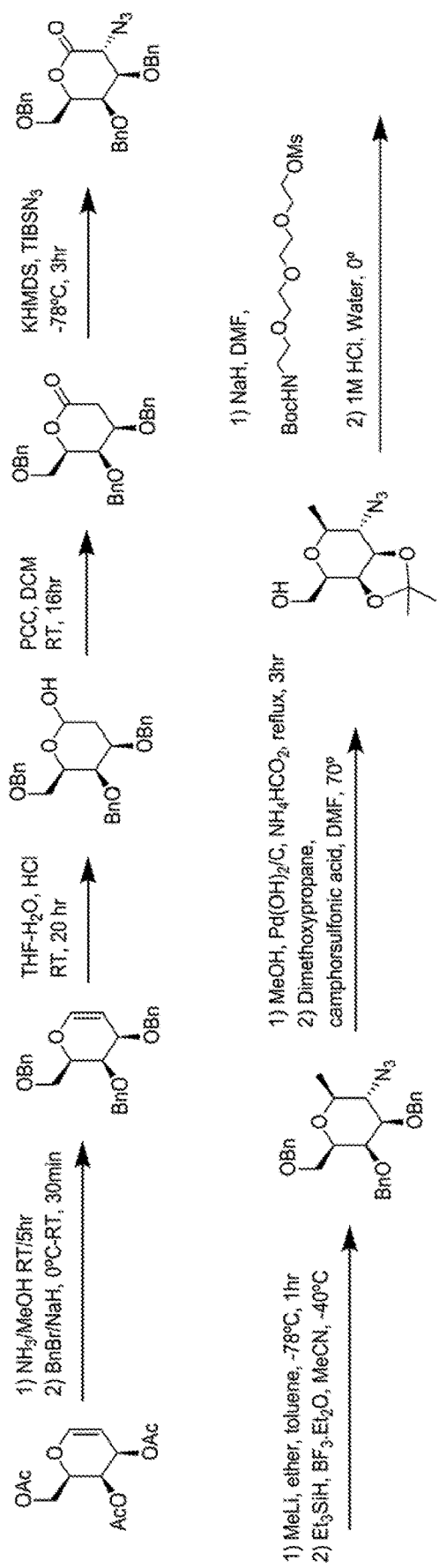
FIG. 47 shows the synthesis of compound MIF-19-3.
Figure 47:
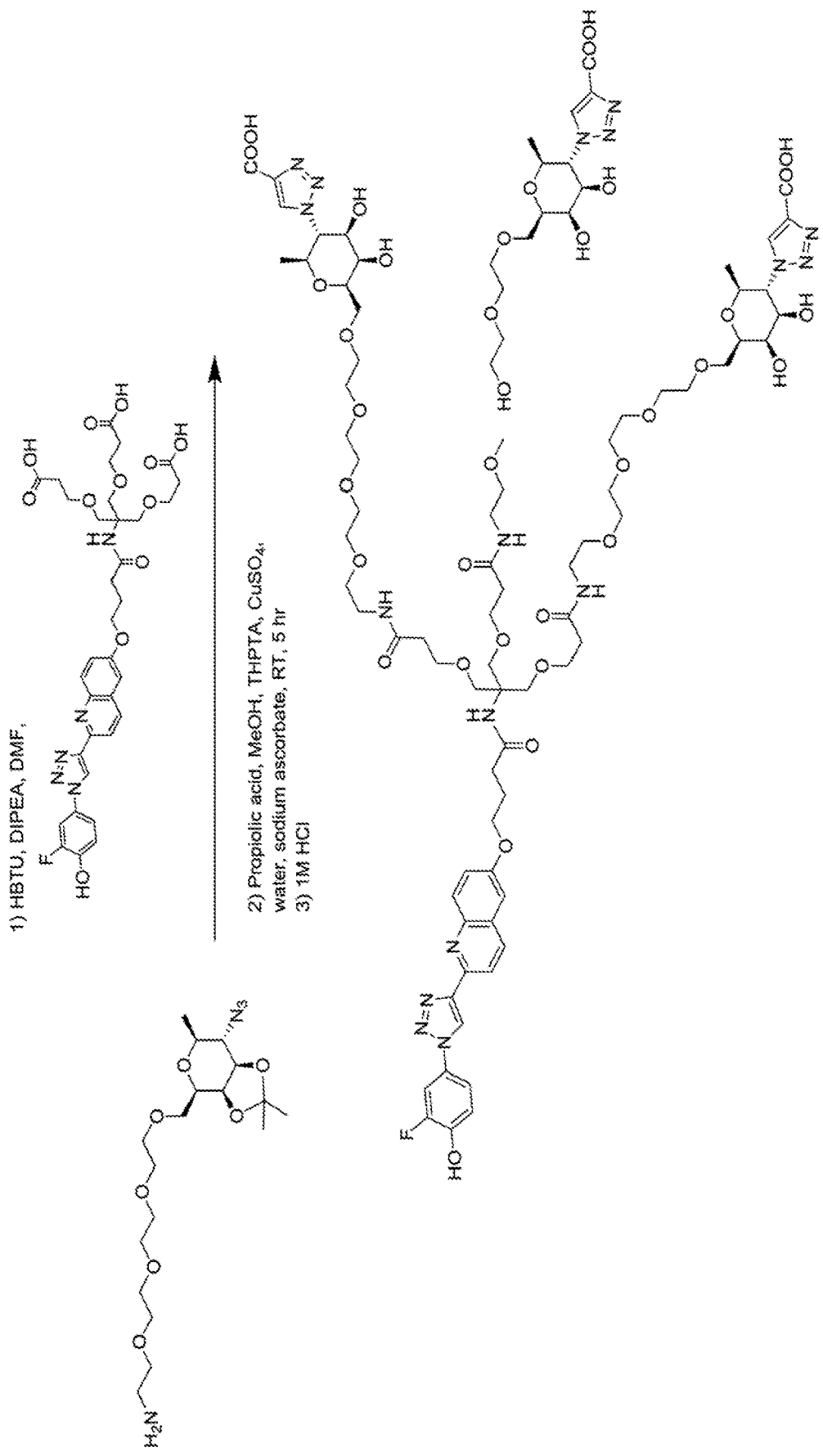

FIG. 47 shows the synthesis of compound MIF-19-3. The molecule is synthesized through a late stage triazole-forming click reaction between the triazide and propiolic acid in methanol in the presence of THPTA, copper sulfate, water, and sodium ascorbate. All other reactions are performed as described above.

Figure 48:
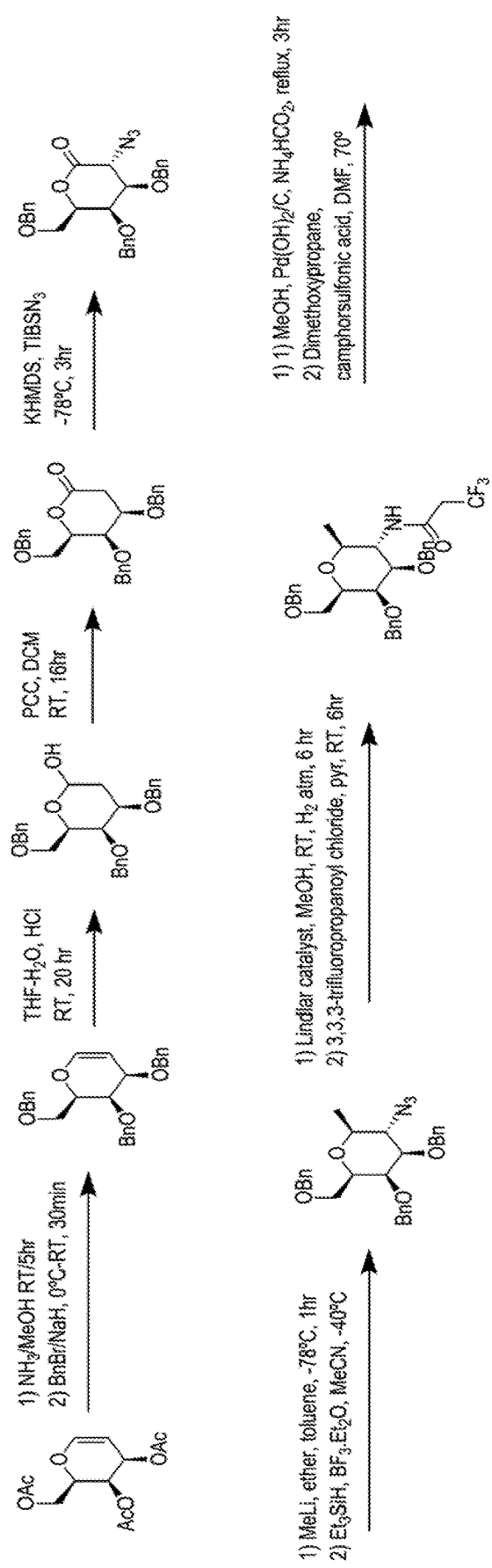
FIG. 48 shows the synthesis of compound MIF-16-3
Figure 48:
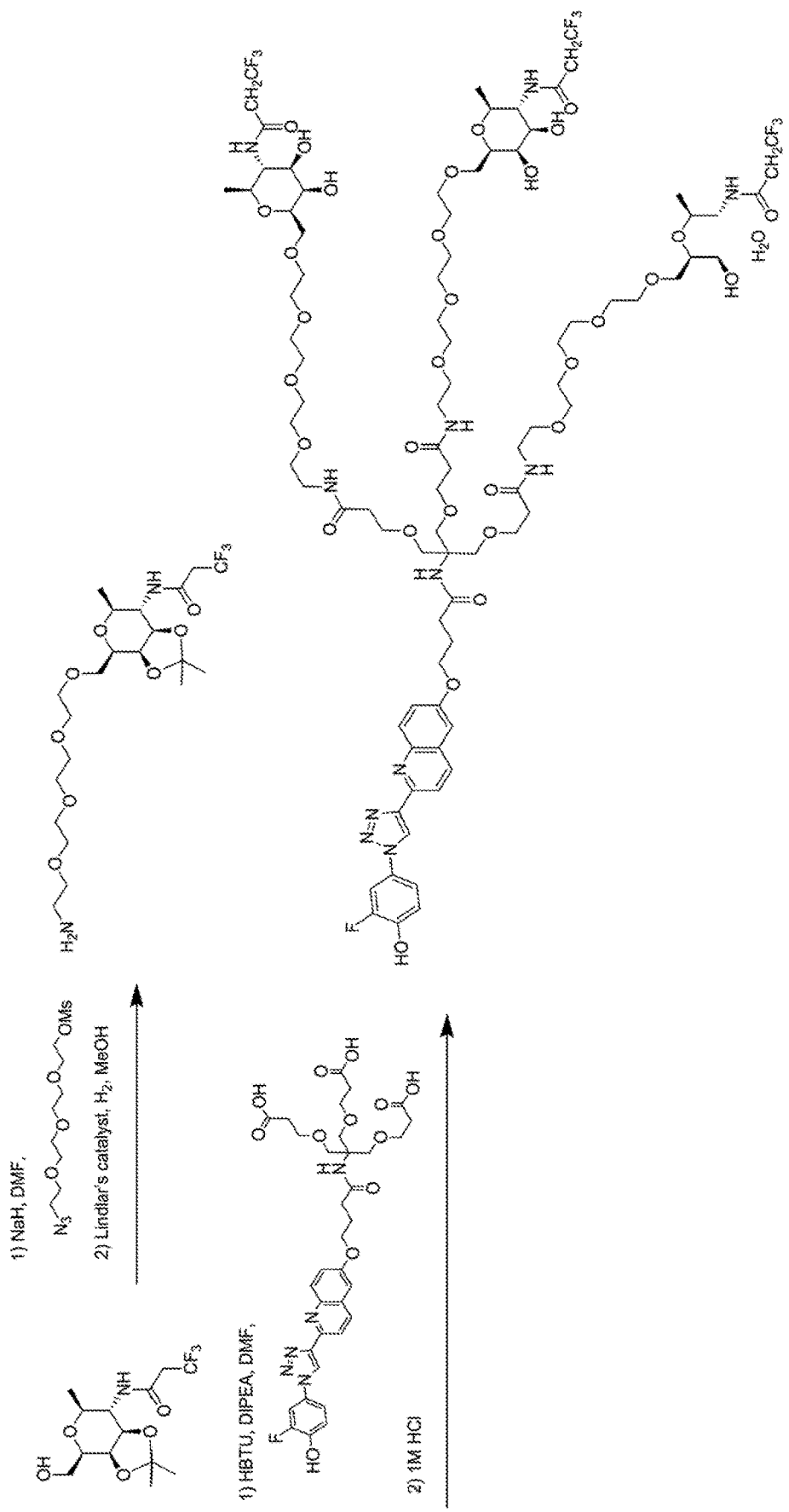

FIG. 48 shows the synthesis of compound MIF-16-3, which was synthesized using procedures analogous to compounds described above.

Figure 49:
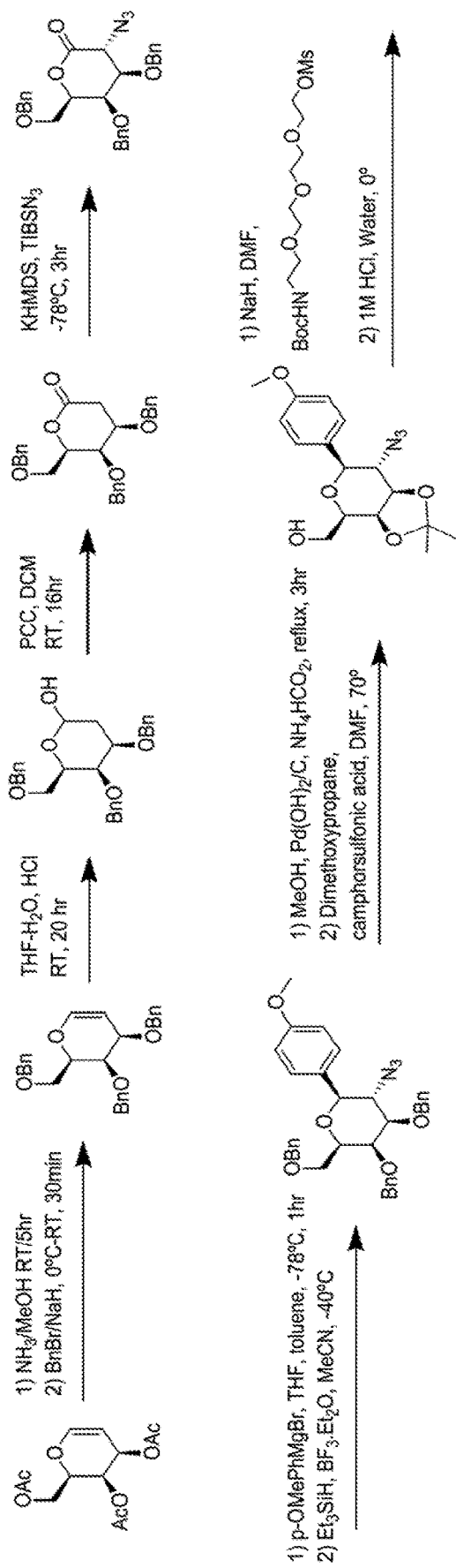
FIG. 49 shows the synthesis of compound MIF-20-3
Figure 49:
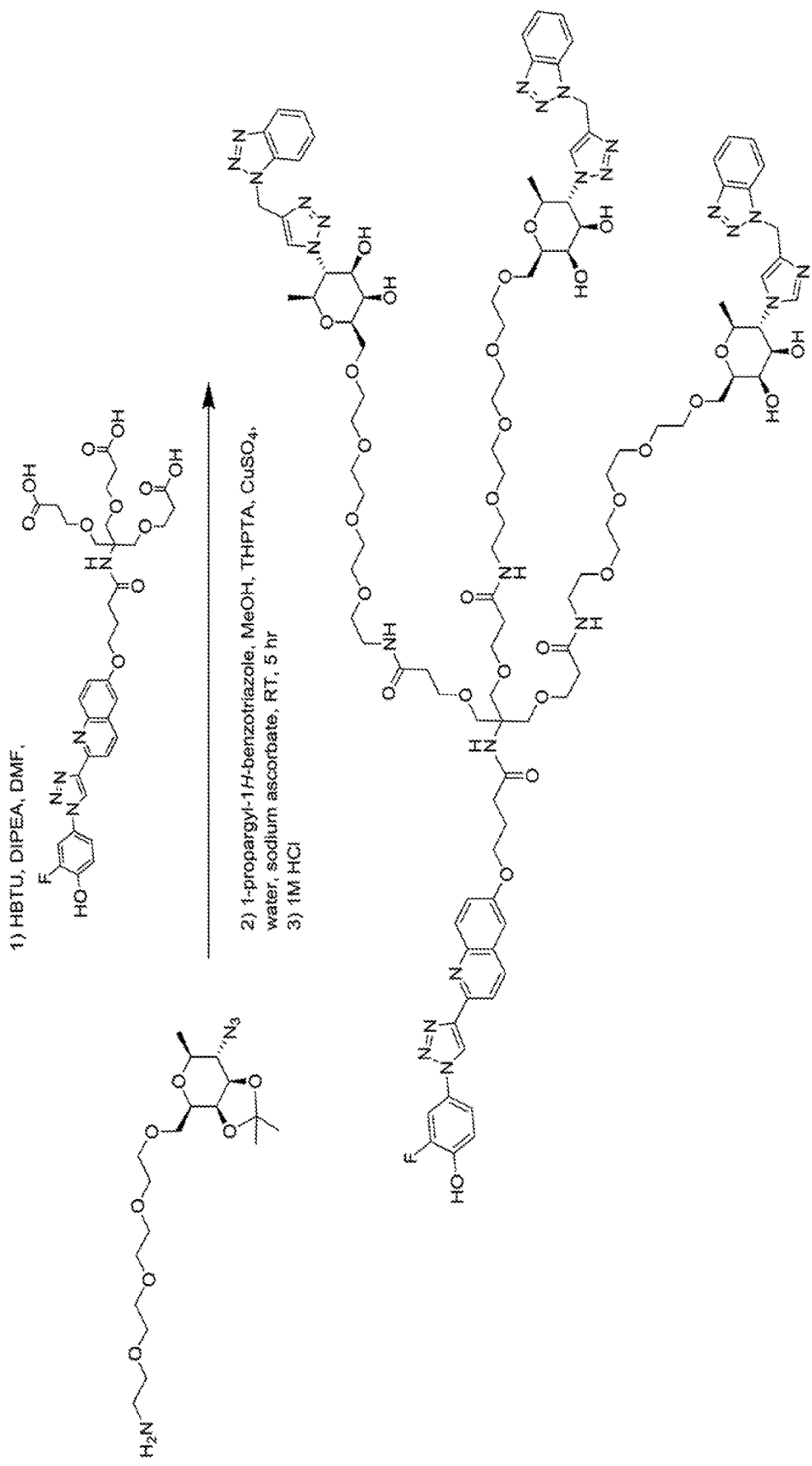

FIG. 49 shows the synthesis of compound MIF-20-3, which was synthesized using procedures analogous to compounds described above.

Figure 50:
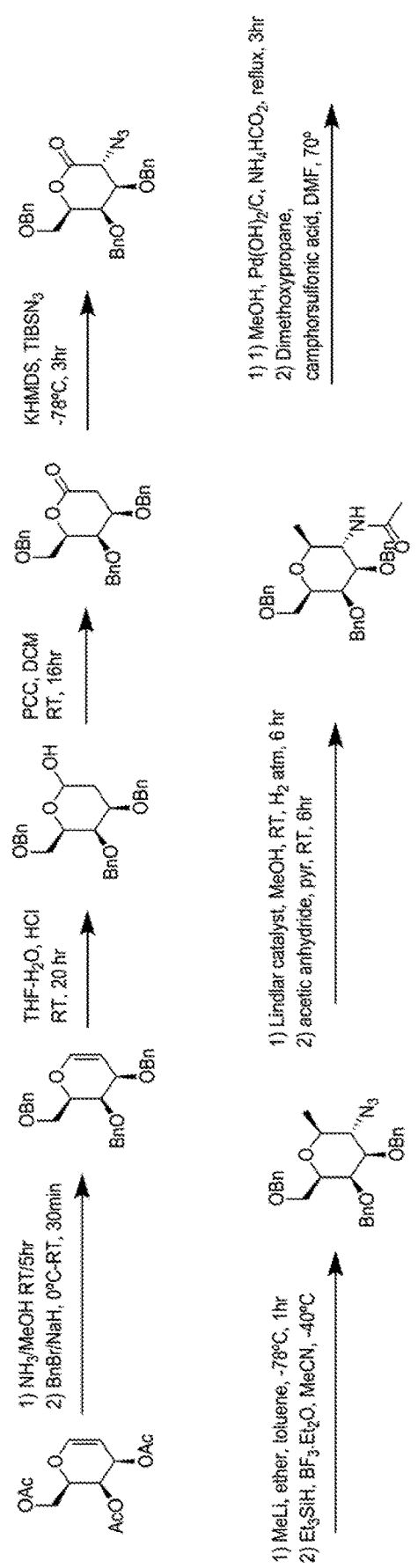
FIG. 50 shows the synthesis of compound MIF-14-3
Figure 50:
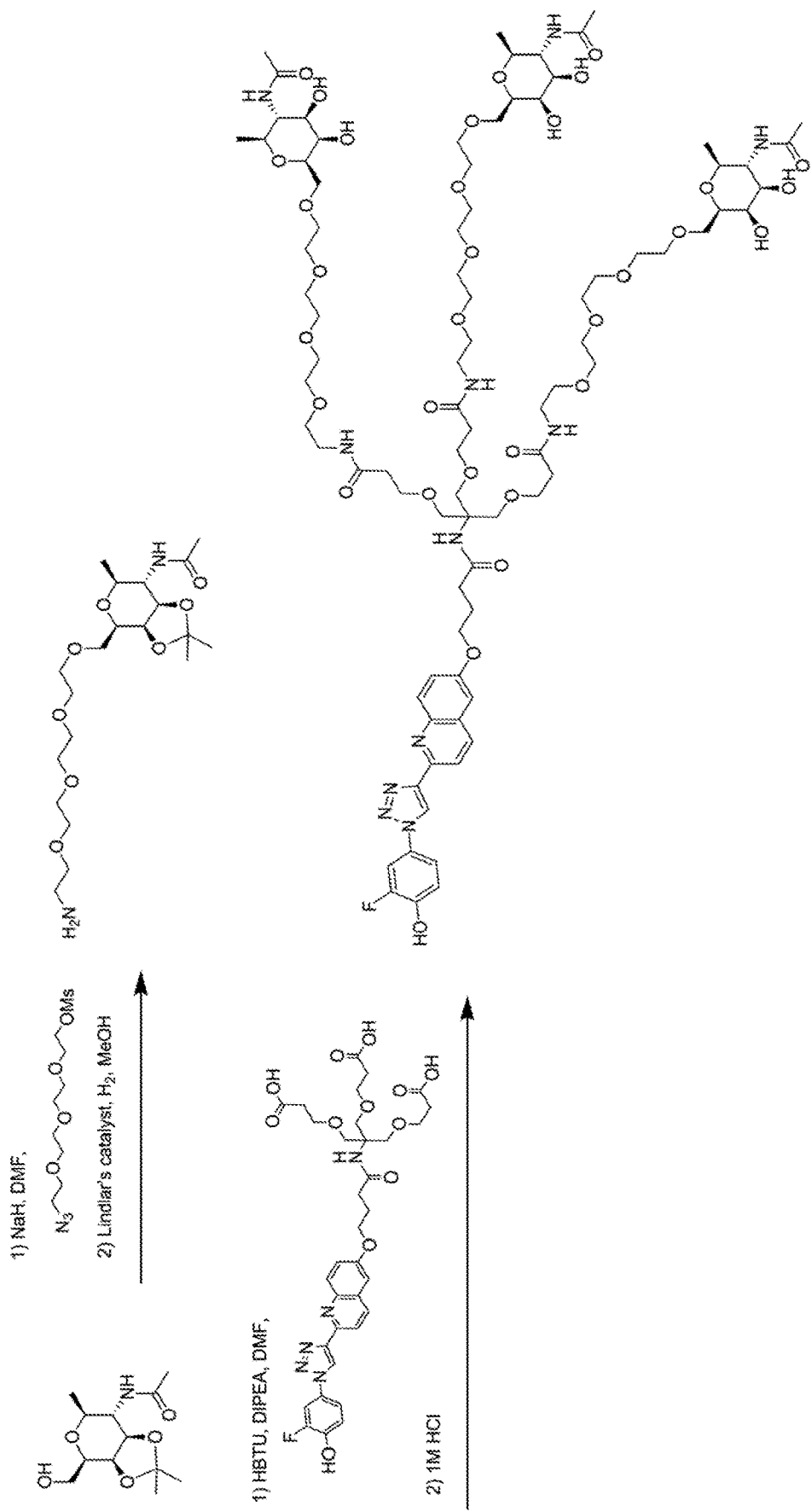

FIG. 50 shows the synthesis of compound MIF-14-3, which was synthesized using procedures analogous to compounds described above.

Figure 51:
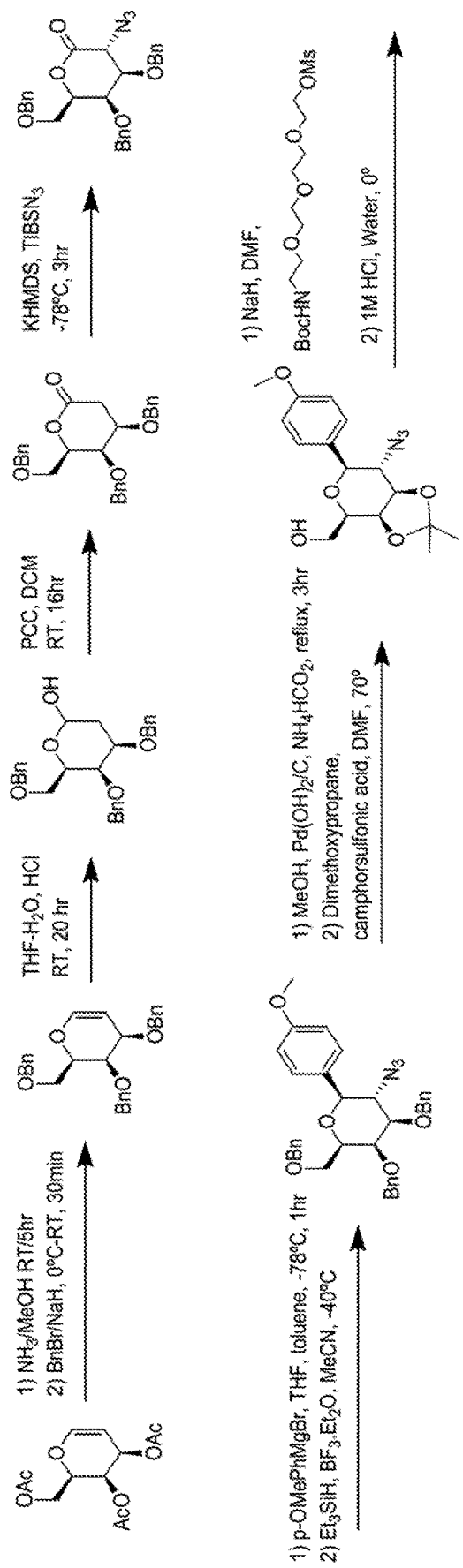
FIG. 51 shows the synthesis of compound MIF-21-3
Figure 51:
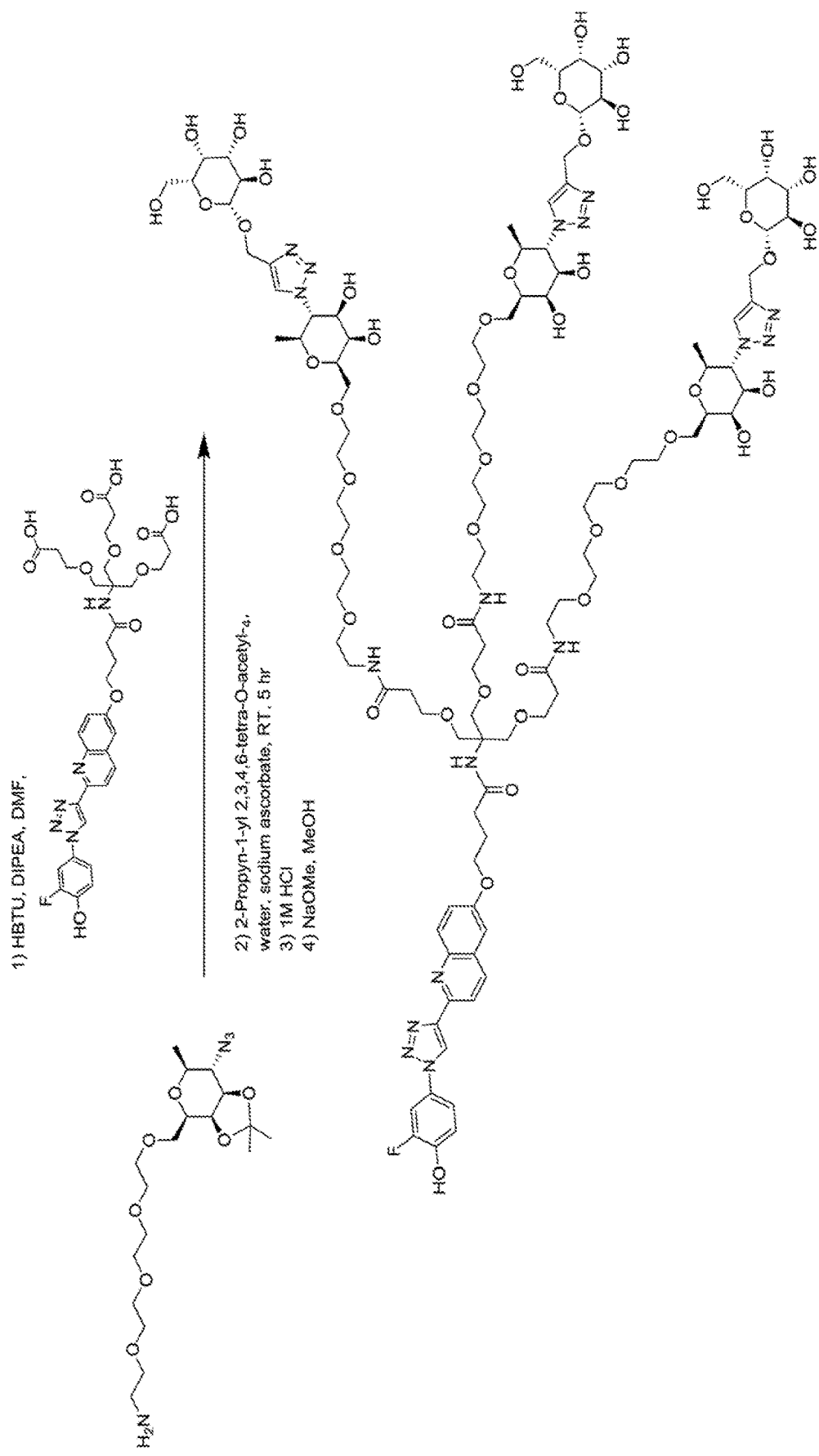
Figure 52:
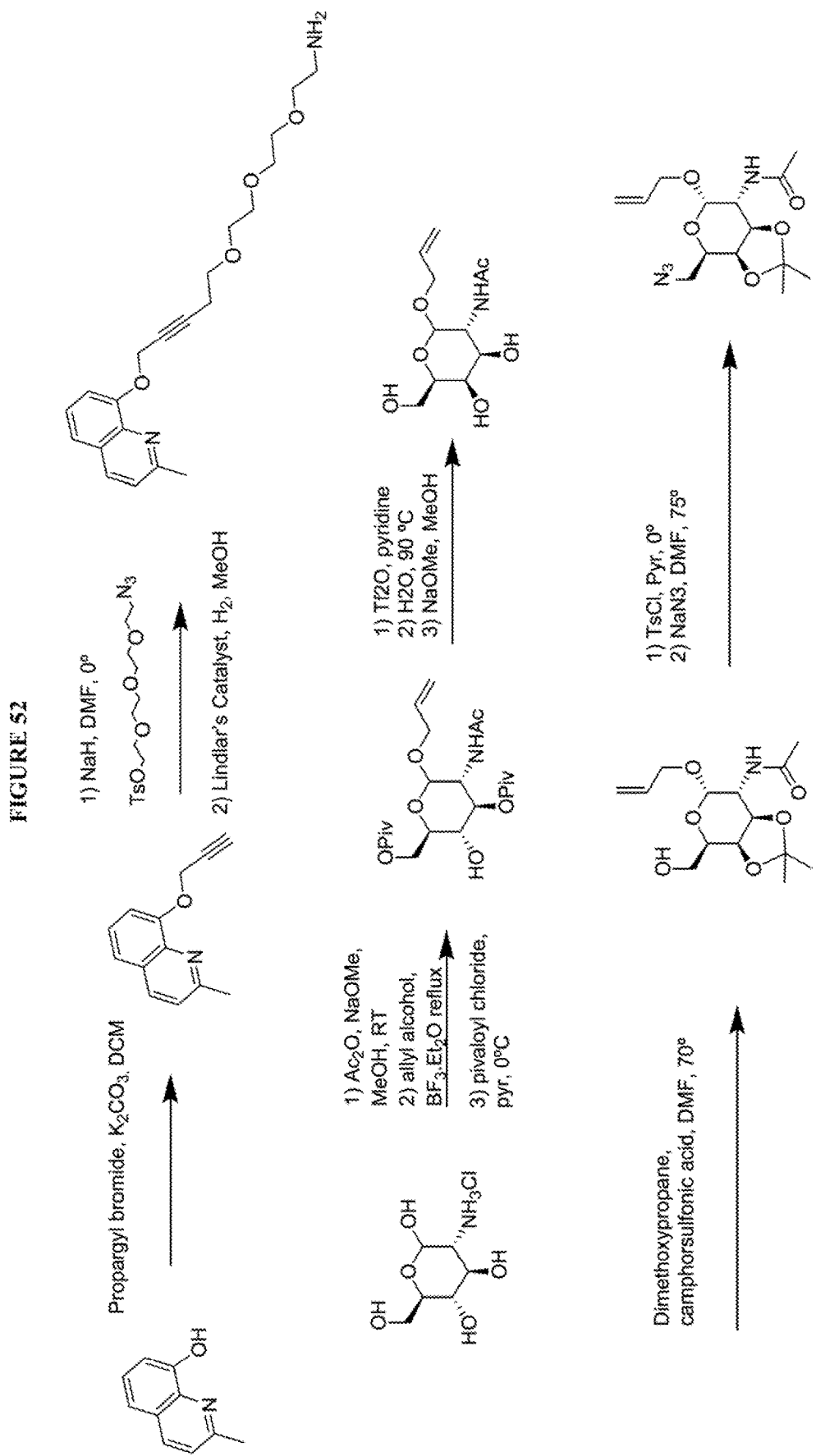
FIGS. 52-66 show the synthesis of a number of MIF-binding compounds with various ASGPRBM moieties.
Figure 52:
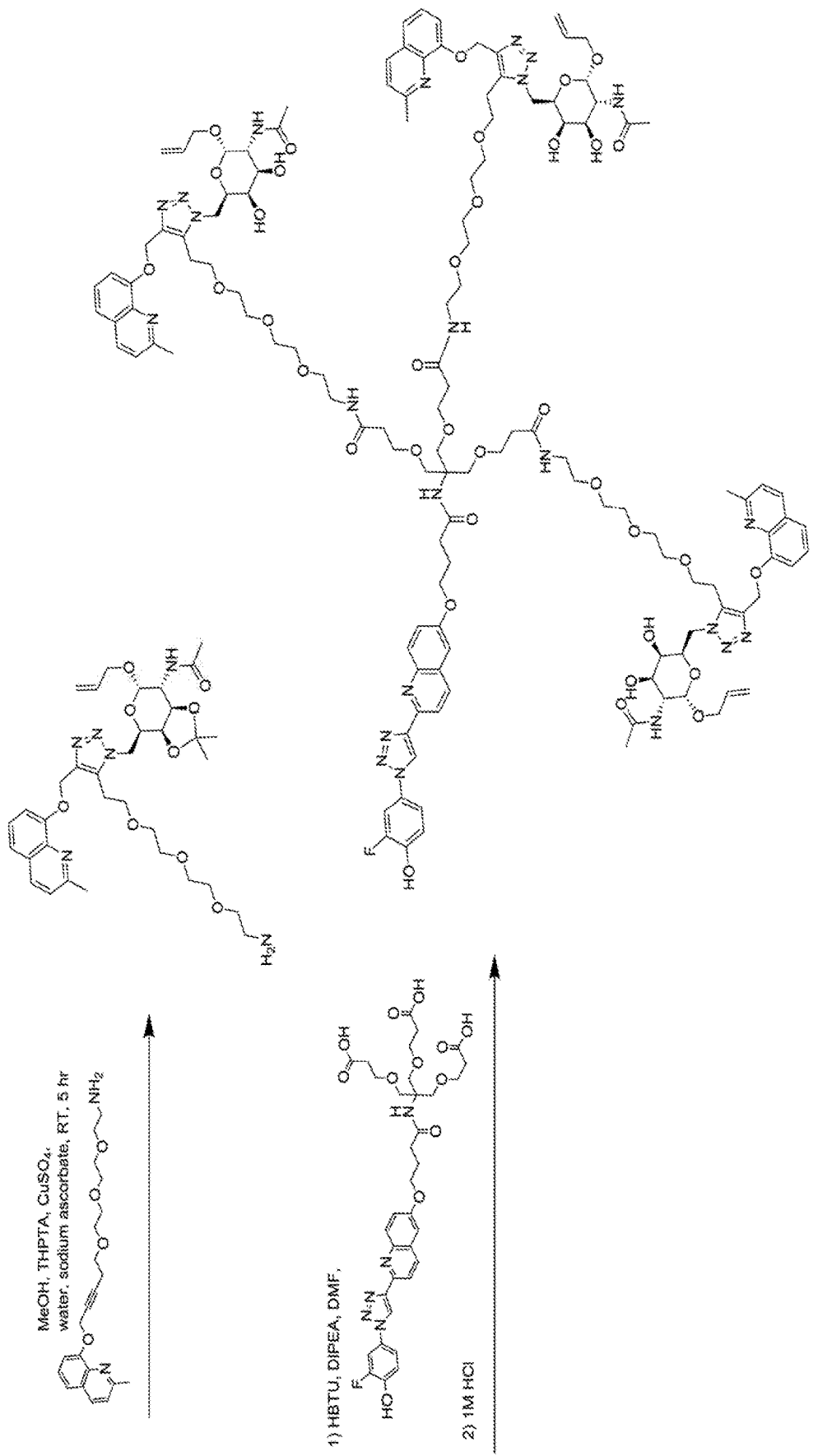
Figure 53:
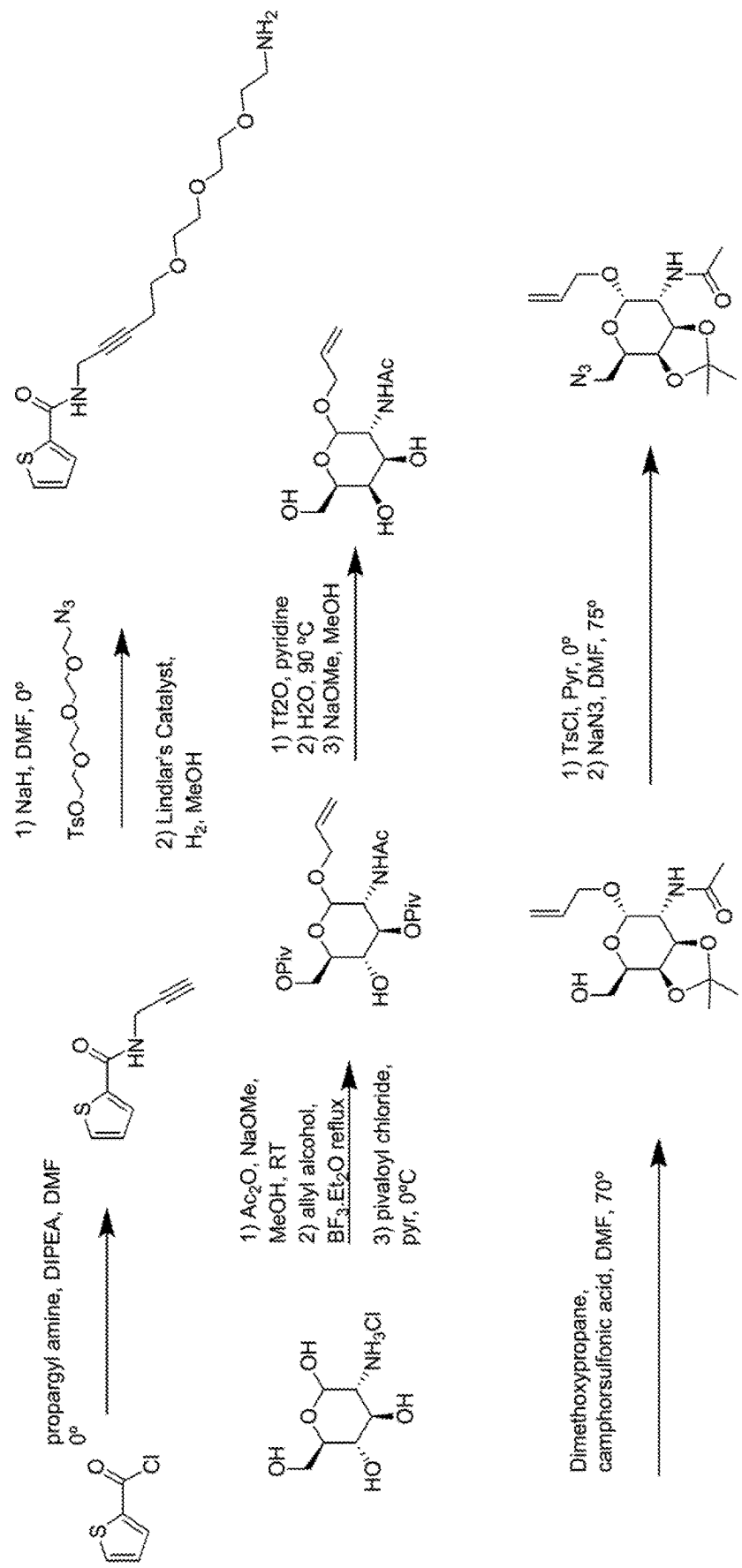
Figure 53:
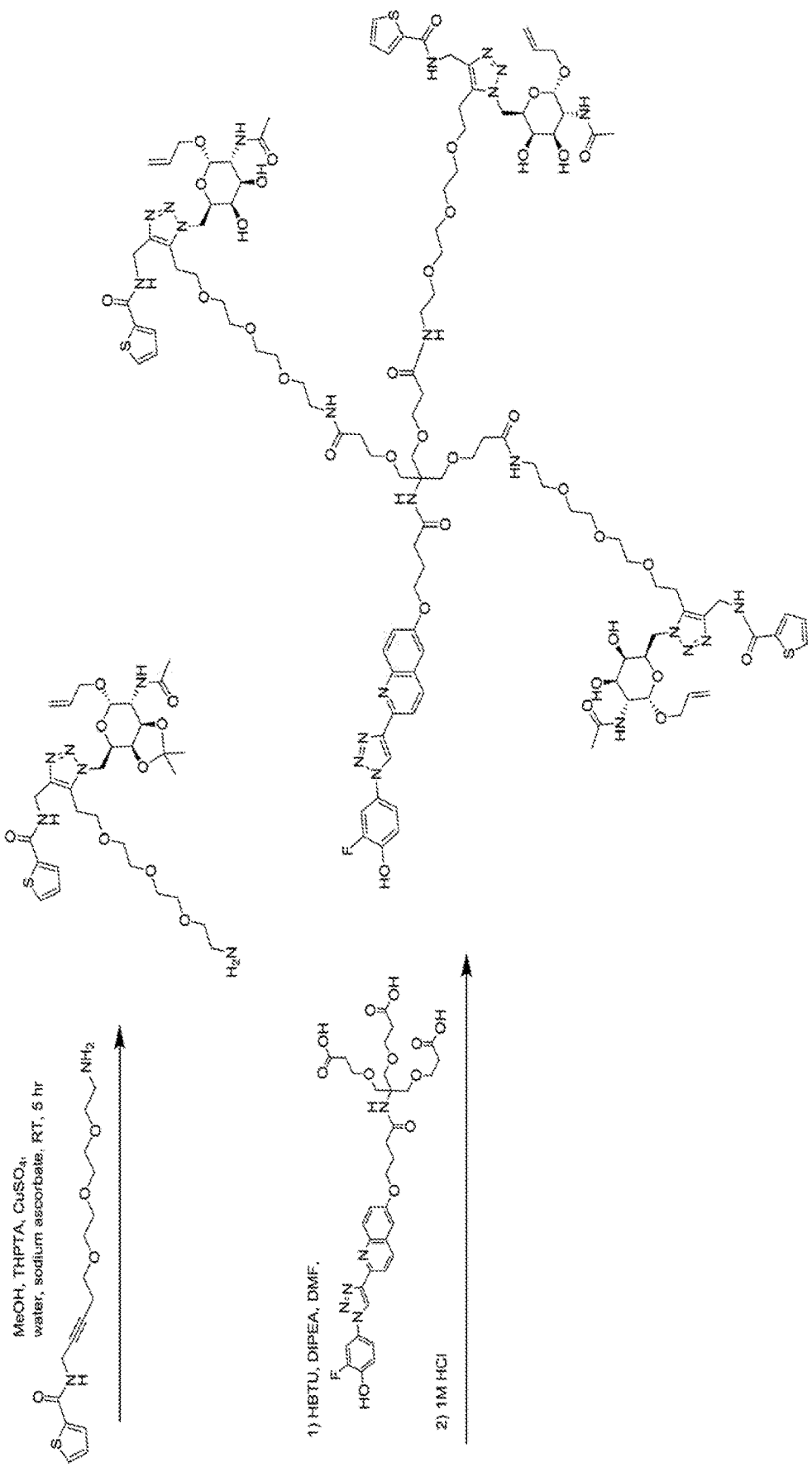
Figure 54:
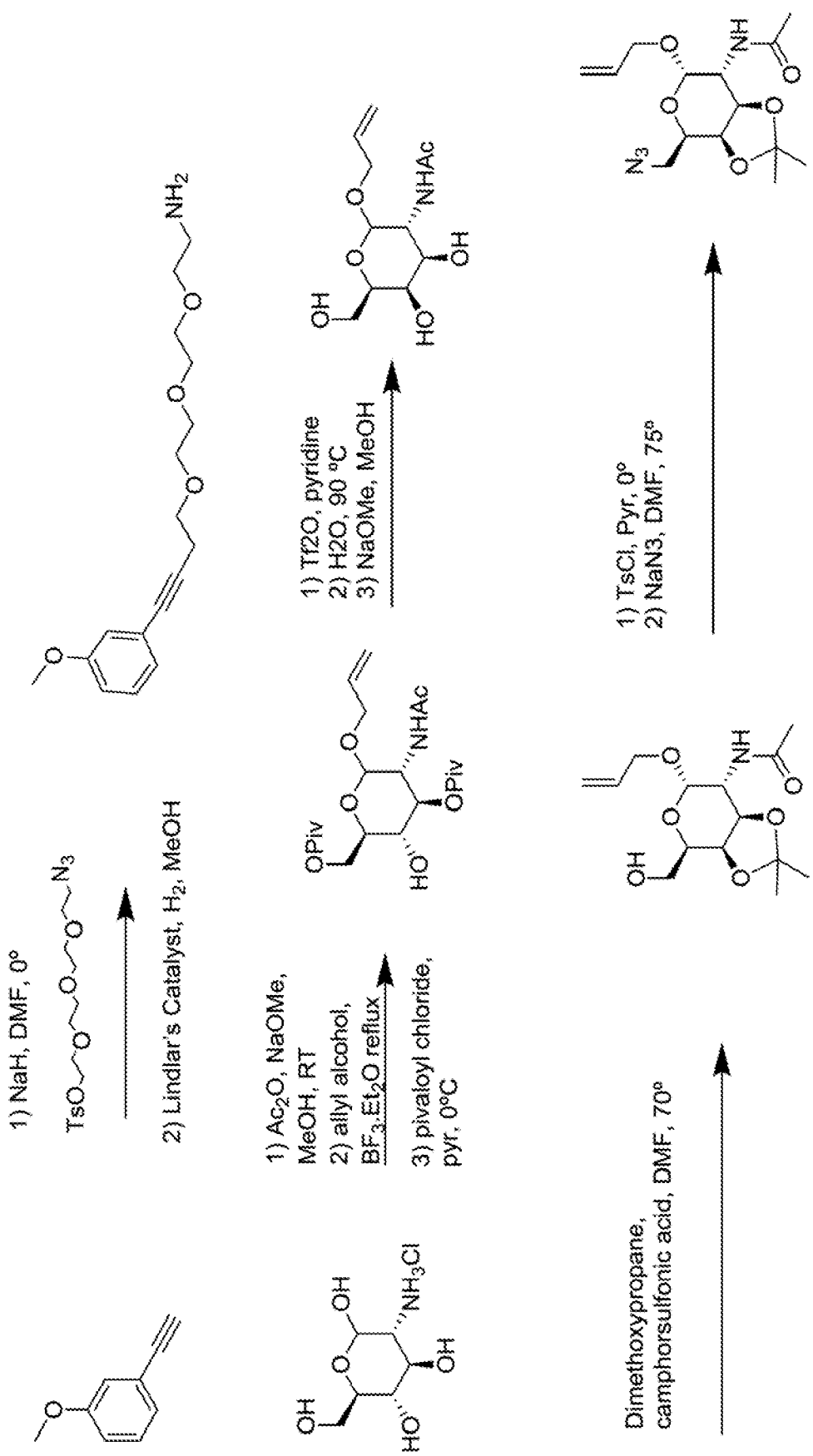
Figure 54:
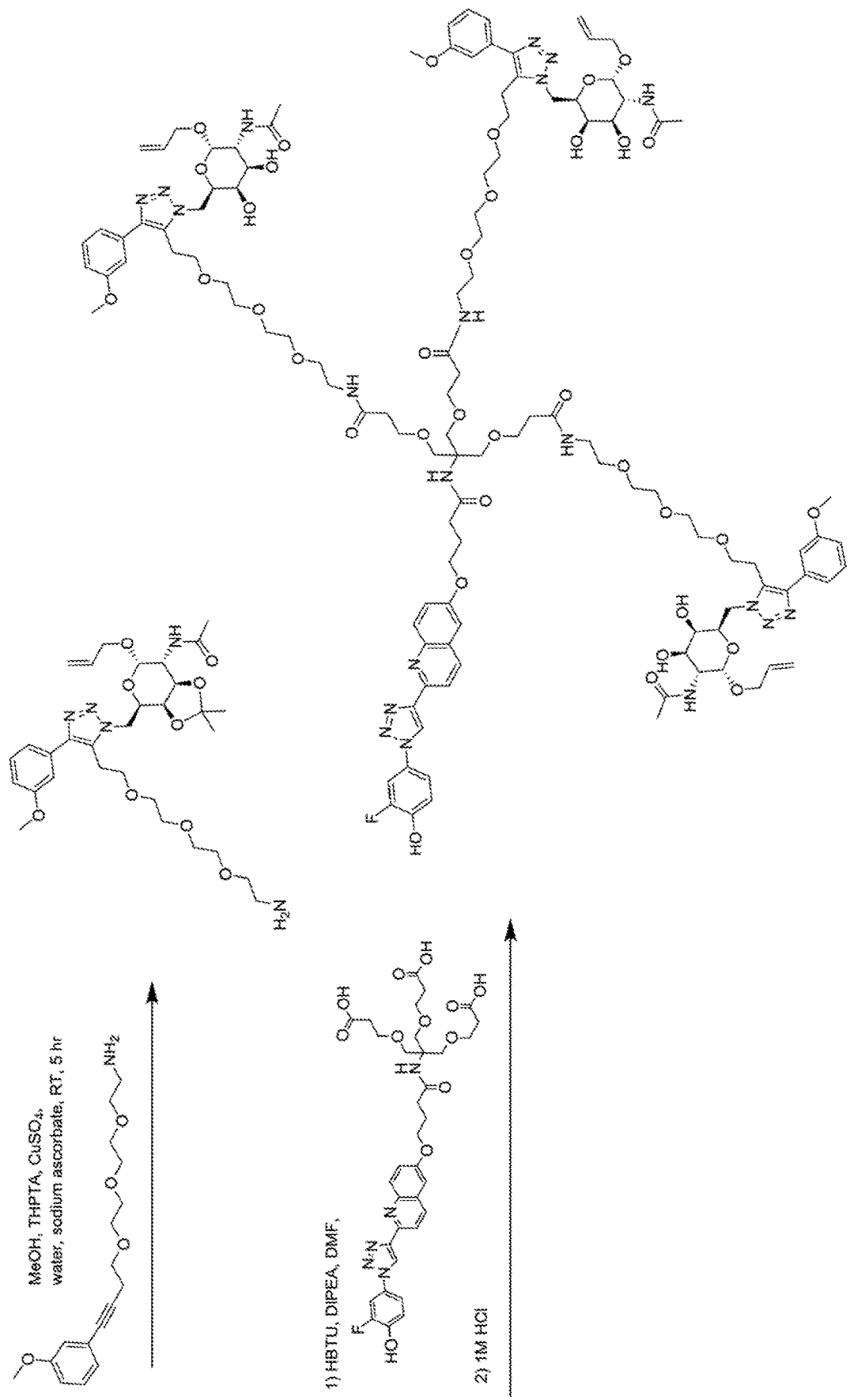
Figure 55:
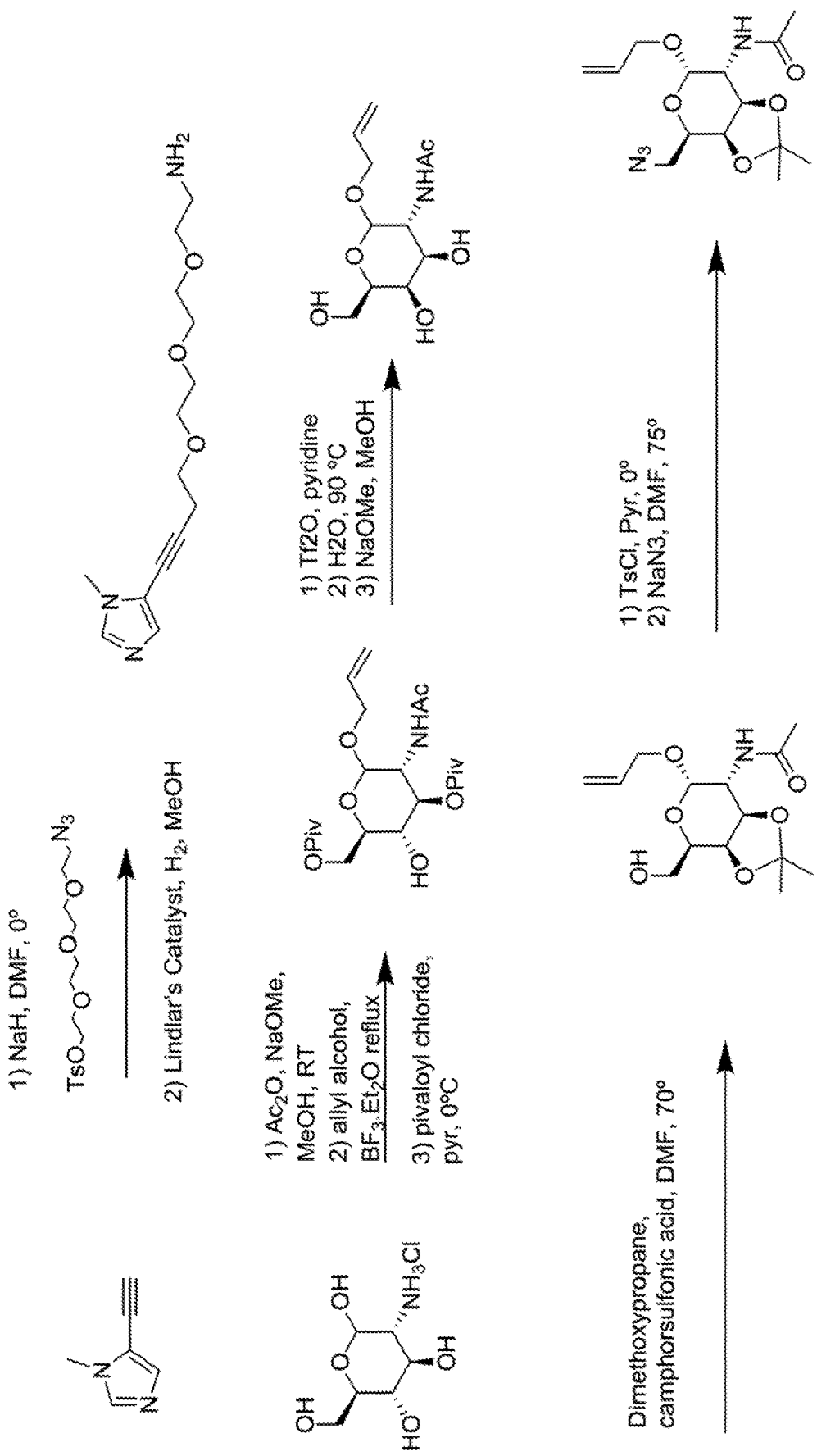
Figure 55:
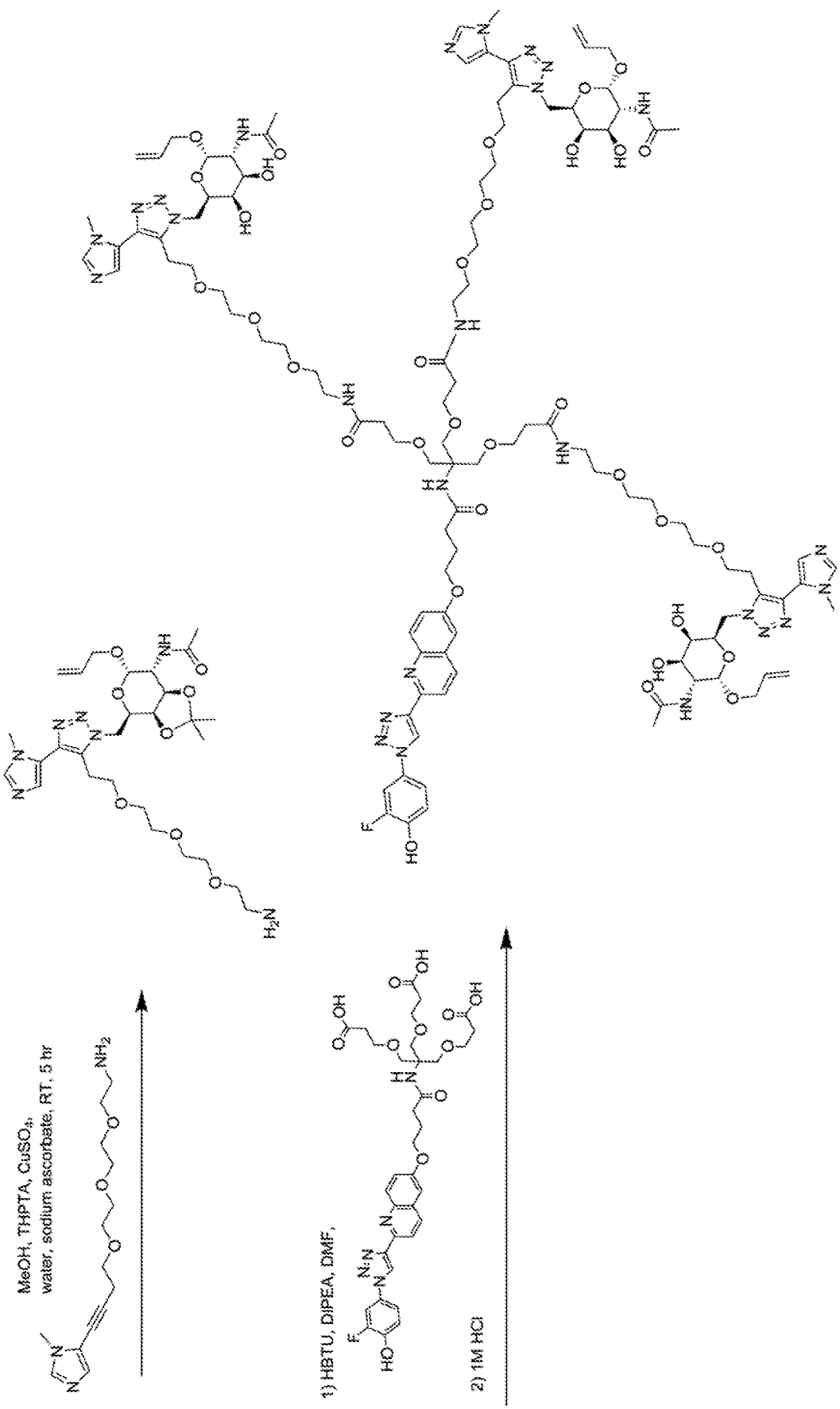
Figure 56:
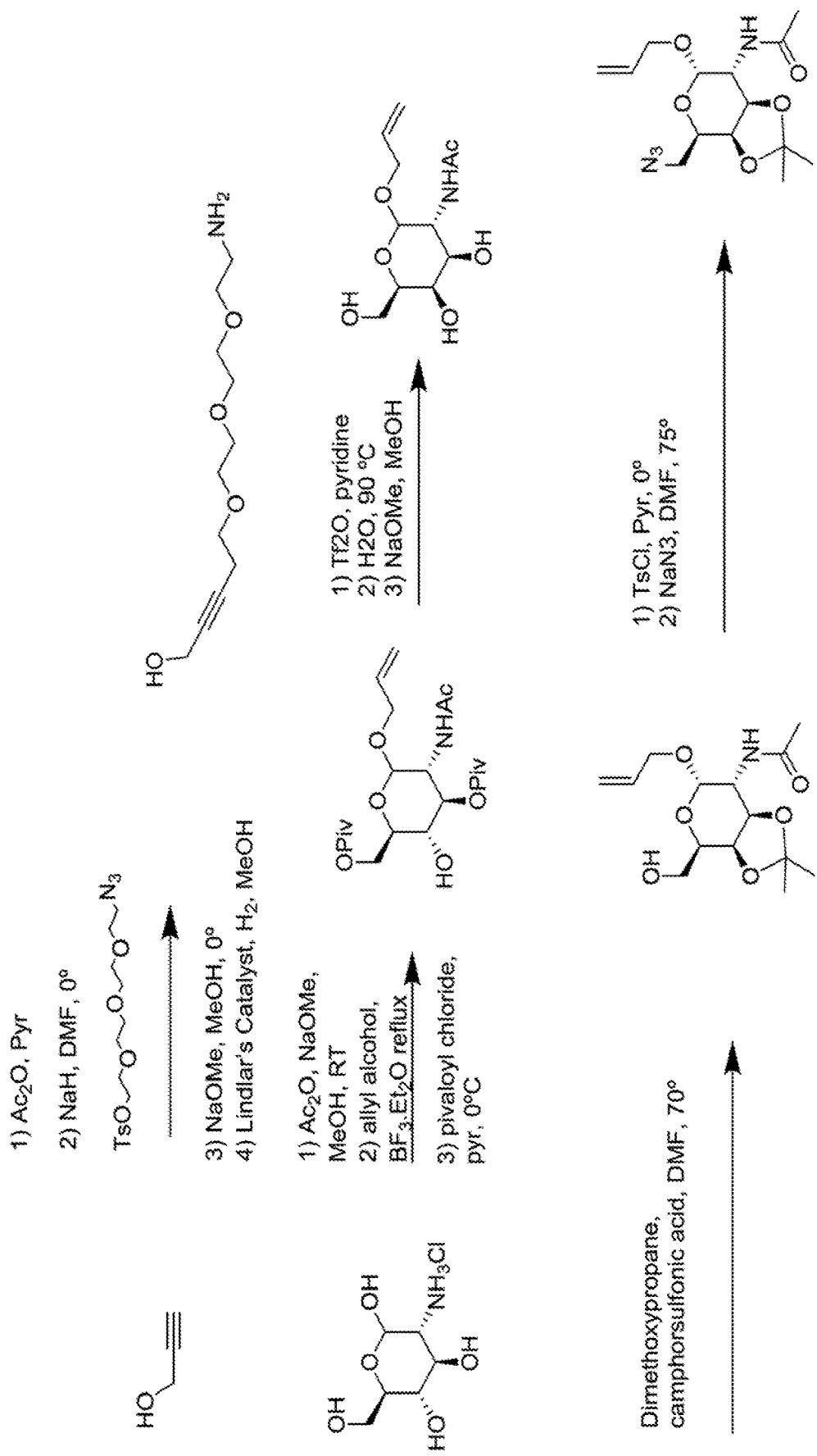
Figure 56:
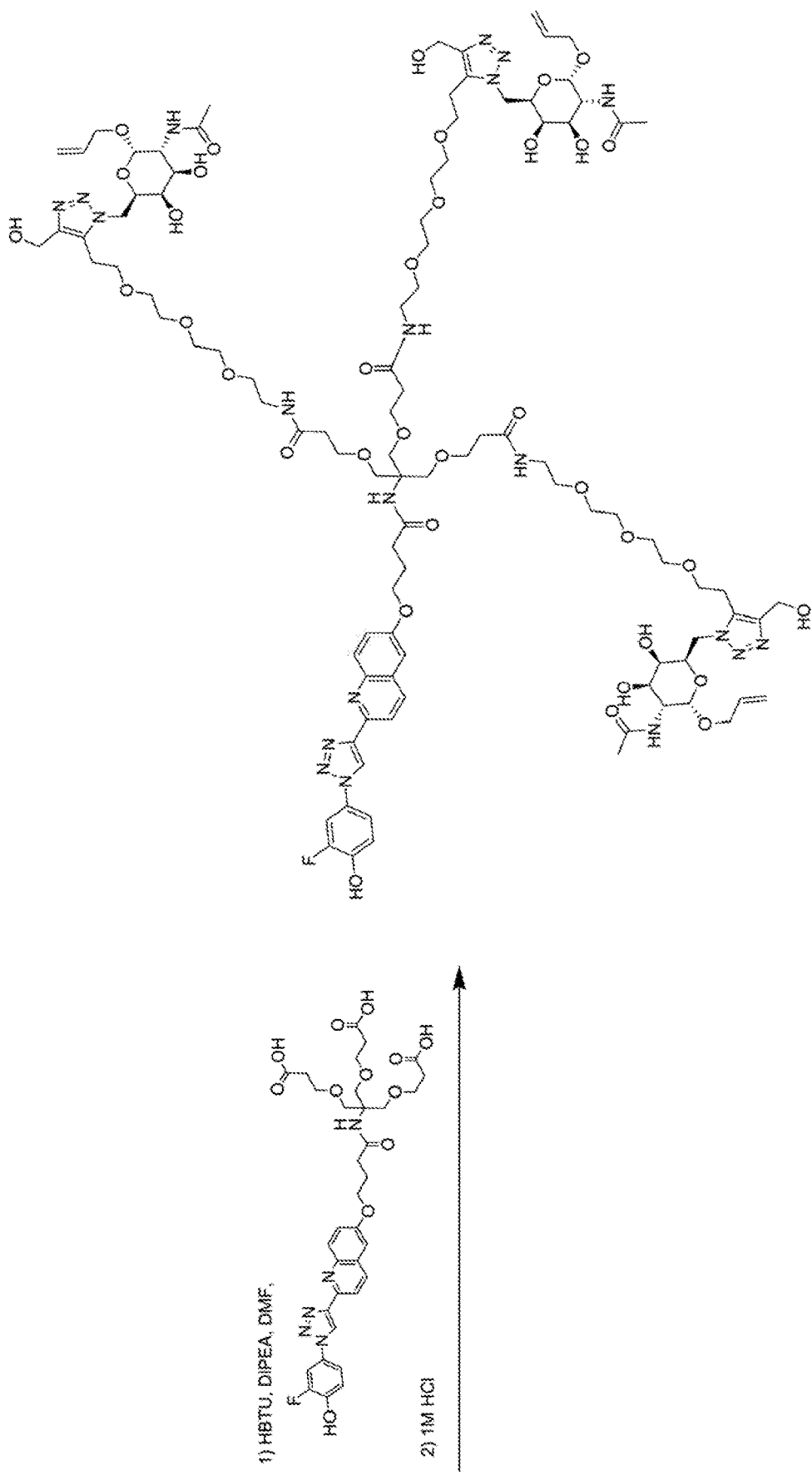
Figure 57:
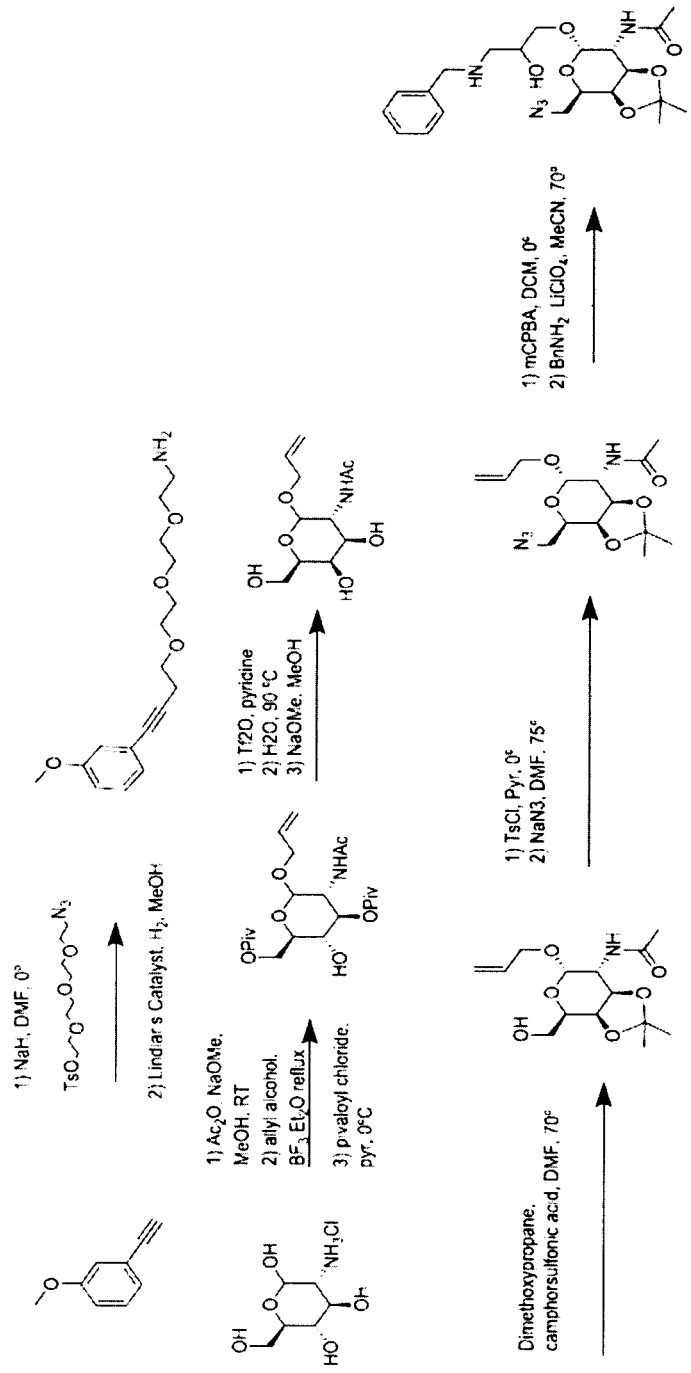
Figure 57:
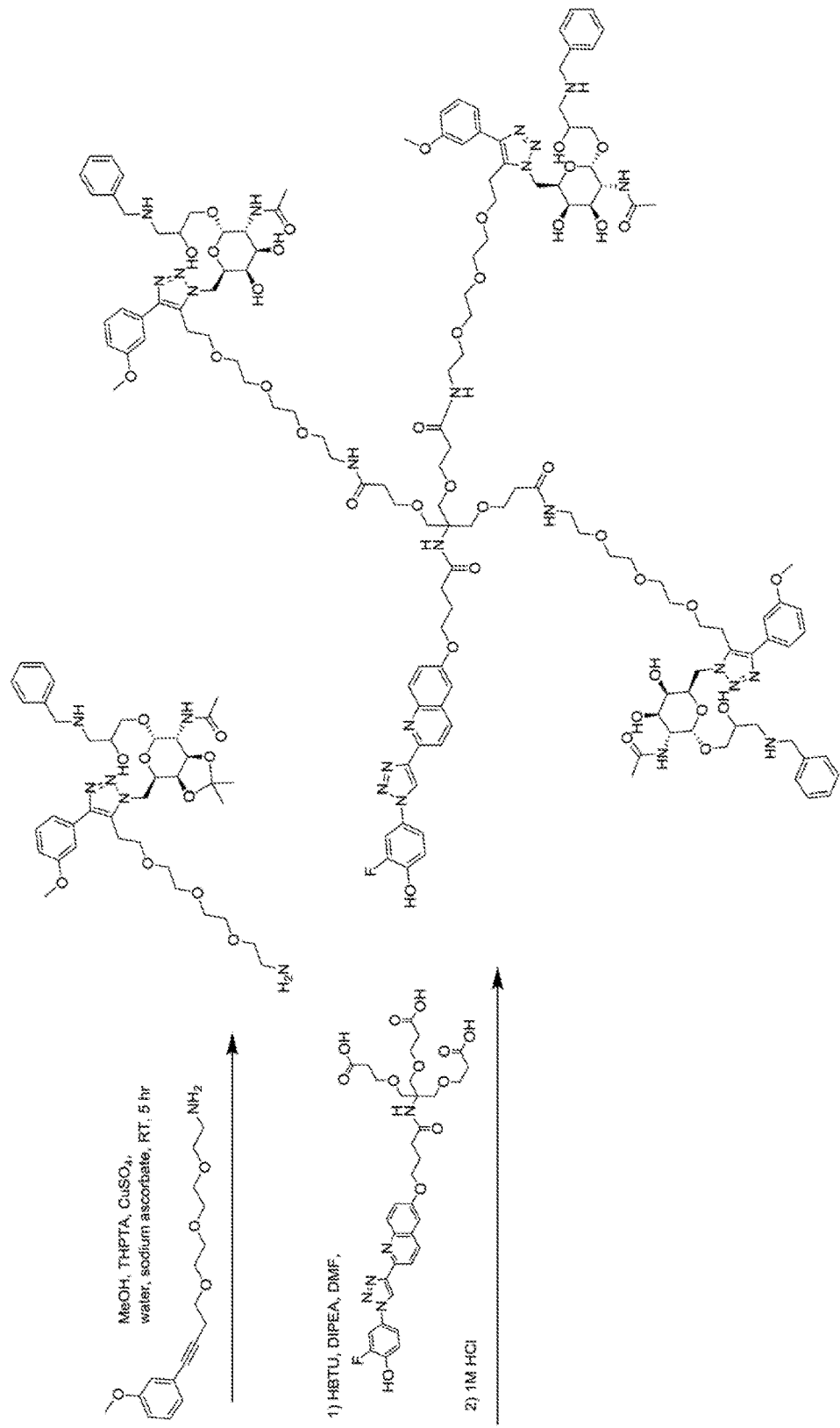
Figure 58:
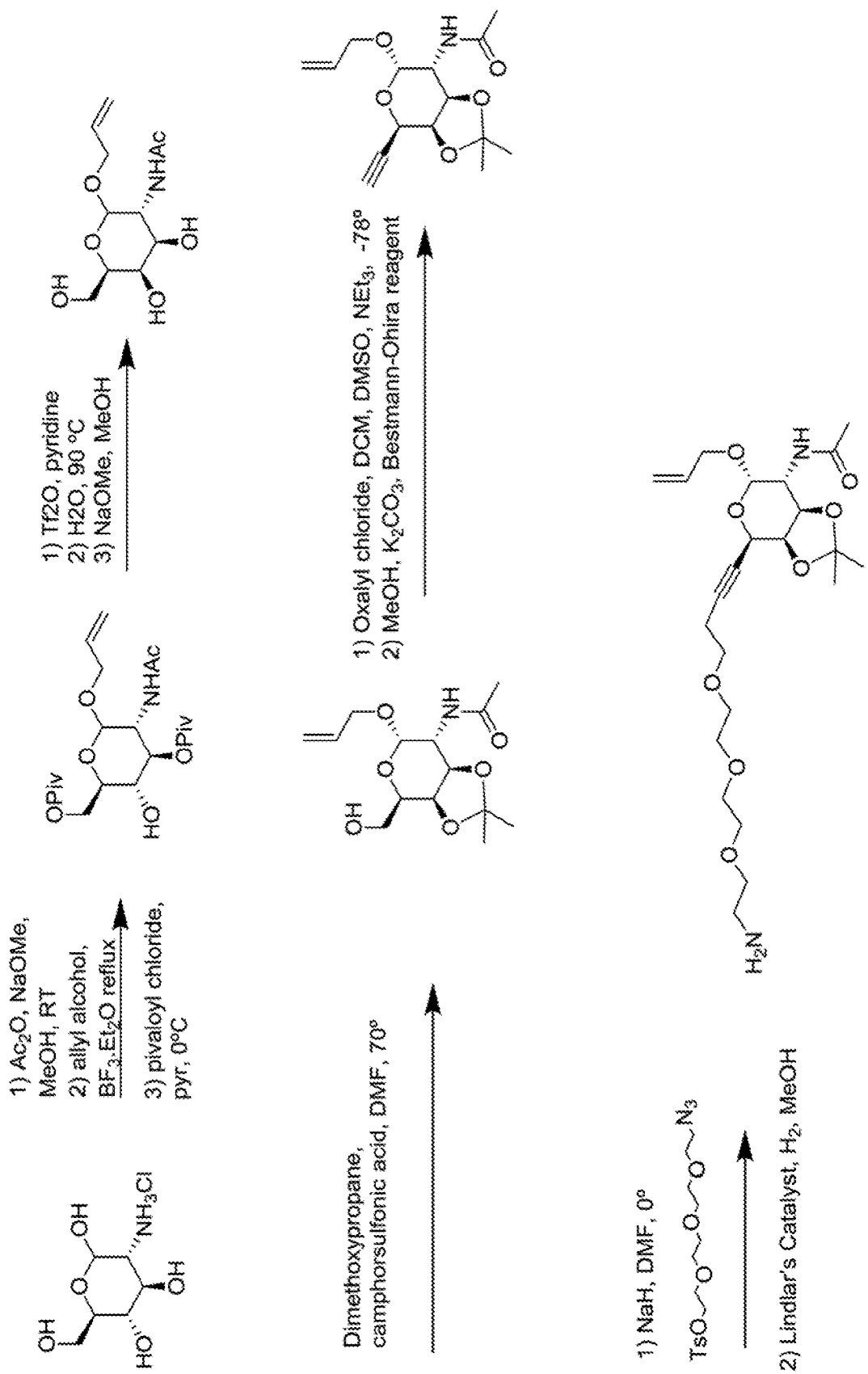
Figure 58:
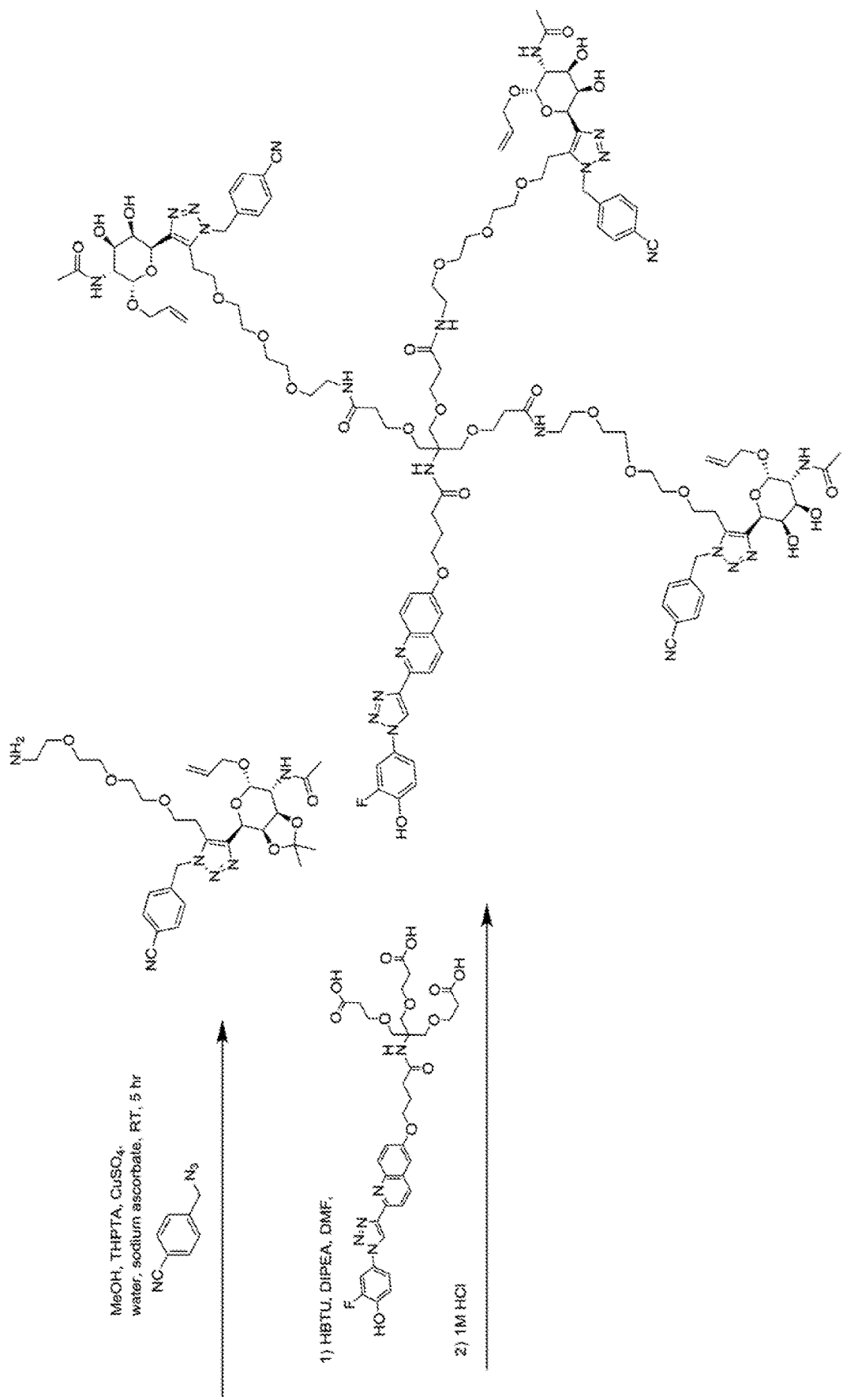
Figure 59:
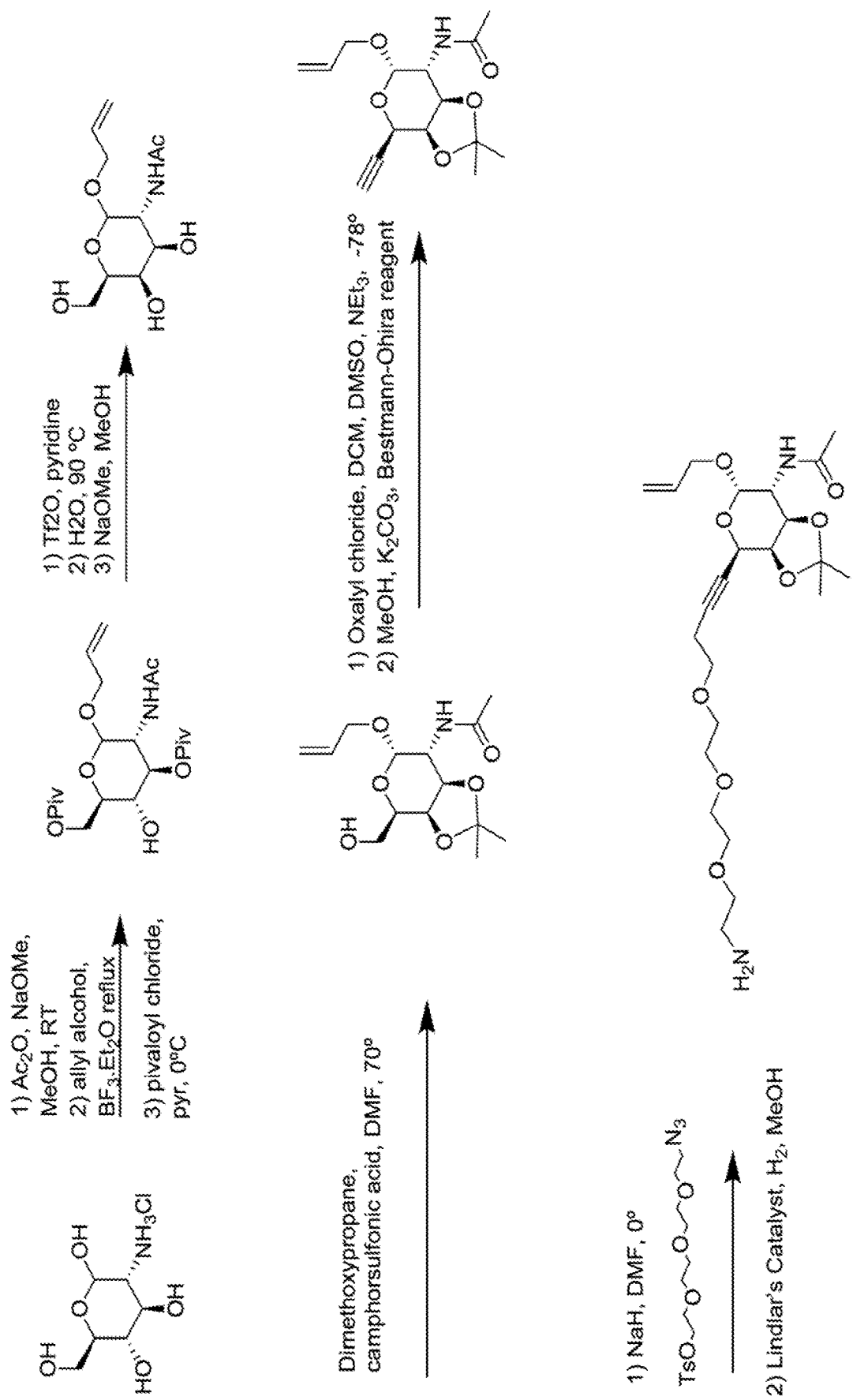
Figure 59:
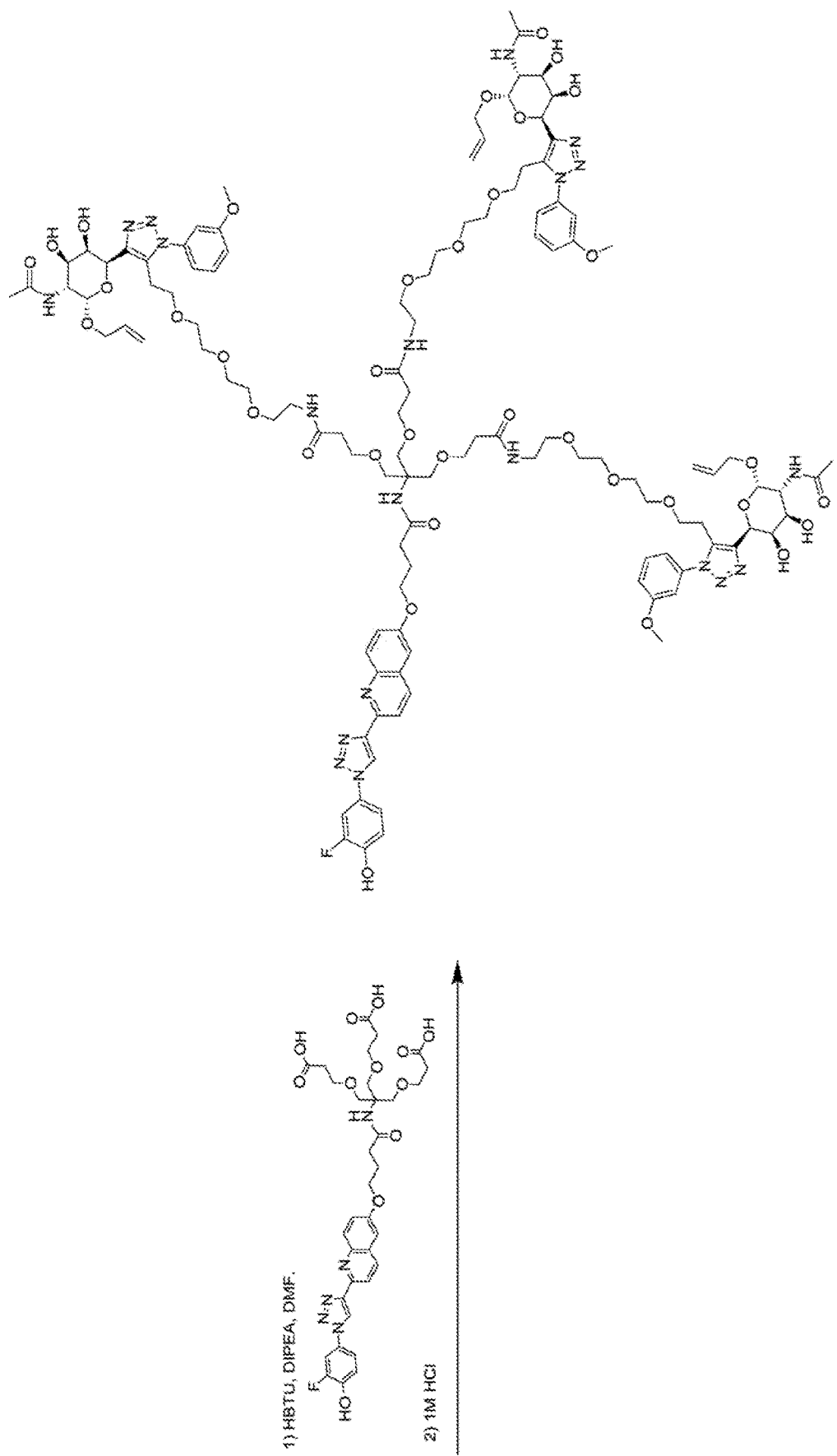
Figure 60:
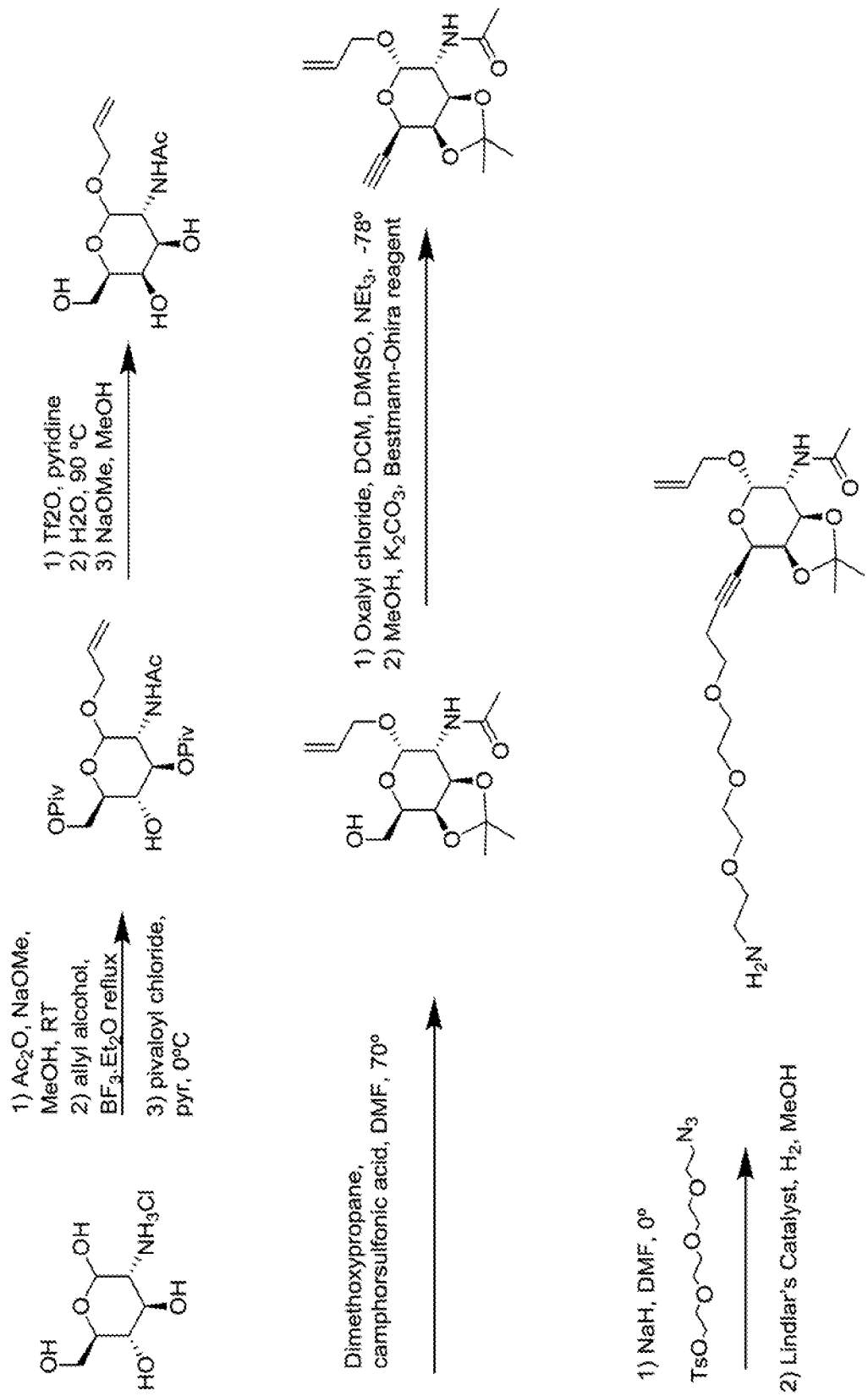
Figure 60:
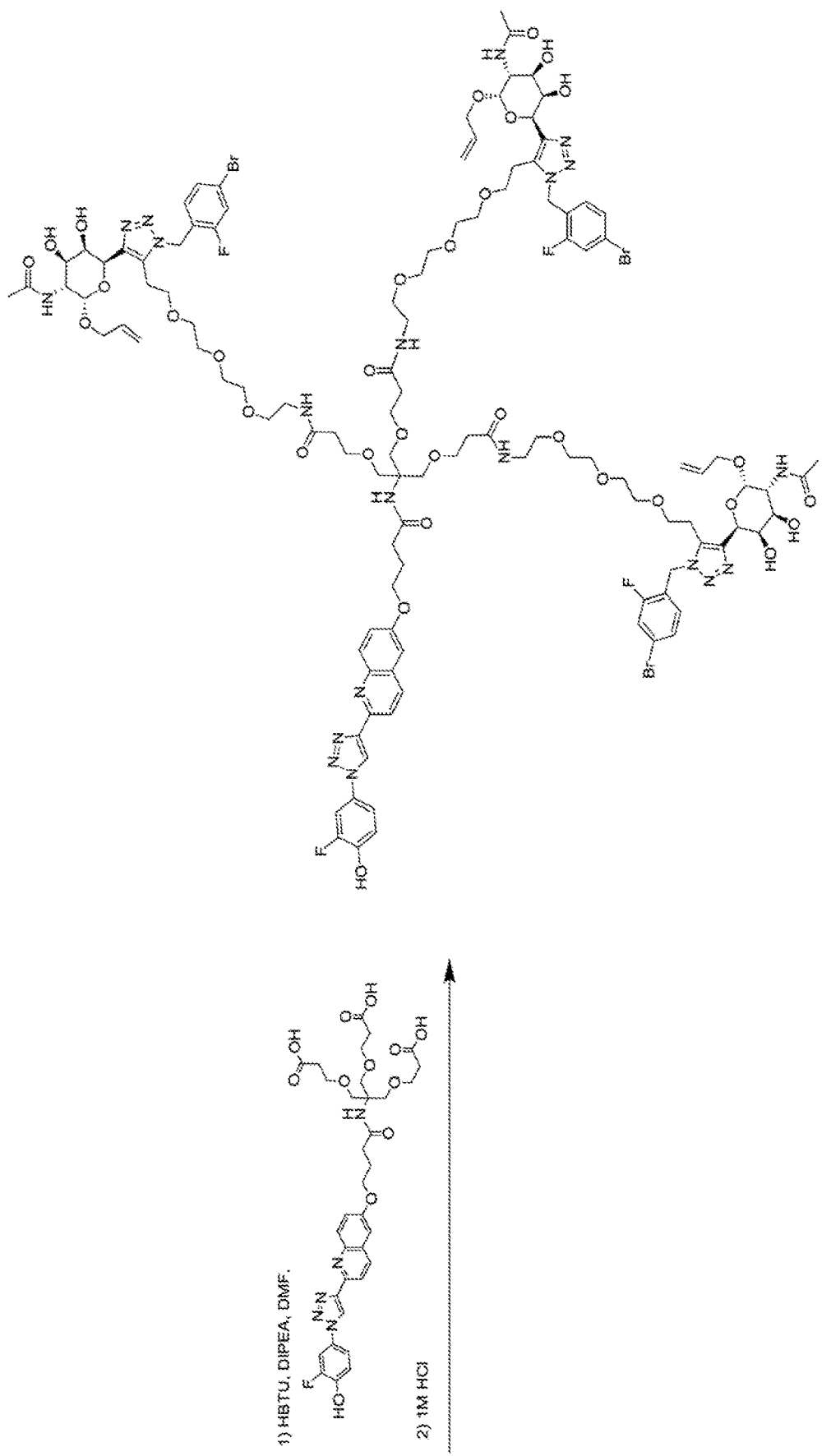
Figure 61:
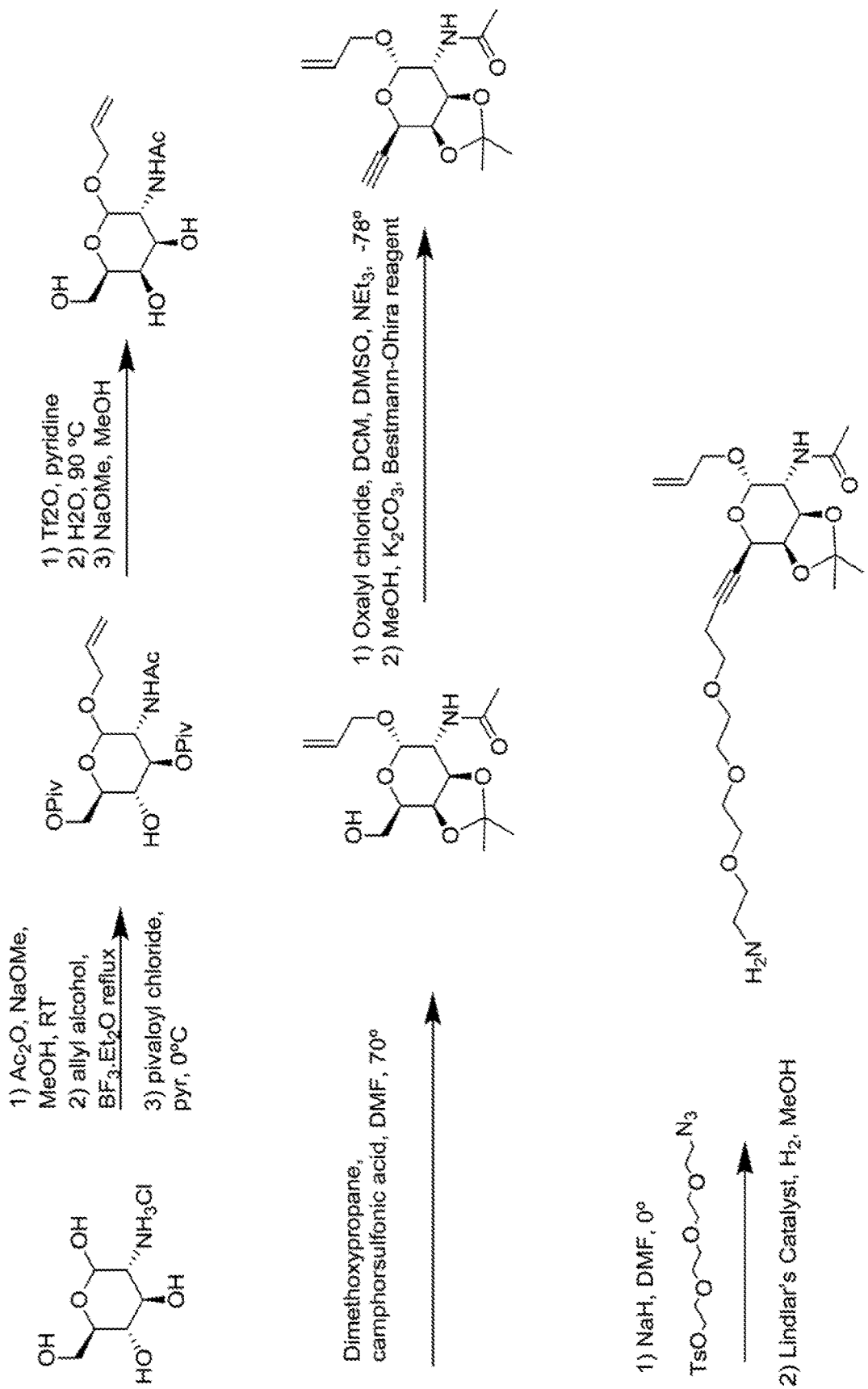
Figure 61:
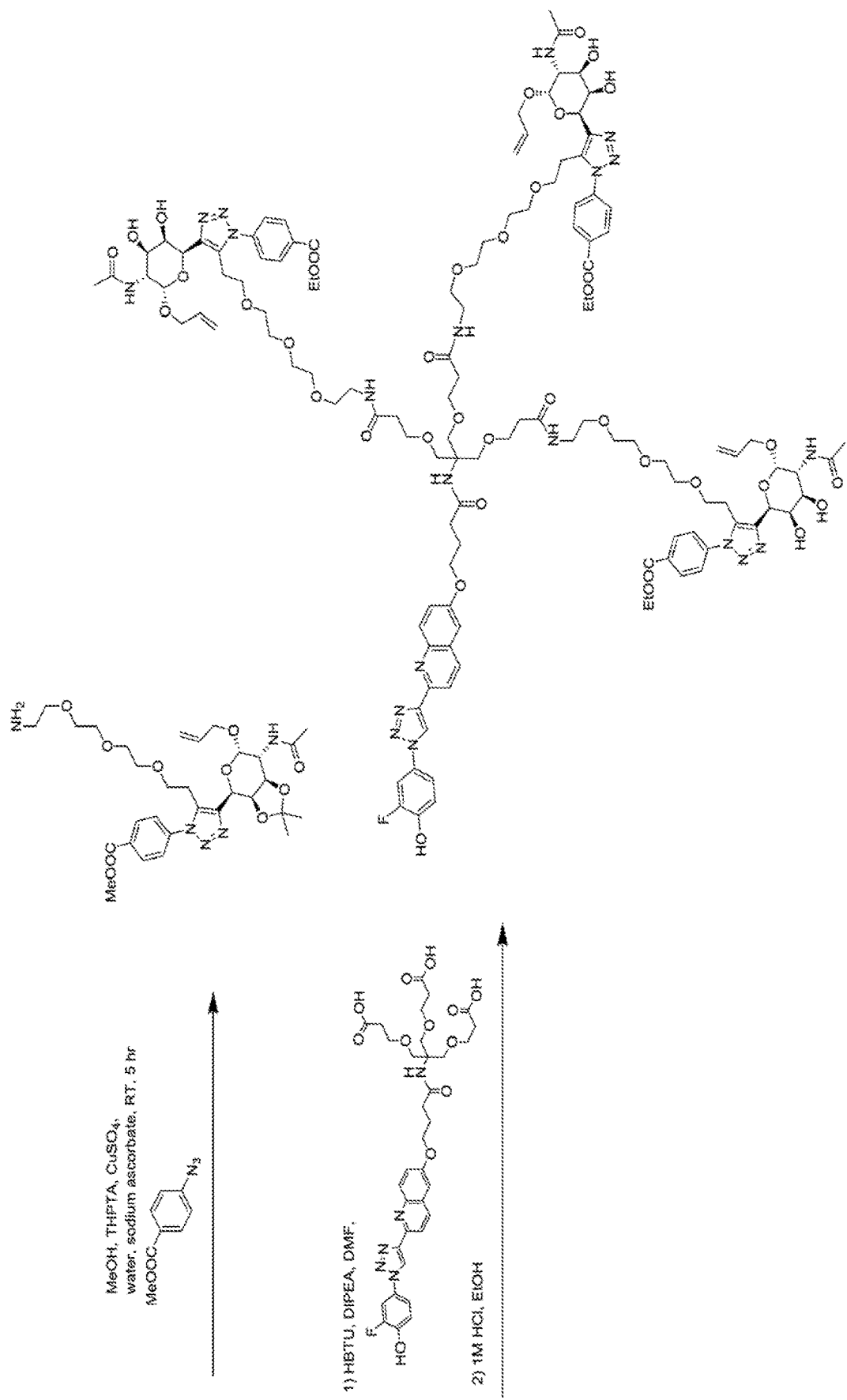
Figure 62:
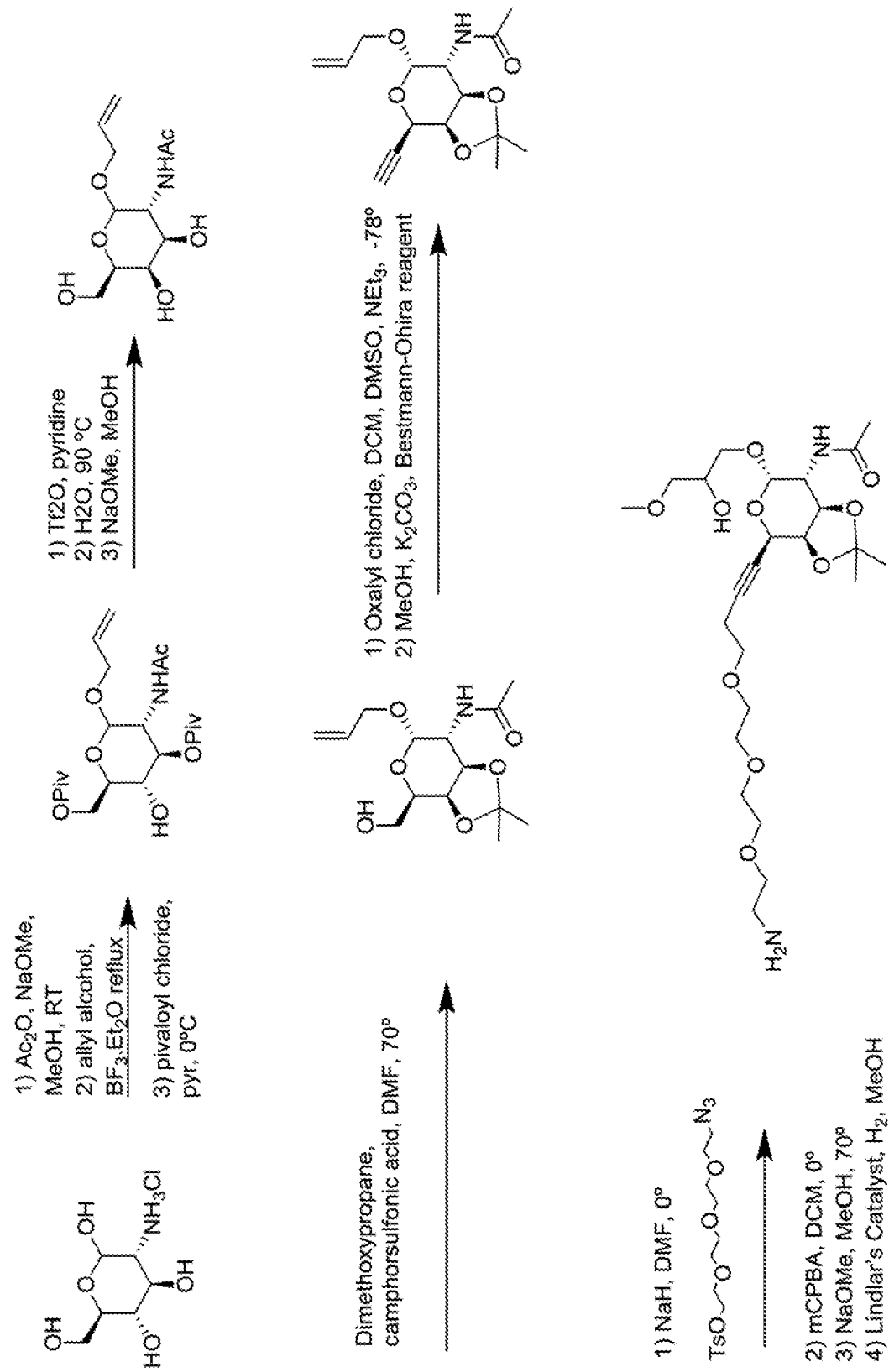
Figure 62:
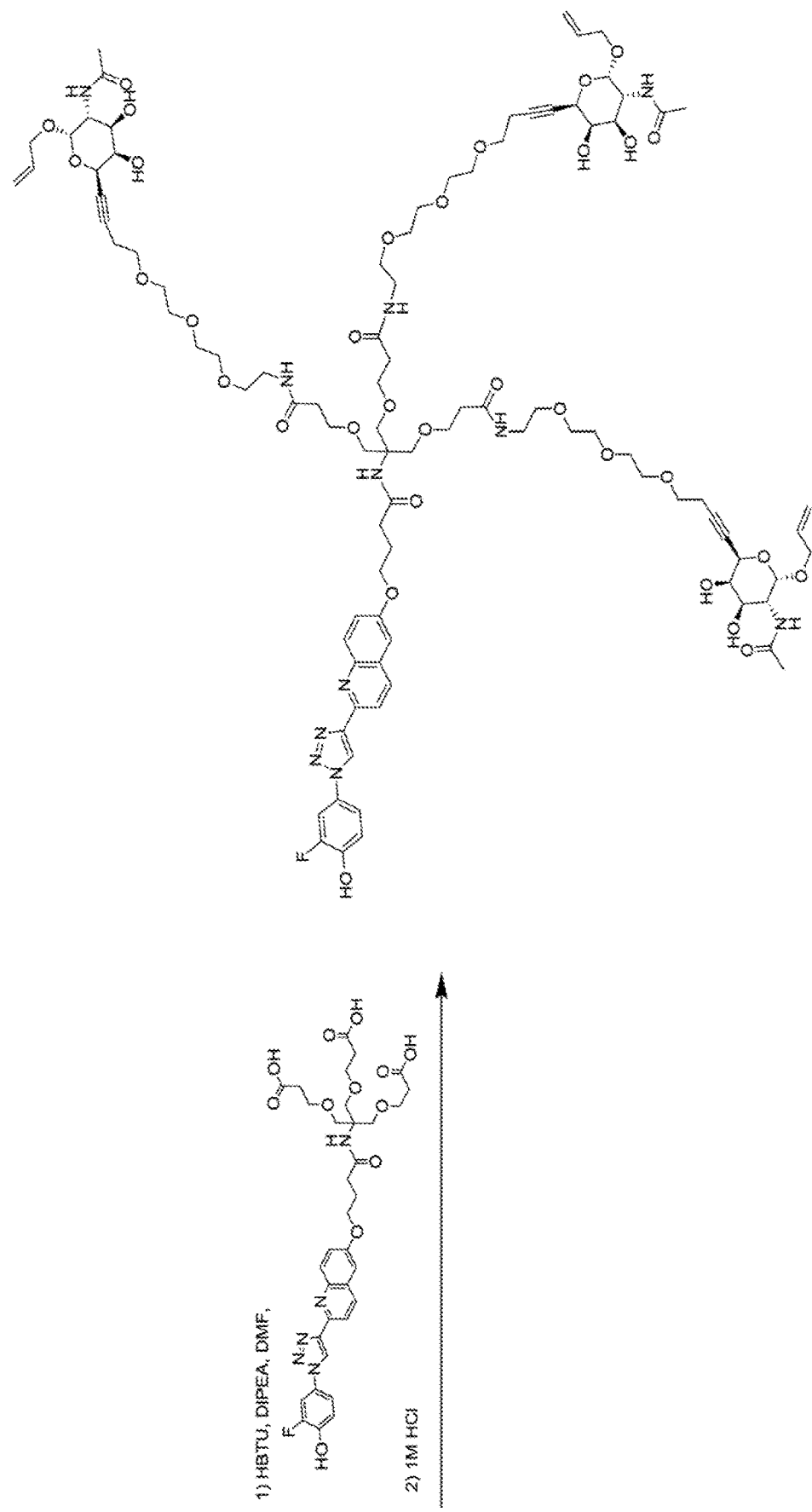
Figure 63:
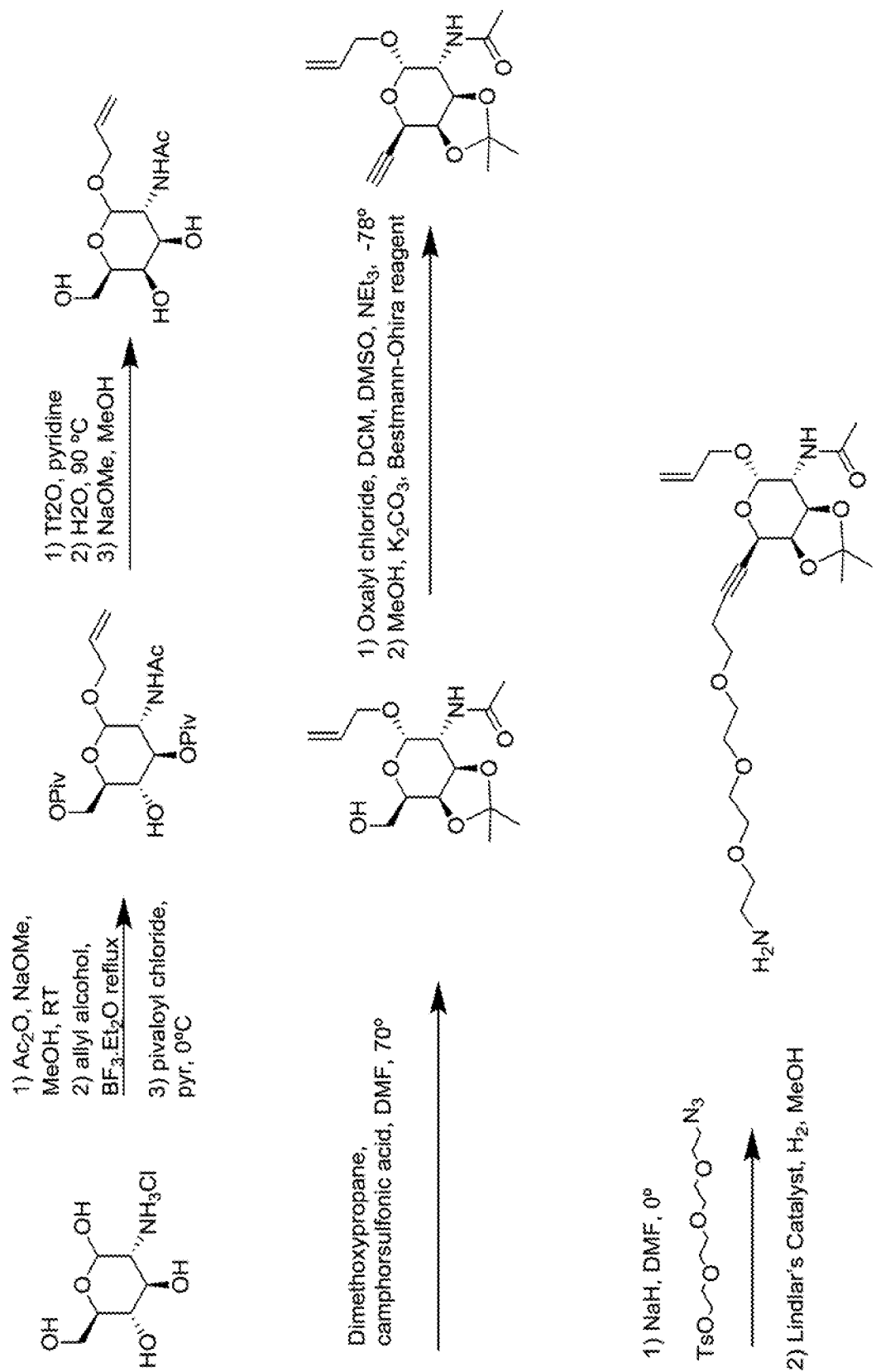
Figure 63:
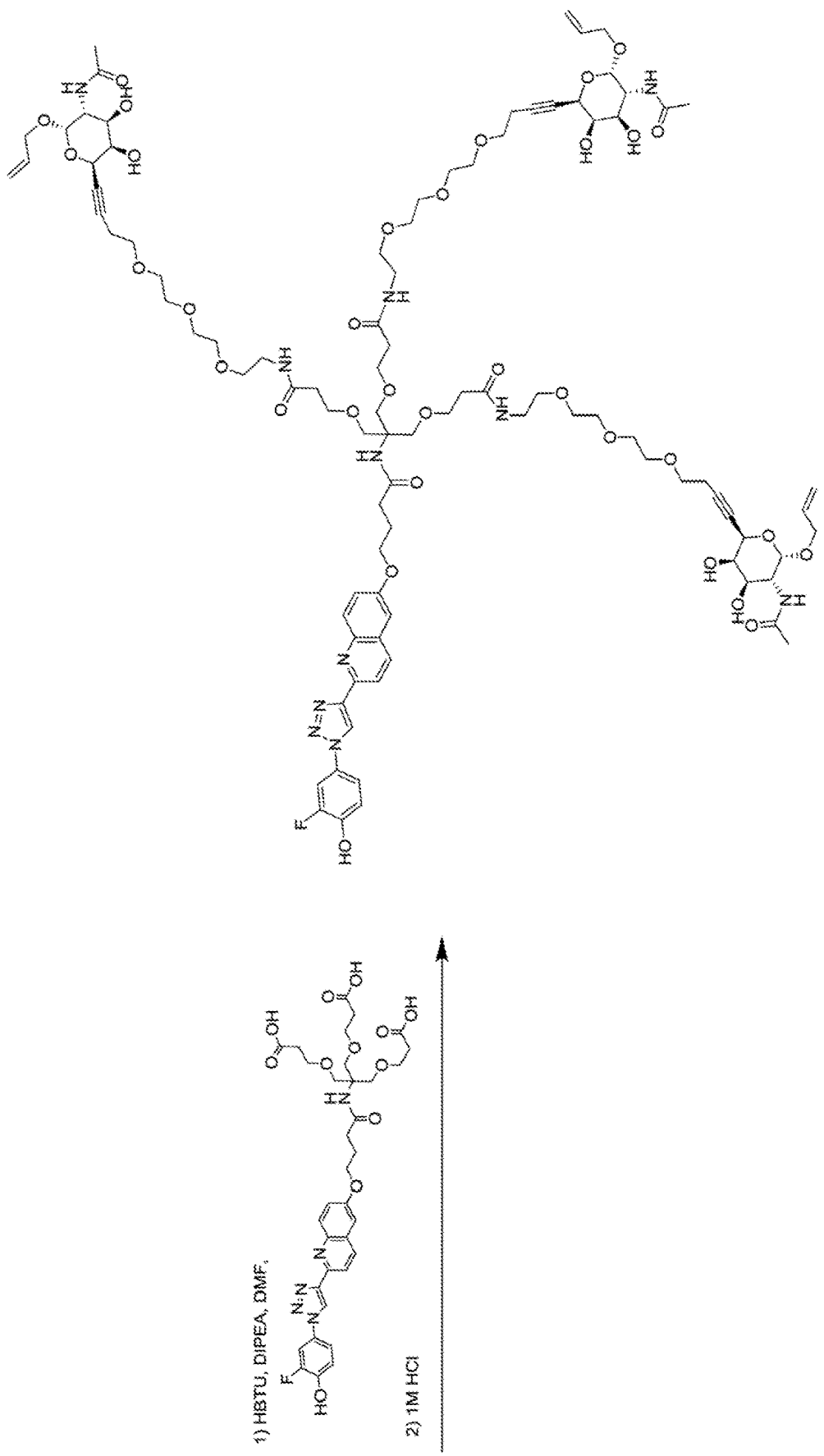
Figure 64:
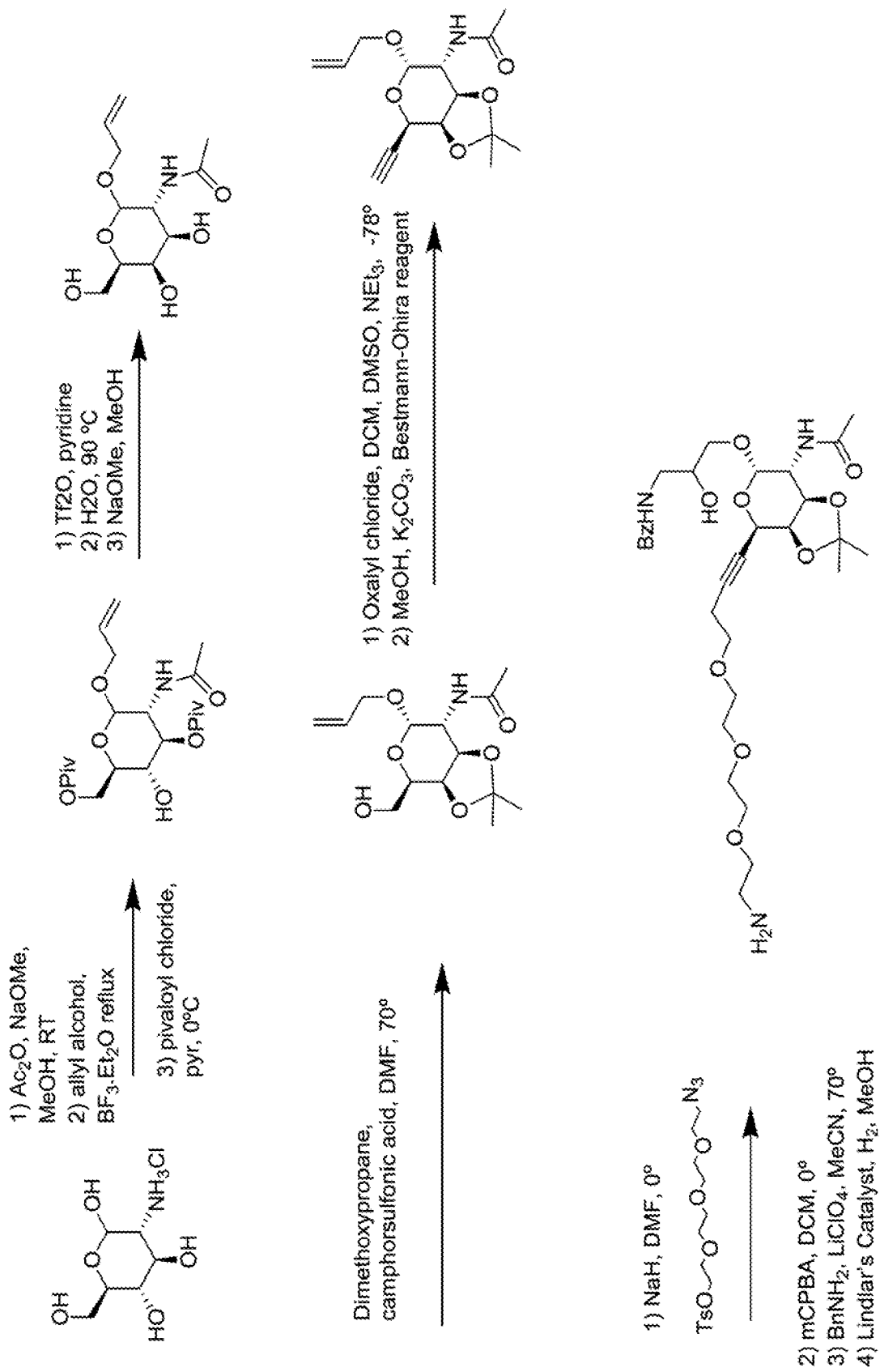
Figure 64:
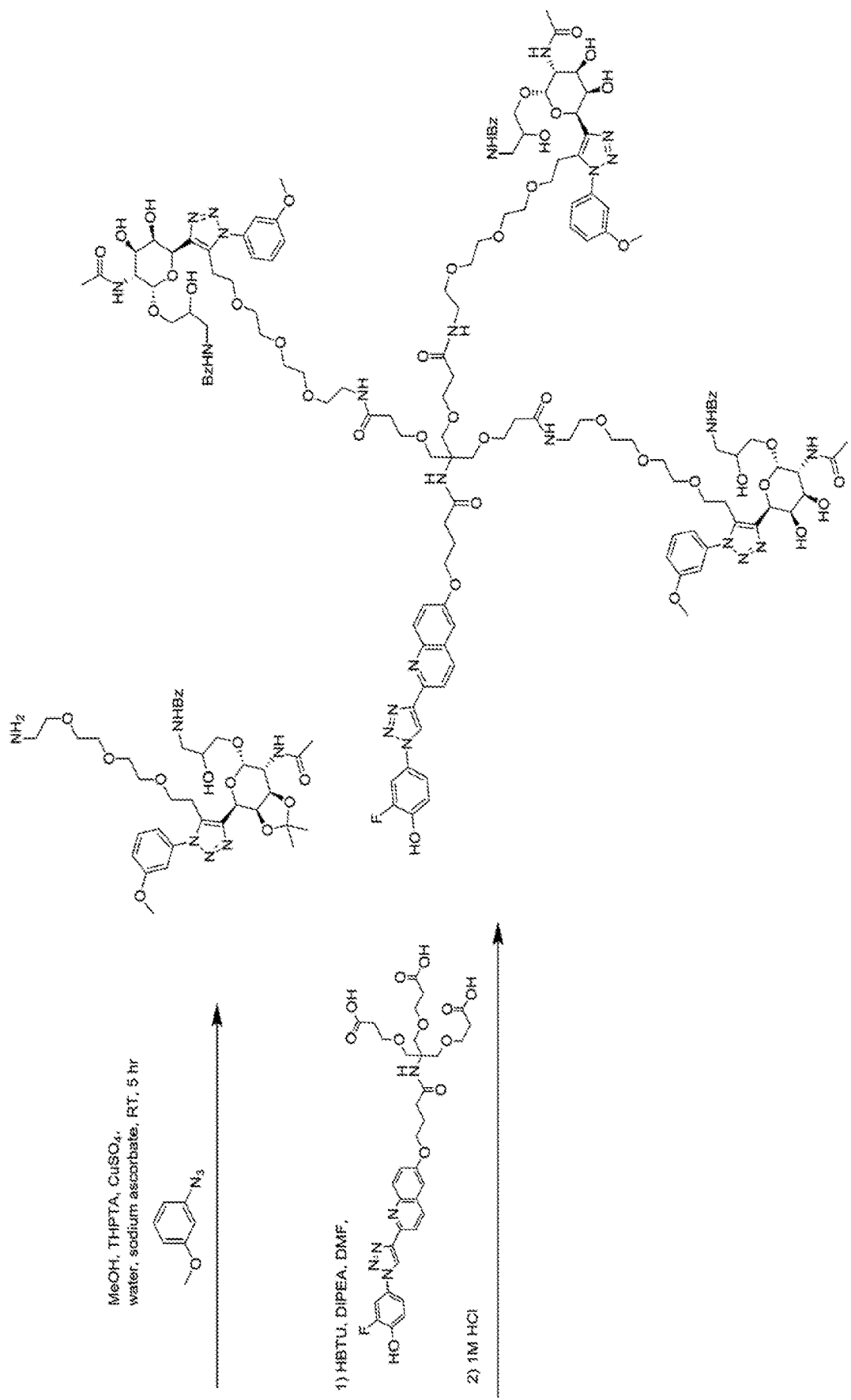
Figure 65:
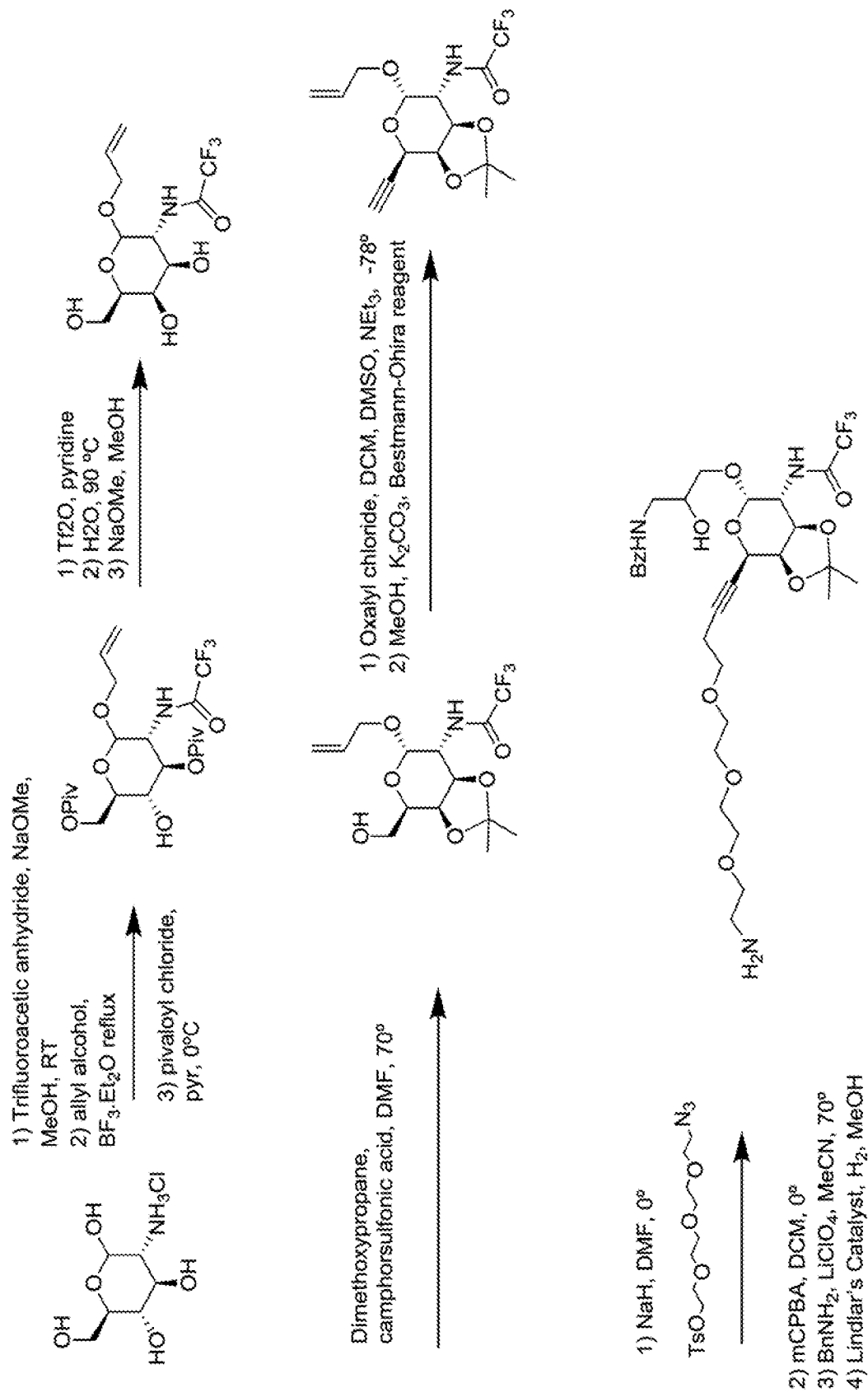
Figure 66:
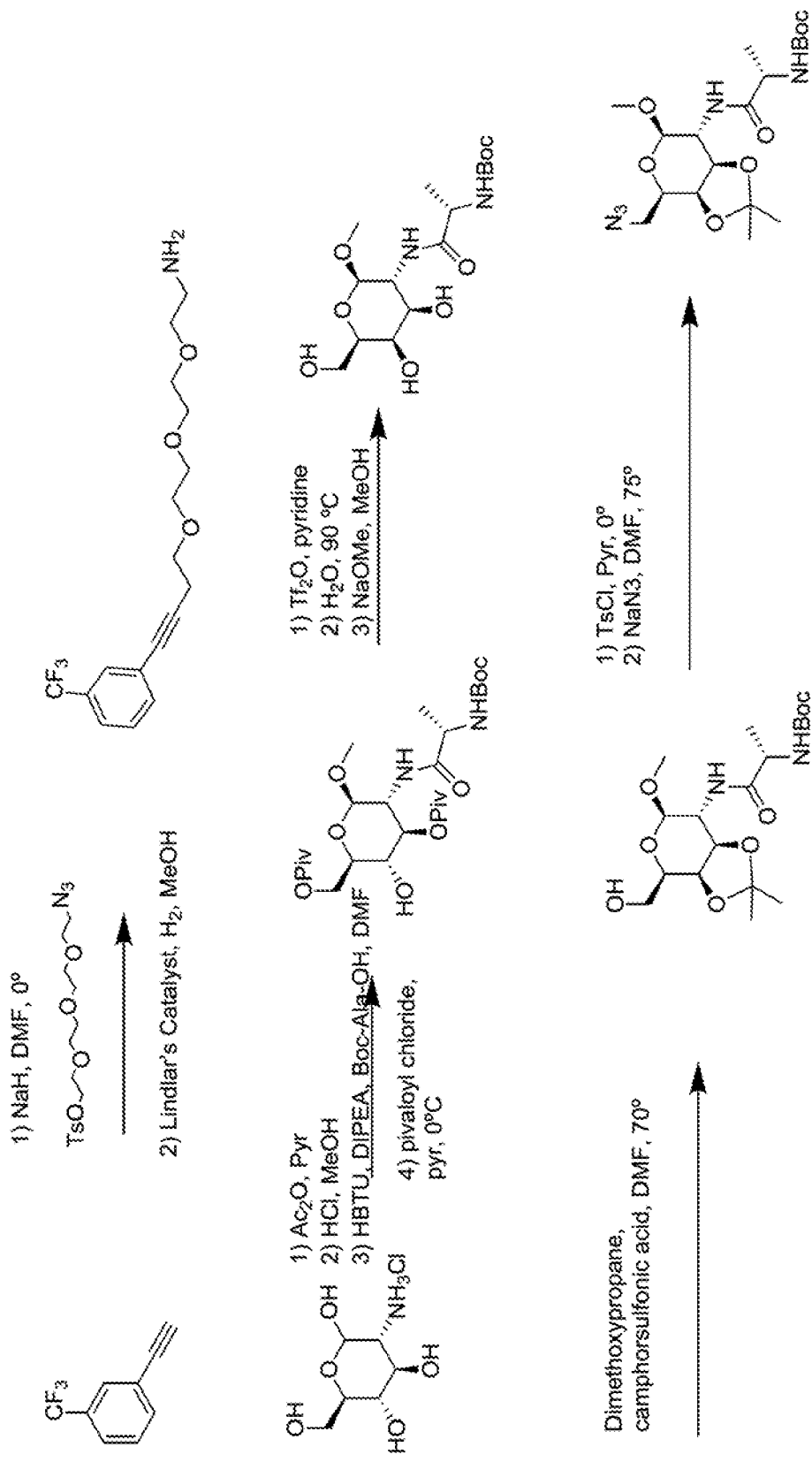
Figure 66:
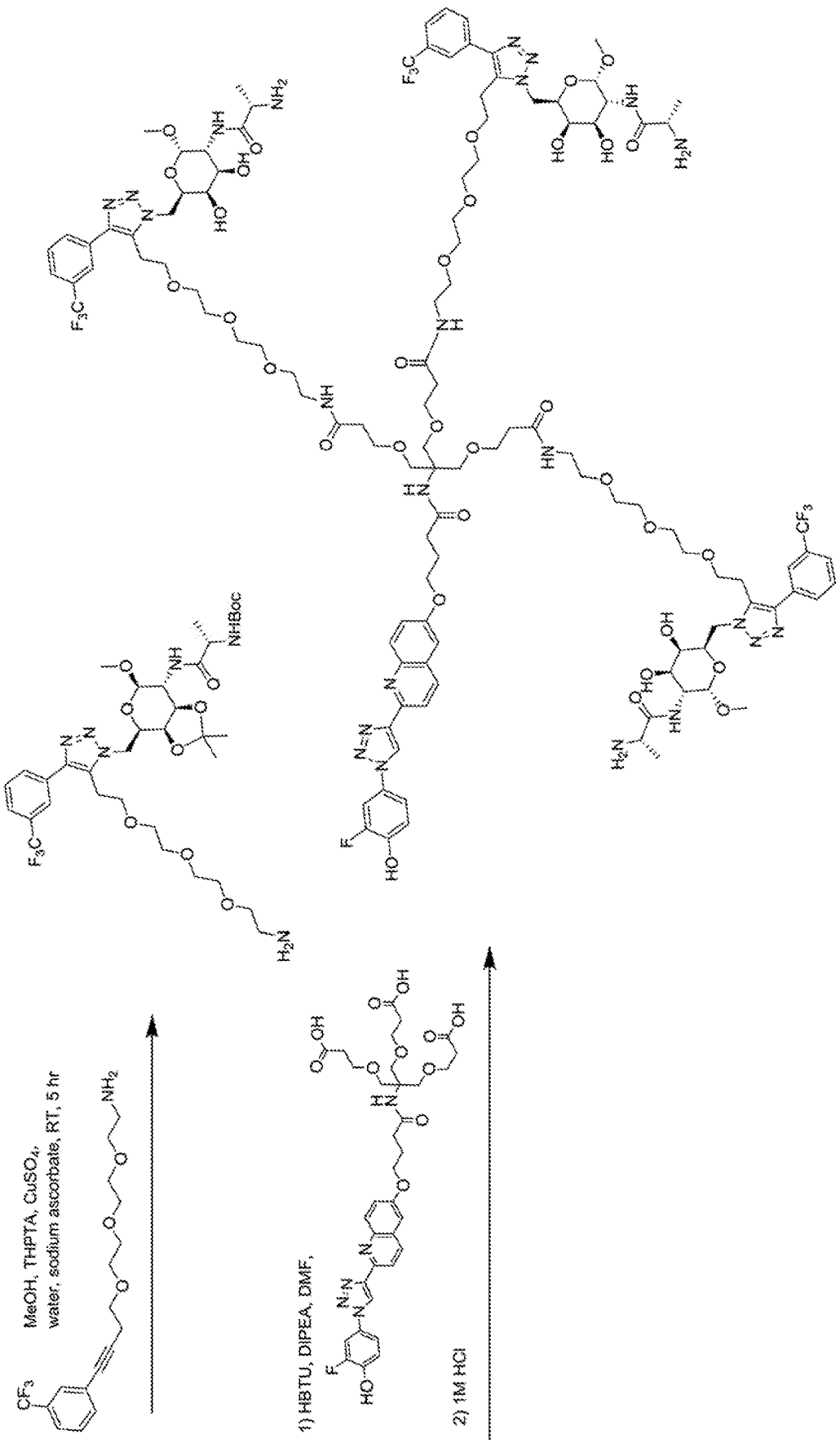
Figure 67:
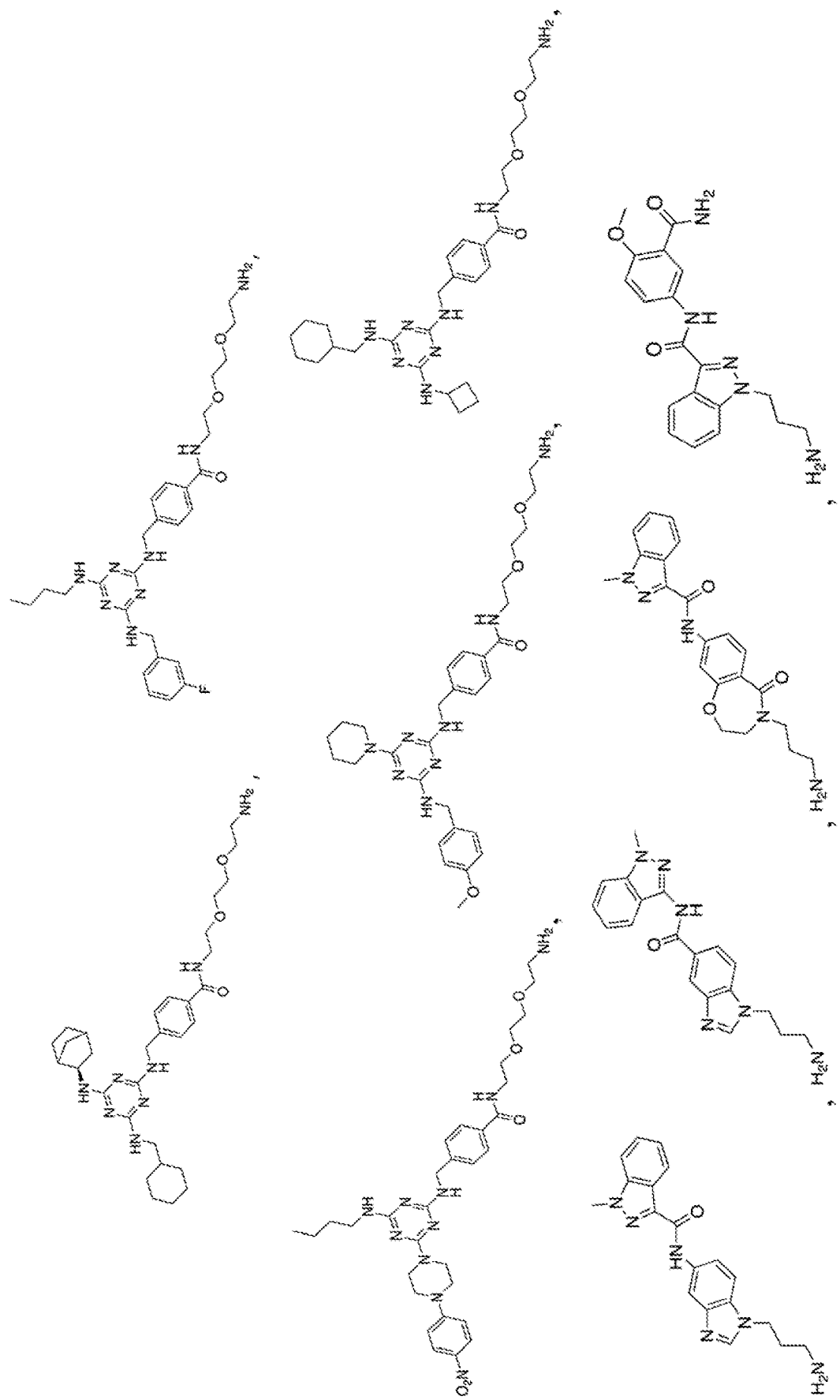
FIG. 67 shows exemplary IgGBM groups each of which is covalently attached to a [CON] group, a [LINKER] group or a [ASGPRBM] group through an amine group, preferably a primary or secondary alkyl amine group which is optionally substituted on the amine group with a $C_1$-$C_3$ alkyl group.
Figure 67:
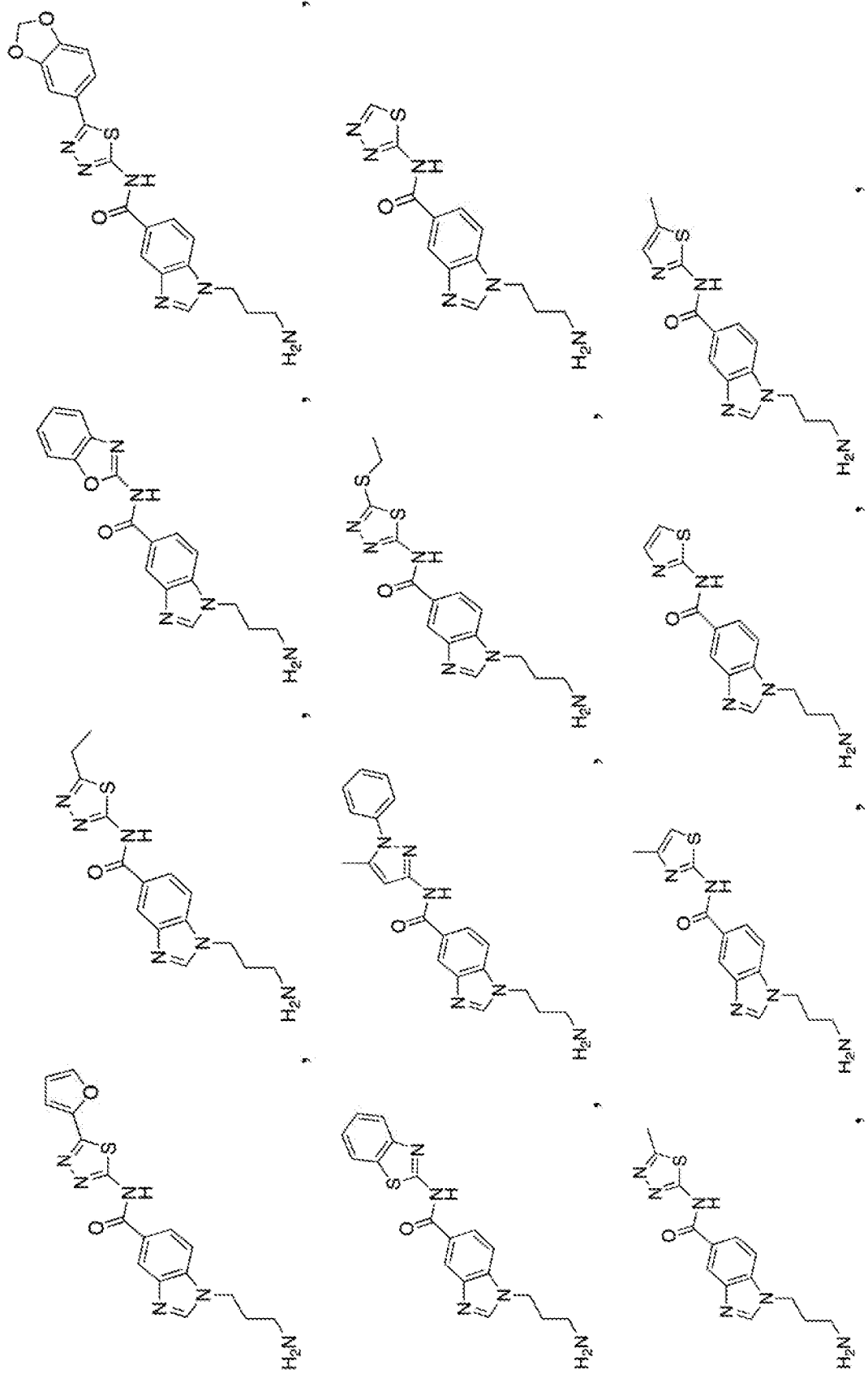
Figure 67:
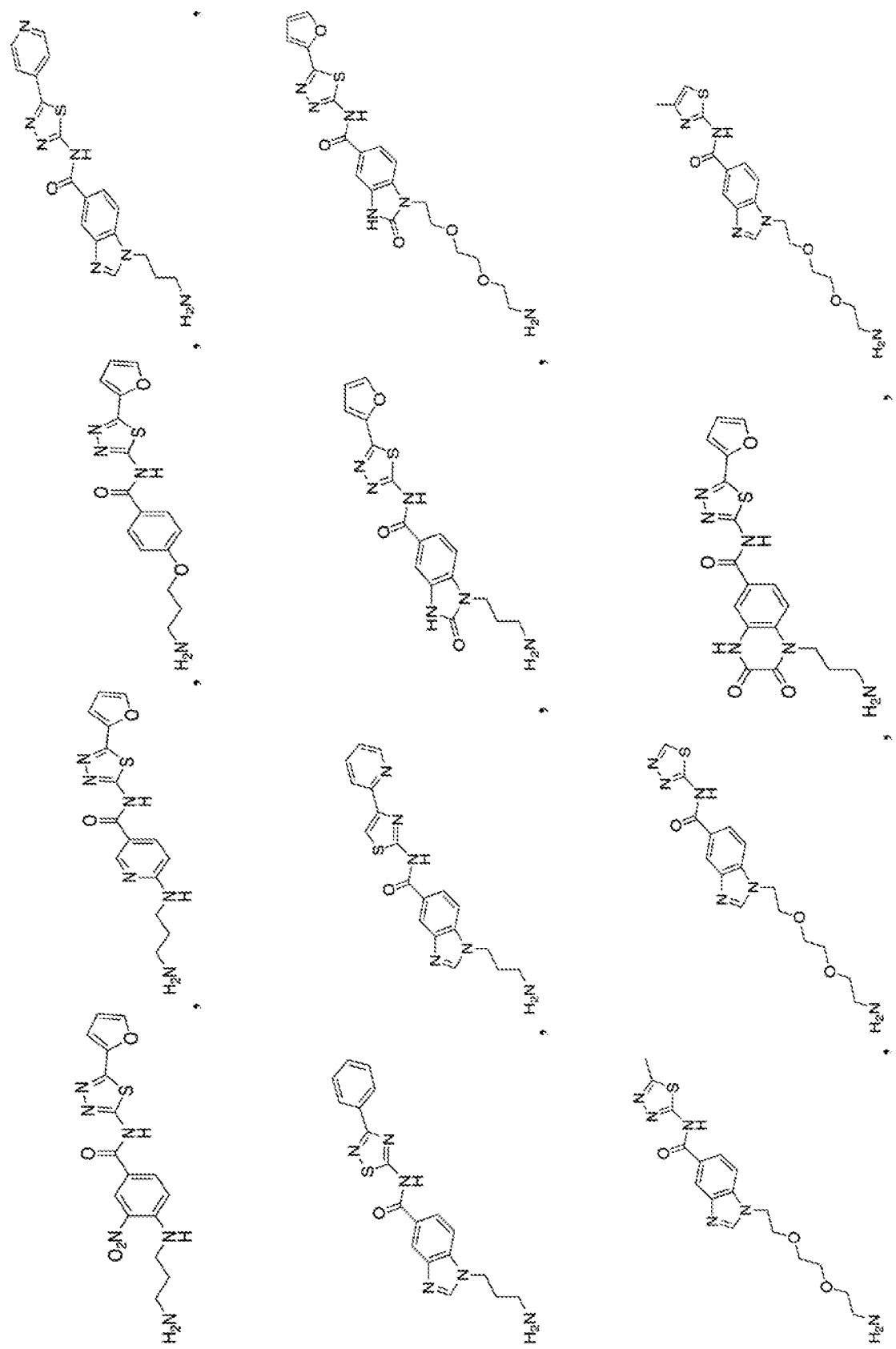
Figure 67:
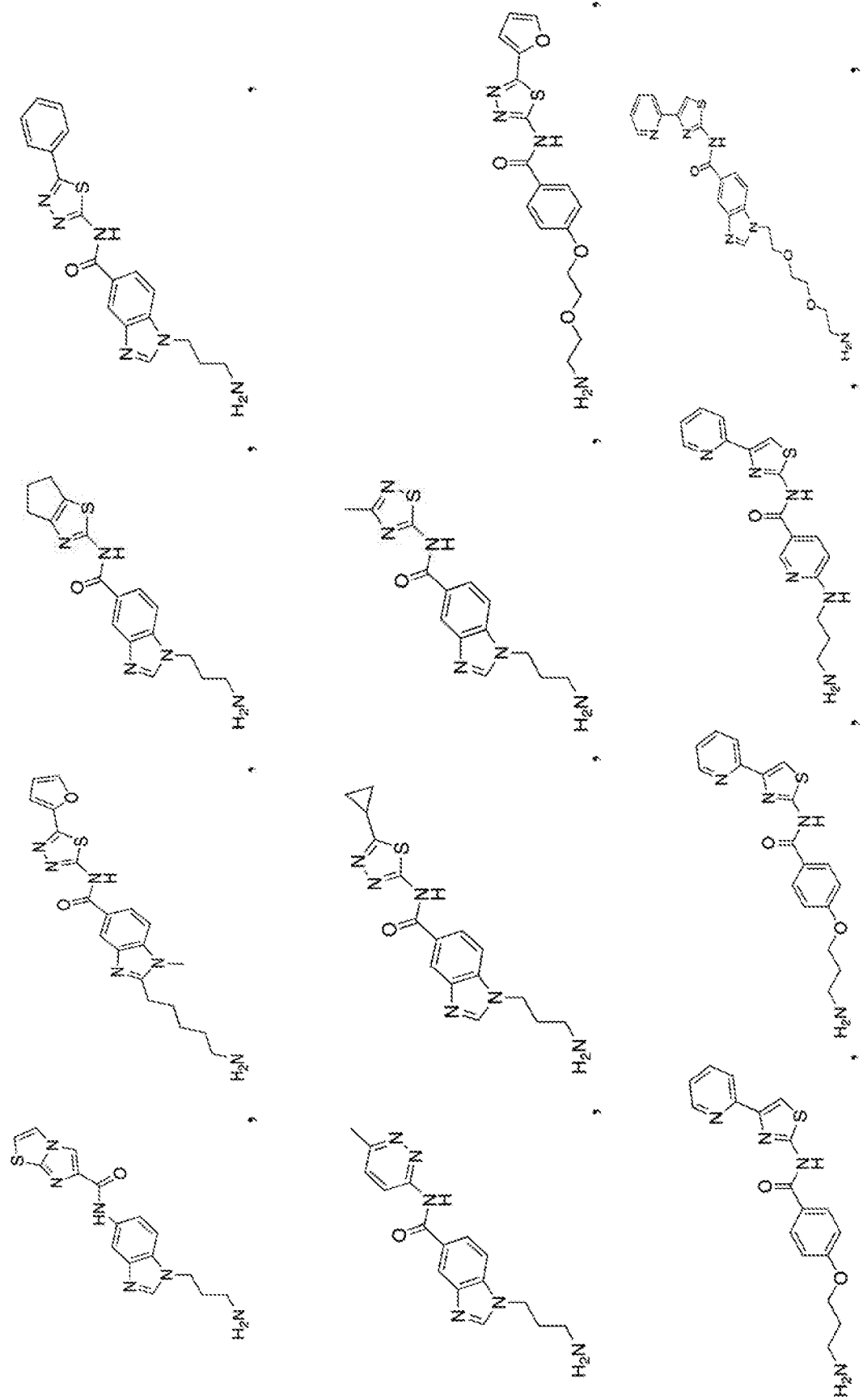
Figure 67:
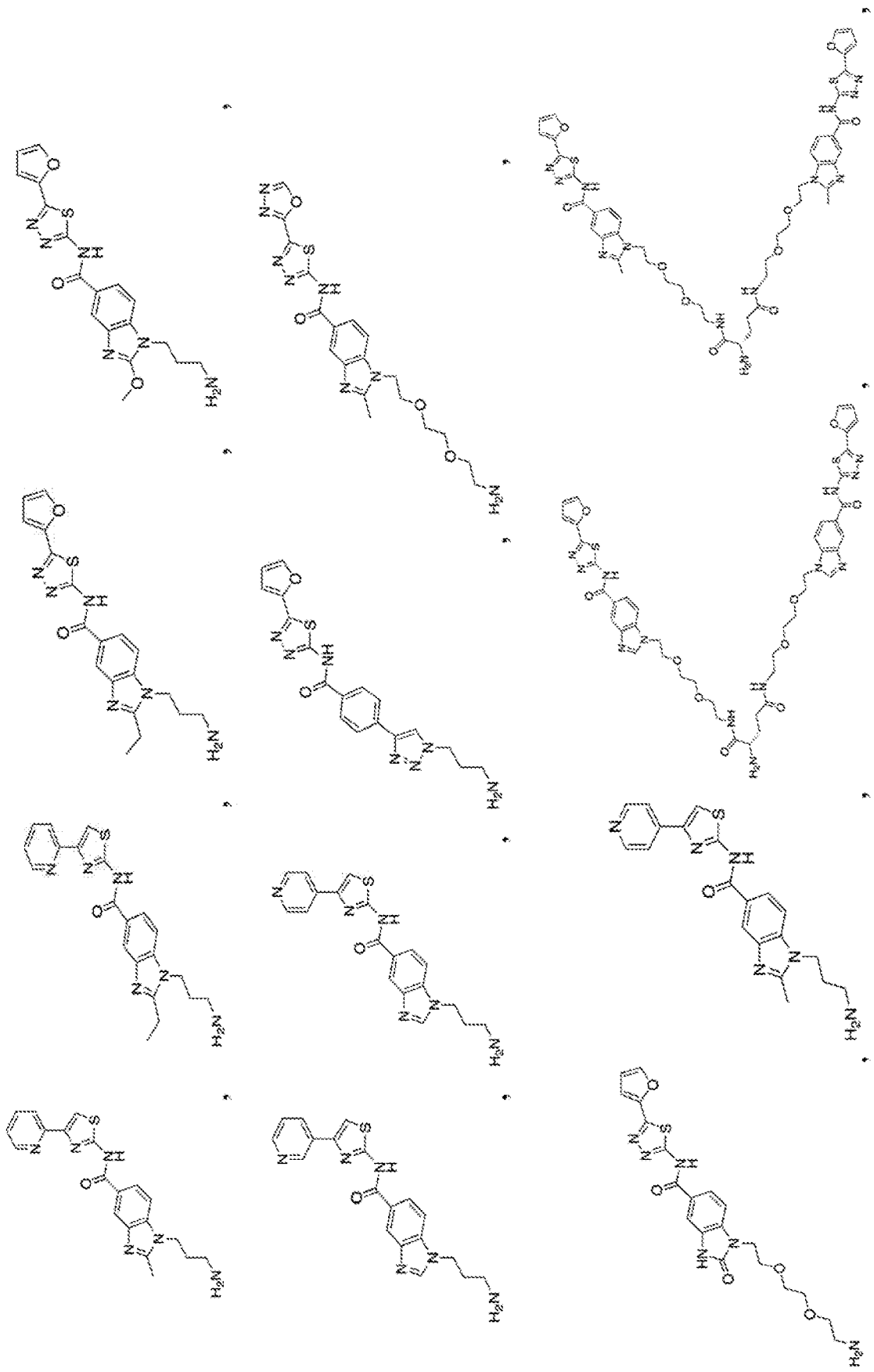
Figure 67:
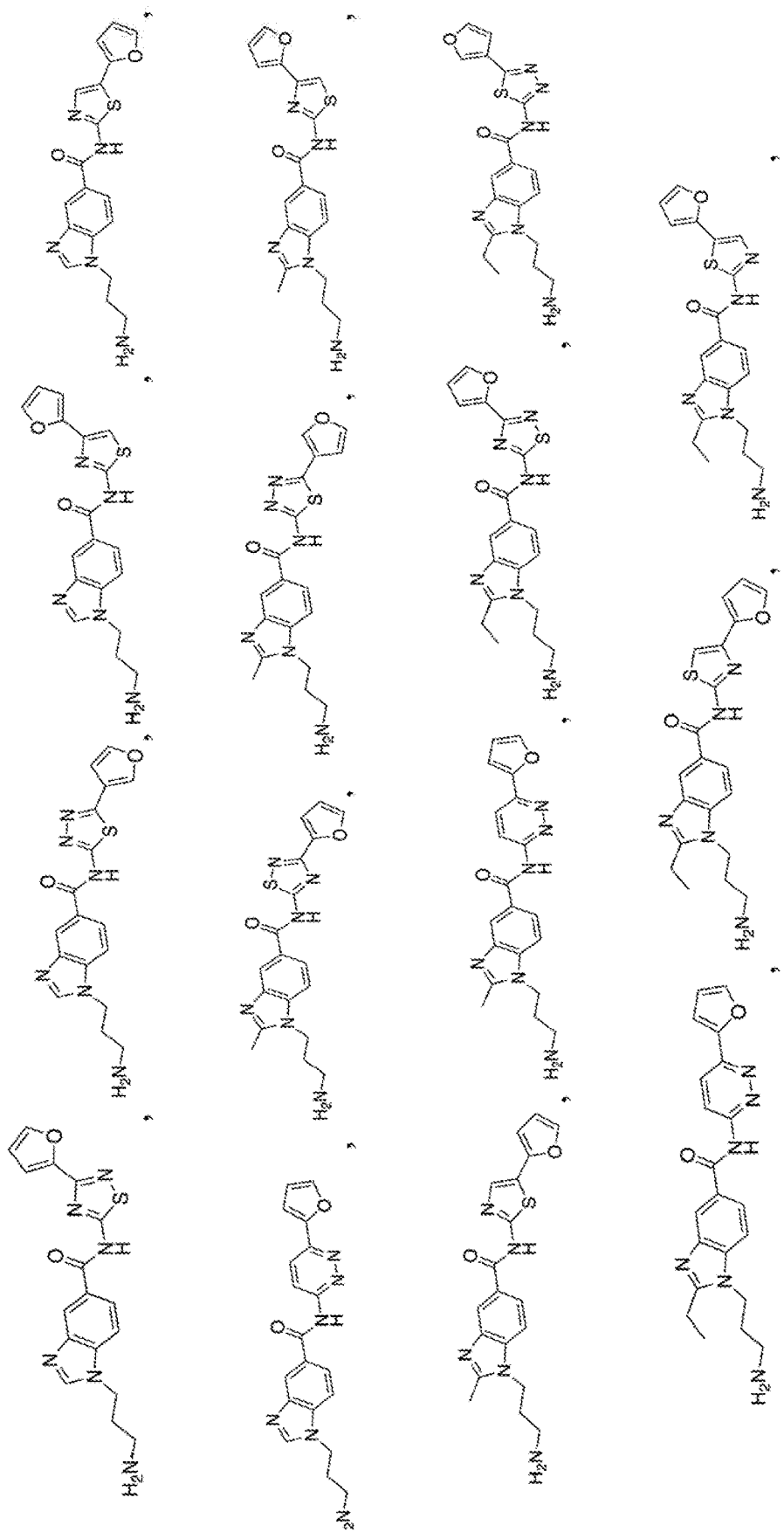
Figure 67:
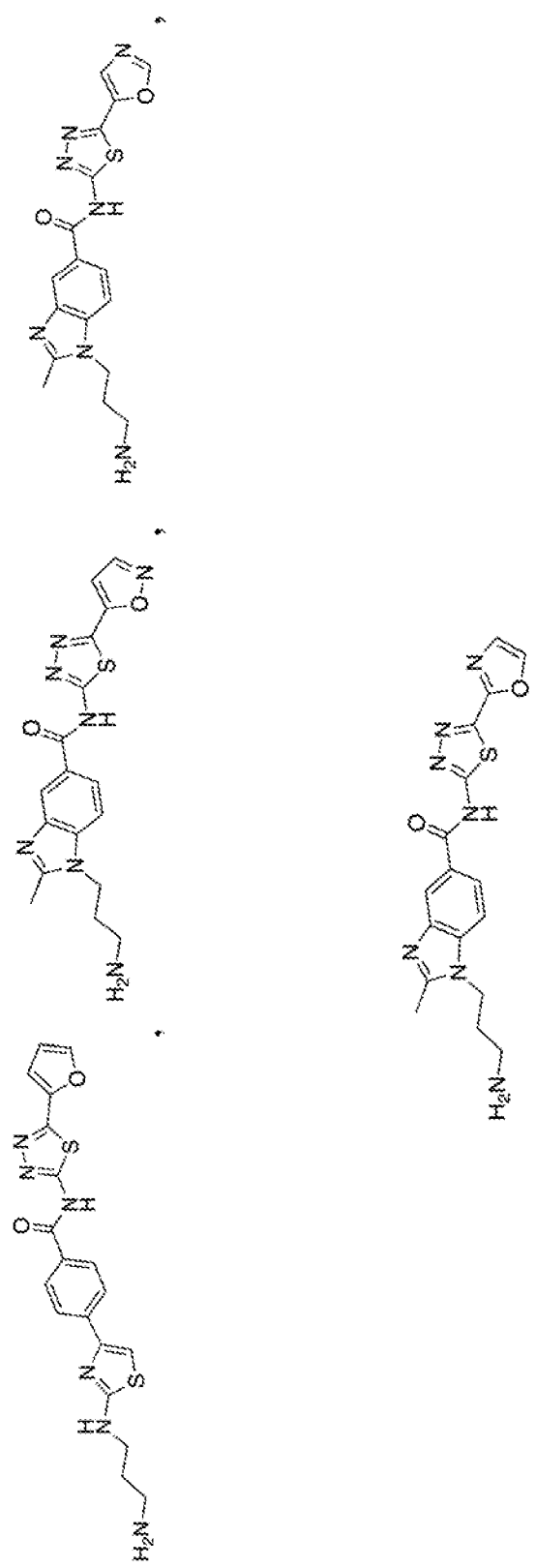
Figure 68:
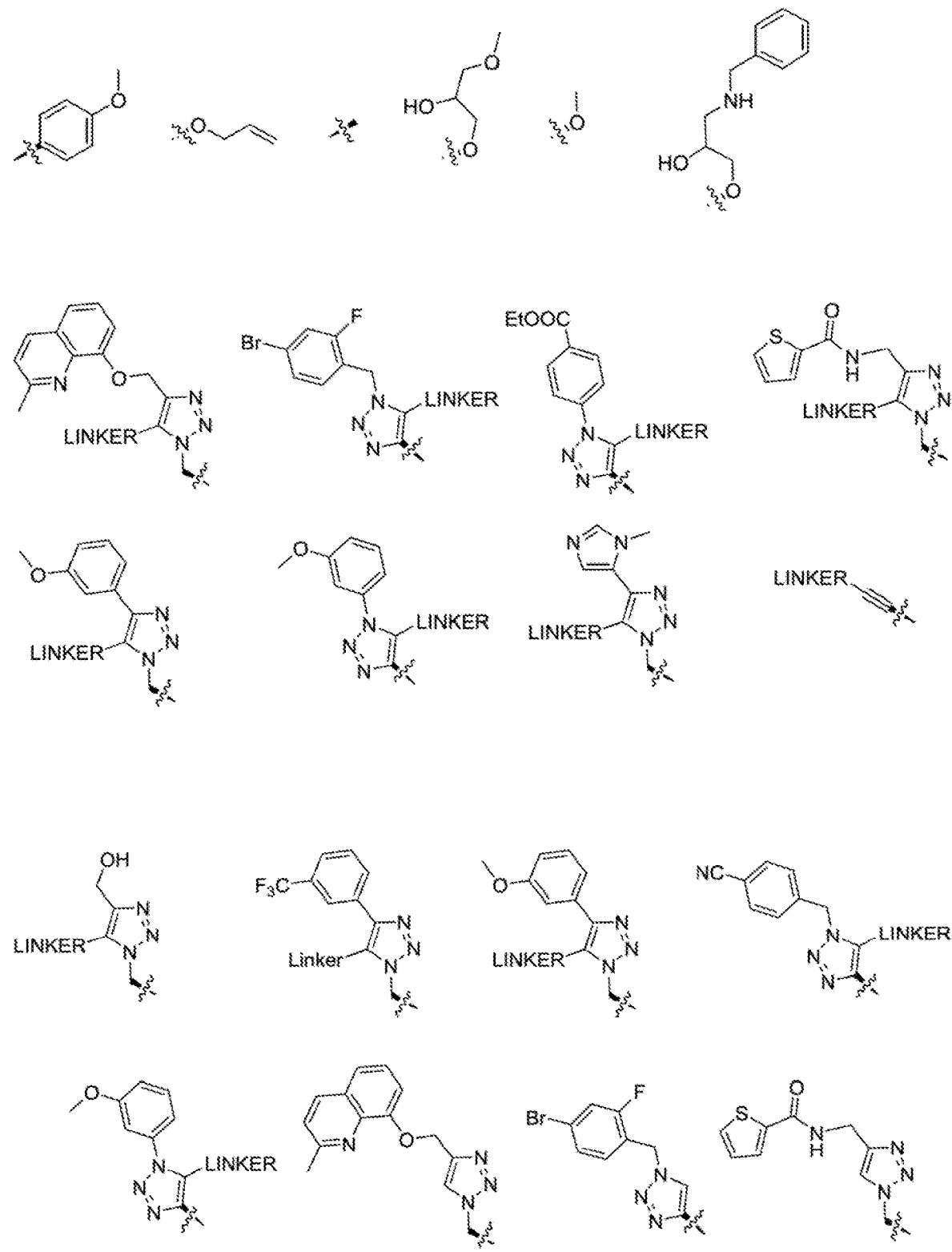
FIG. 68 shows exemplary $R_1$ and $R_3$ substituents on ASGPRBM groups as otherwise described herein.
Figure 68:
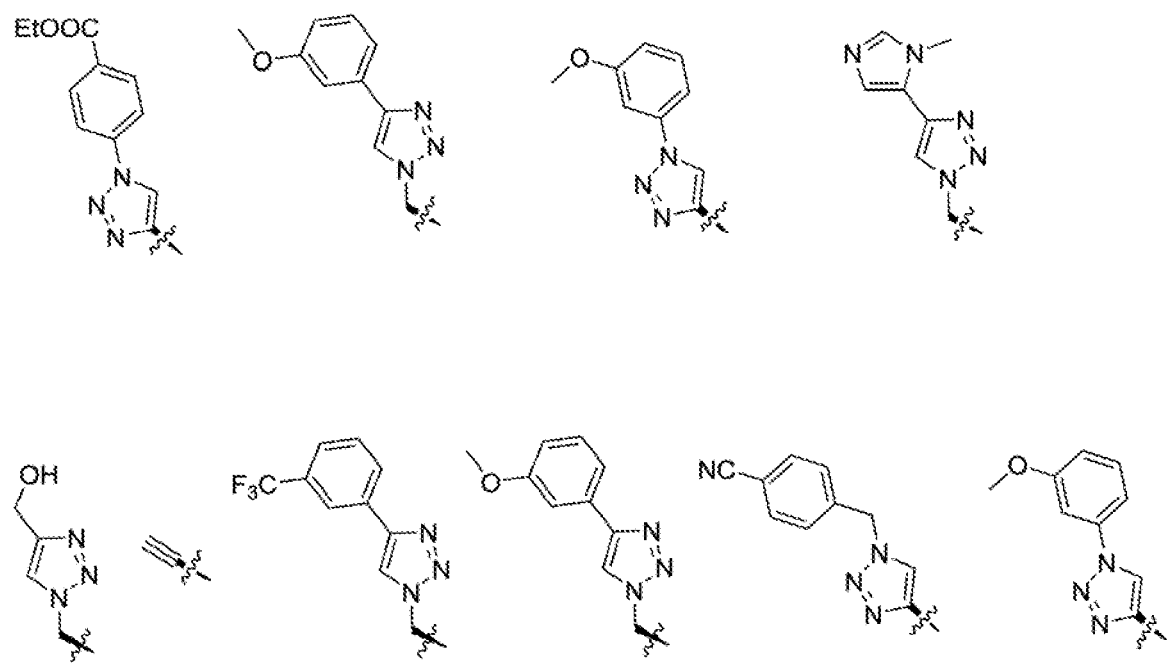

FIG. 51 shows the synthesis of compound MIF-21-3, which was synthesized using procedures analogous to compounds described above.

FIGS. 52-66 show the synthesis of a number of MIF-binding compounds with various ASGPRBM moieties. These are synthesized through methods analogous to those laid out above.

Examples

Proper protein section and turnover is a necessary process for maintaining homeostasis. Newly synthesized proteins targeted for secretion are first trafficked to the endoplasmic reticulum, where they are post-translationally modified with N-linked glycan chains terminating in sialic acids(1). As proteins age, terminal sialic acid residues are removed by circulating endogenous glycosydases(2). This natural protein aging process unmasks galactose and N-acetylgalactose (GalNAc) residues, which bind the asialoglycoprotein receptor (ASGPR) on the surface of hepatocytes(3-5).

The ASGPR is a C-type lectin that removes aged circulating proteins with exposed GalNAc residues from circulation by trafficking them to lysosomes. Multiple galactose or GalNAc residues displayed on the protein surface are necessary for high-affinity binding to—and subsequent endocytosis by—ASGPR(6, 7). Once these proteins are endocytosed, they are released from the ASGPR through depletion of calcium from the endosome and changes in binding site amino acid protonation changes due to a decrease in pH (12); the ASGPR is recycled back to the hepatocyte surface(13). Endocytosed proteins are trafficked to late endosomes, which are fused with lysosomes. Lysosomal proteases then degrade endocytosed proteins, permanently removing them from circulation(14).

Non-glycosylated proteins are not known to be natural target for the ASGPR. One such protein is macrophage inhibitory factor (MIF), a 12.5 kDa protein with possible catalytic activity (15). Genetic depletion or antibody neutralization of MIF has been shown to have positive results in models of sepsis (16), multiple schlorosis (17), rheumatoid arthritis (18), and burn recovery (21). We propose a bifunctional molecule for degrading circulating MIF that takes advantage of ASGPR as an entryway for proteins into the endosomal-lysosomal degradation pathway. The bicyclic ASGPR-binding molecules in MIF-AcF2 and MIF-AcF3 have been reported previously as high affinity binders for the ASGPR (22, 23).

Biological Data

The compounds according to the present invention were tested to determine their biological activity. Active compounds are shown in FIGS. 1, 7 and 13 hereof. The results of the biological experiments are described herein below.

FIG. 1 shows representative compounds according to the present invention. Note that the figure discloses compound 3w (negative control for MIF inhibition), MIF-NVS-PEGnGN3, MIFGN3, MIF-PEGnGN3, MIF-AcF3-1, MIF-AcF3-2 and MIF-AcF3-3. Note that n in the PEG linker preferably ranges from 1-12, 1 to 10, 2 to 8, 2 to 6, 2 to 5 or 1, 2, 3 or 4.

Figure 2:
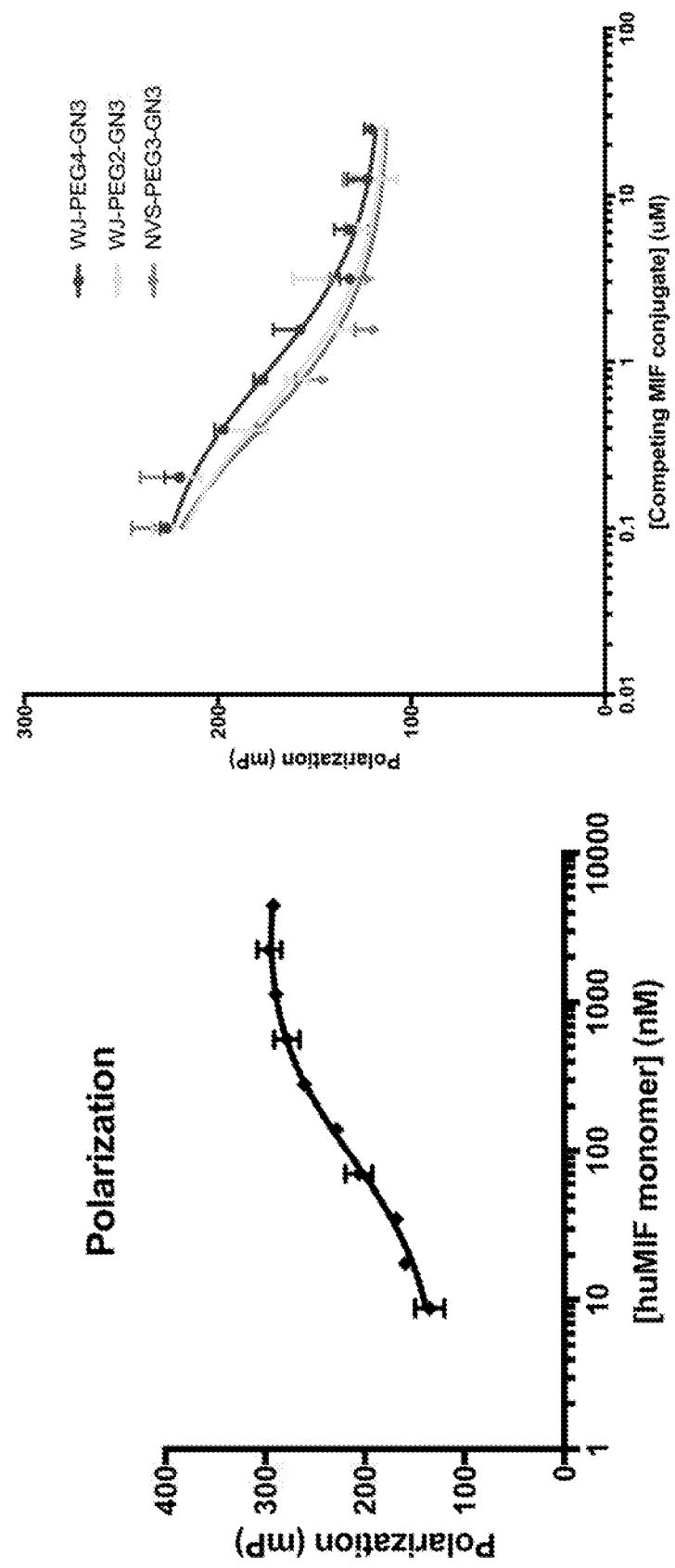
FIG. 2 shows fluorescence polarization data of MIF-FITC binding to human MIF, indicating that our MIF-binding moiety binds MIF. Bifunctional molecules WJ-PEG4-GN3, WJ-PEG2-GN3, and NVS-PEG3-GN3 bound competitively with MIF-FITC, indicating that the bifunctional molecules maintain the ability to bind human MIF.

In an experiment the results of which are shown in FIG. 2, A. fluorescence polarization data of MIF-FITC binding to human MIF indicates that the MIF-binding moiety of the present invention binds MIF. B. Bifunctional molecules WJ-PEG4-GN3, WJ-PEG2-GN3, and NVS-PEG3-GN3 bound competitively with MIF-FITC, indicating that the bifunctional molecules maintain the ability to bind human MIF.

Figure 3:
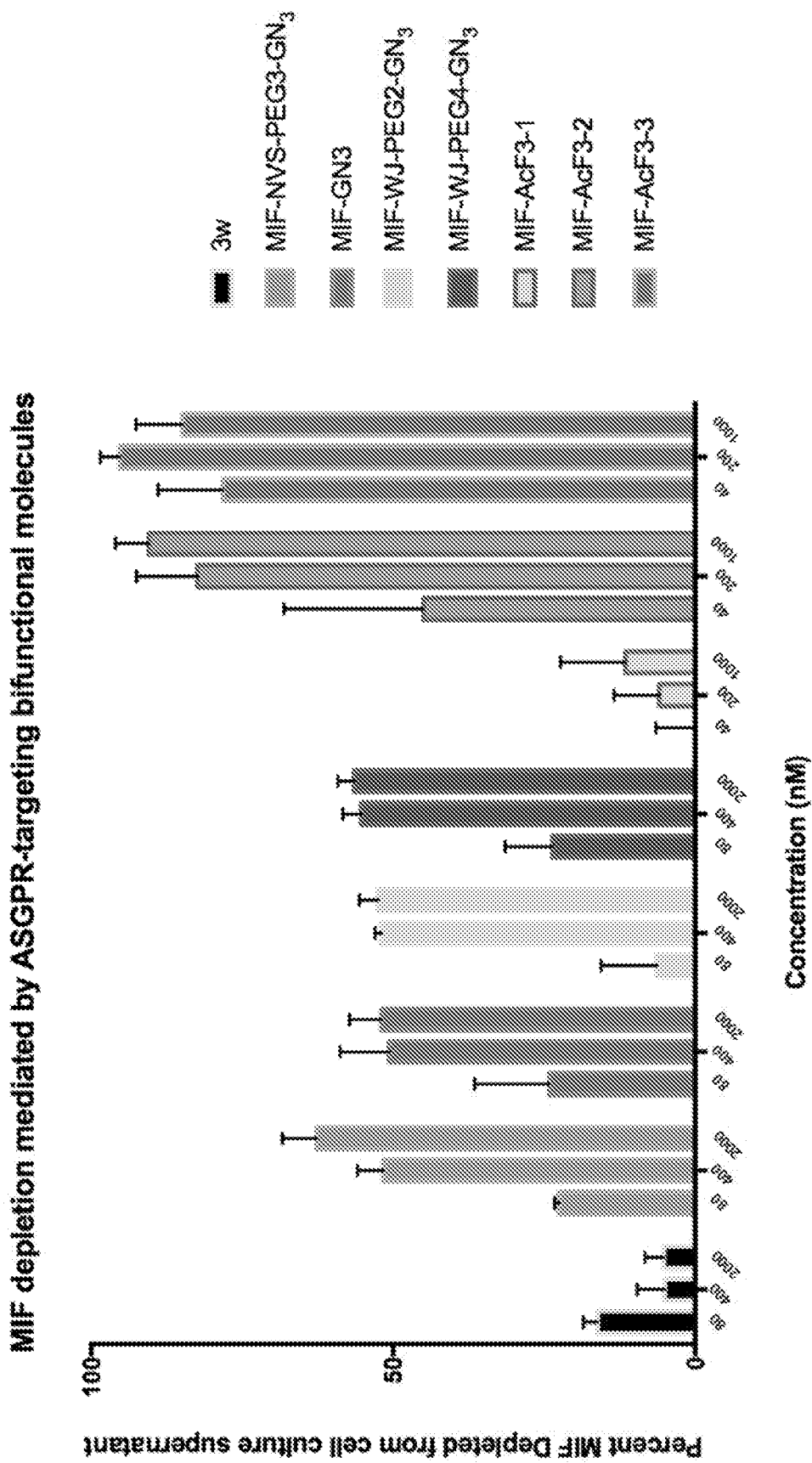
FIG. 3 shows that bifunctional molecules are able to deplete human MIF from the supernatant of culture HepG2 cells.

In an experiment the results of which are presented in FIG. 3, bifunctional molecules were able to deplete human MIF from the supernatant of culture HepG2 cells. Briefly, human MIF (100 nM) was added to cell culture media in the presence of negative control MIF inhibitor 3w as well as bifunctional molecules MIF-NVS-PEGn-GN3, MIF-GN3, MIF-PEGn-Gn3, MIF-AcF3-1, MIF-AcF3-2, and MIF-AcF3-3. All molecules utilized a known MIF-binding ligand. Experiments were performed in 96 well plates (approximate surface area 0.3 cm$^2$). HepG2 cells were grown to 90% confluency in RPMI media, then washed with PBS (2×) and treated with serum-free media (optimem+0.1% BSA, +Pen/Strep) containing 100 nM huMIF (Cayman Chemical) and compounds (when applicable). Compounds were diluted from 1 mM stock solutions in DMSO. After 24 hours, a sample of the supernatant (2 uL) was collected, diluted 1:100, and analyzed for MIF content by sandwich ELISA (and incubated for 24 hours in the presence or absence of compound). Remaining MIF levels were determined by sandwich ELISA (biolegend monoclonal anti-MIF and biotinylated anti-MIF antibodies). Data represents the average of at least 3 biological replicates, and error bars represent a standard deviation. After 24 hours, up to 95.3% of the MIF had been depleted from cell culture media (in the case of MIF-AcF3-3).

Figure 4:
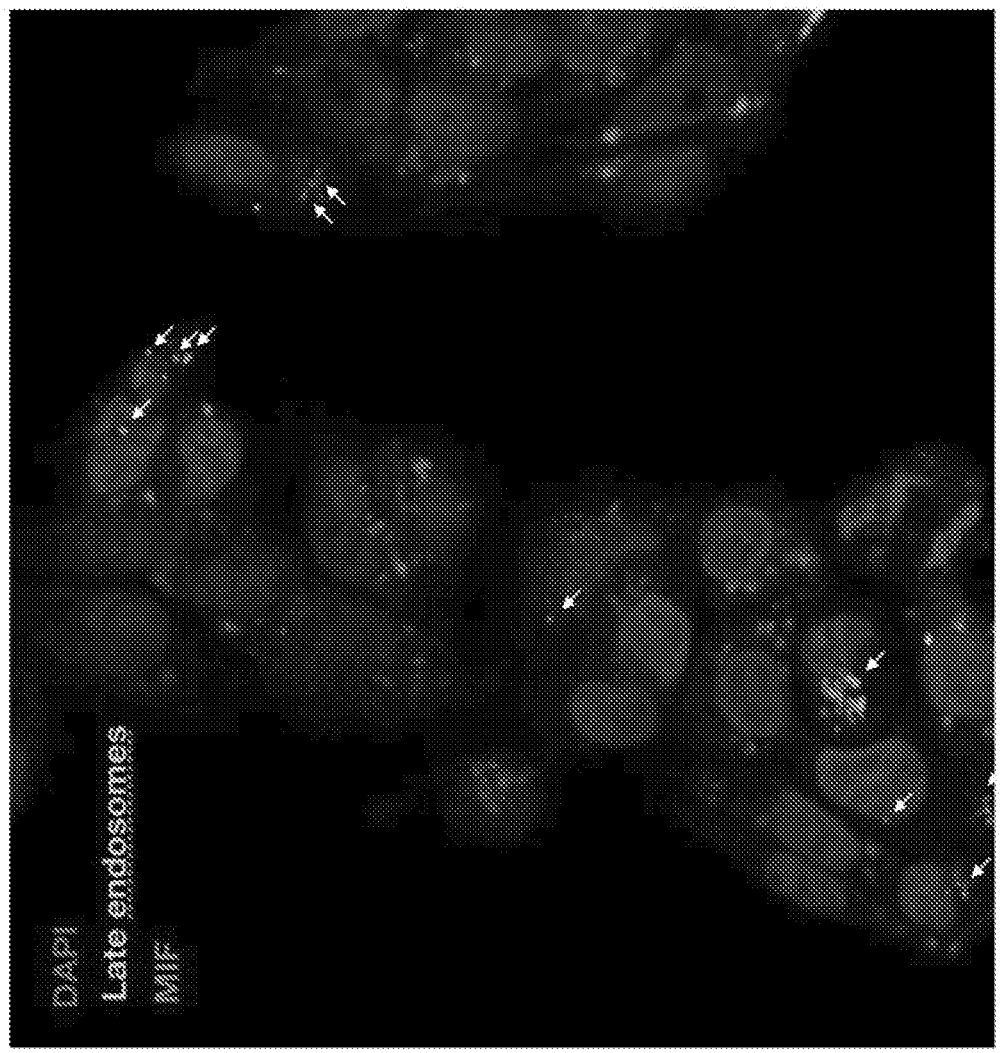
FIG. 4 shows that MIF internalized by HepG2 cells is trafficked to lysosomes.

FIG. 4 shows the results of an experiment to determine whether or not MIF internalized by HepG2 cells is trafficked to lysosomes. In this experiment, cells were incubated with rhuMIF (Cayman) at a concentration of 100 nM with 200 nM MIF-GN$_3$. After 12 hours, cells were fixed with formaldehyde, permeabilized, and probed with anti-Lamp2 antibody (mouse monoclonal, Abeam), polyclonal rabbit anti-MIF antibody (Thermo) and with Alexa-488 labeled anti-mouse antibody and Alexa 568-labeled anti-rabbit antibody, evidencing internalization in lysosomes.

Figure 5:
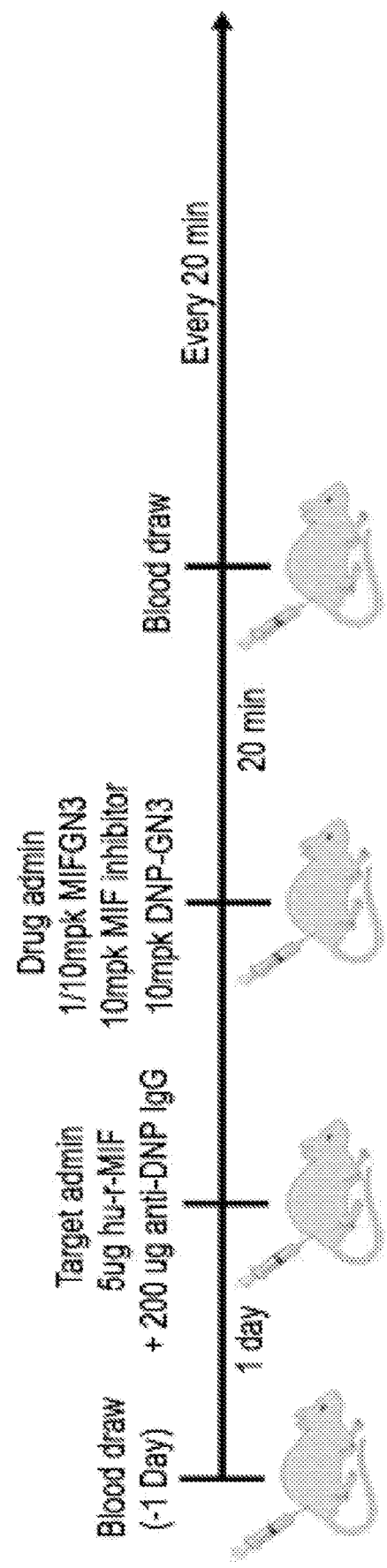
FIG. 5 shows that MIF-GN3 mediates the depletion of injected human MIF from mice.
Figure 5:
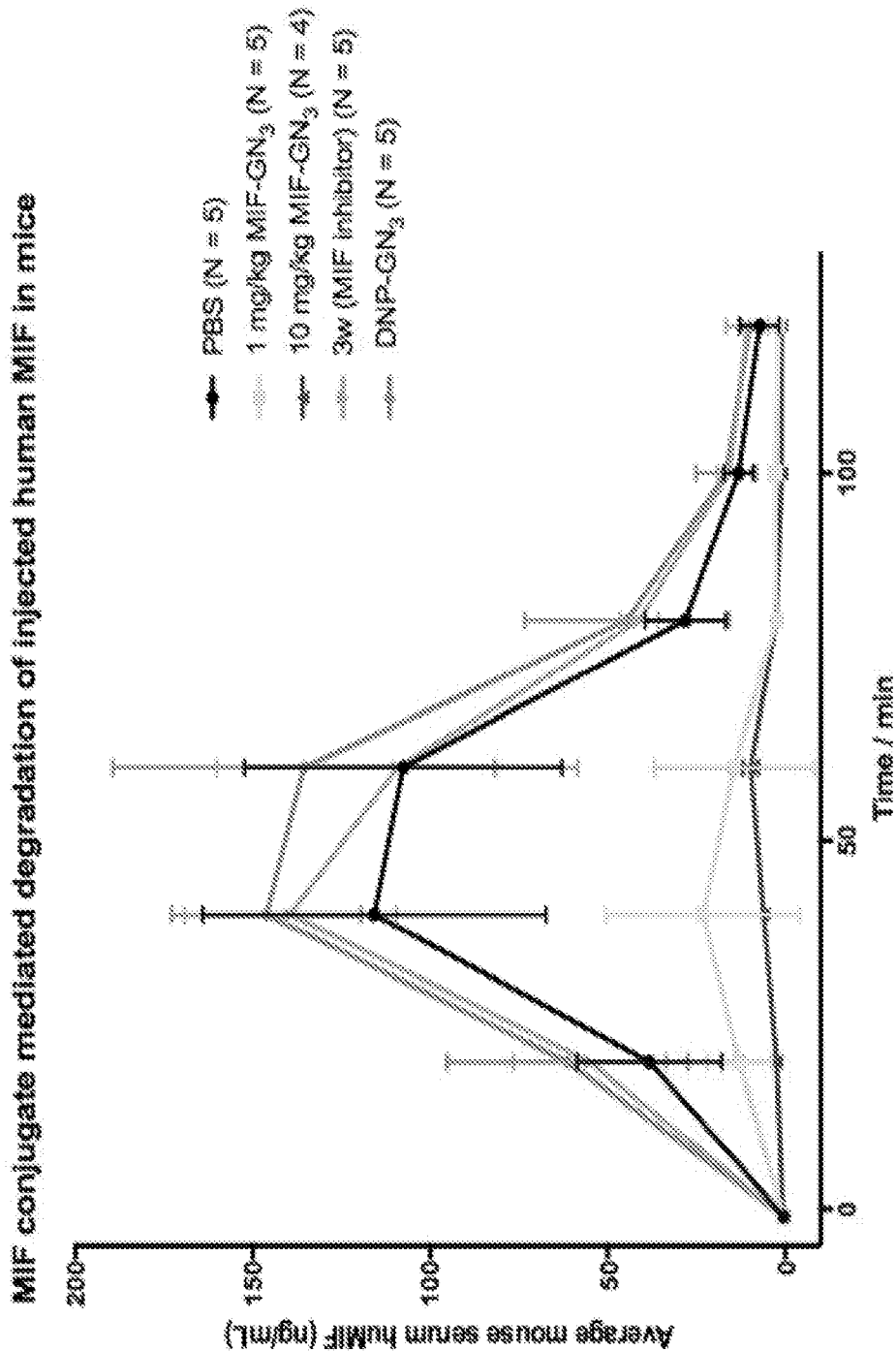
Figure 5:
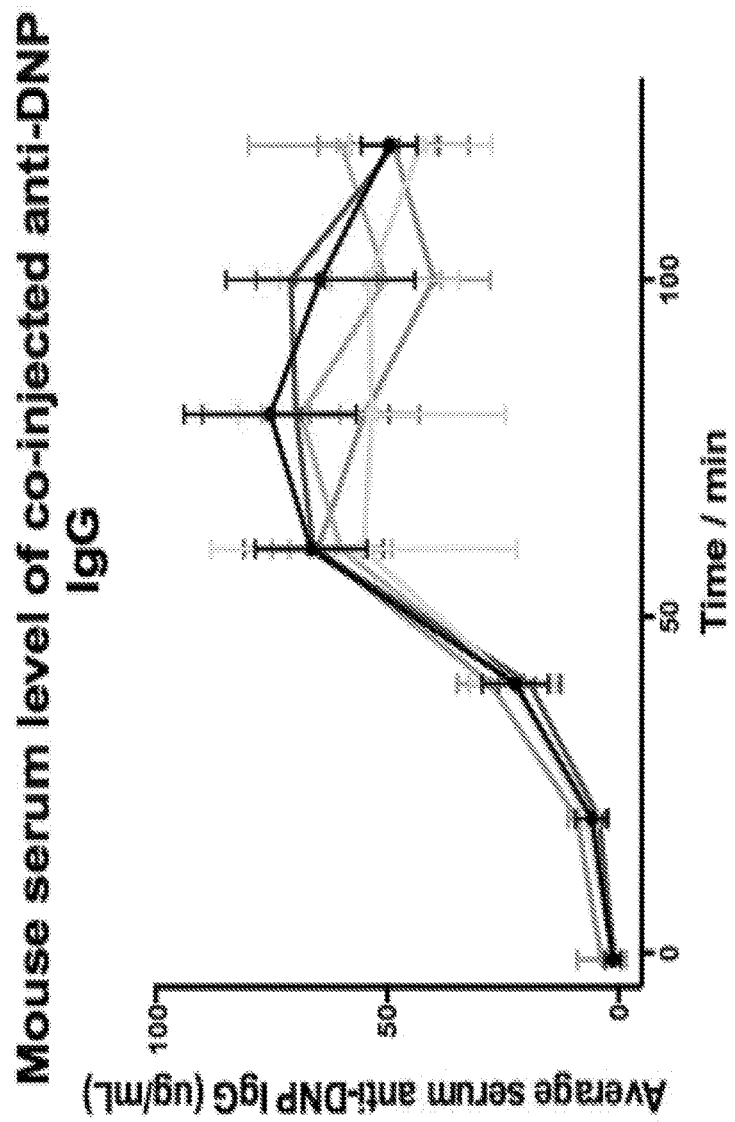

FIG. 5 shows that MIF-GN$_3$ mediates the depletion of injected human MIF from mice. Human MIF has a half-life of approximately 40 minutes in mice. In this experiment, human recombinant MIF (Cayman chemical) was co-injected into mice with an anti-DNP IgG, which was used as an injection positive control. In particular, nude mice were injected with 5 µg recombinant human MIF and 200 µg anti-DNP IgG as an injection control (FIG. 4). MIF-GN$_3$ was then injected at the concentration shown and blood drawn every twenty minutes over the course of two hours. Serum was diluted 1:100 and analyzed for MIF content by sandwich ELISA (biolegend monoclonal anti-MIF and biotinylated anti-MIF antibodies). The levels of the injected IgG were not significantly different between testing groups. In the mice treated with MIF-GN$_3$, a moderate increase in huMIF levels up to 20 ng/ml was seen, while in mice injected with PBS negative control, serum levels of up to 150 ng/ml were observed, evidencing a substantial decrease in huMIF levels as a consequence of the administration of MIF-GN$_3$.

Figure 6:
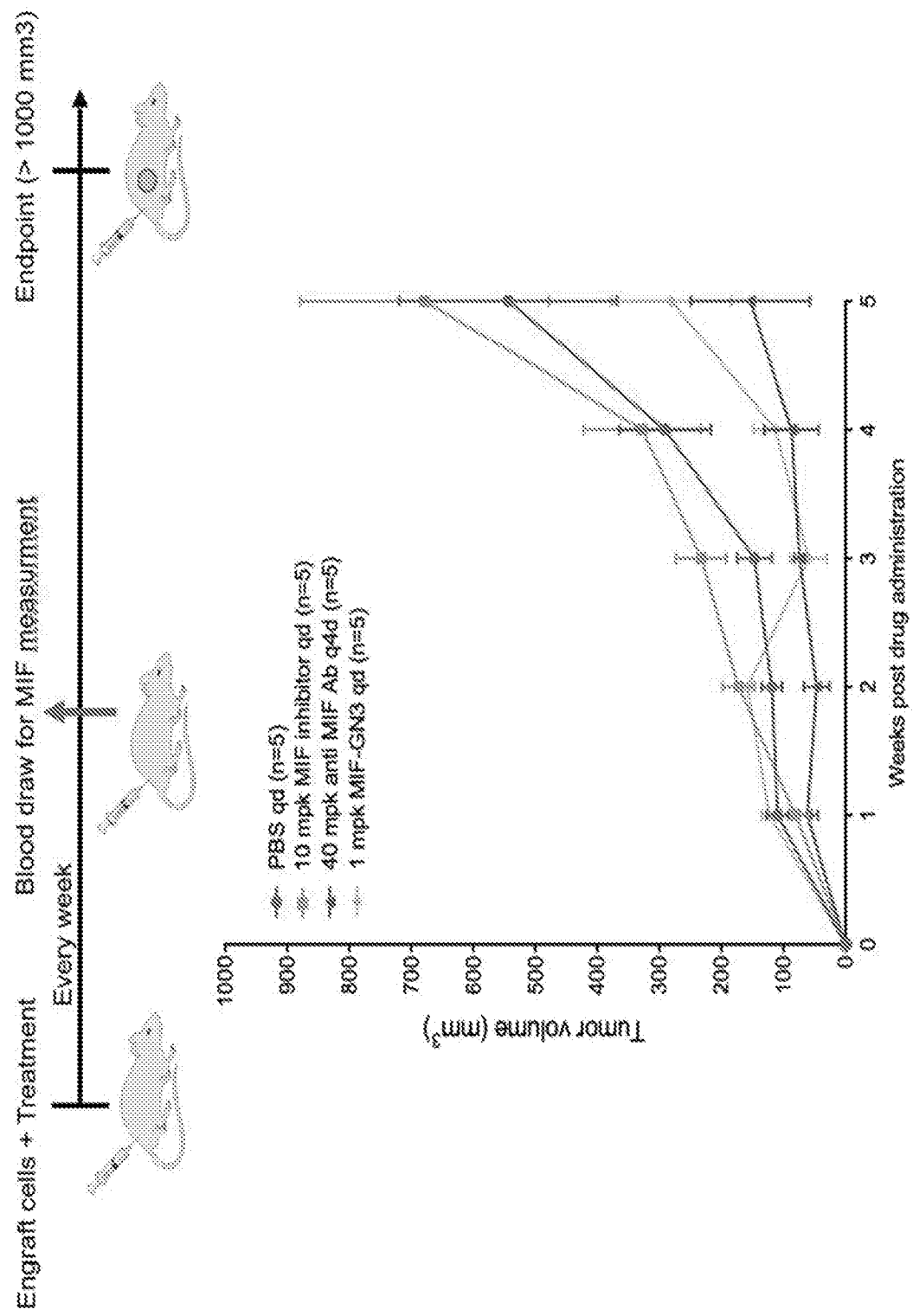
FIG. 6 shows that MIF-GN3 is able to delay tumor growth in a mouse model of prostate cancer.

FIG. 6 shows that MIF-GN$_3$ is able to delay tumor growth in a mouse model of prostate cancer. In this experiment, nude mice were engrafted with PC3 human prostate cancer cells. Treatment was then initiated immediately with either a non-bifunctional MIF inhibitor (3w), an anti-MIF antibody, or MIF-GN$_3$. MIF-GN$_3$ showed a slowing of tumor growth over the course of the experiment, comparable to the MIF-neutralizing antibody. 3w did not inhibit tumor growth, validating the necessity of degrading MIF for therapeutic efficacy.

FIG. 7 shows molecules DNP-GN3 and DNP-AcF3-3, which are bifunctional molecules that bind to anti-DNP IgG and ASGPR. These compounds were used in several of the experiments as described below.

Figure 8:
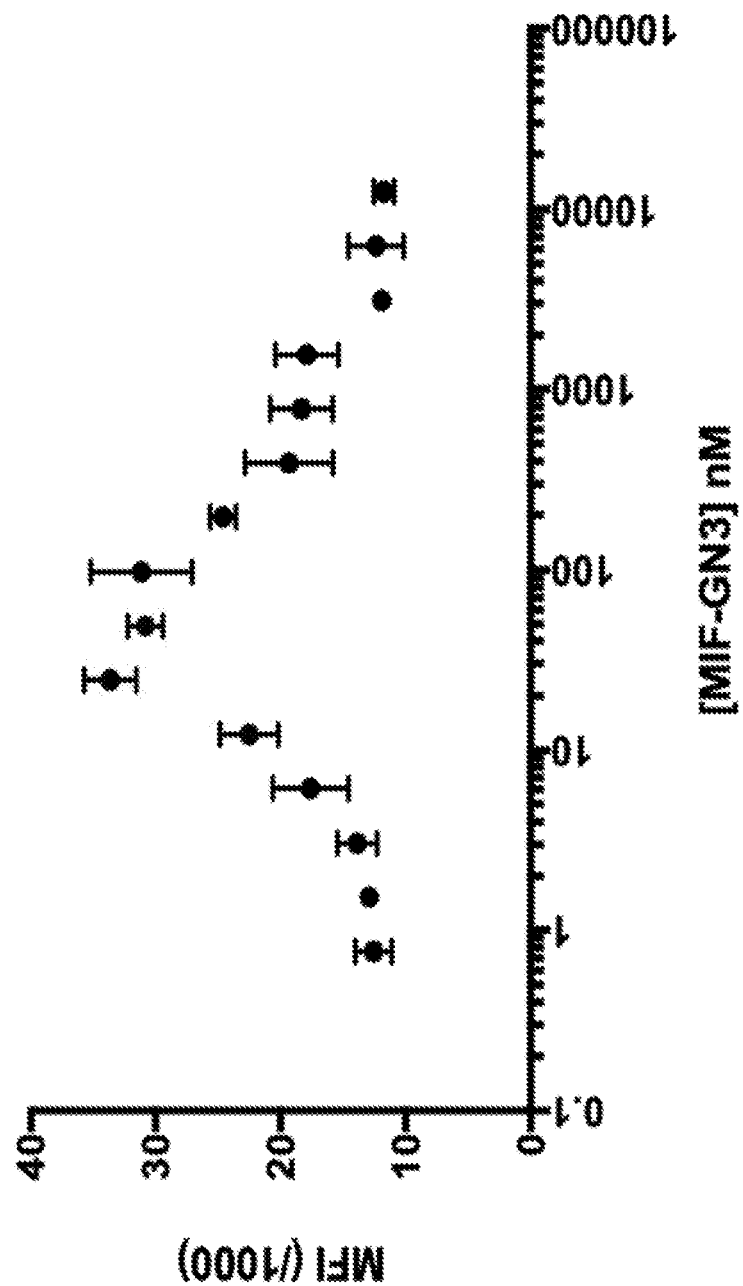
FIG. 8 shows that DNP-GN3 and DNP-AcF3-3 mediate the formation of a ternary complex between HepG2 cells and anti-DNP.
Figure 8:
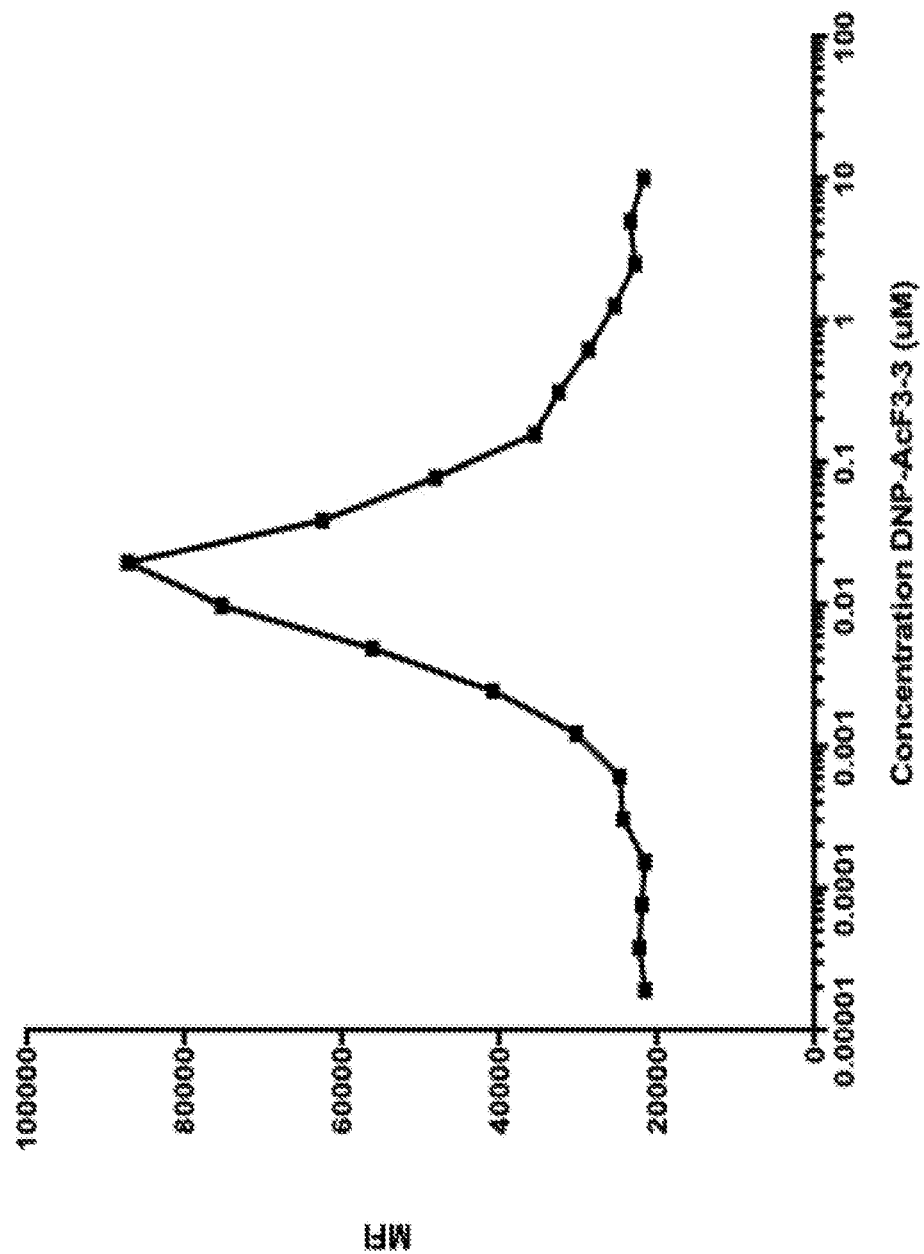

FIG. 8 shows that DNP-GN3 and DNP-AcF3-3 mediate the formation of a ternary complex between HepG2 cells and anti-DNP, thus validating the bifunctional character of the molecules. In this experiment, ASGPR-expressing HepG2 cells were incubated with bifunctional molecules and alexa-488 labeled anti-DNP (Thermo). The readout is mean fluorescence intensity of the cell population. Fluorescence was measured using a flow cytometer.

Figure 9:
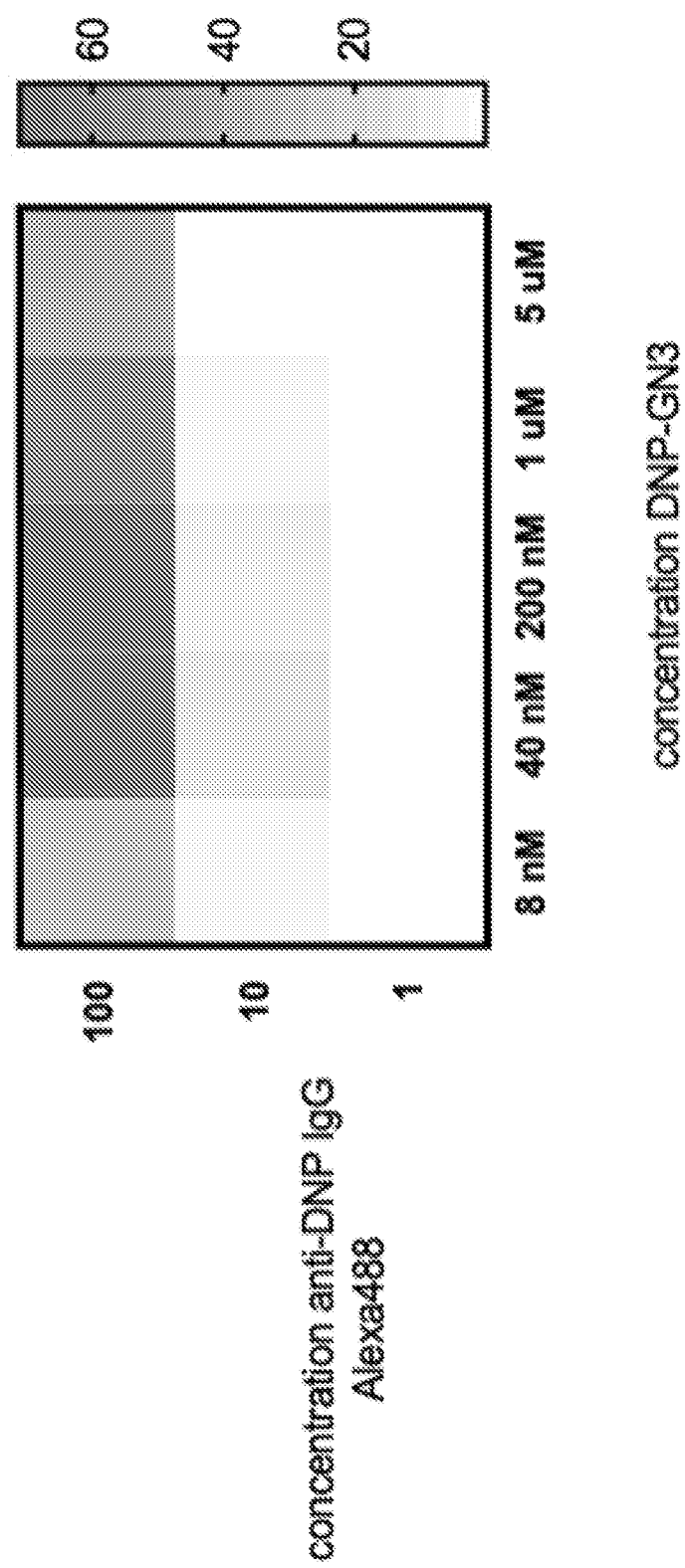
FIG. 9 shows that DNP-GN3 and DNP-AcF3-3 mediate the uptake of alexa 488-labeled anti-DNP by HepG2 cells.
Figure 9:
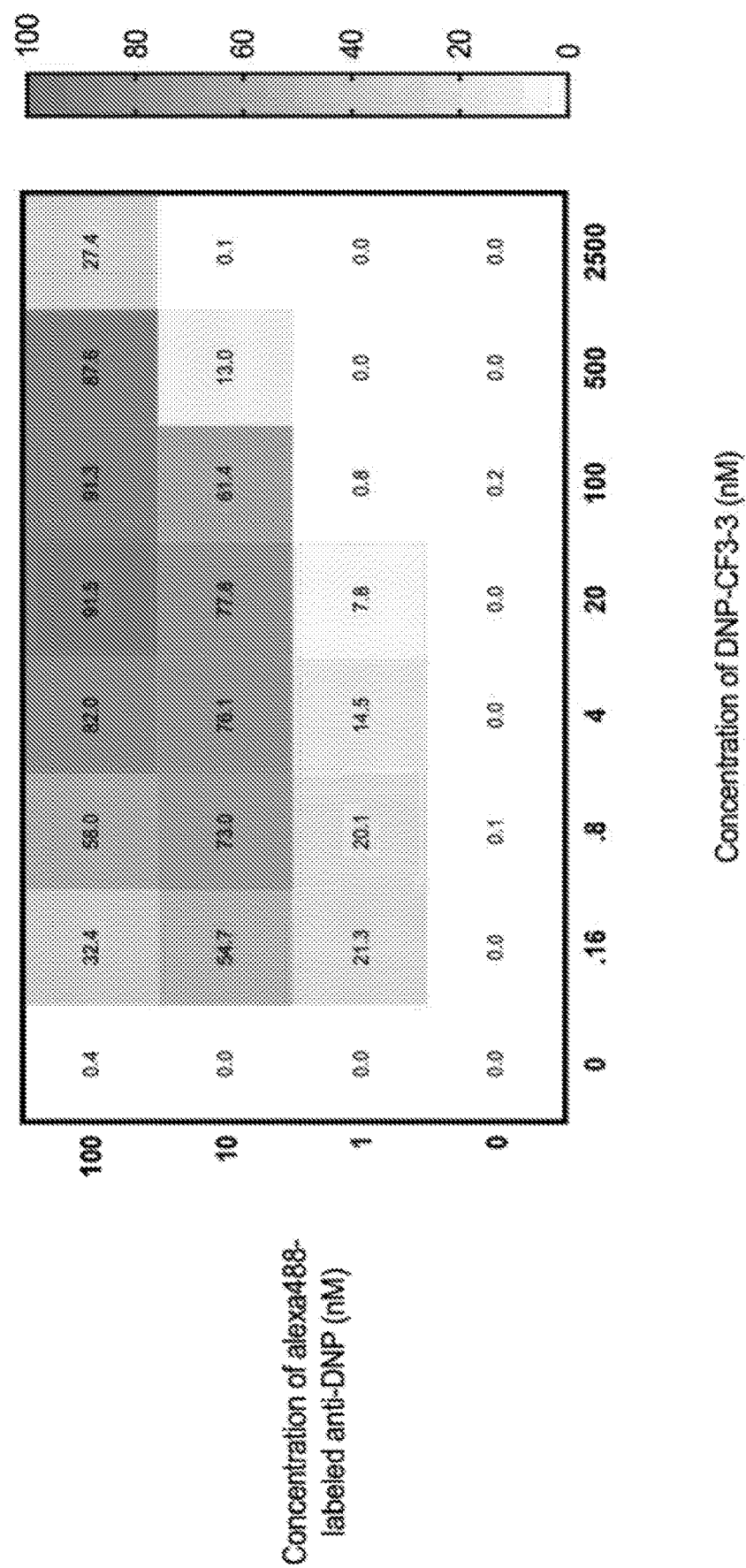

In a further experiment, the results presented in FIG. 9 show that DNP-GN3 and DNP-AcF3-3 mediate the uptake of alexa 488-labeled anti-DNP by HepG2 cells. The assay carried out in this experiment was as is described above for MIF uptake. Readout is percentage of Alexa 488-positive cells after 6 hours. Fluorescence was measured using a flow cytometer.

Figure 10:
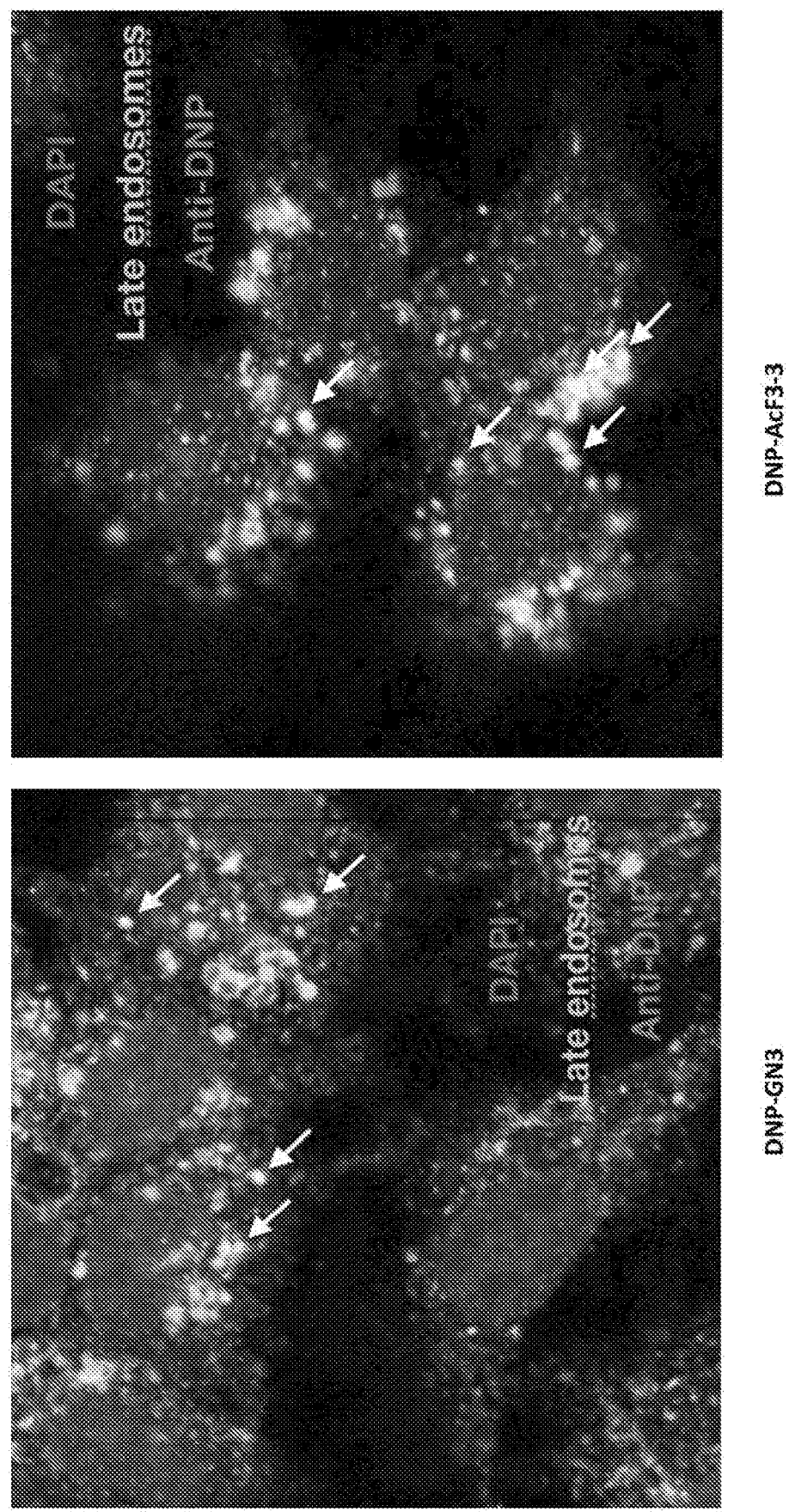
FIG. 10 shows that DNP-GN3 and DNP-AcF3-3 mediate the localization of alexa 568 labeled anti-DNP to late endosomes and lysosomes.

FIG. 10 shows that DNP-GN3 and DNP-AcF3-3 mediate the localization of alexa 568 labeled anti-DNP to late endosomes and lysosomes. This experiment was carried out as described above for the MIF colocalization studies.

Figure 11:
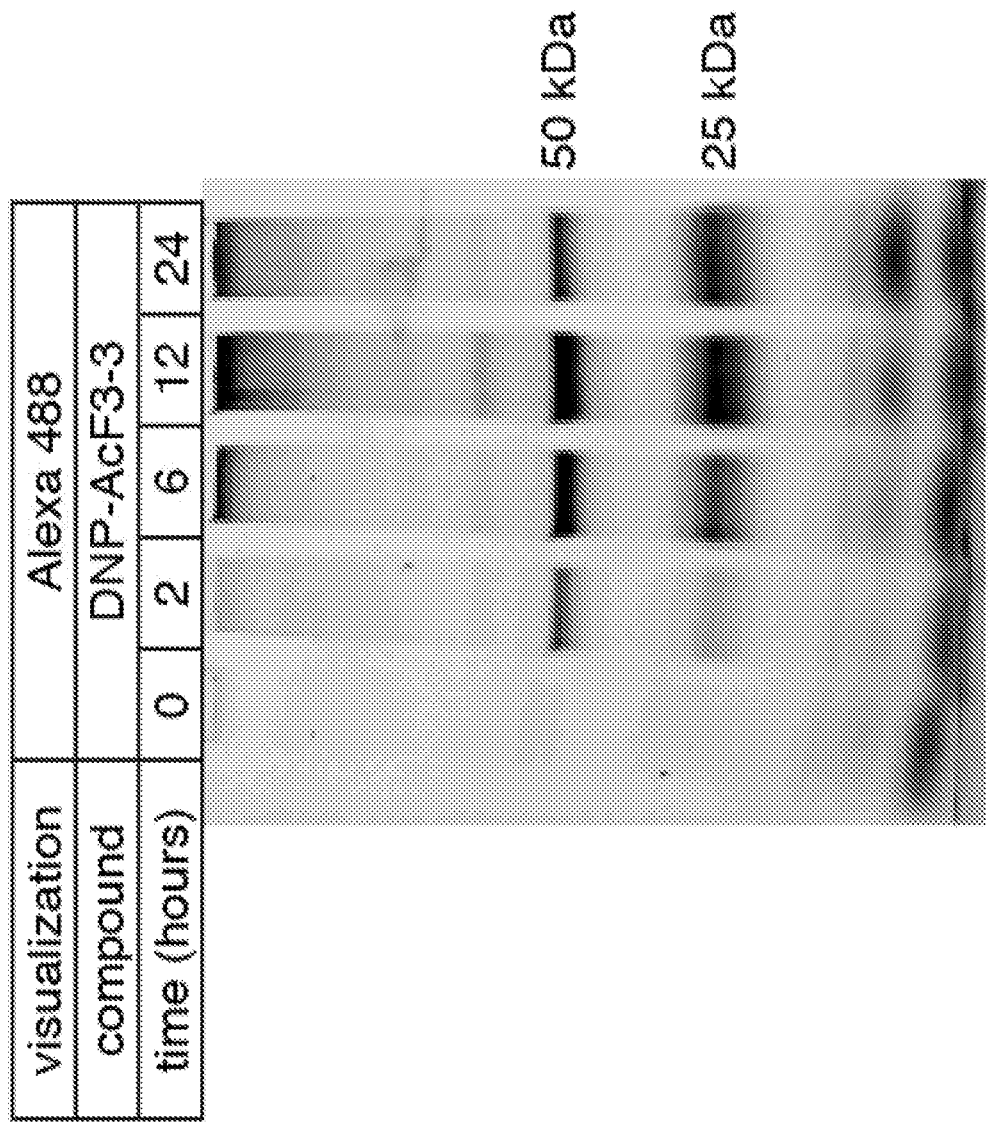
FIG. 11 shows that DNP-AcF3-3 mediates the degradation of alexa 488-labeled anti-DNP in HepG2 cells.

The experimental results presented in FIG. 11 show that DNP-AcF3-3 mediates the degradation of alexa 488-labeled anti-DNP in HepG2 cells. In this experiment, cells were incubated with 1 uM alexa 488-labeled anti-DNP (Thermo) and 200 nM DNP-AcF3-3. Cells were lysed (RIPA in PBS, containing protease inhibitors) at the given time and assayed by SDS-PAGE gel. Readout is fluorescence of protein fragments.

Figure 12:
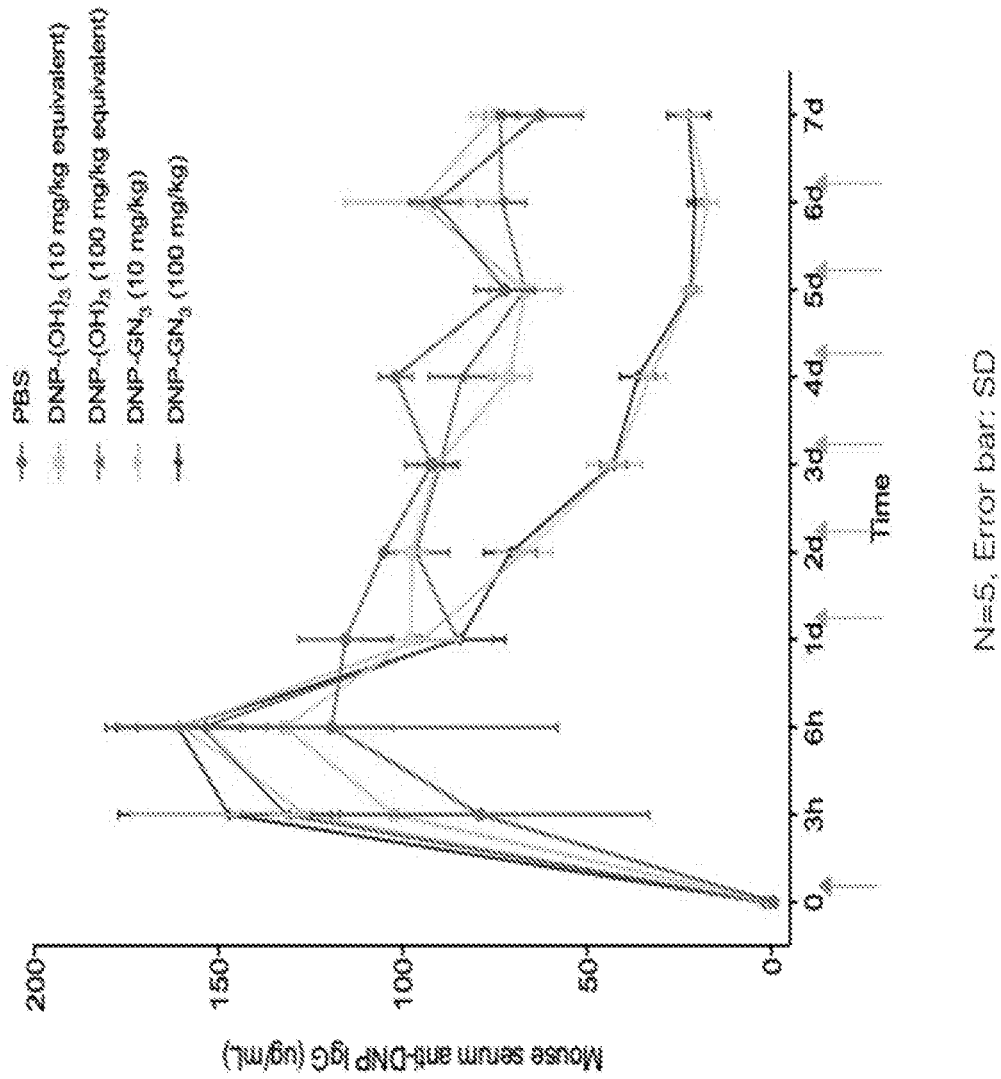
FIG. 12 shows that DNP-GN3 mediates the depletion of anti-DNP from mouse serum.

The results presented in FIG. 12 evidence that DNP-GN3 mediates the depletion of anti-DNP from mouse serum. Mice were injected with anti-DNP on day 0, then treated with the given compounds each day for 6 days. Serum IgG levels were measured by ELISA. DNP-(OH)$_3$ is used as a non-bifunctional control molecule.

FIG. 13 shows the structures of IgG-degrading molecules IBA-GN3, Triazine-GN3, FcIII-GN3, and FcIII-4c-GN3.

Figure 14:
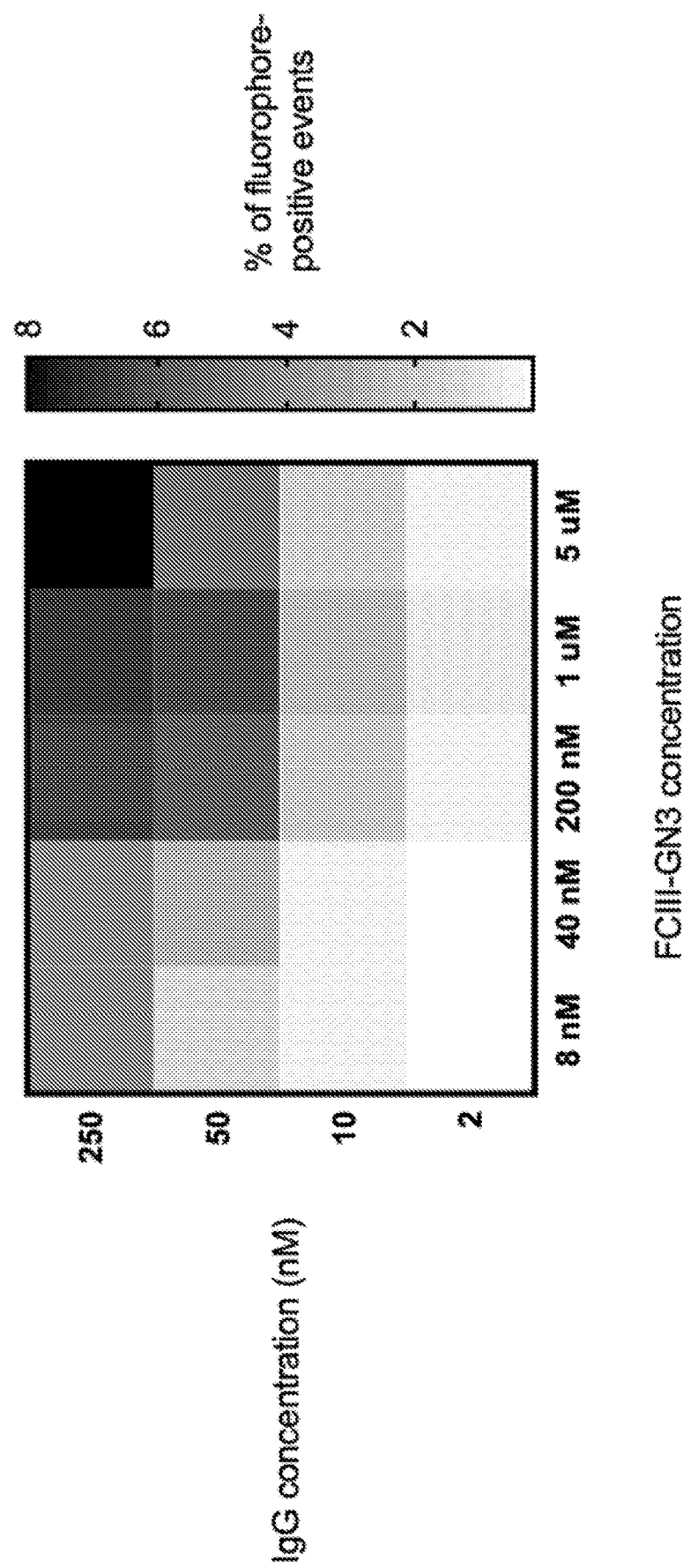
FIG. 14 shows that FcIII-GN3 mediates the uptake of human IgG into HepG2 cells. Experiment performed as described above.

FIG. 14 shows that FcIII-GN3 mediates the uptake of human IgG into HepG2 cells. This experiment was performed as described above.

Figure 15:
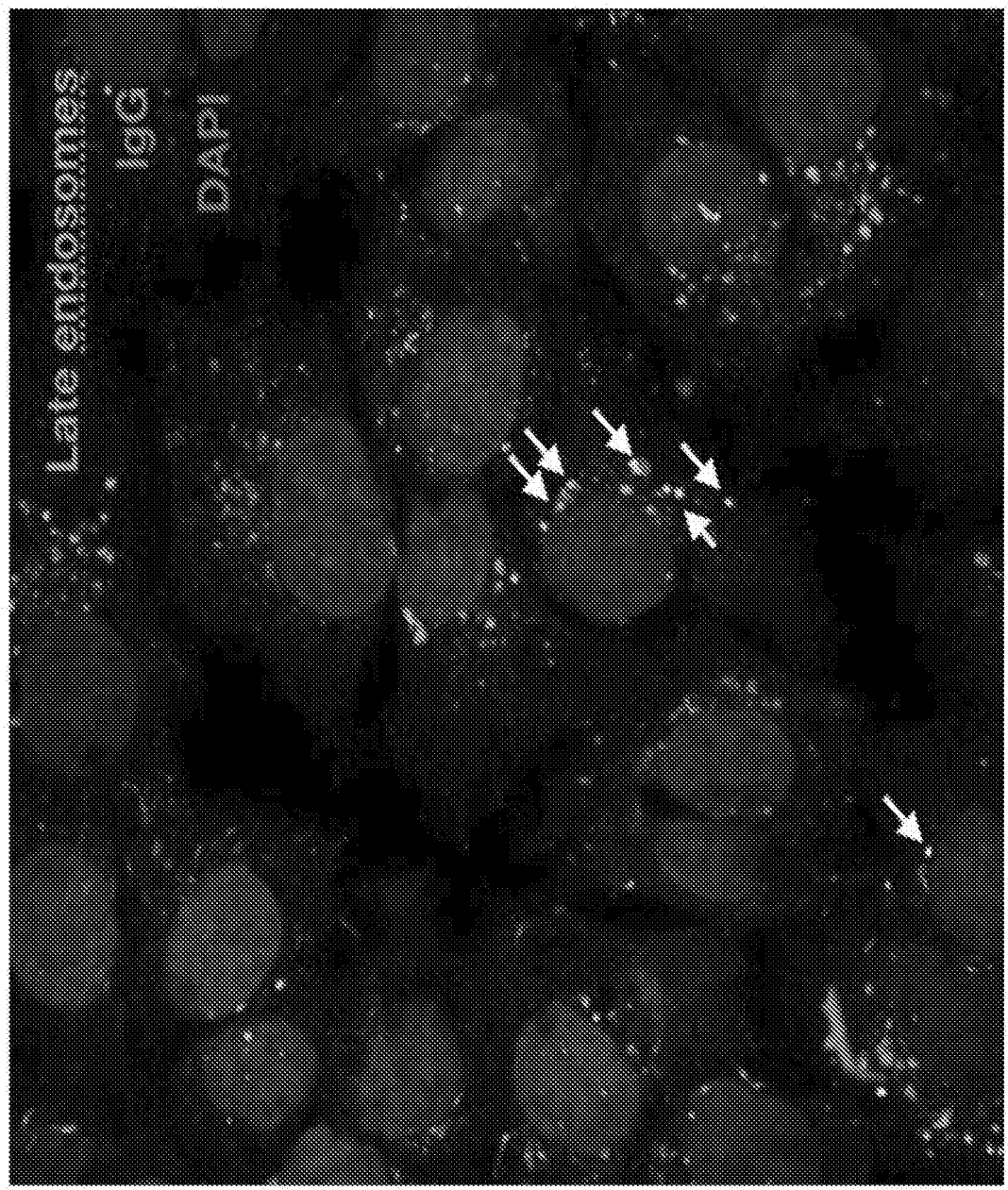
FIG. 15 shows that FcIII-GN3 mediates the localization of IgG to late endosomes in HepG2 cells. Experiment performed as described above.

FIG. 15 shows that FcIII-GN3 mediates the localization of IgG to late endosomes in HepG2 cells. Experiment performed as described above.

Experimental Chemistry
1. MIF Binding Molecule (FIG. 13)
MIF-1

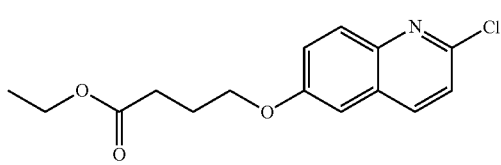 [SMILES: CCOC(=O)CCCOc1ccc2nc(Cl)ccc2c1]

2-chloroquinolin-6-ol (1.00 g, 5.57 mmol) and K$_2$CO$_3$ (1.53 g, 11.1 mmol, 2.0 eq) were dissolved in DMF (20 mL). Ethyl bromobutyrate (1.63 g, 1.2 mL, 8.35 mmol, 1.5 eq) was then added and the mixture stirred at 80° for 12 hours. The reaction was diluted into ethyl acetate and washed with water (2×) and brine (3×). The organic layer was dried over sodium sulfate and evaporated to give compound 30, which was used in the next step without further purification.

$^1$H NMR (400 MHz, Chloroform-d) δ 7.98 (d, J=8.6 Hz, 1H), 7.92 (d, J=9.2 Hz, 1H), 7.40-7.32 (m, 2H), 7.07 (d, J=2.7 Hz, 1H), 4.20-4.09 (m, 5H), 2.56 (t, J=7.2 Hz, 2H), 2.19 (t, J=6.7 Hz, 2H), 1.26 (t, J=7.1 Hz, 4H).

$^{13}$C NMR (101 MHz, cdcl$_3$) δ 173.24, 157.46, 148.18, 143.87, 137.83, 130.05, 128.06, 123.40, 122.67, 106.20, 77.48, 77.16, 76.84, 67.30, 60.69, 30.87, 24.63, 14.39.

HRMS: [M+H]$^+$ Expected 294.090, found 294.11

MIF-2

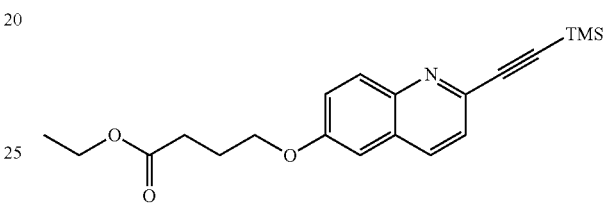

Compound 30 (1.52 g, 5.17 mmol) was dissolved in THF (20 mL) and triethylamine (2.88 mL, 20.7 mmol, 4 eq). Copper (I) iodide (49.0 mg, 0.258 mmol, 0.05 eq), Pd(PPh$_3$)$_2$Cl$_2$ (181 mg, 0.258 mmol, 0.05 eq), and TMS-acetylene (1.07 mL, 762 mg, 7.75 mmol, 1.5 eq) were then added and the reaction was stirred under pressure at 65° for 16 hours. The reaction mixture was filtered through celite, washed ethyl acetate, and evaporated. The residue was purified on silica (50% ethyl acetate in hexanes) to give compound 31.

$^1$H NMR (500 MHz, Chloroform-d) δ 8.00 (d, J=8.4 Hz, 2H), 7.50 (d, J=8.5 Hz, 1H), 7.43-7.33 (m, 1H), 7.04 (d, J=2.2 Hz, 1H), 4.15 (dt, J=12.7, 6.5 Hz, 4H), 2.56 (t, J=7.2 Hz, 2H), 2.24-2.13 (m, 2H), 1.26 (t, J=7.1 Hz, 3H), 0.30 (s, 9H).

$^{13}$C NMR (151 MHz, cdcl$_3$) δ 173.07, 124.73, 105.65, 67.11, 60.51, 30.67, 24.42, 14.21, −0.27.

HRMS: [M+H]$^+$ Expected 356.168, Found 356.505

MIF-3

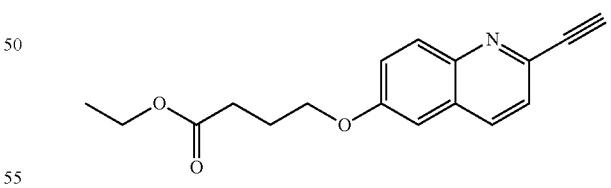

Procedure

Compound 31 (1.57 g, 4.42 mmol) was dissolved in DCM (45 mL) and TBAF (5.3 mL, 1M in THF, 5.30 mmol, 1.2 eq) was added dropwise. After 1 minute of stirring 10% citric acid (50 mL) was added and the reaction stirred for 30 minutes. The organic phase was washed with water (1×), dried, and evaporated to give compound 32, which was used in the next step without further purification.

$^1$H NMR (600 MHz, Chloroform-d) δ 8.11-8.00 (m, 1H), 7.51 (d, J=8.4 Hz, 1H), 7.38 (dd, J=9.3, 2.3 Hz, 1H), 7.05 (d, J=2.4 Hz, 1H), 4.15 (p, J=6.6, 6.0 Hz, 3H), 3.43-3.36 (m, 1H), 2.56 (t, J=7.2 Hz, 1H), 2.22-2.14 (m, 1H), 1.73-1.64 (m, 1H), 1.47 (q, J=7.4 Hz, 1H), 1.26 (t, J=7.1 Hz, 2H), 1.02 (t, J=7.3 Hz, 1H).

CNMR: $^{13}$C NMR (151 MHz, cdcl$_3$) δ 173.06, 137.60, 129.91, 128.64, 124.50, 123.18, 122.48, 105.99, 105.58, 77.20, 76.99, 76.77, 67.12, 60.51, 59.14, 30.67, 24.42, 24.22, 19.80, 14.21, 13.69.

HRMS: [M+H]$^+$ Expected 284.129, Found 284.327

MIF-4

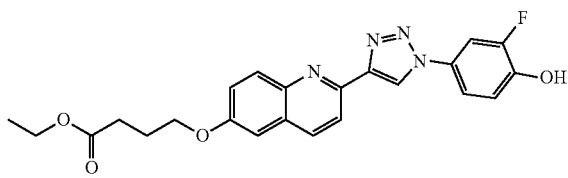 [SMILES: CCOC(=O)CCCOc1ccc2nc(-c3cn(-c4ccc(O)c(F)c4)nn3)ccc2c1]

2-fluoro-4-iodophenol (126 mg, 0.529 mmol) and sodium azide (38 mg, 0.528 mmol, 1.0 eq) were dissolved in DMSO (2.5 mL) and stirred for two hours at 70°. Compound 32 (150 mg, 0.529 mmol, 1 eq), trans-N,N'-dimethylcyclohexane-1,2-diamine (11 mg, 0.079 mmol, 0.15 eq), sodium ascorbate (10 mg, 0.053 mmol, 0.1 eq), copper (I) iodide (15 mg, 0.079 mmol, 0.15 eq), and H$_2$O (2.5 mL) were then added, and the mixture stirred at 70° overnight. The reaction was diluted with ethyl acetate and washed with H$_2$O (1×) and brine (1×). The organic layer was dried over sodium sulfate, evaporated, and purified on silica (DCM/EtOAc) to give compound 33.

$^1$H NMR (600 MHz, DMSO-d$_6$) δ 10.46 (s, 1H), 9.32 (s, 1H), 8.39 (d, J=8.6 Hz, 1H), 8.23 (d, J=8.5 Hz, 1H), 7.95 (dd, J=11.6, 2.6 Hz, 2H), 7.77-7.71 (m, 1H), 7.43 (dd, J=4.8, 2.0 Hz, 2H), 7.16 (t, J=9.0 Hz, 1H), 4.17 (d, J=6.3 Hz, 2H), 4.13-4.07 (m, 3H), 3.17 (d, J=5.2 Hz, 3H), 2.53 (d, J=7.3 Hz, 3H), 2.07 (t, J=6.8 Hz, 2H), 1.19 (d, J=7.1 Hz, 3H), 0.94 (d, J=7.3 Hz, 1H).

$^{13}$C NMR (151 MHz, dmso) δ 172.96, 156.95, 151.95, 150.34, 148.62, 145.98, 143.82, 136.47, 130.40, 129.01, 123.19, 121.83, 119.06, 118.62, 117.31, 109.87, 109.72, 107.12, 67.43, 60.35, 49.03, 40.48, 40.36, 40.22, 40.09, 39.95, 39.81, 39.67, 39.53, 30.61, 24.58, 23.48, 14.56, 13.93.

HRMS: Expected 437.163, Found 437.164

MIF-5

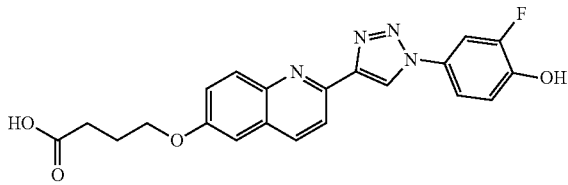 [SMILES: O=C(O)CCCOc1ccc2nc(-c3cn(-c4ccc(O)c(F)c4)nn3)ccc2c1]

Compound 33 (90 mg, 0.206 mmol) was dissolved in dioxane (6 mL) and 2M NaOH (3 mL). The reaction was stirred for 2.5 hours at room temperature, at which time the reaction was diluted with water and the pH adjusted to 3-4 with 1M HCl. The mixture was cooled to 4° and filtered to give compound 34, which was used without further purification.

2. GalNAc Spacer (FIG. 14)

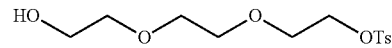 [SMILES: Cc1ccc(S(=O)(=O)OCCOCCOCCO)cc1]

Triethylene glycol (17.5 mL, 19.7 g, 131.13 mmol, 5 eq) was dissolved in DCM (150 mL) and trimethylamine (5.48 mL, 3.98 g, 1.5 eq) and cooled to 0°. TsCl (5.00 g, 26.23 mmol, 1 eq) was then added and the reaction mixture stirred at room temperature for 18 hours. The reaction was diluted into DCM and washed with water (3×) and brine (1×). The organic layer was dried over sodium sulfate and concentrated in vacuo. The crude product was purified on silica (0-5% MeOH in DCM) to give compound 64 (6.89 g, 22.6 mmol) in 85% yield.

$^1$H NMR (400 MHz, Chloroform-d) δ 7.80 (d, J=8.3 Hz, 2H), 7.38-7.30 (m, 2H), 4.23-4.14 (m, 2H), 3.71 (td, J=5.3, 4.3 Hz, 4H), 3.66-3.55 (m, 6H), 2.45 (s, 3H).

$^{13}$CNMR (101 MHZ, cdcl$_3$) δ 144.98, 133.09, 129.95, 128.09, 72.58, 70.91, 70.44, 69.28, 68.84, 61.88, 21.76.

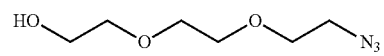 [SMILES: [N-]=[N+]=NCCOCCOCCO]

Compound 64 (2.00 g, 6.57 mmol) and sodium azide (0.470 g, 7.23 mmol, 1.1 eq) were dissolved in DMF (40 mL) and stirred overnight at 60°. 25 mL of DMF was then removed by rotary evaporation, and the resulting mixture diluted into water and extracted with ethyl acetate (2×). The organic layers were washed with brine (3×), dried over sodium sulfate, and evaporated. The crude product was purified on silica (0-5% MeOH in DCM) to give compound 65 (932 mg, 5.32 mmol) in 81% yield.

3. GalNAc ASGPR Ligand (FIG. 15)

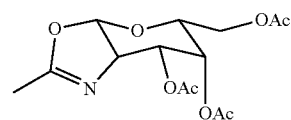 [SMILES: CC(=O)OCC1OC2OC(C)=NC2C(OC(C)=O)C1OC(C)=O]

Galactosamine pentaacetate (100 mg, 0.257 mmol) was dissolved in dichloroethane (1 mL) and stirred at room temperature before the addition of TMSOTf (70 uL, 86.0 mg, 0.387 mmol, 1.5 eq). The reaction was stirred at 50° for 90 minutes, then allowed to cool to room temperature and stirred for a further 12 hours. The reaction was poured into ice cold saturated sodium bicarbonate and extracted into DCM. The organic layer was washed with water (2×), dried over sodium sulfate, and evaporated to give compound 66 (0.236 mmol, 77.7 mmol, 92%) as a dark gum, which was used without further purification.

HNMR $^1$H NMR (400 MHz, Chloroform-d) δ 5.98 (d, J=6.8 Hz, 1H), 5.45 (t, J=3.0 Hz, 1H), 4.90 (dd, J=7.4, 3.3 Hz, 1H), 4.29-4.20 (m, 1H), 4.17 (d, J=6.9 Hz, 1H), 4.10 (dd, J=11.1, 5.7 Hz, 1H), 3.99 (td, J=7.1, 1.4 Hz, 1H), 2.11 (s, 3H), 2.05 (m, J=7.6 Hz, 6H).

CNMR $^{13}$C NMR (101 MHz, cdcl$_3$) δ 170.46, 170.13, 169.78, 166.35, 121.82, 118.64, 101.41, 71.76, 69.44, 65.25, 63.53, 61.56, 46.82, 20.77, 20.68, 20.54, 14.41, 8.64, −0.06.

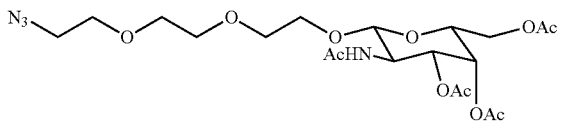 [SMILES: CC(=O)NC1C(OCCOCCOCCN=[N+]=[N-])OC(COC(C)=O)C(OC(C)=O)C1OC(C)=O]

Compound 66 (200 mg, 0.607 mmol) and compound 65 (160 mg, 0.913 mmol, 1.5 eq) were dissolved in 1,2-dichloroethane (5 mL). 4 Å molecular sieves were then added, and the reaction stirred for 30 minutes. TMSOTf (55 uL, 67.5 mg, 0.304 mmol, 0.5 eq) was then added to the mixture, and the reaction stirred overnight. The mixture was diluted into DCM, washed with 1M sodium bicarbonate (1×) and water (1×), then dried over magnesium concentrate and concentrated. The crude oil was purified on silica gel (50-100% EtoAc in DCM) to give compound 67 (245 mg, 0.486 mmol) in 80.1% yield.

$^1$H NMR (400 MHz, Chloroform-d) δ 6.13 (d, J=9.3 Hz, 1H), 5.31 (dd, J=3.4, 1.1 Hz, 1H), 5.05 (dd, J=11.2, 3.4 Hz, 1H), 4.77 (d, J=8.6 Hz, 1H), 4.28-4.04 (m, 3H), 3.93-3.79 (m, 3H), 3.78-3.58 (m, 8H), 3.43 (dt, J=28.2, 4.9 Hz, 4H), 2.15 (s, 3H), 2.04 (s, 3H) 1.98 (s, 3H), 1.97 (s, 3H)

$^{13}$C NMR (101 MHZ, cdcl$_3$) δ 170.24, 170.09, 169.99, 101.84, 72.06, 71.27, 70.50, 70.29, 70.27, 70.20, 70.00, 69.98, 69.67, 69.37, 68.18, 66.30, 61.38, 61.17, 50.32, 50.26, 50.11, 22.80, 20.37, 20.31

HRMS: [M+Na]$^+$ 527.207 found 527.203

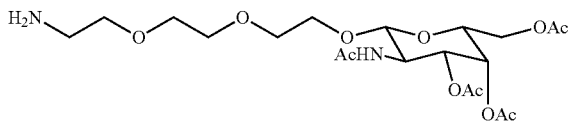 [SMILES: CC(=O)NC1C(OCCOCCOCCN)OC(COC(C)=O)C(OC(C)=O)C1OC(C)=O]

Compound 67 (1.80 g, 3.57 mmol) was dissolved in THF (35 mL). Triphenylphosphine (1.40 g, 5.35 mmol, 1.5 eq) and water (257 uL, 14.28 mmol, 4 eq) were then added and the reaction stirred at room temperature under nitrogen for 36 hours. The solvent was removed and the crude product used in the next step without further purification.

4. Tris Valent Glycine (FIG. 16)

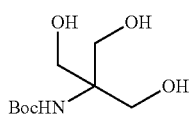

Tris base (5.00 g, 41.3 mmol) was dissolved in dichloromethane (80 mL) and trimethylamine (20 mL). Di-tert-butyl dicarbonate (10.81 g, 49.6 mmol, 1.2 eq) was then added, and the reaction stirred for 4 hours. The mixture was evaporated and the residue portioned between ethyl acetate and water. The organic fraction was washed with water (1×), 1M HCl (2×), saturated sodium bicarbonate (1×), and brine (1×) before drying over sodium sulfate and evaporation to give compound 23 (9.04 g, 40.9 mmol) in 99% yield, which was used without purification in further steps.

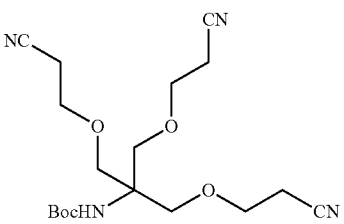 [SMILES: CC(C)(C)OC(=O)NC(COCCC#N)(COCCC#N)COCCC#N]

Compound 27 (9.04 g, 40.9 mmol) was dissolved in a mixture of dioxane (17 mL) and aqueous KOH (4.98 g, 88.7 mmol, 2.46 mL). Acrylonitrilte (8.84 mL, 7.16 g, 135.0 mmol, 3.3 eq) was then added dropwise over a period of 2.5 hours, and the reaction stirred under nitrogen for 24 hours. The reaction was neutralized with the addition of 2M HCl (30 mL) and portioned between DCM and water. The organic layer was washed with water (2×) and brine (1×), dried over sodium sulfate, and evaporated. The crude mixture was purified on silica (0-80% EtOAc in hexanes) to give compound 20 (7.87 g, 20.7 mmol) in 59% yield.

HNMR: $^1$H NMR (400 MHz, Chloroform-d) δ 4.84 (s, 1H), 3.73 (s, 6H), 3.65 (t, J=6.1 Hz, 6H), 2.57 (t, J=6.1 Hz, 6H), 1.35 (s, 9H).

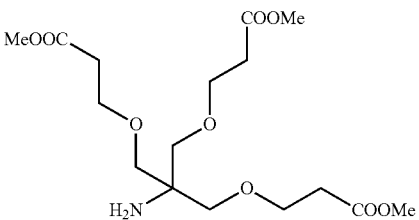

Compound 28 (7.87 g, 20.7 mmol) was dissolved in MeOH (40 mL) and concentrated sulfuric acid (10 mL) was added. The reaction was stirred at reflux under nitrogen for 24 hours, then neutralized with sodium bicarbonate. Methanol was evaporated, and the residue partioned between water and ethyl acetate. The ethyl acetate layer was washed with sodium bicarbonate (1×) and brine (1×), then dried over sodium sulfate. The crude residue was purified on silica (10% MeOH in DCM) to give compound 29 (5.50 g, 14.5 mmol) in 70% yield.

HNMR: ¹H NMR (400 MHz, Chloroform-d) δ 3.79-3.64 (m, 15H), 3.32 (s, 6H), 2.56 (t, J=6.3 Hz, 6H).

CNMR: ¹³C NMR (101 MHz, cdcl₃) δ 172.03, 72.52, 66.77, 56.10, 51.62, 34.80.

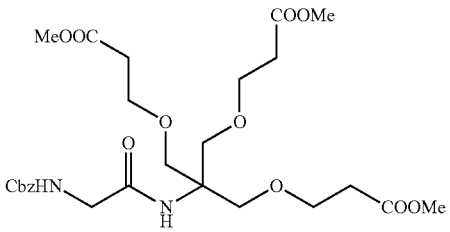 [SMILES: COC(=O)CCOCC(COCCC(=O)OC)(COCCC(=O)OC)NC(=O)CNC(=O)OCc1ccccc1]

Compound 70 (723 mg, 1.90 mmol) was dissolved in MeCN (25 mL). HOBT (291 mg, 1.90 mmol, 1 eq), Cbz-glycine (397 mg, 1.90 mmol, 1 eq), and DCC (392 mg, 1.90 mmol, 1 eq) were then added, and the reaction stirred overnight. MeCN was then evaporated, and the residue adsorbed onto silica and purified using a gradient of 0-75% EtOAc in hexanes. Compound 71 (866 mg, 1.52 mmol) was recovered in 80% yield.

¹H NMR (600 MHz, Chloroform-d) δ 7.33 (dd, J=24.9, 4.4 Hz, 5H), 6.33 (s, 1H), 5.55 (s, 1H), 5.12 (s, 2H), 3.86 (d, J=5.1 Hz, 2H), 3.68 (t, J=5.5 Hz, 21H), 3.49 (s, 1H), 2.53 (t, J=6.1 Hz, 6H).

¹³C NMR (151 MHz, cdcl₃) δ 172.14, 168.67, 156.32, 136.41, 128.45, 128.05, 127.98, 69.04, 66.85, 66.71, 59.83, 51.69, 44.55, 34.64.

Expected: [M+H]⁺ 571.250, found 571.243

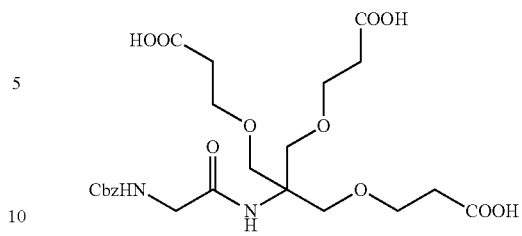

Compound 71 (100 mg, 0.175 mmol) was dissolved in dioxane (2 mL) and 2M NaOH (2 mL). The reaction was stirred for 3 hours, then acidified and extracted twice into ethyl acetate. The organic fraction was washed with 1M HCl, then dried over sodium sulfate and evaporated to give compound 72, which was used in further steps without purification.

5. GalNAc Trivalent (FIG. 17)

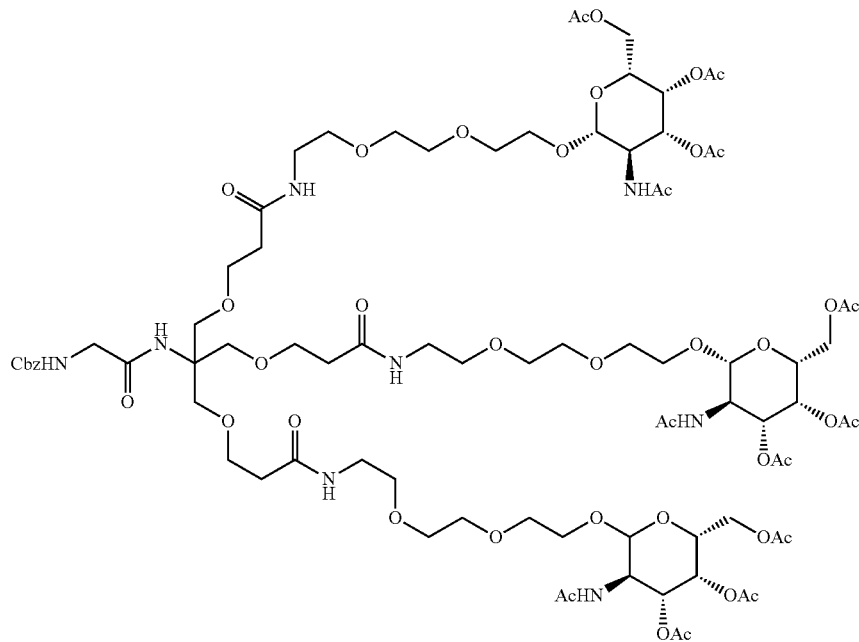 [SMILES: CC(=O)N[C@H]1[C@H](OCCOCCOCCNC(=O)CCOCC(COCCC(=O)NCCOCCOCCOC2O[C@H](COC(C)=O)[C@H](OC(C)=O)[C@H](OC(C)=O)[C@H]2NC(C)=O)(COCCC(=O)NCCOCCOCCO[C@@H]2O[C@H](COC(C)=O)[C@H](OC(C)=O)[C@H](OC(C)=O)[C@H]2NC(C)=O)NC(=O)CNC(=O)OCc2ccccc2)O[C@H](COC(C)=O)[C@H](OC(C)=O)[C@@H]1OC(C)=O]

Compound 72 (372 mg, 0.704 mmol, 1 eq) was dissolved in DMF (40 mL) and DIPEA (981 uL, 728 mg, 5.632 mmol, 8 eq). HBTU (1.01 g, 2.67 mmol, 3.8 eq) was then added, and the reaction stirred for 10 minutes at room temperature before the addition of compound 68 (1.28 g, 2.67 mmol, 3.8 eq). The reaction was stirred for two hours, then diluted into DCM and washed with H3PO4 (1M, 1×), NaHCO3 (1M, 1×), and brine (1×). The organic layer was dried over sodium sulfate and evaporated onto silica. The residue was purified (0-20% MeOH in DCM) to give compound 73 (831 mg, 0.436 mmol) in 62% yield.

$^1$H NMR (500 MHz, DMSO-d$_6$) δ 7.91 (t, J=5.7 Hz, 3H), 7.80 (d, J=9.2 Hz, 3H), 7.39-7.28 (m, 6H), 7.12 (s, 1H), 5.21 (d, J=3.4 Hz, 3H), 5.02 (s, 2H), 4.97 (dd, J=11.2, 3.4 Hz, 3H), 4.55 (d, J=8.5 Hz, 3H), 4.10-3.99 (m, 9H), 3.92-3.84 (m, 3H), 3.81-3.75 (m, 3H), 3.62-3.46 (m, 35H), 3.39 (t, J=6.1 Hz, 6H), 3.23-3.16 (m, 6H), 2.30 (t, J=6.4 Hz, 6H), 2.10 (s, 9H), 1.99 (s, 9H), 1.89 (s, 9H), 1.77 (s, 9H).

$^{13}$C NMR (126 MHz, dmso) δ 170.40, 170.16, 170.09, 169.79, 169.48, 169.04, 156.60, 137.23, 128.50, 127.94, 127.84, 101.12, 72.50, 70.65, 70.07, 69.93, 69.86, 69.77, 69.59, 69.29, 68.50, 67.51, 66.89, 65.59, 61.63, 60.38, 59.84, 49.50, 43.77, 38.68, 36.01, 22.95, 20.68, 20.62, 20.60.

under hydrogen (1 atm) at 0° for 16 hours. Upon completion, the reaction was filtered through celite and methanol evaporated to give compound 74 (657 mg, 0.370 mmol) in 99.5% yield, which was used without further purification.

Compound 74 (441 mg, 0.248 mmol) was dissolved in methanol (15 mL) and cooled to 0°. Sodium methoxide solution (400 uL, 5.4M in MeOH) was then added, and the reaction stirred for 30 minutes. Dowex 50WX8 was then added until the solution was weakly acidic. The resin was filtered off and washed thoroughly with methanol. The combined methanol fractions were evaporated under reduced pressure to give compound 75 (274 mg, 0.196

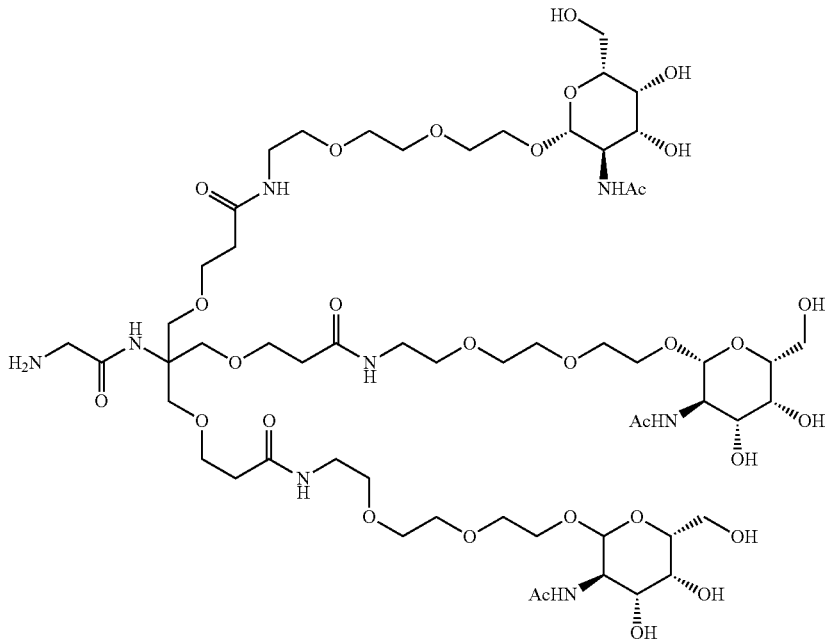 [SMILES: CC(=O)N[C@H]1[C@H](OCCOCCOCCNC(=O)CCOCC(COCCC(=O)NCCOCCOCCOC2O[C@H](CO)[C@H](O)[C@H](O)[C@H]2NC(C)=O)(COCCC(=O)NCCOCCOCCO[C@@H]2O[C@H](CO)[C@H](O)[C@H](O)[C@H]2NC(C)=O)NC(=O)CN)O[C@H](CO)[C@H](O)[C@@H]1O]

Compound 73 (710 mg, 0.372 mmol) was dissolved in dry methanol (90 mL) and cooled to 0° under nitrogen. Pd/C (71.0 mg, 10% w/w) was then added, and the reaction stirred mmol) in 79% yield. Compound 75 was used in further steps without purification.

6. MIF-GN$_3$ (FIG. 18)

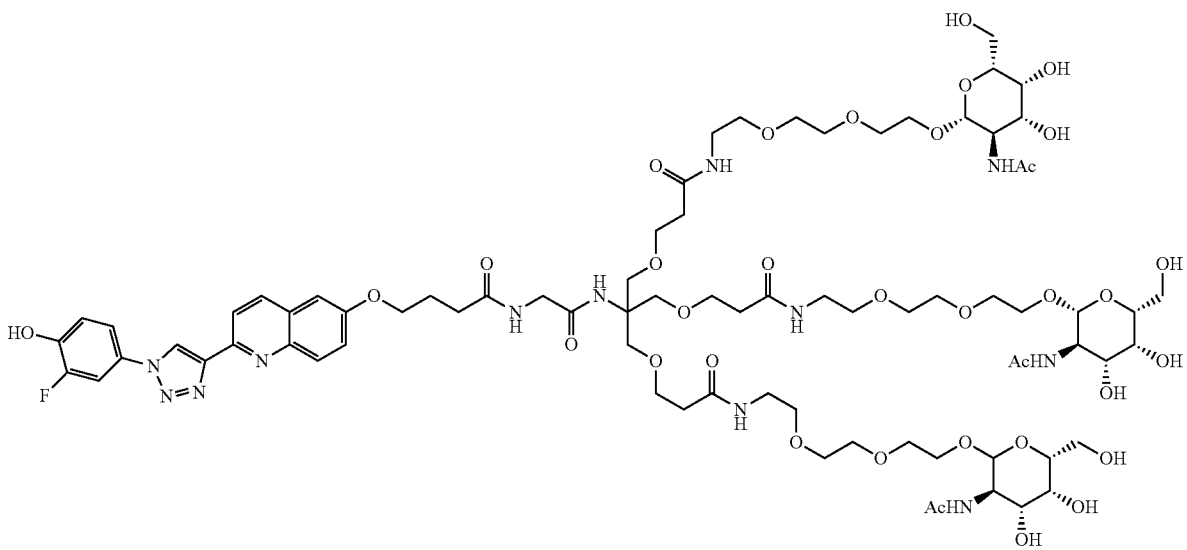 [SMILES: CC(=O)N[C@H]1[C@H](OCCOCCOCCNC(=O)CCOCC(COCCC(=O)NCCOCCOCCOC2O[C@H](CO)[C@H](O)[C@H](O)[C@H]2NC(C)=O)(COCCC(=O)NCCOCCOCCO[C@@H]2O[C@H](CO)[C@H](O)[C@H](O)[C@H]2NC(C)=O)NC(=O)CNC(=O)CCCOc2ccc3nc(-c4cn(-c5ccc(O)c(F)c5)nn4)ccc3c2)O[C@H](CO)[C@H](O)[C@@H]1O]

Compound 34 (23.5 mg, 0.0575 mmol, 1.1 eq) and HATU (20.0 mg, 0.0522 mmol, 1 eq) were dissolved in dry DMF (5 mL) and DIPEA (23.3 uL, 16.9 mg, 0.131 mmol, 2.5 eq) and stirred for 10 minutes at room temperature. Compound 75 (73.0 mg, 0.0522 mmol) was then added, and the reaction stirred for 30 minutes. The mixture was loaded directly onto HPLC and purified (20-30% MeCN in water, 3% TFA) to give compound 76 (12 mg, 0.0067 mmol) in 12.8% yield.

Expected [M+H]$^+$ 1787.801, found 1787.823

7. Bicyclic ASGPR Spacer (FIG. 19)

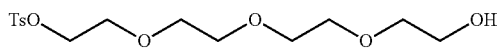 [SMILES: Cc1ccc(S(=O)(=O)OCCOCCOCCOCCO)cc1]

Tetraethylene glycol (50.0 g, 258 mmol) was dissolved in THF (1 mL), cooled to 0°, and stirred. NaOH (1.65 g, 41.3 mmol, 1.6 eq) in water (1 mL) was then added, followed by the dropwise addition of p-toluenesulfonyl chloride (4.92 g, 25.8 mmol, 1 eq) in THF (3 mL). The reaction mixture was stirred at 0° for 4 hours, then diluted into DCM. The organic layer was washed with ice-cold water (2×), brine (1×), and dried over sodium sulfate to give compound 16 (8.84 g, 25.4 mmol, 99% yield), which was used in further steps without purification.

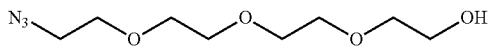 [SMILES: [N-]=[N+]=NCCOCCOCCOCCO]

Compound 16 (8.84 g, 25.4 mmol) was dissolved in 100% ethanol (200 mL) and sodium azide (4.128 g, 63.5 mmol, 2.5 eq) was added. The reaction was heated to reflux for 16 hours, then cooled to room temperature before the addition of water (150 mL). Ethanol was then evaporated under reduced pressure and the product extracted into ethyl acetate (2×). The organic layer was washed with water (1×) and brine (1×), dried over sodium sulfate, and evaporated to give compound 17 (4.82 g, 22.1 mmol) as a yellow oil in 87% yield.

HNMR: $^1$H NMR (400 MHz, Chloroform-J) δ 3.69-3.64 (m, 2H), 3.61 (m, J=4.2 Hz, 10H), 3.57-3.51 (m, 2H), 3.33 (td, J=5.0, 2.3 Hz, 2H), 2.81 (s, 1H).

CNMR: $^{13}$C NMR (101 MHz, cdcl$_3$) δ 72.47, 70.65, 70.63, 70.59, 70.52, 70.28, 69.99, 61.60, 50.59.

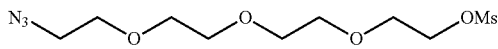 [SMILES: CS(=O)(=O)OCCOCCOCCOCCN=[N+]=[N-]]

Compound 17 (5.00 g, 22.8 mmol) was dissolved in pyridine (50 mL). Methanesulfonyl chloride (3.14 g, 27.4 mmol, 1.2 eq) was then added and the reaction stirred for six hours under nitrogen. The mixture was then diluted into ethyl acetate, washed with water (3×), 0.5M HCl (2×), saturated sodium bicarbonate (1×), and brine (1×), dried over sodium sulfate, and evaporated to give compound 18 (5.71 g, 19.2 mmol) in 84% yield.

HNMR: $^1$H NMR (400 MHz, Chloroform-J) δ 4.41-4.33 (m, 2H), 3.81-3.72 (m, 2H), 3.70-3.59 (m, 10H), 3.38 (t, J=5.0 Hz, 2H), 3.06 (s, 3H).

CNMR: $^{13}$CNMR (101 MHZ, cdcl$_3$) δ 70.79, 70.75, 70.71, 70.15, 69.39, 69.11, 50.77, 37.78.

HRMS: Expected 298.107, found 298.105

8. Bicyclic ASGPR Precursor (FIG. 20)

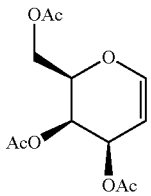 [SMILES: CC(=O)OC[C@H]1OC=C[C@@H](OC(C)=O)[C@H]1OC(C)=O]

Pentaacetyl galactose (25.0 g, 64.0 mmol) was dissolved in 33% HBr in HOAc (30 mL) and stirred under nitrogen for 2 hours. The reaction was diluted into EtOAc (500 mL) and washed with water (3×), saturated sodium bicarbonate (1×), and brine (1×). The organic layer was dried over sodium sulfate and evaporated to give compound 1 as a pale yellow oil in quantitative yield. The compound was used without further purification.

Compound 1 (26.34 g, 64.06 mmol) was dissolved in acetic acid (510 mL) and zinc (67.01 g, 1024 mmol) added. The mixture was stirred vigorously. A solution of CuSO4 (2.96 g, 18.6 mmol) in aqueous NaH2PO4 (128 mL, 1M, 1.53 g) was then added, and the reaction stirred for 1 hour. The reaction mixture was filtered over celite and the resulting water/AcOH mixture evaporated to give a white solid. The white solid was dissolved in EtOAc (2×, 300 mL each), water (300 mL), and EtOAc (1×, 300 mL). The layers were separated and the organic layer further washed with water (2×), saturated sodium bicarbonate (2×), and brine (1×). The organic solution was dried over sodium sulfate, evaporated, and purified on silica (15-25% EtOAc in Hexanes) to give compound 2 in 84% yield (14.64 g, 53.76 mmol).

$^1$HNMR (400 MHz, Chloroform-d) δ 6.46 (dd, J=6.3, 1.8 Hz, 1H), 5.54 (qd, J=2.8, 1.2 Hz, 1H), 5.41 (dt, J=4.7, 1.7 Hz, 1H), 4.71 (ddd, J=6.3, 2.7, 1.5 Hz, 1H), 4.33 (ddt, J=7.0, 5.6, 1.4 Hz, 1H), 4.29-4.15 (m, 2H), 2.11 (s, 3H), 2.06 (s, 3H), 2.00 (s, 3H).

$^{13}$C NMR (101 MHZ, Chloroform-d) δ 170.33, 170.06, 169.97, 145.30, 98.80, 72.69, 63.82, 63.59, 61.85, 20.66, 20.64, 20.58.

HRMS: [M+Na]$^+$ Expected 295.079, found 295.078

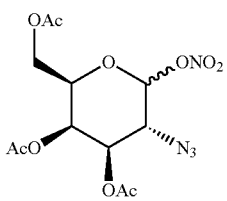

Procedure

Compound 2 (12.0 g, 44 mmol) was dissolved in acetonitrile (250 mL) and cooled to −10°. In a separate nitrogen-flushed flask at −10°, NaN$_3$ (4.3 g, 66 mmol) and ceric ammonium nitrate (87.0 g, 158 mmol) were mixed and stirred vigorously. The solution of compound 2 in acetonitrile was added dropwise via cannula, and the mixture allowed to slowly reach room temperature. The reaction mixture was allowed to stir for a total of 12 hours before dilution with ethyl acetate (500 mL) and washing with water (3x) and brine (1x). The organic layer was dried over sodium sulfate, evaporated, and purified on silica (20-50% EtOAc in Hexanes) to give compound 3 in 79% yield (13.1 g, 34.9 mmol).

$^1$H NMR (400 MHz, Chloroform-d) δ 6.31 (d, J=4.1 Hz, 1H), 5.60 (d, J=8.8 Hz, 1H), 5.43 (dd, J=3.4, 1.3 Hz, 1H), 5.32 (t, J=3.3 Hz, 1H), 5.16 (dt, J=11.6, 3.4 Hz, 1H), 4.96 (dd, J=10.6, 3.3 Hz, 1H), 4.39-4.28 (m, 1H), 4.14-4.00 (m, 5H), 3.76 (ddd, J=13.5, 9.6, 4.7 Hz, 1H), 2.19-2.05 (m, 6H), 2.05-1.88 (m, 12H).

$^{13}$C NMR (101 MHZ, cdcl$_3$) δ 170.15-169.06, 97.91, 97.79, 96.91, 71.68, 71.45, 69.35, 68.42, 66.98, 66.53, 65.85, 64.75, 61.07, 60.84, 57.38, 55.82, 55.08, 20.31-20.20.

HRMS: [M+Na]$^+$ expected 399.076, found 399.073

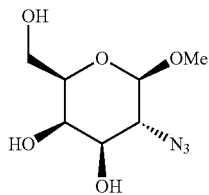 [SMILES: CO[C@@H]1O[C@H](CO)[C@H](O)[C@H](O)[C@H]1N=[N+]=[N-]]

Sodium methoxide solution was prepared from ice-cold dry methanol (50 mL) and sodium hydride (2.296 g, 95.67 mmol) 3 eq) and added to a solution of compound 3 (12.00 g, 31.89 mmol) in dry methanol (100 mL). After thirty minutes of stirring, the reaction was confirmed neutralized by the addition of acetic acid and directly loaded onto silica gel. The reaction mixture was purified over a gradient of 0-20% MeOH in DCM to give compound 4 (6.64 g, 30.3 mmol) in 95% yield.

CNMR:
$^{13}$C NMR (101 MHZ, cd$_3$od) δ 102.60, 100.87, 98.59, 75.65, 74.62, 71.43, 70.41, 68.82, 67.81, 67.69, 67.47, 67.37, 63.73, 62.96, 60.75, 60.43, 59.54, 55.42, 53.69, 45.94.

HRMS: [M+Na]$^+$ expected 242.075, found 242.072

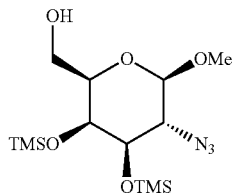

Compound 4 (5.00 g, 22.8 mmol) was dissolved in pyridine (100 mL) and stirred under nitrogen. Trimetylsilylchloride (10.43 mL, 8.929 g, 82.18 mmol, 3.6 eq) was added dropwise and the mixture stirred for 6 hours. The reaction was diluted into ethyl acetate and washed with water (2x) and brine (1x). The organic layer was dried over sodium sulfate and evaporated to give the tri-TMS intermediate. Residual pyridine was removed by coevaporating with toluene (3x). The intermediate was taken up into dry MeOH (45 mL) and cooled to 0° before potassium carbonate (40 mg) was added. The reaction was closely monitored over 1.5 hours and quenched with acetic acid (17 uL) once TLC showed complete consumption of starting material. The product was then dry loaded onto silica and purified with a gradient of 0-50% EtOAc in hexane to give compound 5 (6.55 g, 18.0 mmol) in 79% yield.

$^{13}$C NMR (101 MHZ, cdcl$_3$) δ 103.36, 75.29, 73.71, 72.37, 71.41, 70.94, 70.38, 64.04, 62.49, 62.15, 61.05, 60.36, 57.15, 55.17, 34.60, 31.52, 25.21, 22.59, 20.93, 14.11, 14.05, 0.85, 0.57, 0.55, 0.52, 0.22, 0.14, 0.01, −0.07.

HRMS: [M+Na]$^+$386.154, found 386.156

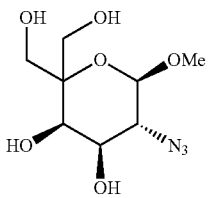 [SMILES: CO[C@@H]1OC(CO)(CO)[C@H](O)[C@H](O)[C@H]1N=[N+]=[N-]]

Compound 5 (7.00 g, 19.3 mmol) was dissolved in DCM (100 mL) and stirred under nitrogen. Dess-Martin periodane (9.82 g, 23.2 mmol, 1.2 eq) was added and the mixture stirred for 2 hours. The reaction was diluted into DCM and washed with water (2x) and brine (1x). The organic layer was dried over sodium sulfate and evaporated to give the intermediate aldehyde.

Compound 6 was dissolved in molecular sieve-dried EtOH (100 mL). Paraformaldehyde (36.50 g, 384.9 mmol, 20 eq) and 21% sodium ethoxide solution (14.5 mL, 38.5 mmol, 2 eq) were added and the reaction stirred for 8 hours. The solvent was evaporated and the product adsorbed onto silica. The product was purified using a gradient of 0-25% MeOH in DCM to afford compound 7 (2.981 g, 11.97 mmol) in 62% yield.

HRMS: [M+Na]$^+$ expected 272.086 (+Na), found 272.083

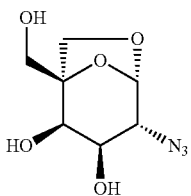 [SMILES: [N-]=[N+]=N[C@H]1[C@H]2OC[C@](CO)(O2)[C@H](O)[C@@H]1O]

L6-7 (500 mg, 2.00 mmol) was dissolved in water (4.5 mL) and sulfuric acid (0.5 mL). The reaction was sealed in a microwave vial and heated at 100° for 40 minutes. The reaction was cooled to 0°, then diluted with MeOH (10 mL) and neutralized by the addition of concentrated ammonia solution. Salts were filtered off and washed several times with methanol. The filtrate was adsorbed onto silica and purified on a gradient of 0-15% MeOH in DCM to give compound L6-8 (347 mg, 1.60 mmol) in 80% yield.

$^{13}$C NMR (101 MHZ, cd$_3$od) δ 102.70, 85.32, 71.03, 69.59, 69.49, 66.07, 61.85

9. Bicyclic ASGPR ligand CF3 (FIG. 21)

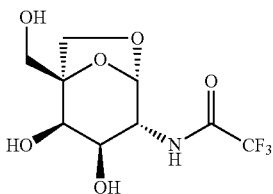 [SMILES: O=C(N[C@H]1[C@H]2OC[C@](CO)(O2)[C@H](O)[C@@H]1O)C(F)(F)F]

Compound (400 mg, 1.84 mmol) was dissolved in methanol (30 mL) and the reaction flask purged with nitrogen. Lindlar's catalyst (40.0 mg, 10 wt %) was then added, and the reaction mixture stirred under a 1 atm hydrogen atmosphere (balloon) for 6 hours. The reaction was filtered over celite and evaporated to give compound 10 (351 mg, 1.84 mmol) in quantitative yield, which was used in the next reaction without further purification.

Compound (351 mg, 1.84 mmol) was dissolved in pyridine (15 mL) and treated with trifluoroacetic anhydride (1.24 mL, 1.85 g, 8.83 mmol, 4.8 eq). The reaction was stirred for 6 hours, then diluted into ethyl acetate and washed with 1M HCl (1×), saturated sodium bicarbonate (1×), and brine (1×). The organic layer was dried over sodium sulfate and evaporated to give compound 11 (1.01 g, 1.75 mmol) in 95% yield, which was used in further steps without purification.

Compound 11 (1.01 g, 1.75 mmol) was dissolved in methanol (25 mL) and dry sodium methoxide (86.2 mg, 1.60 mmol, 4 eq) was added. The reaction was stirred for one hour at room temperature, then neutralized with acetic acid and evaporated onto silica. The crude mixture was purified on silica (0-15% MeOH in DCM) to give compound 12 (482 mg, 1.68 mmol) in 96% yield.

$^1$H NMR (400 MHz, DMSO-t/e) δ 9.51 (d, J=6.6 Hz, 1H), 5.15 (s, 1H), 4.98-4.90 (m, 1H), 4.87 (d, J=5.6 Hz, 1H), 4.75-4.70 (m, 1H), 3.86-3.80 (m, 2H), 3.80-3.70 (m, 2H), 3.67-3.54 (m, 3H).

$^{13}$C NMR (101 MHZ, dmso) δ 157.47, 157.11, 117.74, 114.87, 100.28, 84.21, 68.77, 68.28, 66.00, 60.51, 55.95, 40.56, 40.35, 40.15, 39.94, 39.73, 39.52, 39.31.

HRMS: [M+H]$^+$ Expected 288.069, found 288.064

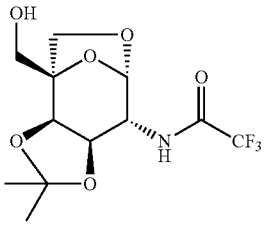 [SMILES: CC1(C)O[C@@H]2[C@@H](NC(=O)C(F)(F)F)[C@H]3OC[C@](CO)(O3)[C@@H]2O1]

Compound 12 (110 mg, 0.383 mmol) was dissolved in DMF (8 mL) and dimethoxypropane (236 uL, 200 mg, 1.92 mmol, 5 eq) and camphorsulfonic acid (45 mg, 0.192 mmol, 0.5 eq) were added. The reaction was stirred at 70° overnight, then DMF evaporated under reduced pressure. The residue was dissolved in ethyl acetate, washed with saturated sodium bicarbonate (1×) and brine (1×), then evaporated onto silica and purified (0-5% MeOH in DCM) to give compound 13 (99.1 mg, 0.303 mmol) in 79% yield.

HNMR:

$^1$H NMR (400 MHz, Chloroform-d) δ 6.87 (d, J=9.0 Hz, 1H), 5.35 (d, J=2.1 Hz, 1H), 4.18-4.11 (m, 2H), 4.11-4.03 (m, 2H), 3.84 (t, J=8.2 Hz, 2H), 3.74 (d, J=7.9 Hz, 1H), 2.66 (d, J=6.6 Hz, 1H), 1.52 (s, 3H), 1.32 (s, 3H).

CNMR:

$^{13}$C NMR (101 MHz, cdcl$_3$) δ 157.87, 157.50, 157.12, 156.75, 119.93, 117.07, 114.21, 112.04, 111.35, 100.22, 81.55, 75.57, 75.00, 68.44, 60.96, 55.16, 27.67, 26.16.

HRMS: [M+H]$^+$ Expected 328.101, found 328.095

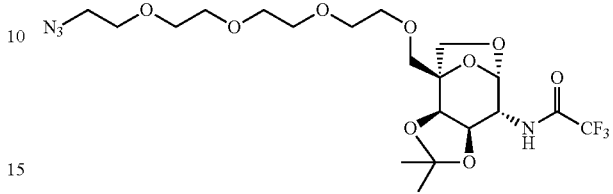

Compound 13 (99.1 mg, 0.303 mmol) was dissolved in DMF (5 mF) and treated with sodium hydride (8.7 mg, 0.364 mmol, 1.2 eq), then stirred under nitrogen for 15 minutes. Compound 18 (108 mg, 0.364 mmol, 1.2 eq) was then added, and the reaction stirred for 1 hour. The reaction was neutralized by the dropwise addition of acetic acid. The solvent was removed under reduced pressure and the residue taken up into ethyl acetate and washed with brine (4×), and the organic layer was dried over sodium sulfate and evaporated onto silica. The crude mixture was purified on silica (50-100% EtOAc in hexanes) to give compound 14 (131 mg, 0.248 mmol) in 82% yield.

HNMR: $^1$H NMR (400 MHz, DMSO-t/e) δ 9.75 (d, J=8.3 Hz, 1H), 5.29 (s, 1H), 4.40 (t, J=6.7 Hz, 1H), 4.30 (d, J=5.9 Hz, 1H), 3.88-3.66 (m, 5H), 3.64-3.48 (m, 14H), 3.39 (t, J=5.0 Hz, 2H), 1.41 (s, 3H), 1.28 (s, 3H).

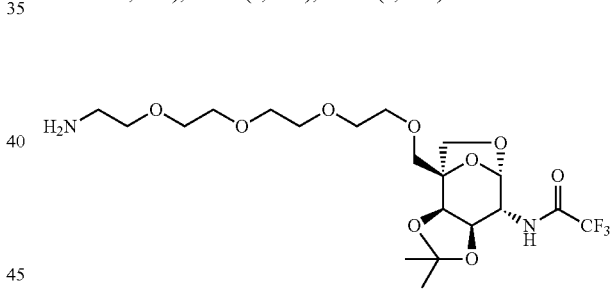

Compound 14 (131 mg, 0.240 mmol) was dissolved in methanol (10 mL) and stirred under a nitrogen atmosphere. Lindlar catalyst (13.1 mg, 10 wt %) was then added, and the reaction stirred for 6 hours under H$_2$ atmosphere (1 atm). The reaction was then filtered over celite and the solvent evaporated to give compound 15 (120 mg, 0.240 mmol) in quantitative yield, which was used without further purification.

HRMS: [M+H]$^+$ Expected 503.222, found 503.223

10. MIF binding divalent (FIG. 23)

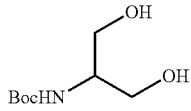

Serinol (2.00 g, 22.0 mmol) was dissolved in dichloromethane (40 mL) and trimethylamine (10 mL). Di-tert-butyl dicarbonate (5.76 g, 26.4 mmol, 1.2 eq) was then added, and the reaction stirred for 4 hours. The mixture was evaporated and the residue portioned between ethyl acetate and water. The organic fraction was washed with water (1×), 1M HCl (2×), saturated sodium bicarbonate (1×), and brine (1×) before drying over sodium sulfate and evaporation to give compound 23 (3.99 g, 20.9 mmol) in 95% yield, which was used without purification in further steps.

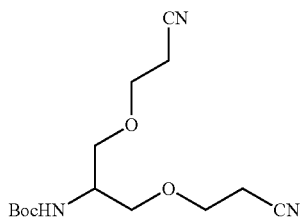 [SMILES: CC(C)(C)OC(=O)NC(COCCC#N)COCCC#N]

Compound 23 (3.99 g, 20.9 mmol) was dissolved in a mixture of dioxane (12 mL) and aqueous KOH (1.63 g, 29 mmol, 2.4 mL). Acrylonitrilte (3.02 mL, 2.44 g, 46.0 mmol, 2.2 eq) was then added dropwise over a period of 2.5 hours, and the reaction stirred under nitrogen for 24 hours. The reaction was neutralized with the addition of 2M HCl (16 mL) and portioned between DCM and water. The organic layer was washed with water (2×) and brine (1×), dried over sodium sulfate, and evaporated. The crude mixture was purified on silica (20-100% EtOAc in hexanes) to give compound 20 (4.96 g, 16.7 mmol) in 80% yield.

HNMR: $^1$H NMR (400 MHz, Chloroform-d) δ 4.91 (d, J=8.9 Hz, 1H), 3.94-3.81 (m, 1H), 3.68 (t, J=6.1 Hz, 4H), 3.65-3.48 (m, 4H), 2.60 (t, J=6.1 Hz, 4H), 1.42 (s, 9H).

CNMR: $^{13}$C NMR (101 MHz, cdcl$_3$) δ 171.11, 117.88, 79.70, 69.12, 65.53, 49.24, 28.30, 18.83, 14.16.

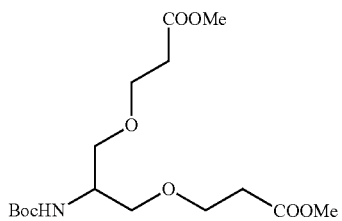

HNMR:

Compound 24 (4.96 g, 16.7 mmol) was dissolved in methanol (40 mL) and concentrated sulfuric acid (10 mL) was added. The mixture was heated at reflux for 24 hours under a nitrogen atmosphere, then cooled to room temperature. Excess sodium bicarbonate was then added, followed by di-tert-butyl dicarbonate (4.37 g, 20.04 mmol, 1.2 eq), and the reaction stirred at room temperature for 6 hours. The cloudy mixture was portioned between water and ethyl acetate, and the organic fraction washed with water (1×), 0.5M HCl (2×), saturated sodium bicarbonate (1×), and brine (1×), dried over sodium sulfate, and evaporated. Compound 20 was purified over a gradient of 0-10% MeOH in DCM on silica, and recovered in 74% yield (4.50 g, 12.4 mmol).

HNMR: $^1$H NMR (400 MHz, Chloroform-J) δ 4.90 (d, J=8.6 Hz, 1H), 3.82 (br s, 1H), 3.70-3.59 (m, 10H), 3.51-3.34 (m, 4H), 2.51 (t, J=6.3 Hz, 4H), 1.38 (s, 9H).

CNMR: $^{13}$C NMR (101 MHz, cdcl$_3$) δ 171.86, 155.34, 79.20, 69.19, 66.41, 51.58, 49.29, 34.75, 28.28.

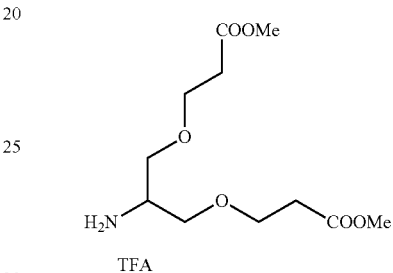

Compound 25 (1.00 g, 2.75 mmol) was dissolved in dry MeOH (10 mL) and TFA (1 mL) and stirred for 15 minutes. Volatiles were evaporated under reduced pressure to give compound 26 as the TFA salt (1.04 g) in quantitative yield.

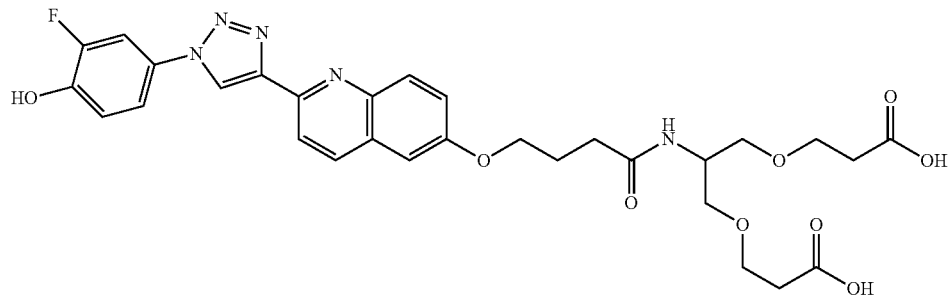 [SMILES: O=C(O)CCOCC(COCCC(=O)O)NC(=O)CCCOc1ccc2nc(-c3cn(-c4ccc(O)c(F)c4)nn3)ccc2c1]

Compound 34 (50.0 mg, 0.123 mmol) was dissolved in DMF (5 mL) and DIPEA (214 uL, 159 mg, 1.23 mmol, 10 eq) and stirred under nitrogen. HBTU (102.4 mg, 0.270 mmol, 2.2 eq) was then added, and the reaction stirred for 15 minutes. Compound 26 (102 mg, 0.270 mmol, 2.2 eq) dissolved in DMF (1 mL) was then added dropwise, and the reaction stirred for 1 hour. The mixture was diluted into ethyl acetate, and washed with 1M HCl (2×) and brine (5×). The organic layer was evaporated to give a gummy residue, which was purified on reverse phase HPLC (35-45% MeCN in water, 0.1% TFA) to give compound 40 (62.6 mg, 0.0959 mmol) in 78% yield.

HRMS: expected 654.258, found 654.259

Compound 40 (62.6 mg, 0.0959 mmol) was dissolved in dioxane (1.8 mL) and 1M NaOH (0.2 mL) was added. The solution was stirred at room temperature for 2 hours, then acidified (pH 3) and evaporated. The residue was resuspended in EtOAc, washed with 1M HCl, and dried over sodium sulfate. The organic layer was evaporated to give compound 41 as an oil (57.6 mg, 0.0921 mmol) in 96% yield, which was used without further purification.

11. MIF Binding Trivalent (FIG. 23)

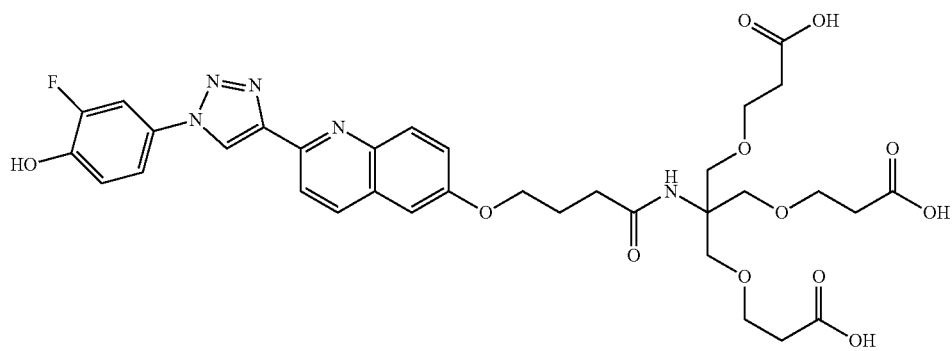 [SMILES: O=C(O)CCOCC(COCCC(=O)O)(COCCC(=O)O)NC(=O)CCCOc1ccc2nc(-c3cn(-c4ccc(O)c(F)c4)nn3)ccc2c1]

Procedure

Compound 34 (50.0 mg, 0.123 mmol) was dissolved in DMF (5 mL) and DIPEA (214 uL, 159 mg, 1.23 mmol, 10 eq) and stirred under nitrogen. HBTU (154 mg, 0.405 mmol, 3.3 eq) was then added, and the reaction stirred for 15 minutes. Compound 29 (200 mg, 0.405 mmol, 3.3 eq) dissolved in DMF (1 mL) was then added dropwise, and the reaction stirred for 1 hour. The mixture was diluted into ethyl acetate, and washed with 1M HCl (2×) and brine (5×). The organic layer was evaporated to give a gummy residue, which was purified on reverse phase HPLC (35-50% MeCN in water, 0.1% TFA) to give compound 44 (79.3 mg, 0.103 mmol) in 84% yield.

HRMS: $[M+H]^+$ expected 770.305, found 770.308

Compound 44 (79.3 mg, 0.103 mmol) was dissolved in dioxane (1.8 mL) and 1M NaOH (0.2 mL) was added. The solution was stirred at room temperature for 2 hours, then acidified (pH 3) and evaporated. The residue was resuspended in EtOAc, washed with 1M HCl, and dried over sodium sulfate. The organic layer was evaporated to give compound 41 as an oil (68.9 mg, 0.0948 mmol) in 92% yield, which was used without further purification.

12. MIF-AcF3-2 (FIG. 24)

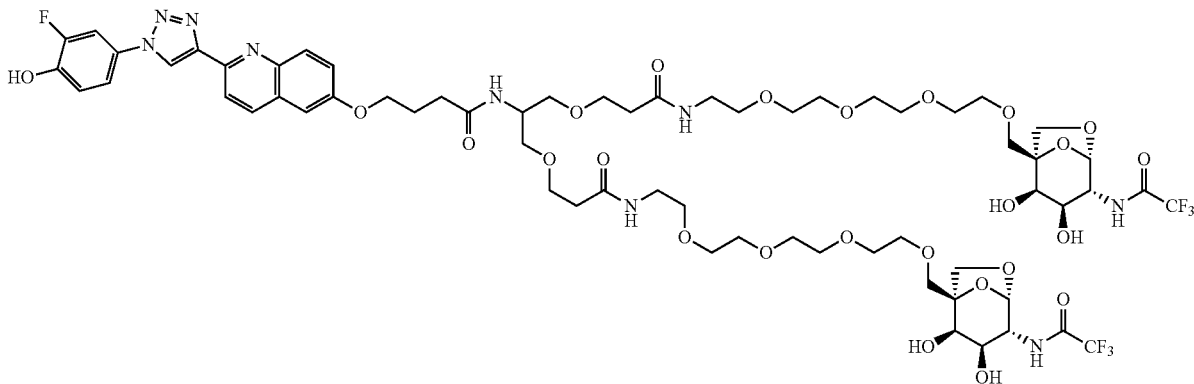 [SMILES: O=C(CCOCC(COCCC(=O)NCCOCCOCCOCCOC[C@@]12CO[C@@H](O1)[C@H](NC(=O)C(F)(F)F)[C@@H](O)[C@H]2O)NC(=O)CCCOc1ccc2nc(-c3cn(-c4ccc(O)c(F)c4)nn3)ccc2c1)NCCOCCOCCOCCOC[C@@]12CO[C@@H](O1)[C@H](NC(=O)C(F)(F)F)[C@@H](O)[C@H]2O]

Compound 41 (57.6 mg, 0.0921 mmol) was dissolved in DMF (1.8 mL) and DIPEA (0.2 mL). HBTU (84.0 mg, 0.222 mmol, 2.4 eq) was then added, and the reaction stirred for 15 minutes before the addition of compound 15 (111 mg, 0.222 mmol, 2.4 eq). The reaction was stirred for 1 hour, then evaporated to give a red residue which was used in the next reaction without purification.

Compound 42 (crude, 0.0921 mmol scale) was dissolved in 1M HCl (1 mL) and stirred for 2 hours. The reaction was purified directly by HPLC (20-40% MeCN in $H_2O$, +3% TFA) to give compound 43 (44.66 mg, 0.0295 mmol) in 32% yield.

Expected (H) 1514.570, found 1514.561

13. MIF-AcF3-3 (FIG. 25)

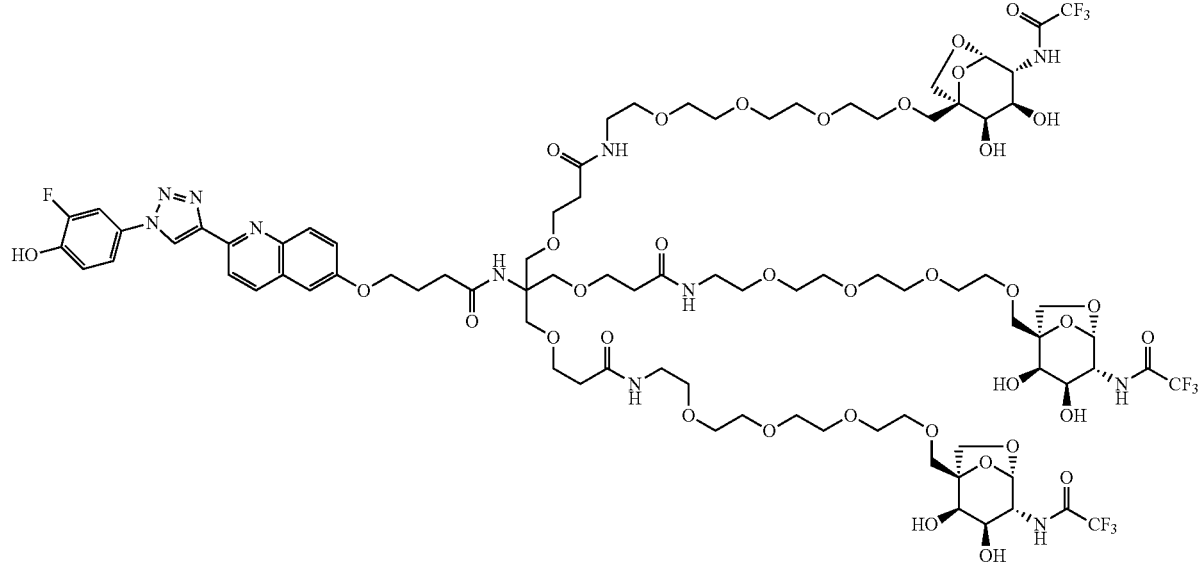 [SMILES: O=C(CCOCC(COCCC(=O)NCCOCCOCCOCCOC[C@@]12CO[C@@H](O1)[C@H](NC(=O)C(F)(F)F)[C@@H](O)[C@H]2O)(COCCC(=O)NCCOCCOCCOCCOC[C@@]12CO[C@@H](O1)[C@H](NC(=O)C(F)(F)F)[C@@H](O)[C@H]2O)NC(=O)CCCOc1ccc2nc(-c3cn(-c4ccc(O)c(F)c4)nn3)ccc2c1)NCCOCCOCCOCCOC[C@@]12CO[C@@H](O1)[C@H](NC(=O)C(F)(F)F)[C@@H](O)[C@H]2O]

Compound 45 (68.9 mg, 0.0948 mmol) was dissolved in DMF (1.8 mL) and DIPEA (0.2 mL). HBTU PGP-150 $C_1$ (126 mg, 0.333 mmol, 3.6 eq) was then added, and the reaction stirred for 15 minutes before the addition of compound 15 (167 mg, 0.333 mmol, 3.6 eq). The reaction was stirred for 1 hour, then evaporated to give a reddish residue which was used in the next reaction without purification.

Procedure

Compound 38 (crude, 0.0948 mmol scale) was dissolved in 1M HCl (1 mL) and stirred for 2 hours. The reaction was purified directly by HPLC (20-40% MeCN in $H_2O$, +3% TFA) to give compound 39 (78.1 mg, 0.0379 mmol) in 40% yield.

Expected (2H, 12) 1030.891 Found 1030.903

Synthesis of MIF-AcF2-3, MIF-Ac-3, MIF-Et-3

Set forth in FIGS. 26-29 are the chemical syntheses of MIF-AcF2-3, MIF-Ac-3, MIF-Et-3 and MIF-EtF3-3 produced using analogous methods to those presented above with minor variation.

REFERENCES

1. Stove S, Welte T, Wagner T, Kola A, Klos A, Bautsch W, et al. Circulating complement proteins in patients with sepsis or systemic inflammatory response syndrome. Clinical and diagnostic laboratory immunology. 1996; 3(2): 175-83.
2. Chuang T-Y, Chang H-T, Chung K-P, Cheng H-S, Liu C-Y, Liu Y-C, et al. High levels of serum macrophage migration inhibitory factor and interleukin 10 are associated with a rapidly fatal outcome in patients with severe sepsis. International Journal of Infectious Diseases. 2014; 20:13-7.
3. Henderson B, Pockley A G. Proteotoxic stress and circulating cell stress proteins in the cardiovascular diseases. Cell Stress and Chaperones. 2012; 17(3):303-11.
4. Leander K, Mälarstig A, van't Hooft F M, Hyde C, Hellenius M-L, Troutt J S, et al. Circulating proprotein convertase subtilisin/kexin type 9 (PCSK9) predicts future risk of cardiovascular events independently of established risk factors. Circulation. 2016; 133(13): 1230-9.
5. Benham A M. Protein secretion and the endoplasmic reticulum. Cold Spring Harbor perspectives in biology. 2012; 4(8):a012872.
6. Yang W H, Aziz P V, Heithoff D M, Mahan M J, Smith J W, Marth J D. An intrinsic mechanism of secreted protein aging and turnover. Proceedings of the National Academy of Sciences. 2015; 112(44):13657-62.
7. Winkelhake J L, Nicolson G. Aglycosylantibody. Effects of exoglycosidase treatments on autochthonous antibody survival time in the circulation. Journal of Biological Chemistry. 1976; 251(4): 1074-80.
8. Sarkar M, Liao J, Kabat E A, Tanabe T, Ashwell G. The binding site of rabbit hepatic lectin. Journal of Biological Chemistry. 1979; 254(9):3170-4.
9. Ashwell G, Harford J. Carbohydrate-specific receptors of the liver. Annual review of biochemistry. 1982; 51(1): 531-54.
10. Connolly D T, Townsend R, Kawaguchi K, Bell W, Lee Y C. Binding and endocytosis of cluster glycosides by rabbit hepatocytes. Evidence for a short-circuit pathway that does not lead to degradation. Journal of Biological Chemistry. 1982; 257(2):939-45.
11. Lee R T, Lee Y C. Affinity enhancement by multivalent lectin-carbohydrate interaction. Glycoconjugate journal. 2000; 17(7-9):543-51.

12. Wragg S, Drickamer K. Identification of amino acid residues that determine pH dependence of ligand binding to the asialoglycoprotein receptor during endocytosis. Journal of Biological Chemistry. 1999; 274(50):35400-6.
13. Schwartz A, Fridovich S, Lodish H. Kinetics of internalization and recycling of the asialoglycoprotein receptor in a hepatoma cell line. Journal of Biological Chemistry. 1982; 257(8):4230-7.
14. Wall D A, Wilson G, Hubbard A L. The galactose-specific recognition system of mammalian liver: the route of ligand internalization in rat hepatocytes. Cell. 1980; 21(1):79-93.
15. Watarai H, Nozawa R, Tokunaga A, Yuyama N, Tomas M, Hinohara A, et al. Posttranslational modification of the glycosylation inhibiting factor (GIF) gene product generates bioactive GIF. Proceedings of the National Academy of Sciences. 2000; 97(24): 13251-6.
16. Calandra T, Echtenacher B, Le Roy D, Pugin J, Metz C N, Hiiltner L, et al. Protection from septic shock by neutralization of macrophage migration inhibitory factor. Nature medicine. 2000; 6(2): 164-70.
17. Benedek G, Meza-Romero R, Jordan K, Zhang Y, Nguyen H, Kent G, et al. MIF and D-DT are potential disease severity modifiers in male MS subjects. Proceedings of the National Academy of Sciences. 2017; 114(40): E8421-E9.
18. Kim K-W, Kim H-R. Macrophage migration inhibitory factor: a potential therapeutic target for rheumatoid arthritis. The Korean journal of internal medicine. 2016; 31(4): 634.
19. Hussain F, Freissmuth M, Volkel D, Thiele M, Douillard P, Antoine G, et al. Human anti-macrophage migration inhibitory factor antibodies inhibit growth of human prostate cancer cells in vitro and in vivo. Molecular cancer therapeutics. 2013; 12(7): 1223-34.
20. Reidy T, Rittenberg A, Dwyer M, D'Ortona S, Pier G, Gadjeva M. Homotrimeric macrophage migration inhibitory factor (MIF) drives inflammatory responses in the corneal epithelium by promoting caveolin-rich platform assembly in response to infection. Journal of Biological Chemistry. 2013; 288(12):8269-78.
21. Willis M S, Carlson D L, DiMaio J M, White M D, White D J, Adams G A, et al. Macrophage migration inhibitory factor mediates late cardiac dysfunction after burn injury. American Journal of Physiology-Heart and Circulatory Physiology. 2005; 288(2):H795-H804.
22. Sanhueza, C. A.; Baksh, M. M.; Thuma, B.; Roy, M. D.; Dutta, S.; Preville, C.; Chrunyk, B. A.; Beaumont, K.; Dullea, R.; Ammirati, M., Efficient Liver Targeting by Polyvalent Display of a Compact Ligand for the Asialoglycoprotein Receptor. Journal of the American Chemical Society 2017, 139 (9), 3528-3536.
23. Maschitti, V., Patent WO 2015/I 77668 A1 2015.
24. Schwartz A, Fridovich S E, Knowles B B, Lodish H. Characterization of the asialoglycoprotein receptor in a continuous hepatoma line. Journal of Biological Chemistry. 1981; 256(17): 8878-81.
25. Geuze H J, Slot J W, Strous G J, Lodish H F, Schwartz A L. Intracellular site of asialoglycoprotein receptor-ligand uncoupling: double-label immunoelectron microscopy during receptor-mediated endocytosis. Cell. 1983; 32(1):277-87.

The invention claimed is:

1. A bifunctional compound according to the chemical structure:

wherein [IgGBM] is a peptide IgG binding moiety selected from the group consisting of
PAM;
D-PAM;
D-PAM-Φ;

TWKTSRISIF; (SEQ ID NO: 1)

FGRLVSSIRY; (SEQ ID NO: 2)

Fc-III;
FcBP-1;
FcBP-2;
Fc-III-4c;

EPIHRSTLTALL; (SEQ ID NO: 3)

APAR; (SEQ ID NO: 4)

FcRM;

HWRGWV; (SEQ ID NO: 5)

HYFKFD; (SEQ ID NO: 6)

-continued

HFRRHL; (SEQ ID NO: 7)

HWCitGWV; (SEQ ID NO: 8)

D2AAG;

DAAG;

cyclo[(N-Ac)S(A)-RWHYFK-Lact-E]; (SEQ ID NO: 9)

cyclo[(N-Ac)-Dap(A)-RWHYFK-Lact-E]; (SEQ ID NO: 10)

cyclo[Link-M-WFRHYK]; (SEQ ID NO: 11)

NKFRGKYK; (SEQ ID NO: 12)

NARKFYKG; (SEQ ID NO: 13)

FYWHCLDE; (SEQ ID NO: 14)

FYCHWALE; (SEQ ID NO: 15)

FYCHTIDE; (SEQ ID NO: 16)

Dual 1/3;

RRGW; and (SEQ ID NO: 17)

KHRFNKD; (SEQ ID NO: 18)

wherein [ASGPRBM] is an asialoglycoprotein receptor binding moiety according to the chemical structure:

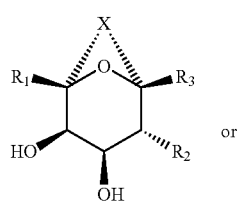 or 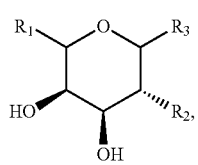

wherein X is 1 to 4 atoms in length and is independently at each occurrence selected from the group consisting of O, S, N($R^{N1}$), and C($R^{N1}$)($R^{N1}$), provided that:
  when X is 1 atom in length, X is O, S, N($R^{N1}$), or C($R^{N1}$)($R^{N1}$),
  when X is 2 atoms in length, no more than 1 atom of X is O, S, or N($R^{N1}$),
  when X is 3 or 4 atoms in length, no more than 2 atoms of X are O, S, or N($R^{N1}$);
wherein $R^{N1}$ is H or $C_1$-$C_3$ alkyl optionally substituted with 1 to 3 halogen groups;
wherein:
  $R_1$ and $R_3$ are each independently H, —$(CH_2)_K$OH, —$(CH_2)_K$O($C_1$-$C_4$ alkyl) optionally substituted with 1 to 3 halogen groups, $C_1$-$C_4$ alkyl optionally substituted with 1 to 3 halogen groups, —$(CH_2)_K$vinyl, —O—$(CH_2)_K$vinyl, —$(CH_2)_K$alkynyl, —$(CH_2)_K$COOH, —$(CH_2)_K$C(O)O—($C_1$-$C_4$ alkyl) optionally substituted with 1 to 3 halogen groups, O—C(O)—($C_1$-$C_4$ alkyl) optionally substituted with 1 to 3 halogen groups, —C(O)—($C_1$-$C_4$ alkyl) optionally substituted with 1 to 3 halogen groups, or $R_1$ and $R_3$ are each independently

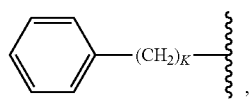

which is optionally substituted with up to three halogen groups; $C_1$-$C_4$ alkyl, each of which alkyl group is optionally substituted with from one to three halogen groups or one or two hydroxyl groups: or O—($C_1$-$C_4$ alkyl), each of which alkyl groups is optionally substituted with from one to three halogen groups or one or two hydroxyl groups:

$R_1$ and $R_3$ are each independently a group according to the chemical structure:

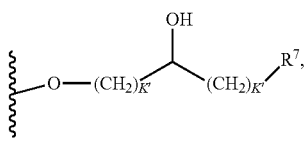

wherein $R^7$ is O—($C_1$-$C_4$ alkyl) optionally substituted with 1 to 3 halogen groups or 1-2 hydroxy groups, —$NR^{N3}R^{N4}$, or

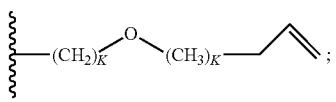

$R_1$ and $R_3$ are each independently a group according to the structure:

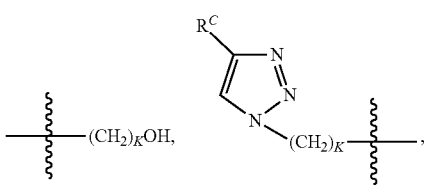

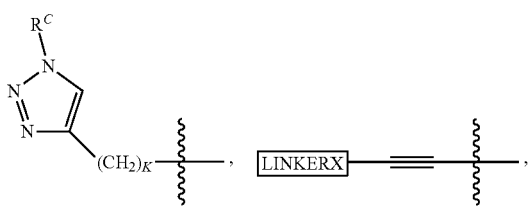

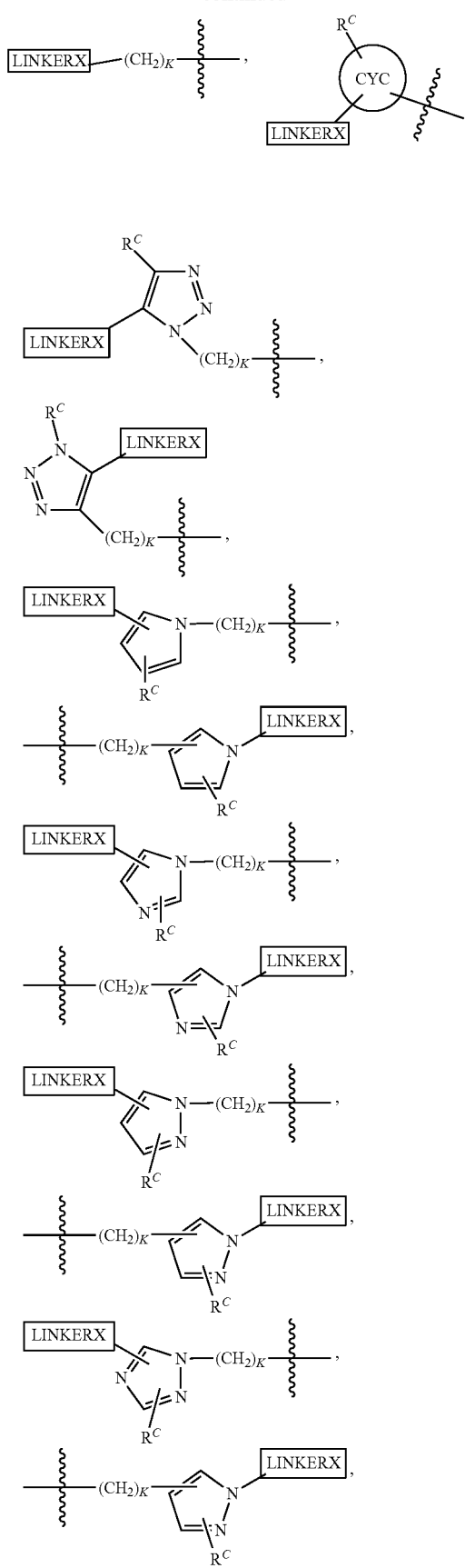
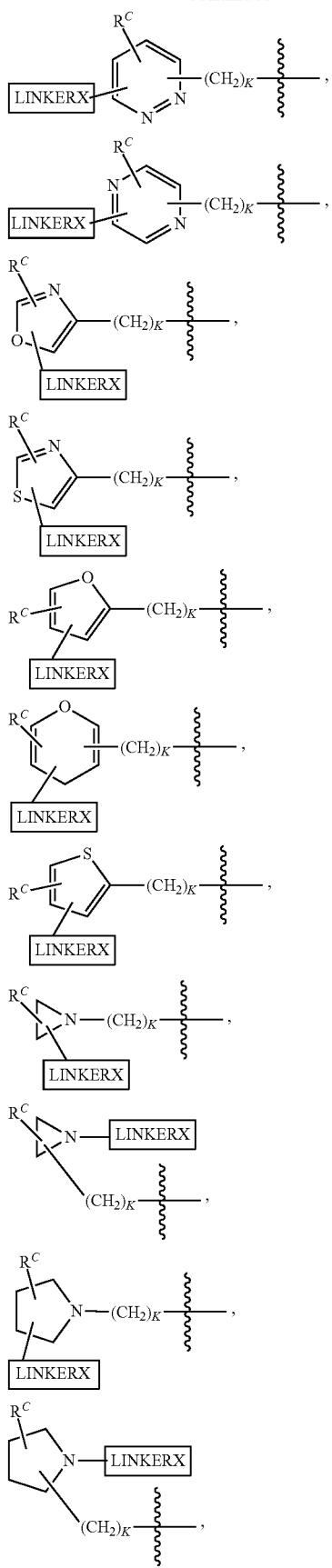

-continued

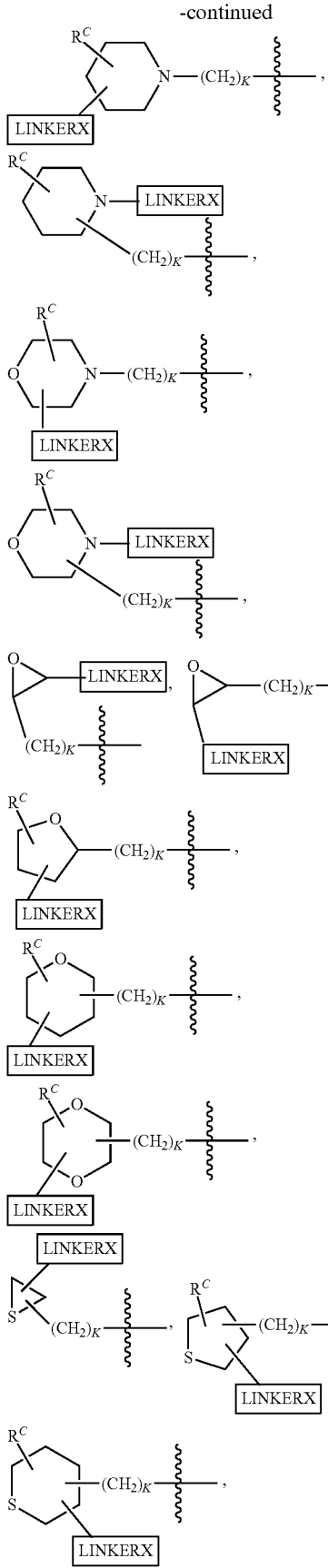

or $R_1$ and $R_3$ are each independently

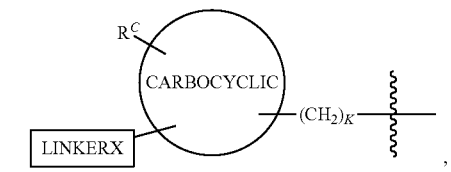

wherein

is a $C_3$-$C_8$ saturated carbocyclic group;

wherein:

$R^C$ is absent, H, $C_1$-$C_4$ alkyl optionally substituted with from 1 to 3 halogen groups or 1 to 2 hydroxyl groups, or a group according to the structure:

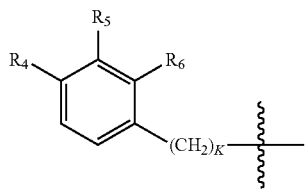

wherein $R_4$, $R_5$ and $R_6$ are each independently, H, halogen, CN, $NR^{N1}R^{N2}$, —$(CH_2)_K$OH, —$(CH_2)_K$O($C_1$-$C_4$ alkyl) optionally substituted with 1-3 halogen groups, $C_1$-$C_3$ alkyl optionally substituted with 1-3 halogen groups, —O—($C_1$-$C_3$-alkyl) optionally substituted with 1-3 halogen groups, —$(CH_2)_K$COOH, —$(CH_2)_K$C(O)O—($C_1$-$C_4$ alkyl) optionally substituted with 1-3 halogen groups, O—C(O)—($C_1$-$C_4$ alkyl) optionally substituted with 1-3 halogen groups, or —C(O)—($C_1$-$C_4$ alkyl) optionally substituted with 1-3 halogen groups, or wherein $R^C$ is

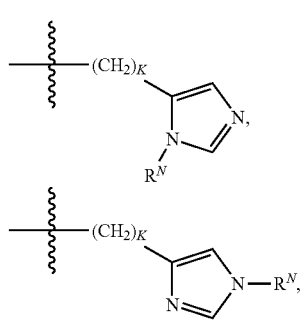

-continued

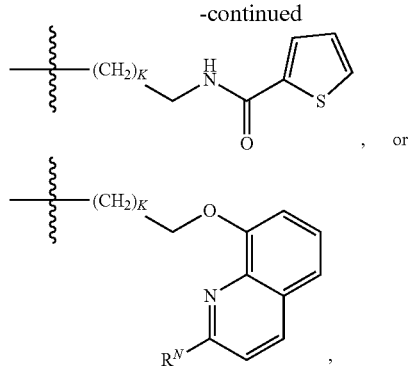

wherein $R^N$, $R^{N1}$, and $R^{N2}$ are each independently H or $C_1$-$C_3$ alkyl optionally substituted with 1 to 3 halogen groups or 1 or 2 hydroxyl groups:

wherein each K is independently 0, 1, 2, 3, or 4:

wherein each —$(CH_2)K$ group is optionally substituted with 1 to 4 $C_1$-$C_3$ alkyl groups which are optionally substituted with 1 to 3 fluoro groups or 1 to 2 hydroxyl groups;

wherein each K' is independently 1, 2, 3, or 4;

wherein $R^{N3}$ is H, or $C_1$-$C_3$ alkyl optionally substituted with 1 to 3 halogen groups or 1 to 2 hydroxy groups;

wherein $R^{N4}$ is H, $C_1$-$C_3$ alkyl optionally substituted with 1 to 3 halogen groups or 1 to 2 hydroxy groups, or

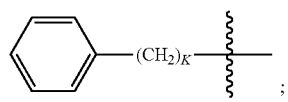

wherein

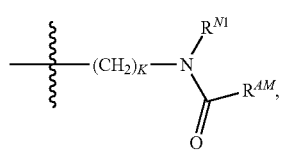

is a linker group comprising at least one [IgGBM] group and links the at least one [IgGBM] group to the [ASGPRBM] through one or more optional [CON] groups,
or

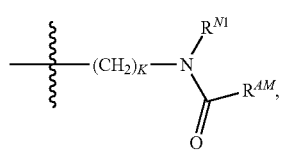

is a linker group comprising at least one or more functional groups that covalently bond the linker group to at least one [IgGBM] group or optional [CON] group;

wherein:
$R_2$ is

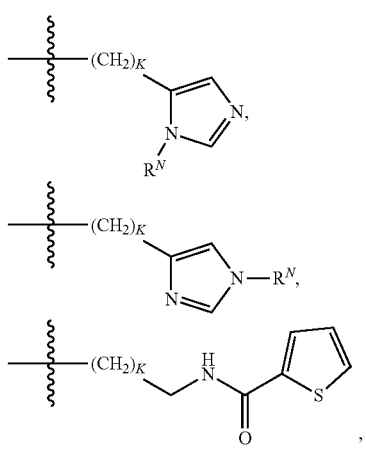

wherein $R^{AM}$ is H, $C_1$-$C_4$ alkyl optionally substituted with up to 3 halogen groups and one or two hydroxyl groups, —$(CH_2)_K COOH$, —$(CH_2)_K C(O)O$—$(C_1$-$C_4$ alkyl) optionally substituted with 1 to 3 halogen groups, —O—C(O)—$(C_1$-$C_4$ alkyl) optionally substituted with 1 to 3 halogen groups, —C(O)—$(C_1$-$C_4$ alkyl) optionally substituted with 1 to 3 halogen groups, —$(CH_2)_K$—$NR^{N3}R_{N4}$;
or
$R_2$ is

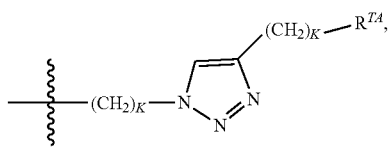

wherein:
$R^{TA}$ is H, CN, $NR^{N1}R^{N2}$, —$(CH_2)_K OH$, —$(CH_2)_K O(C_1$-$C_4$ alkyl) optionally substituted with 1 to 3 halogen groups, $C_1$-$C_4$ alkyl optionally substituted with 1 to 3 halogen groups, —$(CH_2)_K COOH$, —$(CH_2)_K C(O)O$—$(C_1$-$C_4$ alkyl) optionally substituted with 1 to 3 halogen groups, —O—C(O)—$(C_1$-$C_4$ alkyl) optionally substituted with 1 to 3 halogen groups, or —C(O)—$(C_1$-$C_4$ alkyl) optionally substituted with 1 to 3 halogen groups, or $R^{TA}$ is $C_3$-$C_{10}$ aryl or a three- to ten-membered heteroaryl group containing up to 5 heteroatoms, each of the aryl or heteroaryl groups being optionally substituted with up to three CN, $NR^{N1}R^{N2}$, —$(CH_2)_K OH$, —$(CH_2)_K O(C_1$-$C_4$ alkyl) optionally substituted with 1 to 3 halogen groups, $C_1$-$C_3$ alkyl optionally substituted with 1 to 3 halogen groups or 1 to 2 hydroxy groups, —O—$(C_1$-$C_3$-alkyl) optionally substituted from 1-3 halogen groups, —$(CH_2)_K COOH$, —$(CH_2)_K C(O)O$—$(C_1$-$C_4$ alkyl) optionally substituted with 1 to 3 halogen groups, O—C(O)—$(C_1$-$C_4$ alkyl) optionally substituted with 1 to 3 halogen groups, or —$(CH_2)_K C(O)$—$(C_1$-$C_4$ alkyl) optionally substituted with 1 to 3 halogen groups, or $R^{TA}$ is

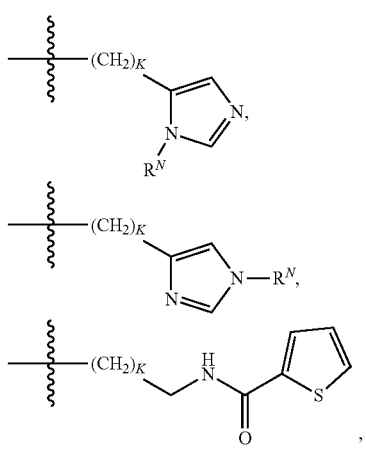

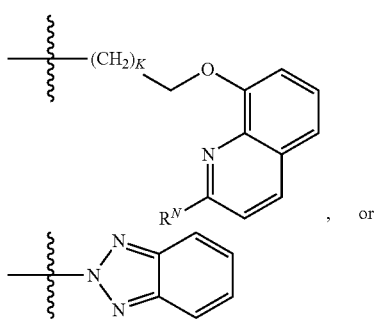

, or

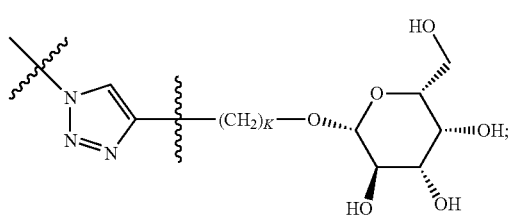

optionally substituted with up to three $C_1$-$C_3$ alkyl groups which are optionally substituted with up to three halogen groups, or $R^{TA}$ is

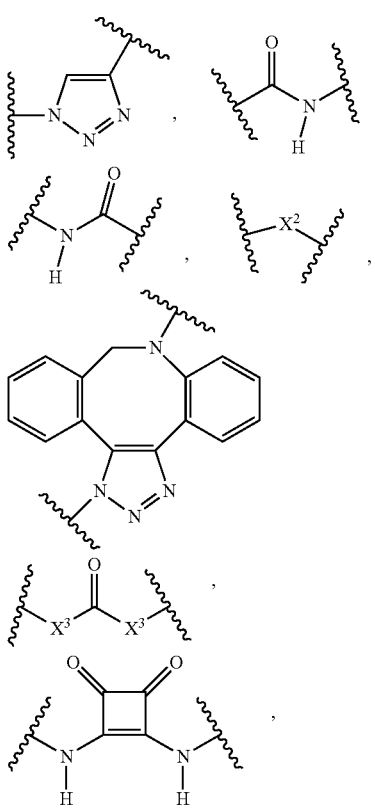

each [CON] is an optional connector chemical moiety which, when present, is a group according to the structure:

i) a group according to:

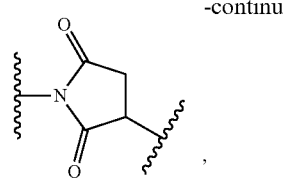

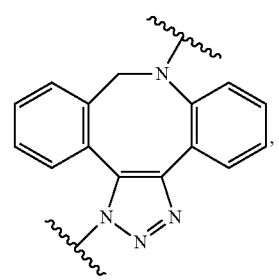

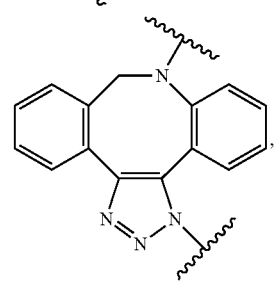

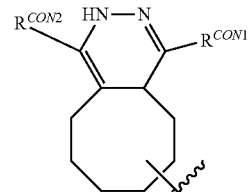

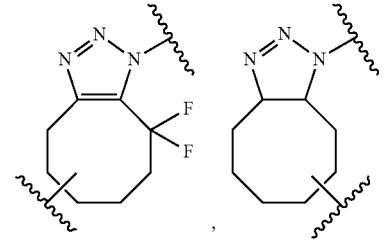

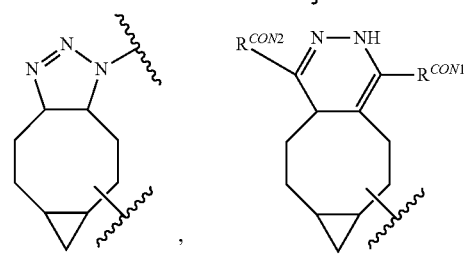

wherein:

$R^{CON1}$ and $R^{CON2}$ are each independently H, methyl, or a bond;

$X^2$ is $CH_2$, O, S, $NR^4$, C(O), S(O), $S(O)_2$, —$S(O)_2O$, —$OS(O)_2$, or $OS(O)_2O$;

$X^3$ is O, S, or $NR^4$; and $R^4$ is H, $C_1$-$C_3$ alkyl or alkanol, or —$C(O)(C_1$-$C_3$ alkyl); or ii) a group according to the structure:

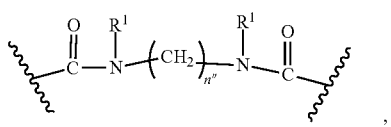

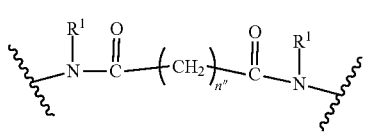

or

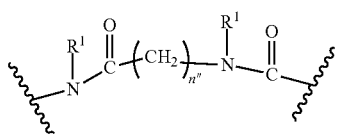

wherein:

R$^1$ is H or C$_1$-C$_3$ alkyl, and n" is independently an integer from 0 to 8;

or iii) a group according to the chemical structure:

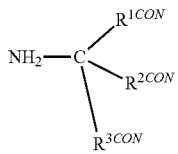

wherein R$^{1CON}$, R$^{2CON}$, and R$^{3CON}$ are each independently H, —(CH$_2$)$_{MC1}$—, —(CH$_2$)$_{MC1a}$C(O)$_{XA}$(N$^4$)$_{XA}$—(CH$_2$)$_{MC1a}$—, —(CH$_2$)$_{MC1a}$(NR$^4$)$_{XA}$C(O)$_{XA}$—(CH$_2$)$_{MC1a}$—, or —(CH$_2$)$_{MC1a}$O—(CH$_2$)$_{MC1}$—C(O)NR$^4$—, with the proviso that R$_{1CON}$, R$^{2CON}$, and R$^{3CON}$ are not simultaneously H;

each MC1 is independently 1, 2, 3, or 4;

each MC1a is independently 1, 2, 3, or 4;

each XA is independently 0 or 1; and

R$^4$ is H, C$_1$-C$_3$ alkyl, C$_1$-C$_3$ alkanol, or —C(O)(C$_1$-C$_3$ alkyl), with the proviso that MC1a and XA in a moiety are not all simultaneously 0;

wherein [LINKER] is:

i) a polyethyleneglycol linker having from 1 to 12 ethylene glycol residues, ii) a polypropylene glycol or polypropylene-co-polyethylene glycol linker containing 1 to 100 alkylene glycol units, iii) a group according to the chemical structure:

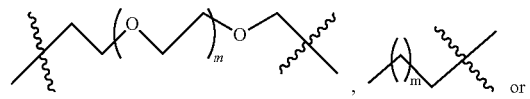

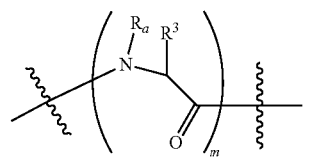

wherein

R$_a$ is H, C$_1$-C$_3$ alkyl or alkanol, or R$_a$ taken together with R$^3$ forms a pyrrolidine ring or a hydroxypyrrolidine ring, m is independently an integer from 1 to 15, and R$^3$ is an amino acid side chain from a D- or L-amino acid selected from the group consisting of alanine (methyl), arginine (propyleneguanidine), asparagine (methylenecarboxyamide), aspartic acid (ethanoic acid), cysteine (thiol, reduced or oxidized di-thiol), glutamine (ethylcarboxyamide), glutamic acid (propanoic acid), glycine (H), histidine (methyleneimidazole), isoleucine (1-methylpropane), leucine (2-methylpropane), lysine (butyleneamine), methionine (ethylmethylthioether), phenylalanine (benzyl), proline, hydroxyproline (R$^3$ forms a cyclic ring with R$_a$ and the adjacent nitrogen group to form a pyrrolidine or hydroxypyrrolidine group), serine (methanol), threonine (ethanol, 1-hydroxyethane), tryptophan (methyleneindole), tyrosine (methylene phenol) and valine (isopropyl);

iv) a group according to the chemical structure:

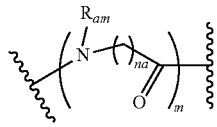

wherein:

R$_{am}$ is H or C$_1$-C$_3$ alkyl optionally substituted with one or two hydroxyl groups;

na is an integer from 1 to 15; and m is an integer from 1 to 100;

v) a group according to the chemical formula:

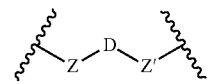

wherein:

Z and Z' are each independently a bond, —(CH$_2$)$_i$—O—, —(CH$_2$)$_i$—S—, —(CH$_2$)$_i$—N(R)—,

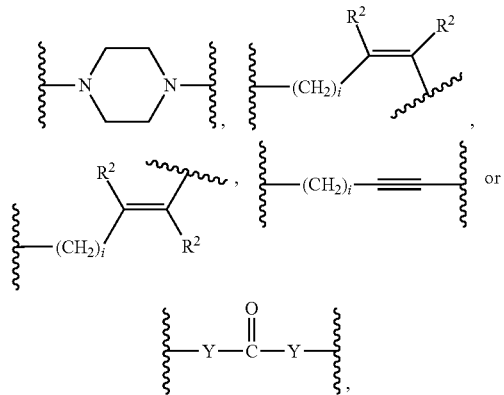

wherein:
the —(CH$_2$)$_i$ group, if present in Z or Z', is bonded to a connector group [CON], [IgGBM], or [ASGPRBM];

each R is H, or C$_1$-C$_3$ alkyl or alkanol;

each R$^2$ is independently H or C$_1$-C$_3$ alkyl;

each Y is independently a bond, O, S, or N—R;

each i is independently 0 to 100;

D is

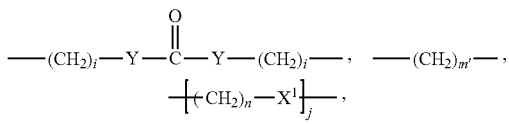

or a bond, with the proviso that Z, Z', and D are not each simultaneously bonds;

j is an integer from 1 to 100:

m' is an integer from 1 to 100 n is an integer from 1 to 100;

X$^1$ is O, S, or N—R:

R is H, C$_1$-C$_3$ alkyl, or C$_1$-C$_3$ alkanol; and vi) a group with the chemical structure:

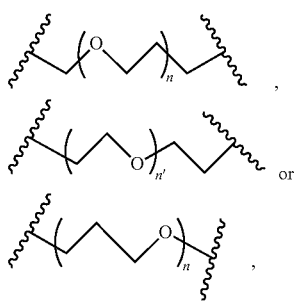

wherein n is an integer from 1 to 25;

n' is an integer from 1 to 25;

n" is an integer from 0 to 8; or vii) a group with the chemical formula: PEG-[CON]-PEG, wherein each PEG is independently at each occurrence 1 to 12 ethylene glycol residues and [CON] is a triazole group

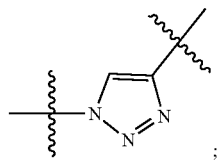

wherein k' is independently 1, 2, or 3;

wherein j' is independently 1, 2, or 3;

wherein h is independently 1, 2, or 3;

wherein h' is independently 1, 2, or 3, wherein i$_L$ is independently 1, 2, or 3, or a salt, stereoisomer, or solvate thereof.

2. The compound of claim 1, wherein:

X in [ASGPRBM] is —O—C(R$^{N1}$)(R$^{N1}$)—, —C(R$^{N1}$)(R$^{N1}$)—O—, —S—C(R$^{N1}$)(R$^{N1}$)—, —C(R$^{N1}$)(R$^{N1}$)—S—, —N(R$^{N1}$)—C(R$^{N1}$)(R$^{N1}$)—, —C(R$^{N1}$)(R$^{N1}$)—N(R$^{N1}$)—, or —C(R$^{N1}$)(R$^{N1}$)—C(R$^{N1}$)(R$^{N1}$)—, when X is 2 atoms in length, X in [ASGPRBM] is —O—C(R$^{N1}$)(R$^{N1}$)—C(R$^{N1}$)(R$^{N1}$)—, —C(R$^{N1}$)(R$^{N1}$)—O—C(R$^{N1}$)(R$^{N1}$), —O—C(R$^{N1}$)(R$^{N1}$)—O—, —O—C(R$^{N1}$)(R$^{N1}$)—S—, —O—C(R$^{N1}$)(R$^{N1}$)—N(R$^{N1}$)—, —S—C(R$^{N1}$)(R$^{N1}$)—C(R$^{N1}$)(R$^{N1}$)—, —C(R$^{N1}$)(R$^{N1}$)—S—C(R$^{N1}$)(R$^{N1}$)—, —C(R$^{N1}$)(R$^{N1}$)—C(R$^{N1}$)(R$^{N1}$), —S—C(R$^{N1}$)(R$^{N1}$)—S—, —S—C(R$^{N1}$)(R$^{N1}$)—O—, —S—C(R$^{N1}$)(R$^{N1}$)—N(R$^{N1}$)—, —N(R$^{N1}$)—C(R$^{N1}$)(R$^{N1}$)—C(R$^{N1}$)(R$^{N1}$)—, —C(R$^{N1}$)(R$^{N1}$)—N(R$^{N1}$)—C(R$^{N1}$)(R$^{N1}$)—, —C(R$^{N1}$)—C(R$^{N1}$)(R$^{N1}$)—N(R$^{N1}$)—, —N(R$^{N1}$)—C(R$^{N1}$)(R$^{N1}$)—N(R$^{N1}$)—, or —C(R$^{N1}$)(R$^{N1}$)—C(R$^{N1}$)(R$^{N1}$)—C(R$^{N1}$)(R$^{N1}$), when X is 3 atoms in length, and X in [ASGPRBM] is —O—C(R$^{N1}$)(R$^{N1}$)—C(R$^{N1}$)(R$^{N1}$)—C(R$^{N1}$)(R$^{N1}$)—, —C(R$^{N1}$)(R$^{N1}$)—O—C(R$^{N1}$)(R$^{N1}$)—C(R$^{N1}$)(R$^{N1}$)—, —O—C(R$^{N1}$)(R$^{N1}$)—O—C(R$^{N1}$)(R$^{N1}$)—, —S—C(R$^{N1}$)(R$^{N1}$)—C(R$^{N1}$)(R$^{N1}$)—C(R$^{N1}$)(R$^{N1}$)—, —C(R$^{N1}$)(R$^{N1}$)—S—C(R$^{N1}$)(R$^{N1}$)—C(R$^{N1}$)(R$^{N1}$)—, —C(R$^{N1}$)(R$^{N1}$)—C(R$^{N1}$)(R$^{N1}$)—S—C(R$^{N1}$)(R$^{N1}$)—, —S—C(R$^{N1}$)(R$^{N1}$)—S—C(R$^{N1}$)(R$^{N1}$)—, —N(R$^{N1}$)—C(R$^{N1}$)(R$^{N1}$)—C(R$^{N1}$)(R$^{N1}$)—C(R$^{N1}$)(R$^{N1}$)—, or —C(R$^{N1}$)(R$^{N1}$)—N(R$^{N1}$)—C(R$^{N1}$)(R$^{N1}$)—C(R$^{N1}$)(R$^{N1}$)— when X is 4 atoms in length.

3. The compound of claim 1, wherein X in [ASGPRBM] is OCH$_2$ or CH$_2$O and wherein R$^{N1}$ is H.

4. The compound of claim 1, wherein the [ASGPRBM] group is a group according to the chemical structure:

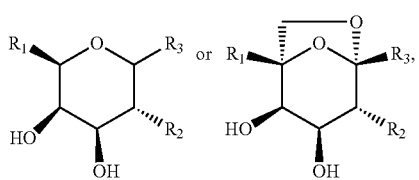

or a salt, stereoisomer, or solvate thereof.

5. The compound of claim 1, wherein the [ASGPRBM] group is a group according to the chemical structure:

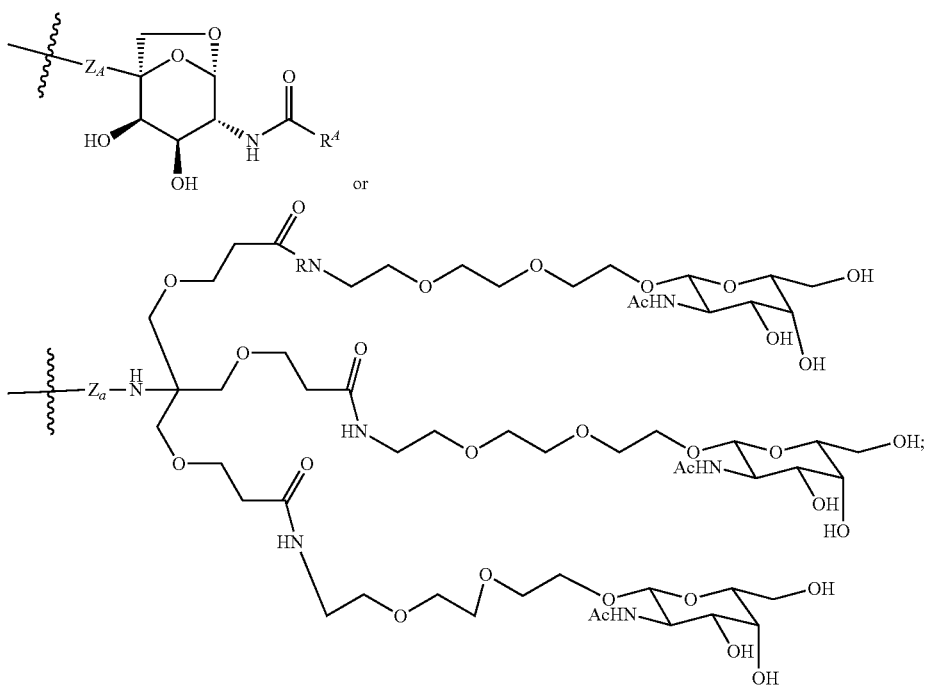

wherein:

$R^A$ is $C_1$-$C_3$ alkyl optionally substituted with 1-5 halogen groups;

$Z_A$ is —$(CH_2)_{IM}$—, —O—$(CH_2)_{IM}$—, —S—$(CH_2)_{IM}$—, —$NR_M$—$(CH_2)_{IM}$—, —C(O)—$(CH_2)_{IM}$—, a PEG group containing from 1 to 8 ethylene glycol residues, or —C(O)$(CH_2)_{IM}$—$NR_M$—; and $Z_B$ is absent, —$(CH_2)_{IM}$—, —C(O)—$(CH_2)_{IM}$—, or —C(O)—$(CH_2)_{IM}$—$NR_M$—;

wherein IM is independently 0, 1, 2, 3, 4, 5, or 6, and wherein $R_M$ is H or a $C_1$-$C_3$ alkyl group which is optionally substituted with one or two hydroxyl groups.

6. The compound of claim 5, wherein at least one applies:

$R^A$ is a methyl or ethyl group, either of which is optionally substituted with 1-3 fluoro groups;

$Z_A$ is a PEG group containing from 1 to 4 ethylene glycol residues.

7. The compound of claim 1, wherein $R_1$ and $R_3$ of the [ASGPRBM] are each independently a group according to the chemical structure:

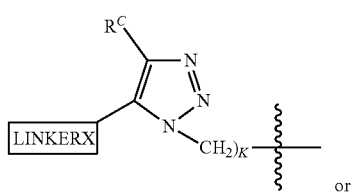

or

-continued

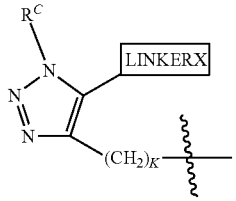

8. The compound of claim 1, wherein $R_1$ and $R_3$ of the [ASGPRBM] group are each independently a moiety selected from the group consisting of

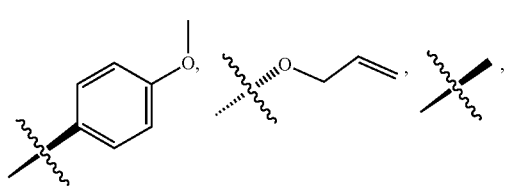

-continued
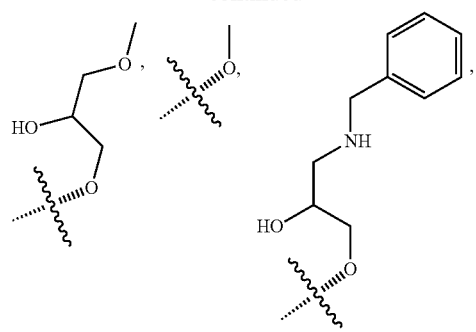
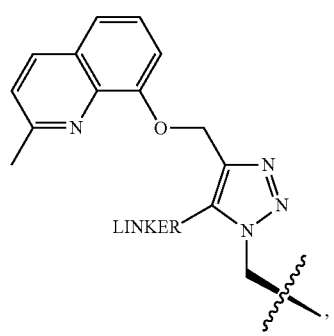
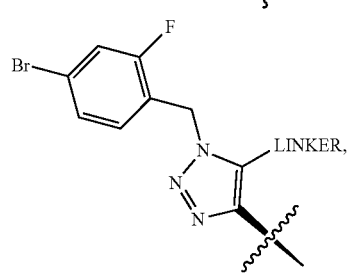
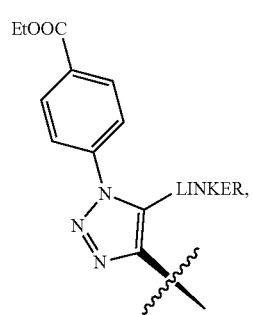
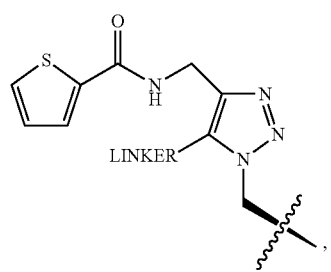
-continued
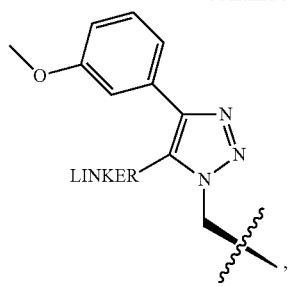
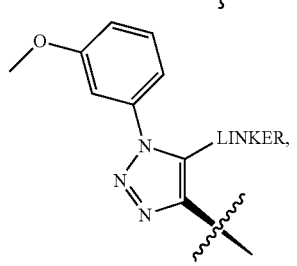
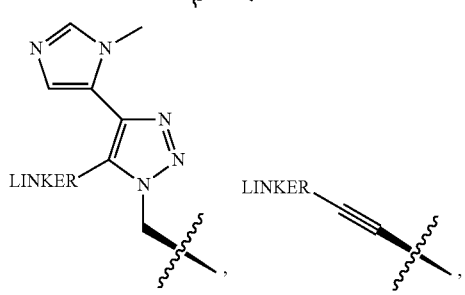
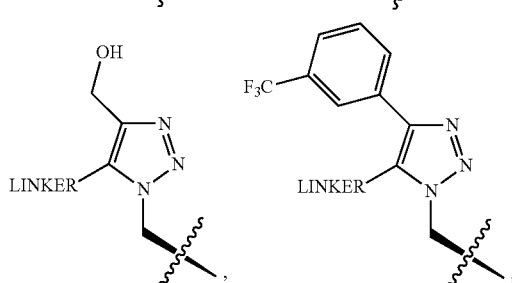
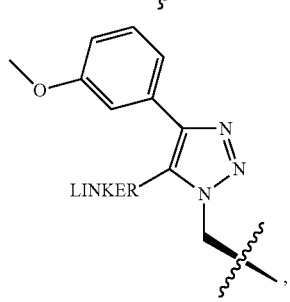
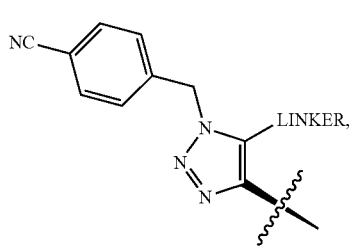

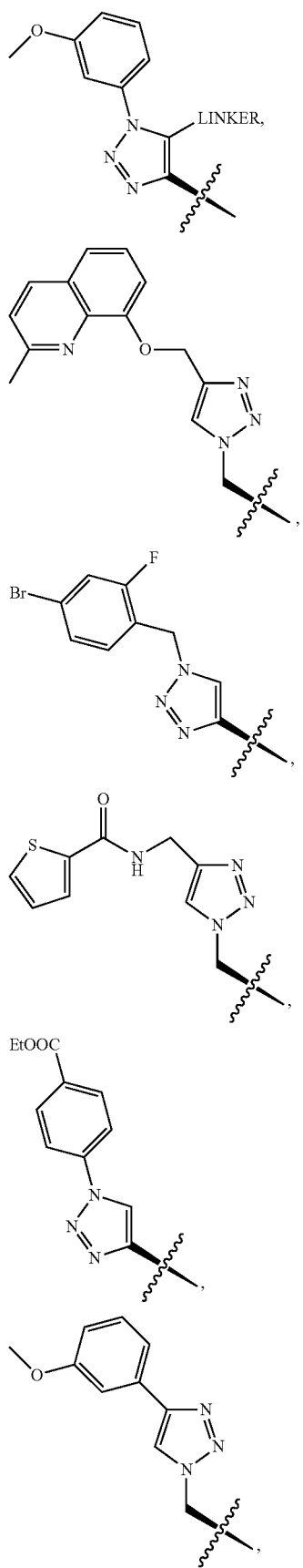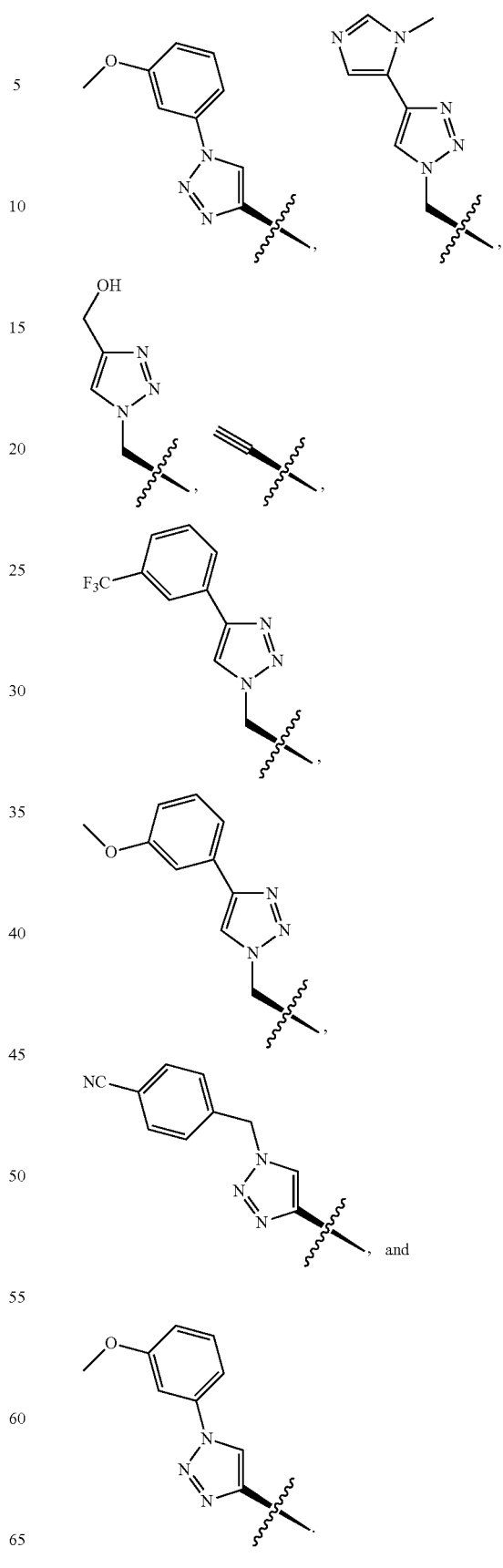

9. The compound of claim 1, where $R_2$ of the [ASGPRBM] group is a moiety selected from the group consisting of

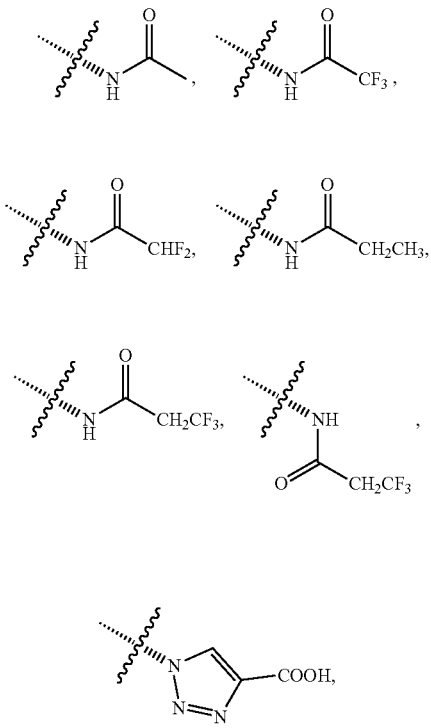

10. The compound of claim 1, wherein the [IgGBM] group is a peptide moiety according to the chemical structure:

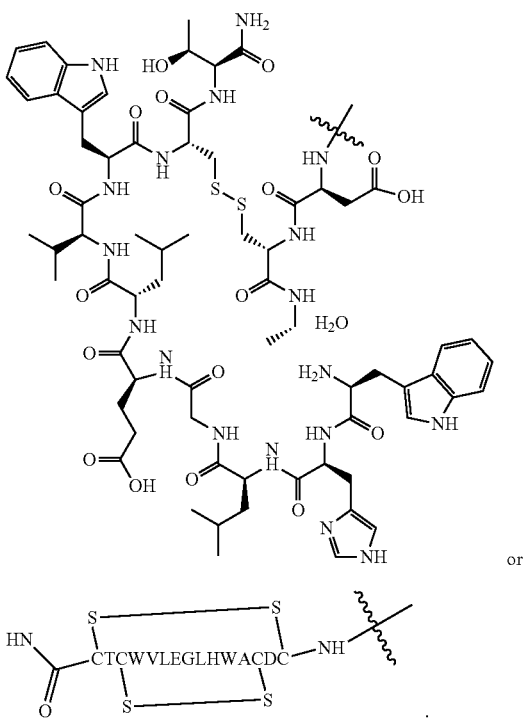

or

11. The compound of claim 1, wherein the linker is a group according to the chemical structure:

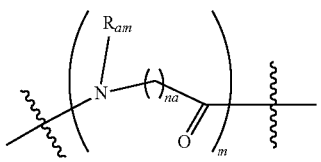

wherein:
$R_{am}$ is H or $C_1$-$C_3$ alkyl optionally substituted with one or two hydroxyl groups;
na is an integer from 1 to 15; and
m is an integer from 1 to 100; or
wherein the linker is a group according to the chemical formula:

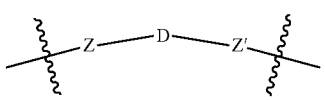

wherein:

Z and Z' are each independently a bond, —(CH$_2$)$_i$—O—, —(CH$_2$)$_i$—S—, —(CH$_2$)$_i$—N(R)—,

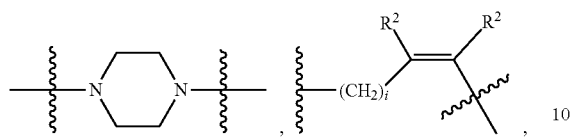

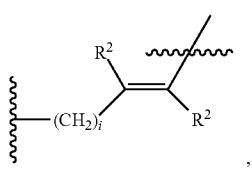

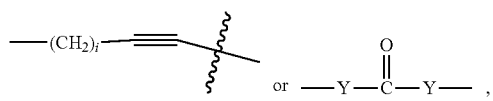

wherein the —(CH$_2$)$_i$ group, if present in Z or Z', is bonded to a connector group [CON], [IgGBM] or [ASGPRBM];

each R is H, or C$_1$-C$_3$ alkyl or alkanol;

each R$^2$ is independently H or C$_1$-C$_3$ alkyl;

each Y is independently a bond, O, S, or N—R;

each i is independently 0 to 100;

D is

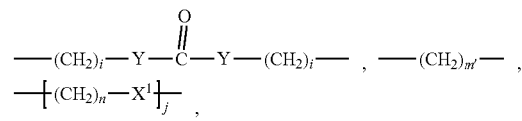

or a bond, with the proviso that Z, Z' and D are not each simultaneously bonds;

j is an integer from 1 to 100;

m' is an integer from 1 to 100;

n is an integer from 1 to 100;

X$^1$ is O, S, or N—R; and

R is H, C$_1$-C$_3$ alkyl, or alkanol.

12. The compound of claim 1, wherein the [CON] is a group according to the chemical structure:

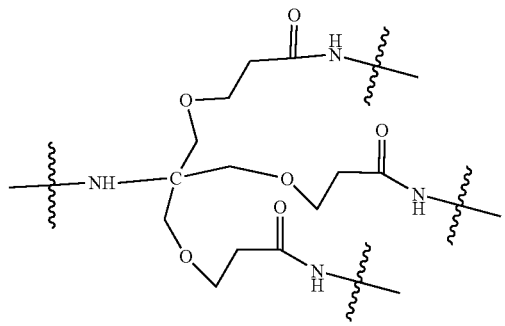

13. A compound selected from the group consisting of:

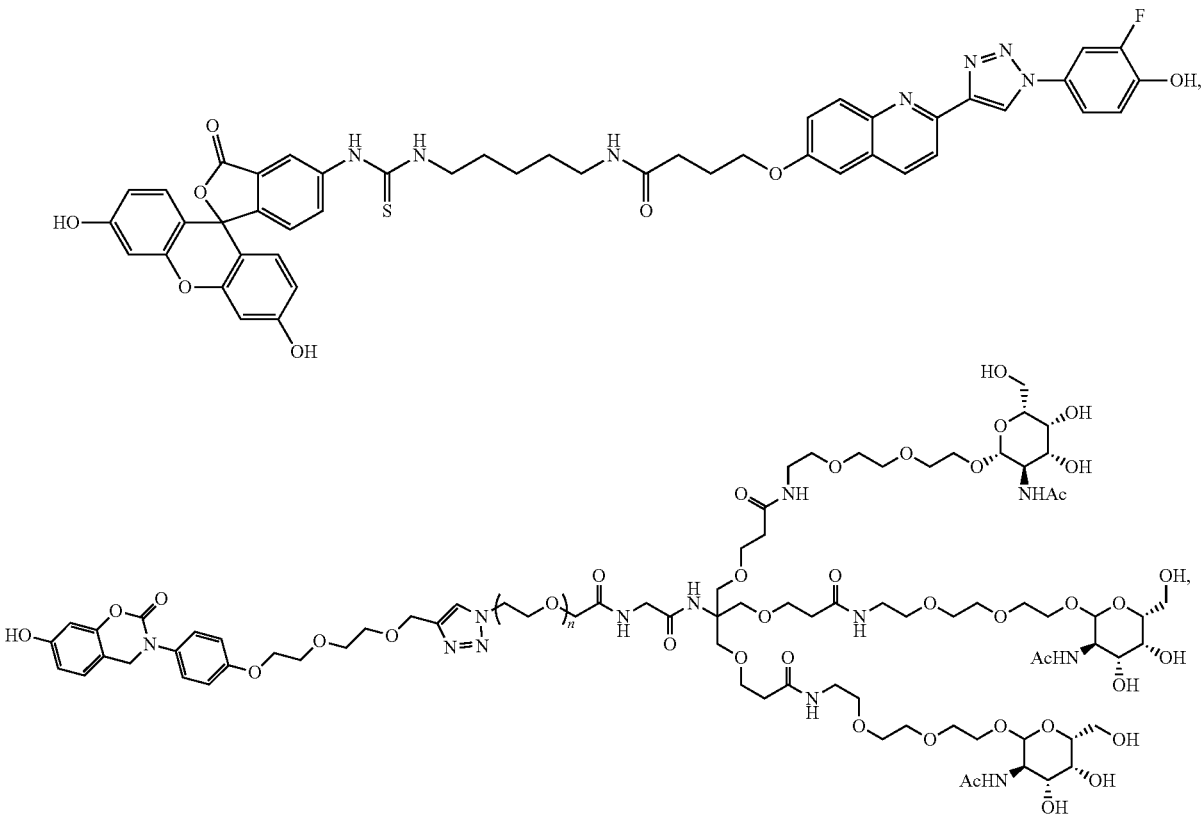

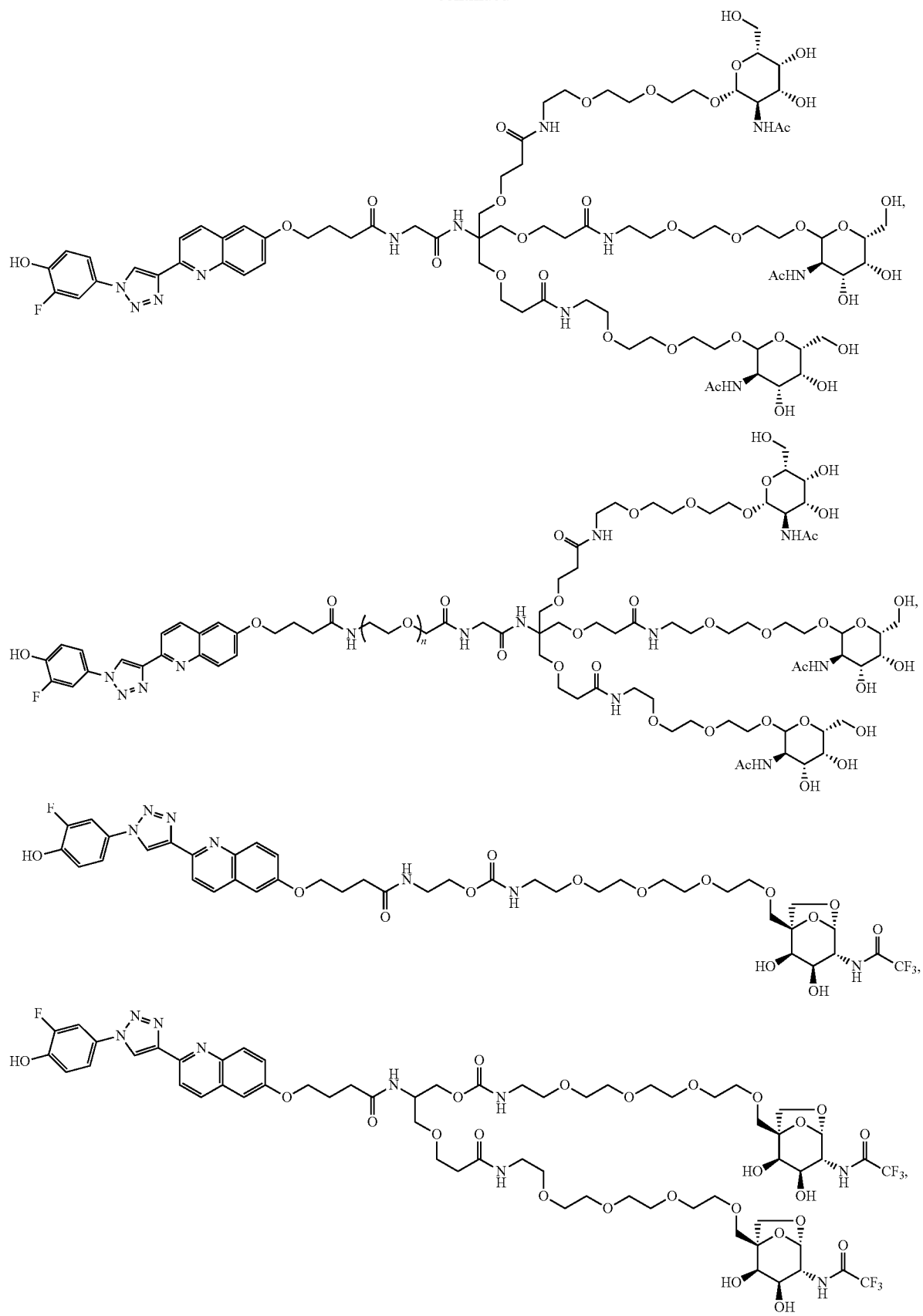

-continued
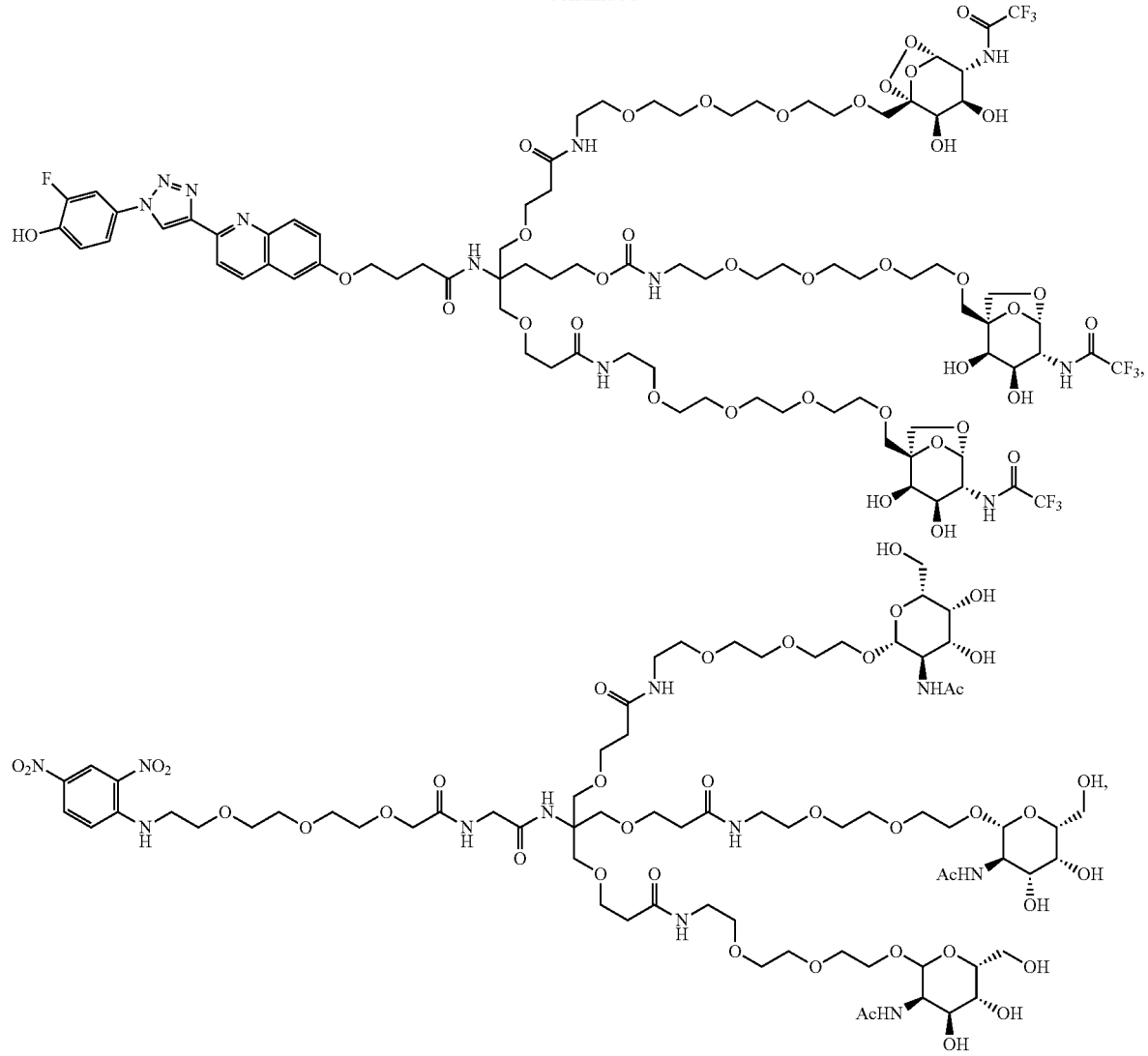
DNP-GN3
DNP-AcF3-3

-continued
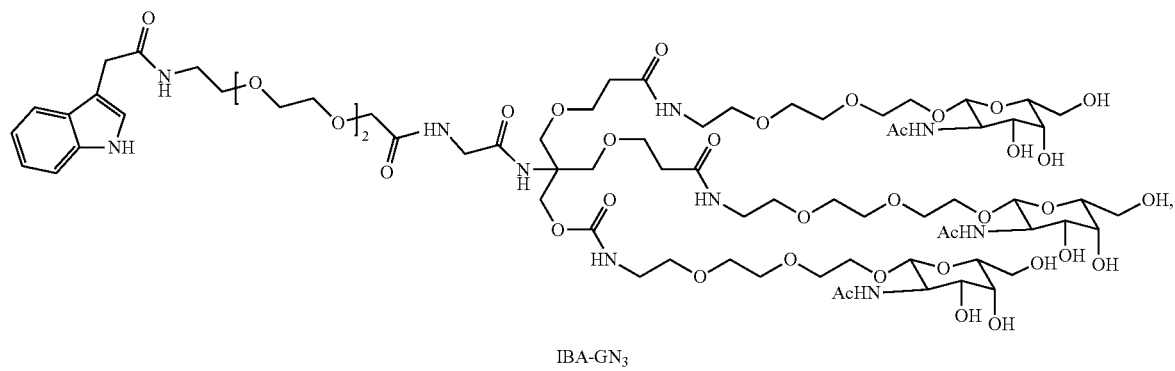
IBA-GN₃
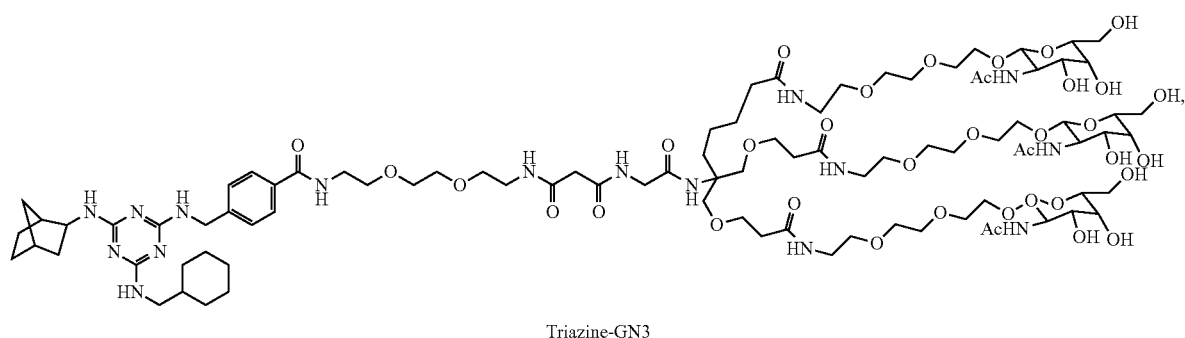
Triazine-GN3
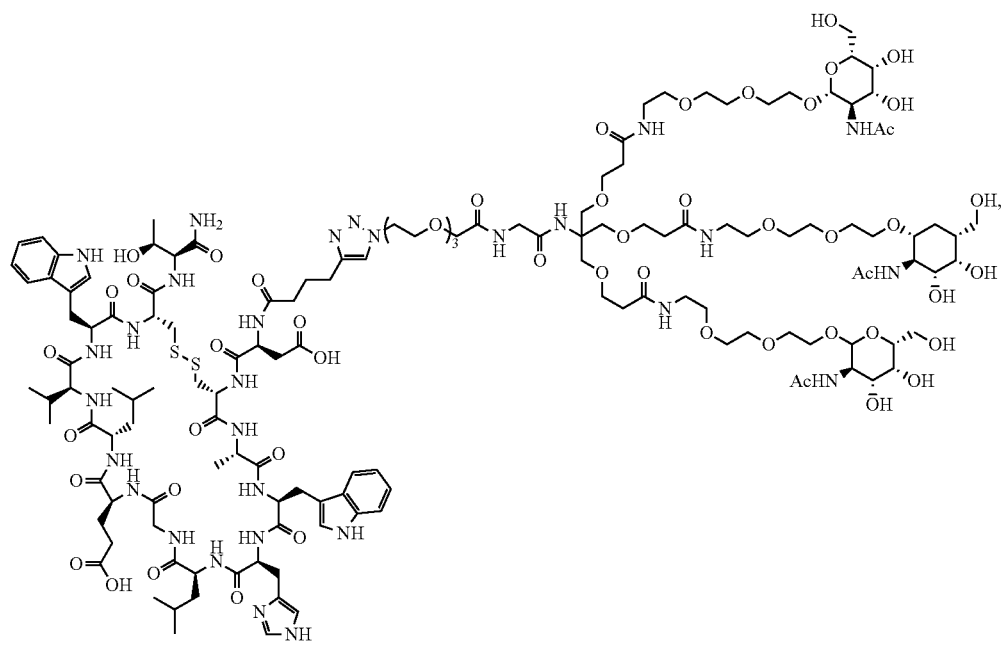
FcIII-GN3

-continued
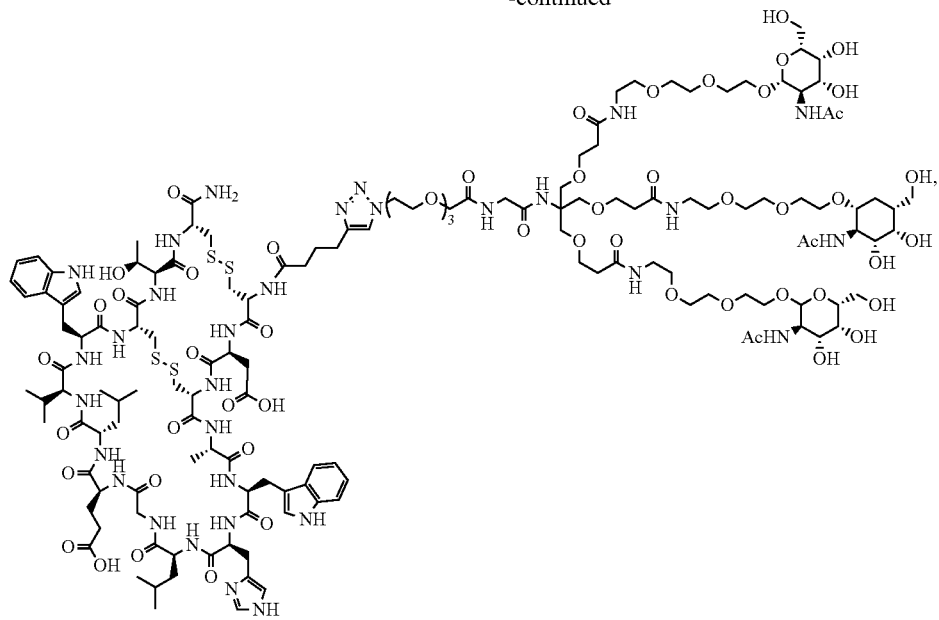
FcIII-4c-GN3
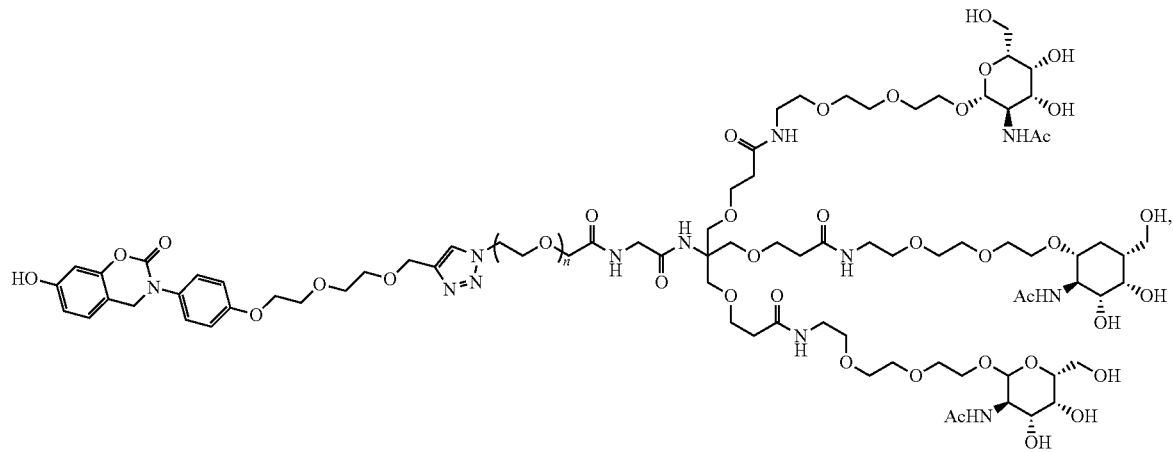
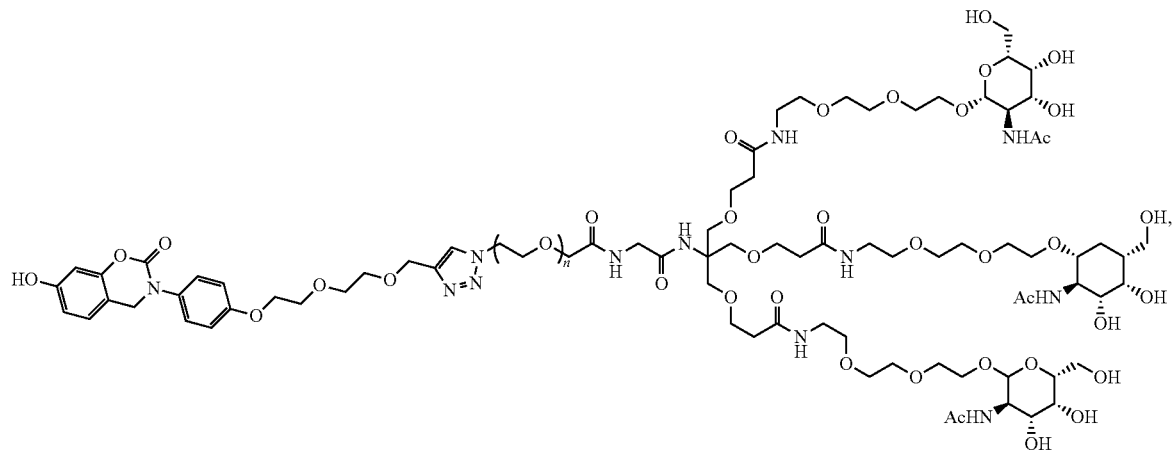

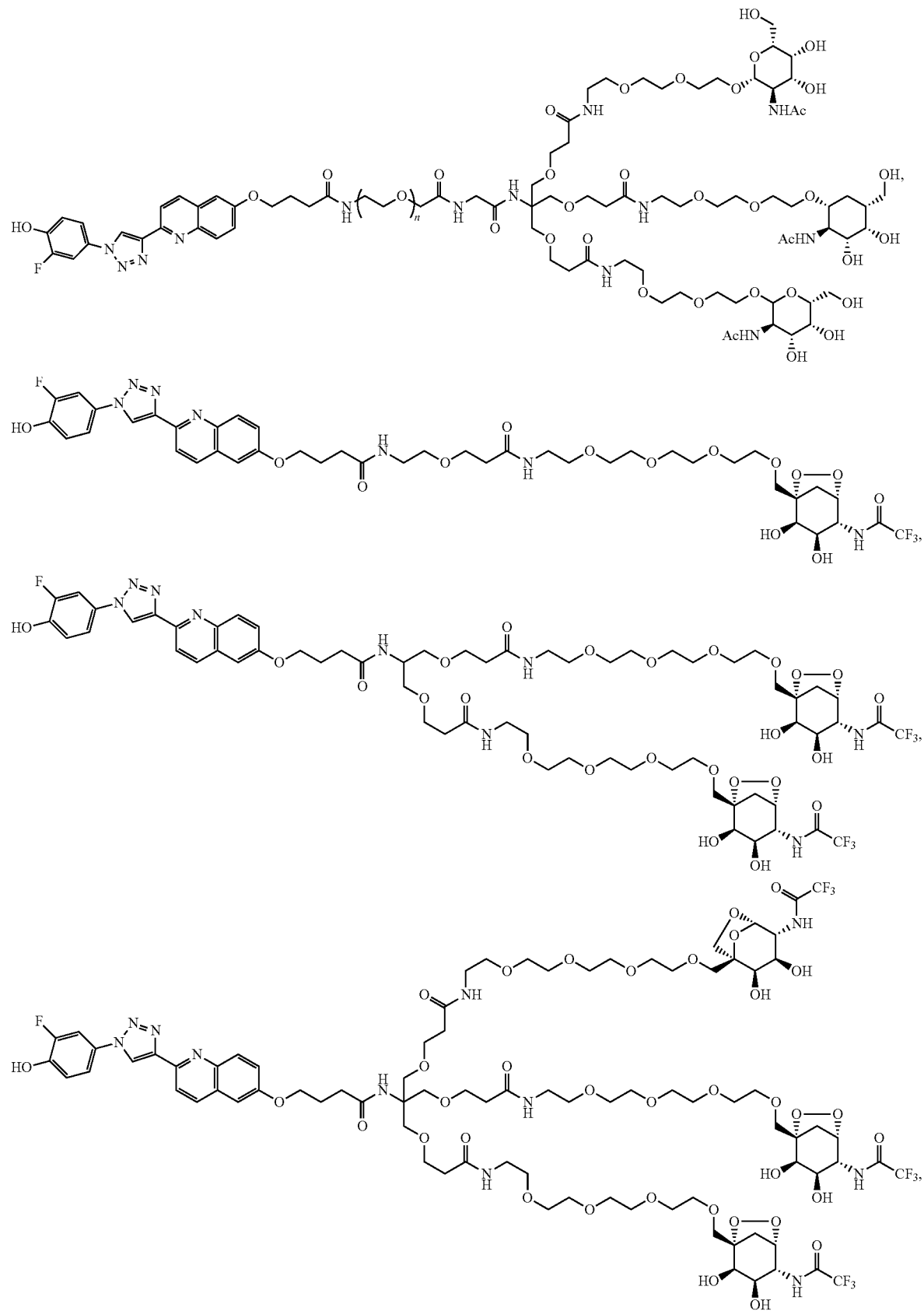

127 128
-continued
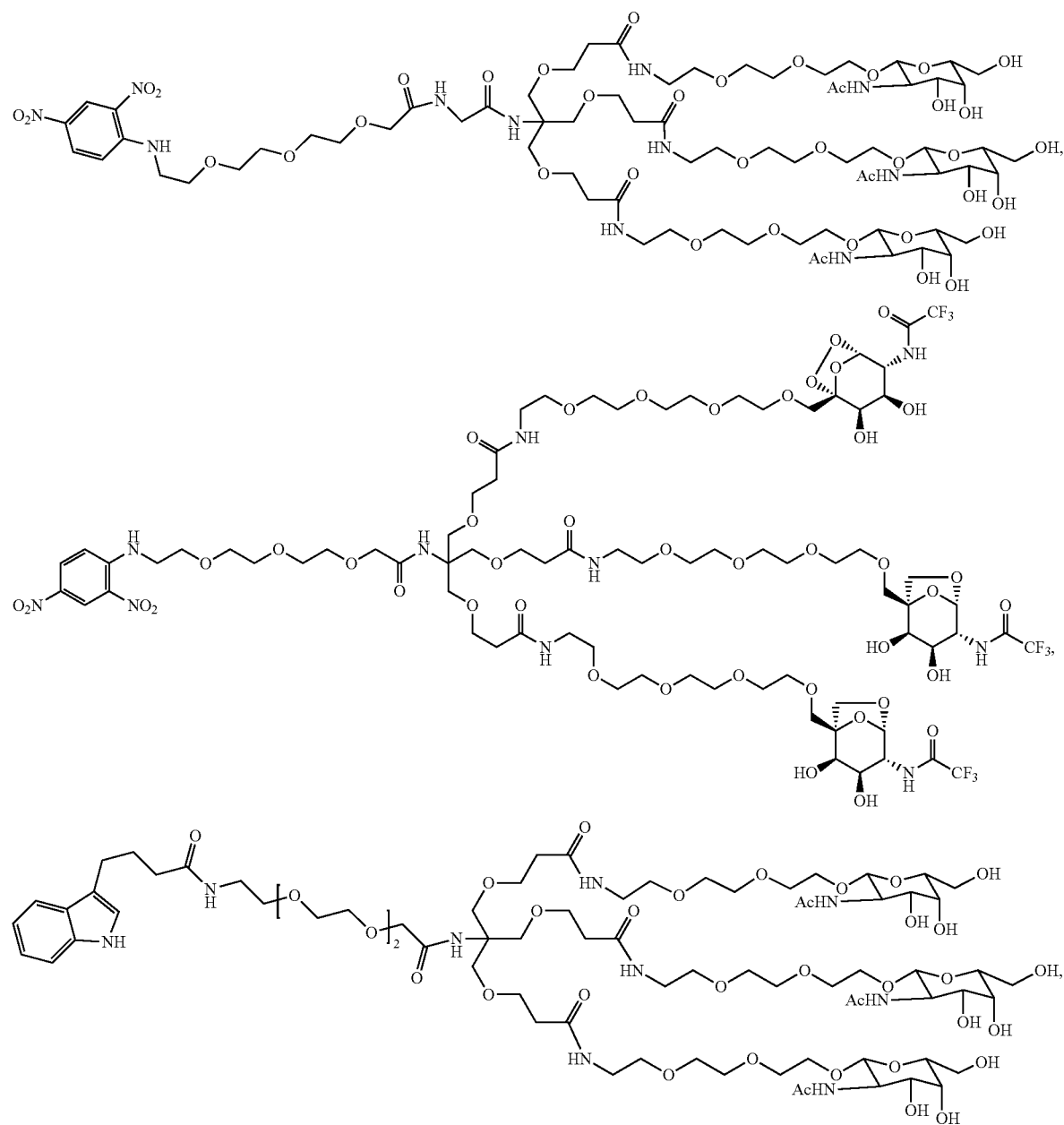
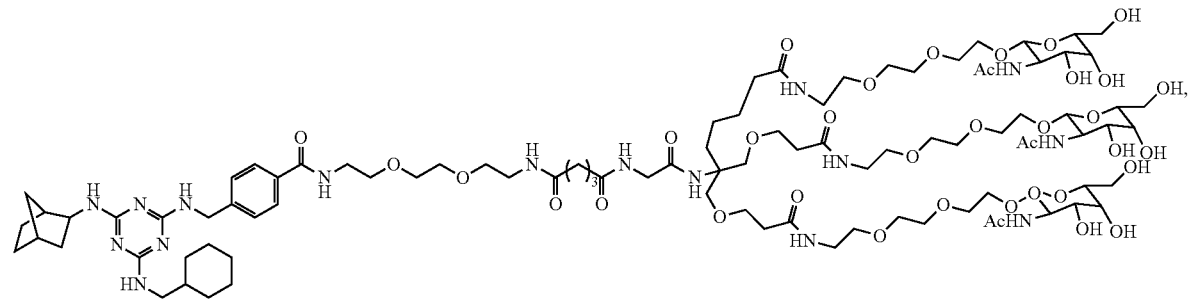
Triazine-GN3

-continued
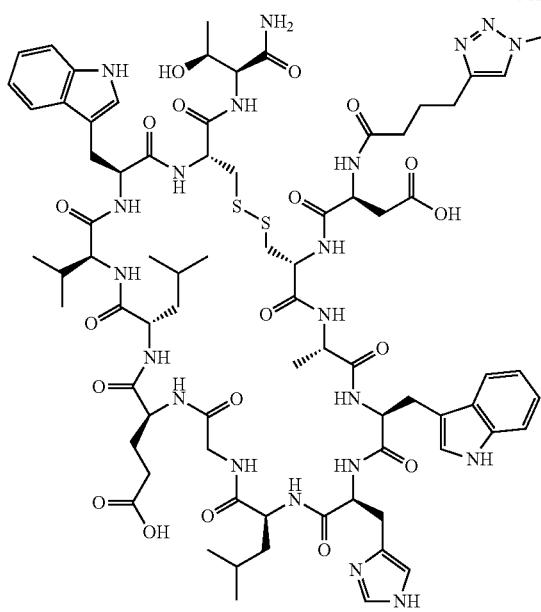
129
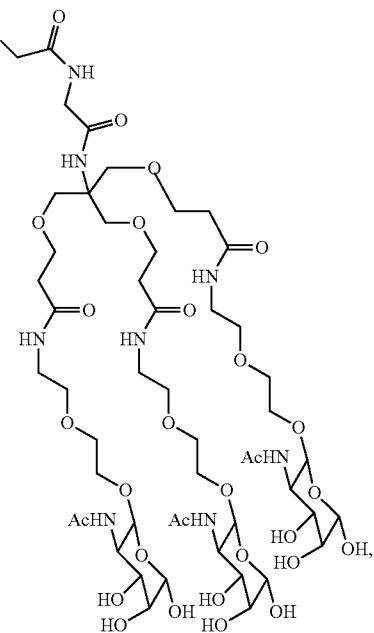
130
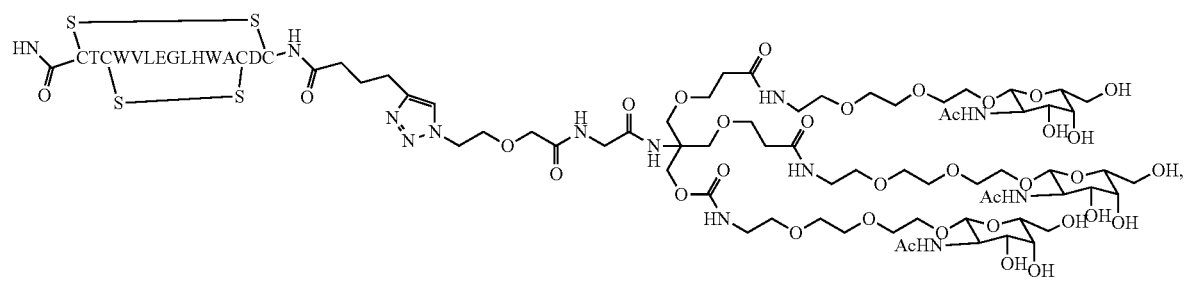
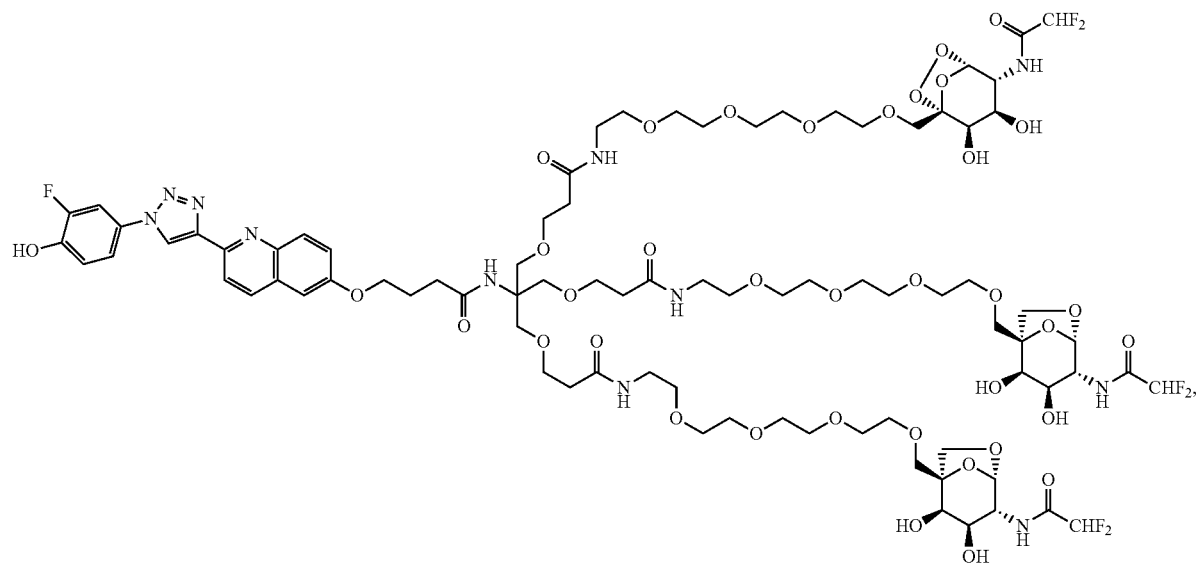

-continued
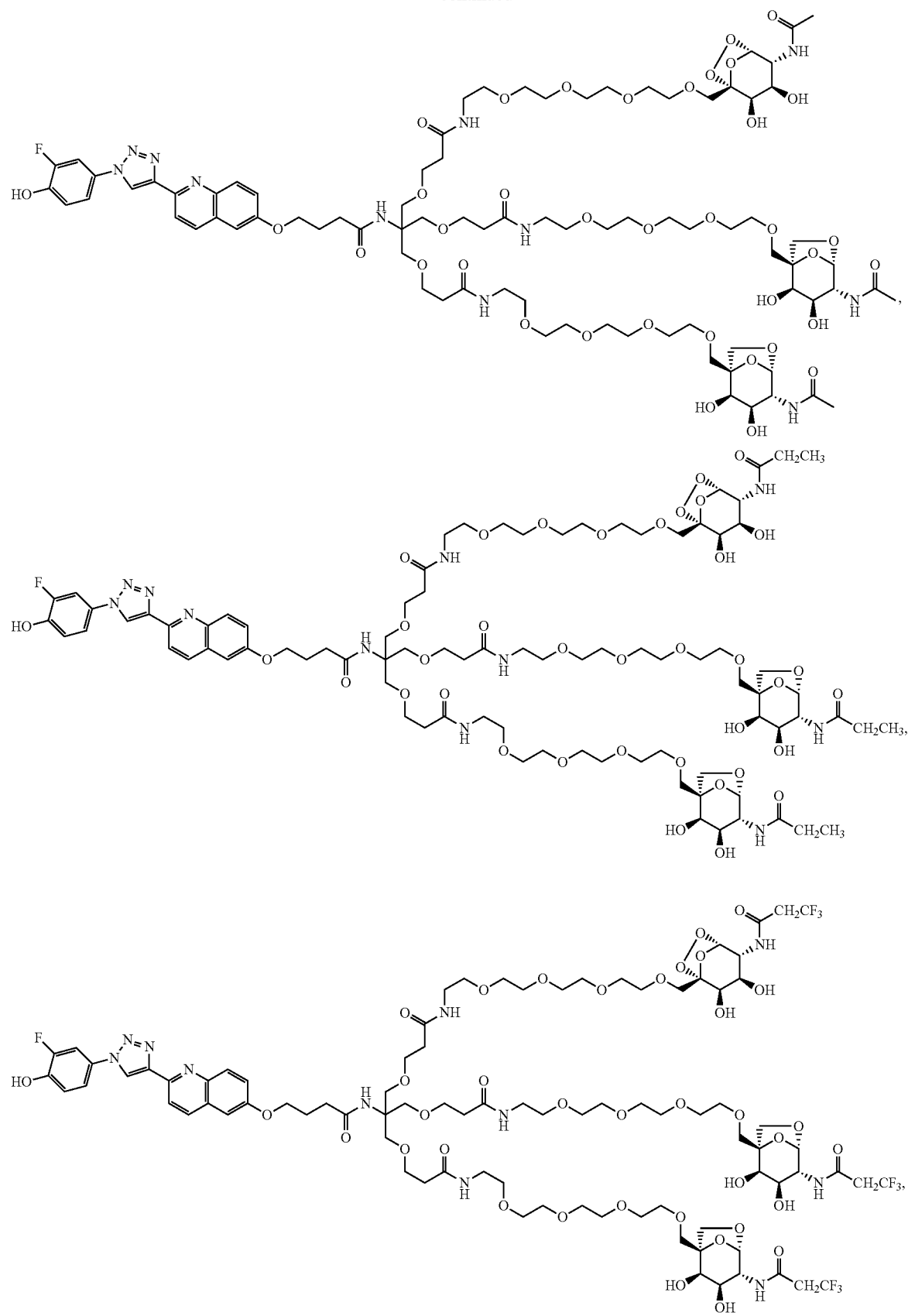

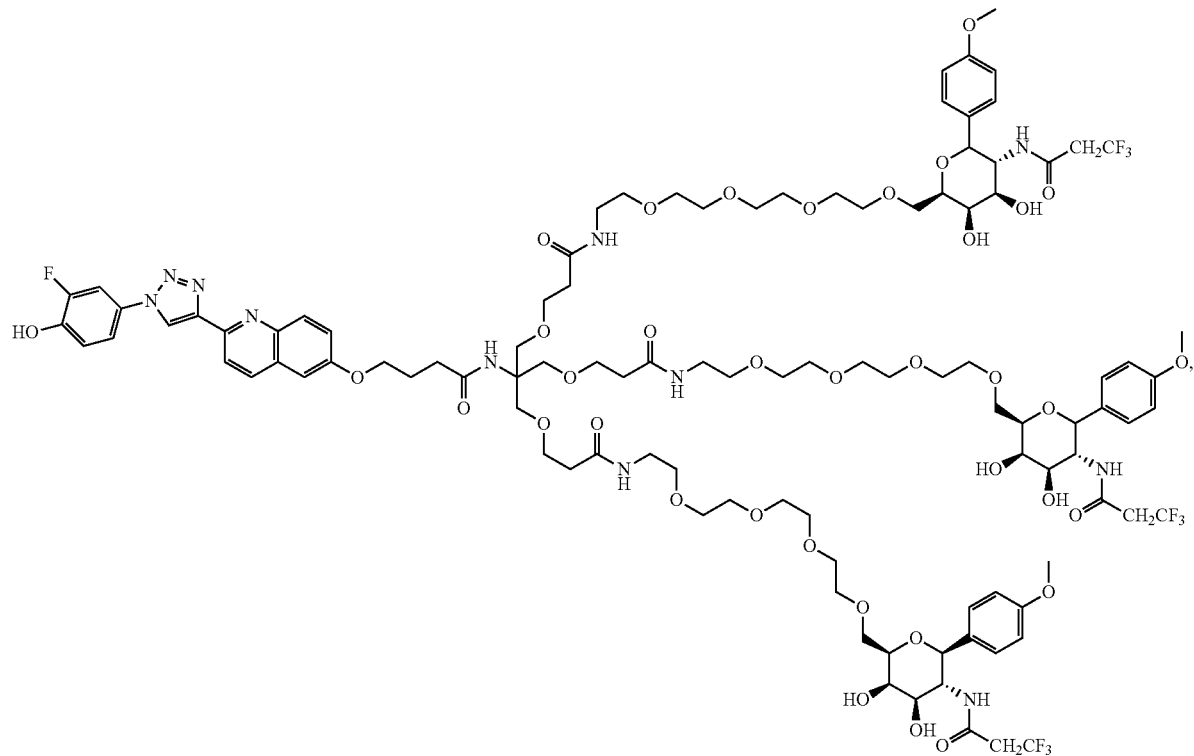
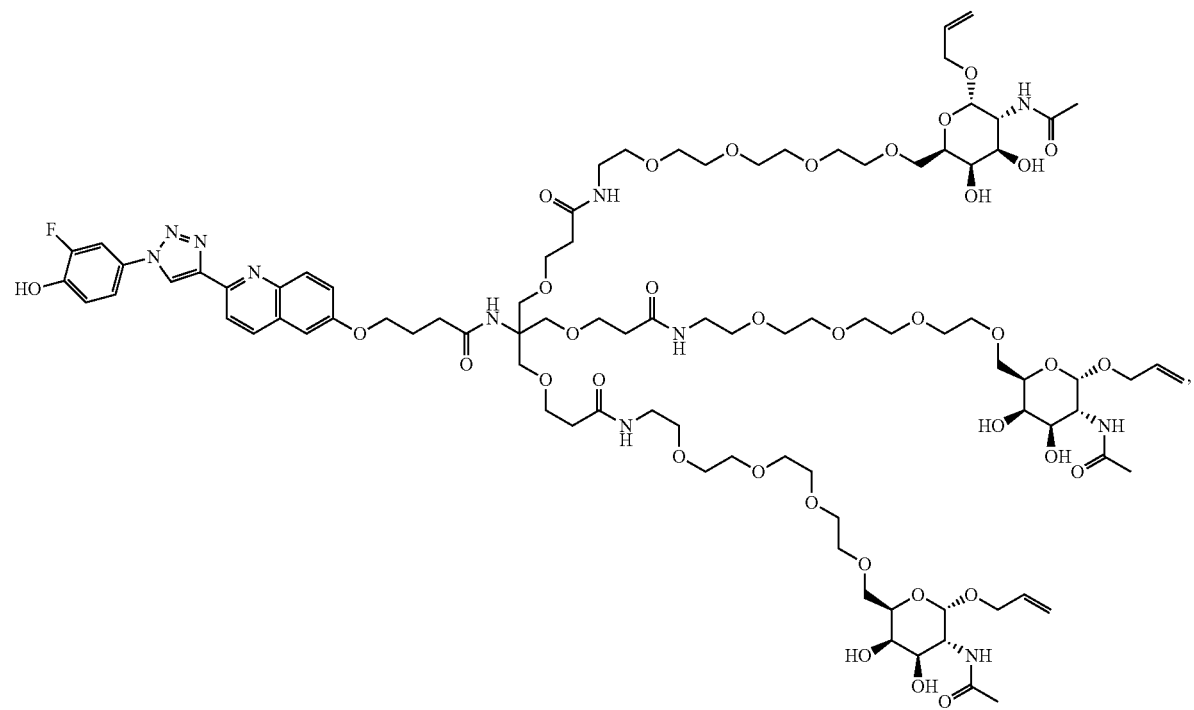

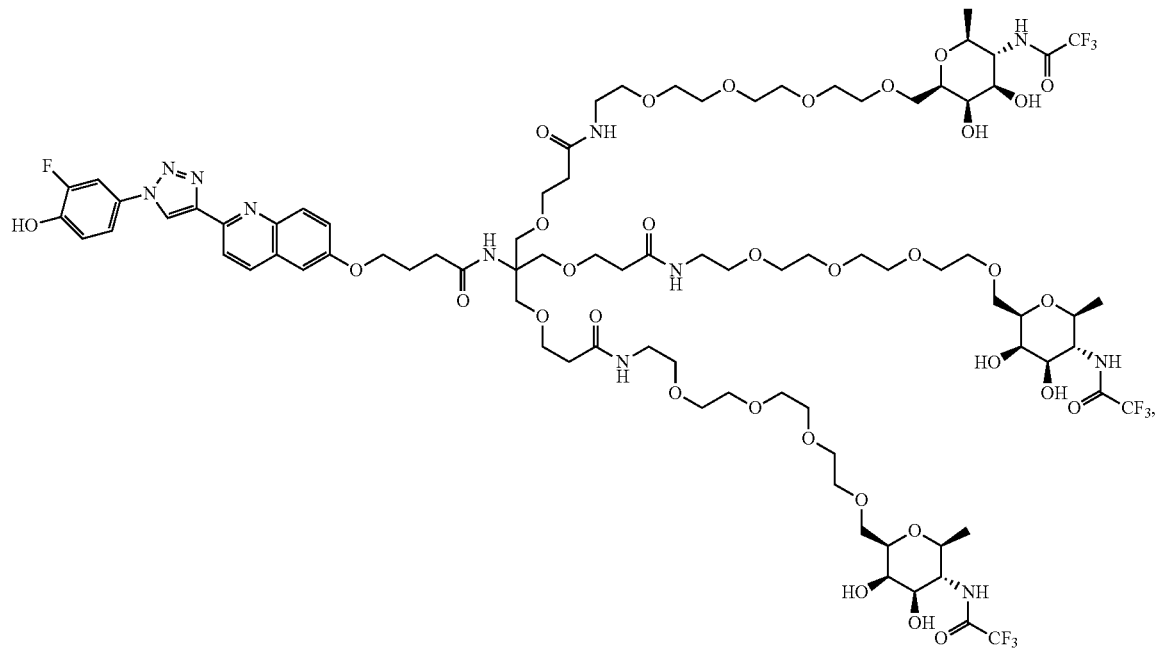
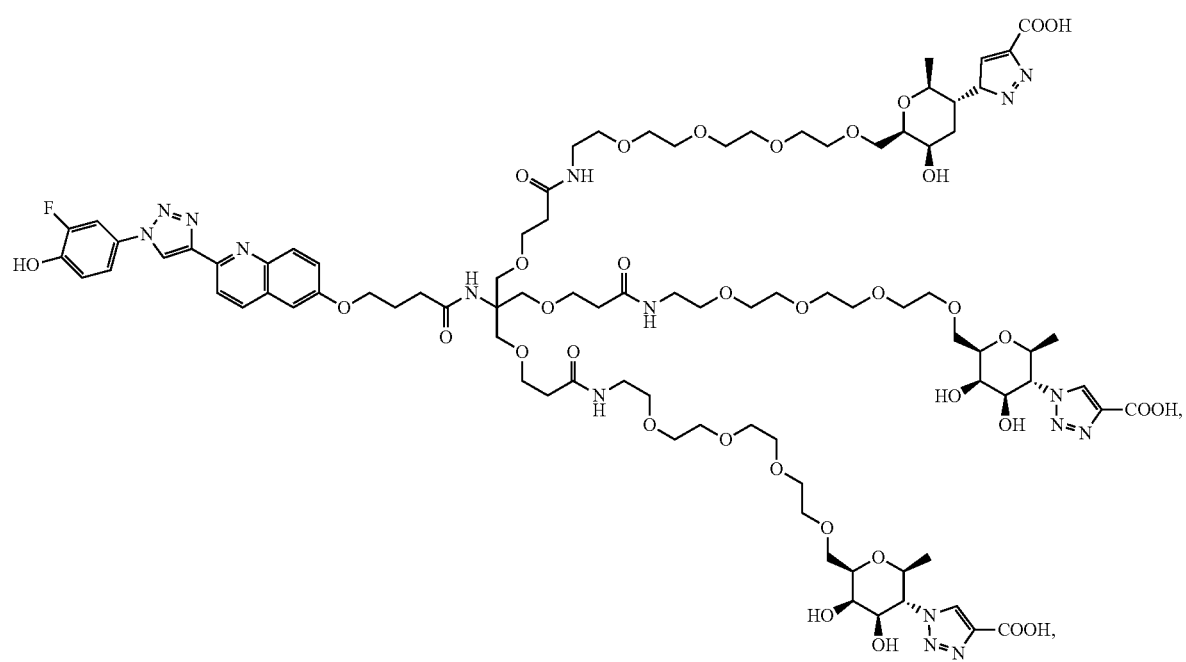

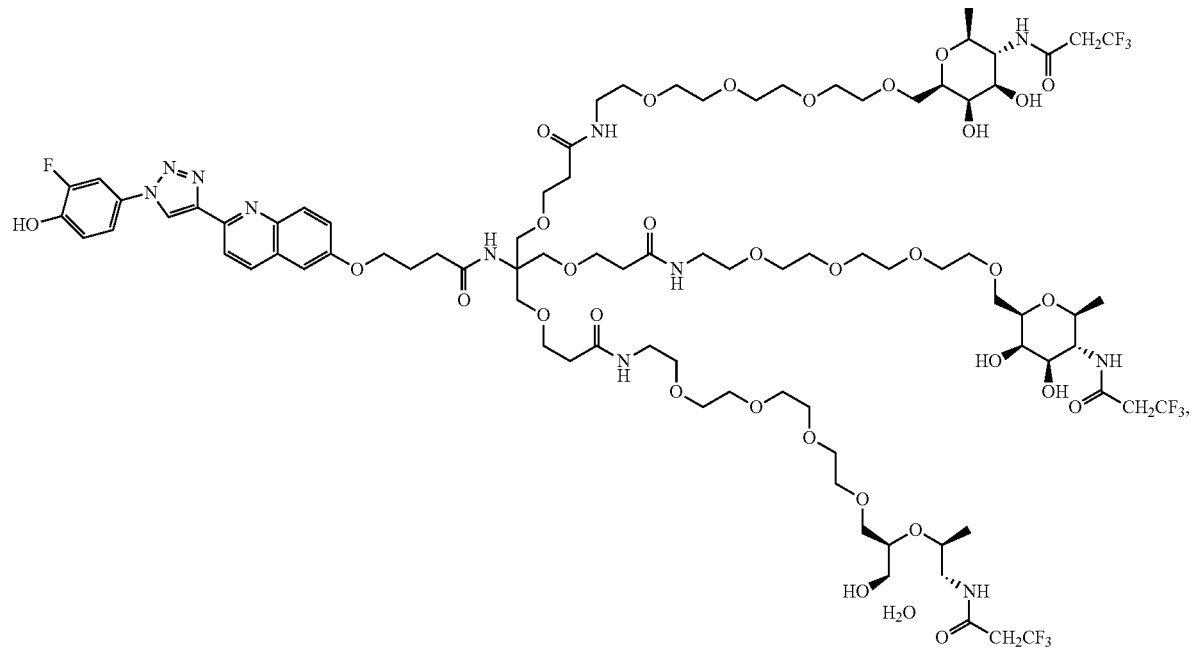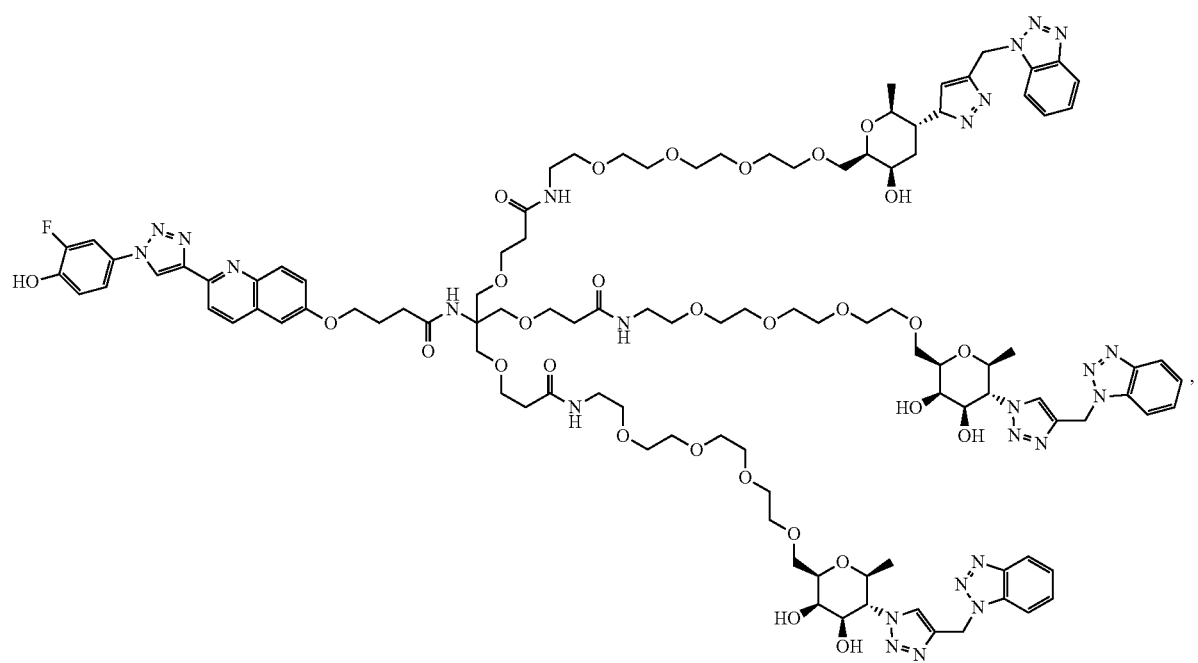

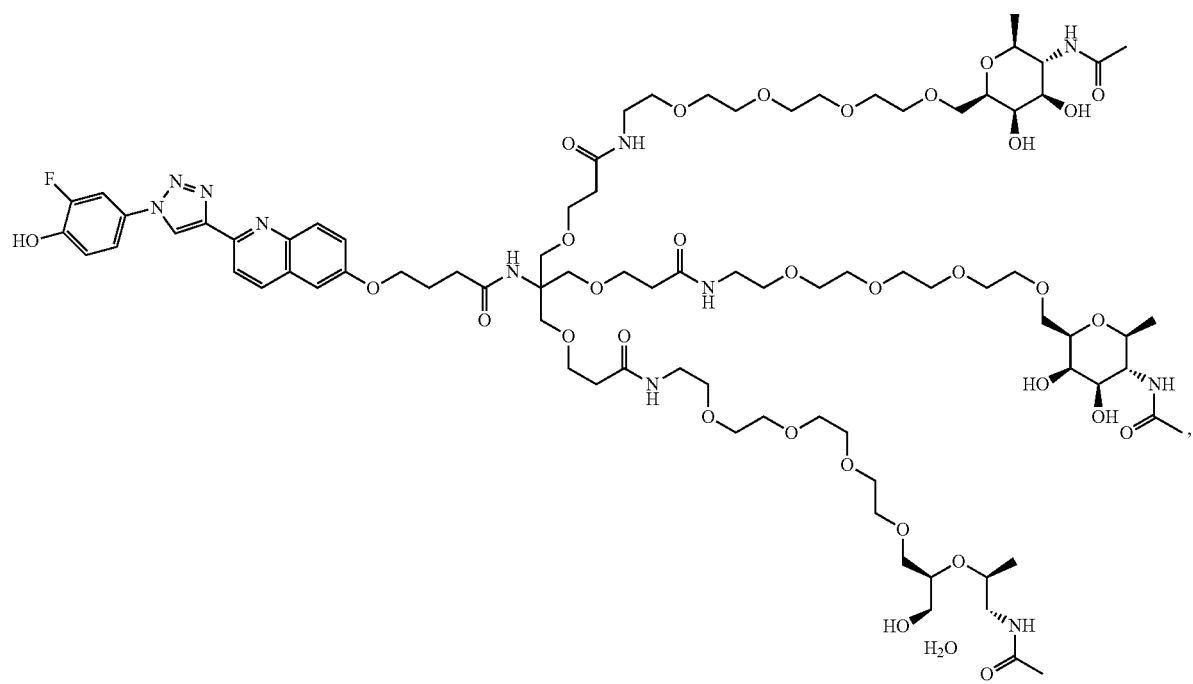
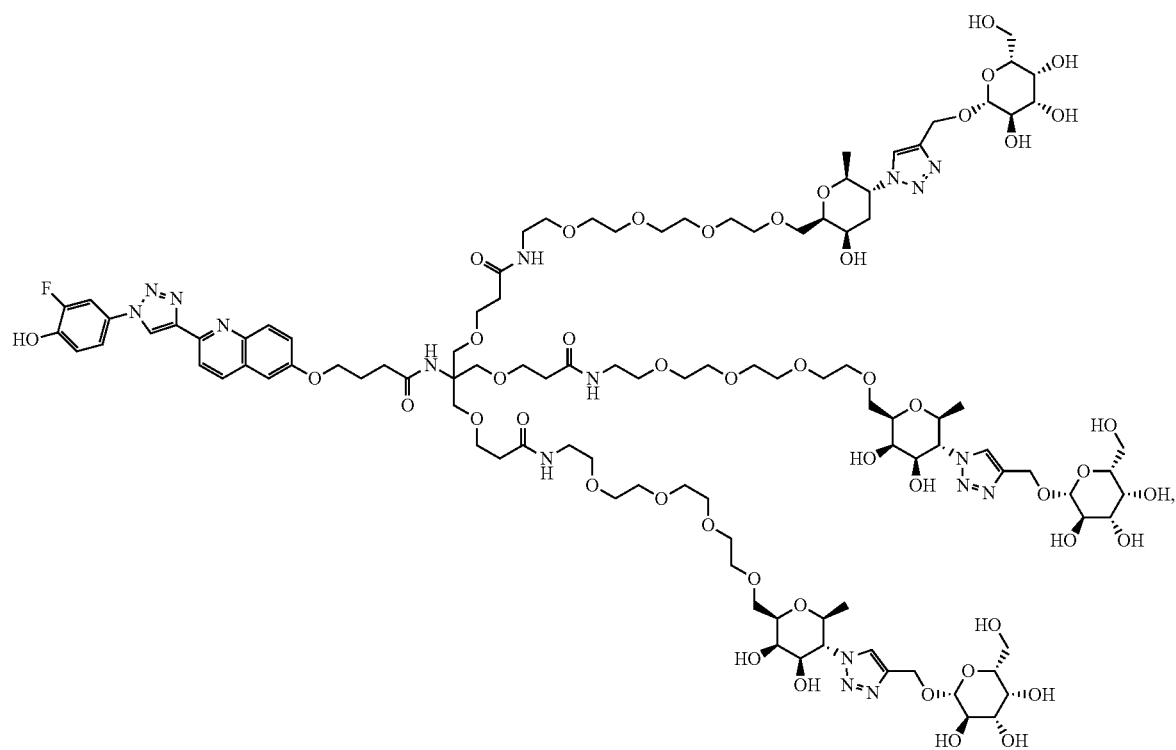

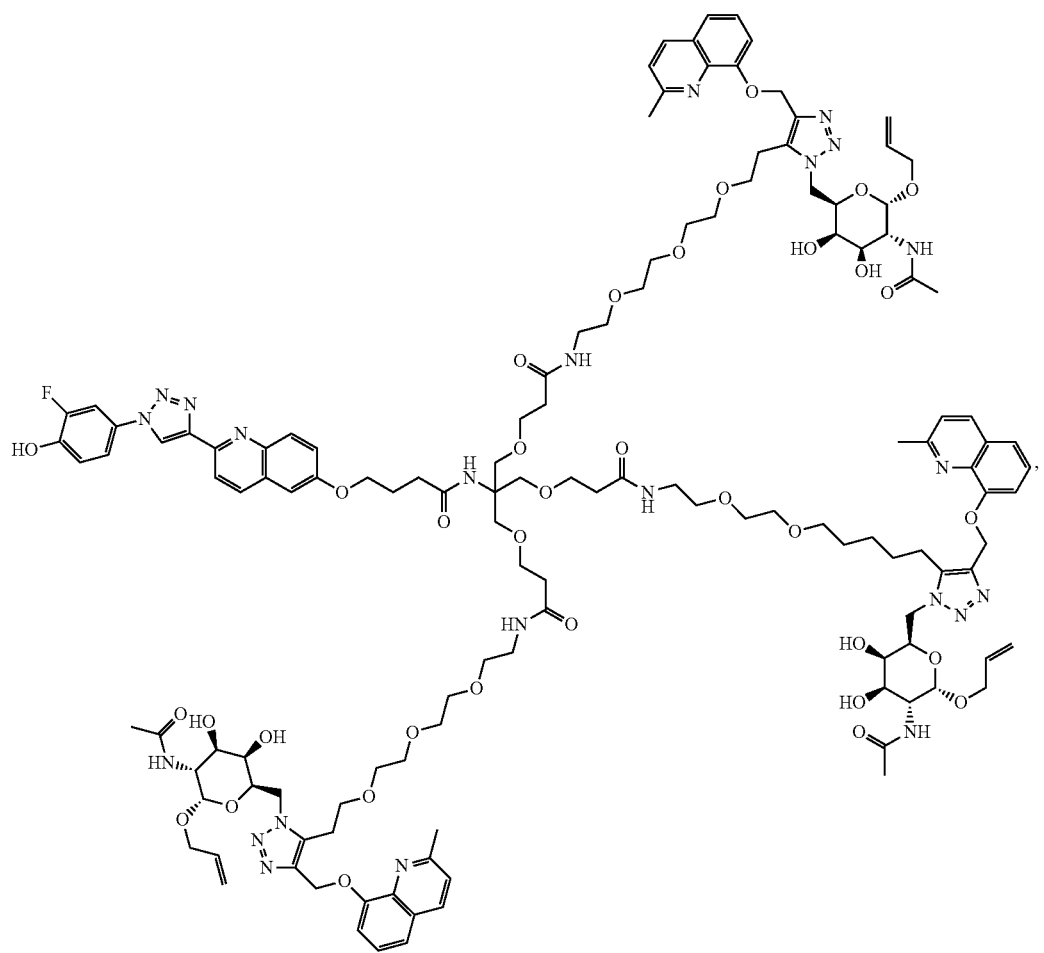 [SMILES: C=CCO[C@H]1O[C@H](Cn2nnc(COc3cccc4ccc(C)nc34)c2CCCCCOCCOCCNC(=O)CCOCC(COCCC(=O)NCCOCCOCCOCCc2c(COc3cccc4ccc(C)nc34)nnn2C[C@H]2O[C@H](OCC=C)[C@H](NC(C)=O)[C@@H](O)[C@H]2O)(COCCC(=O)NCCOCCOCCOCCc2c(COc3cccc4ccc(C)nc34)nnn2C[C@H]2O[C@H](OCC=C)[C@H](NC(C)=O)[C@@H](O)[C@H]2O)NC(=O)CCCOc2ccc3nc(-c4cn(-c5ccc(O)c(F)c5)nn4)ccc3c2)[C@H](O)[C@H](O)[C@H]1NC(C)=O]

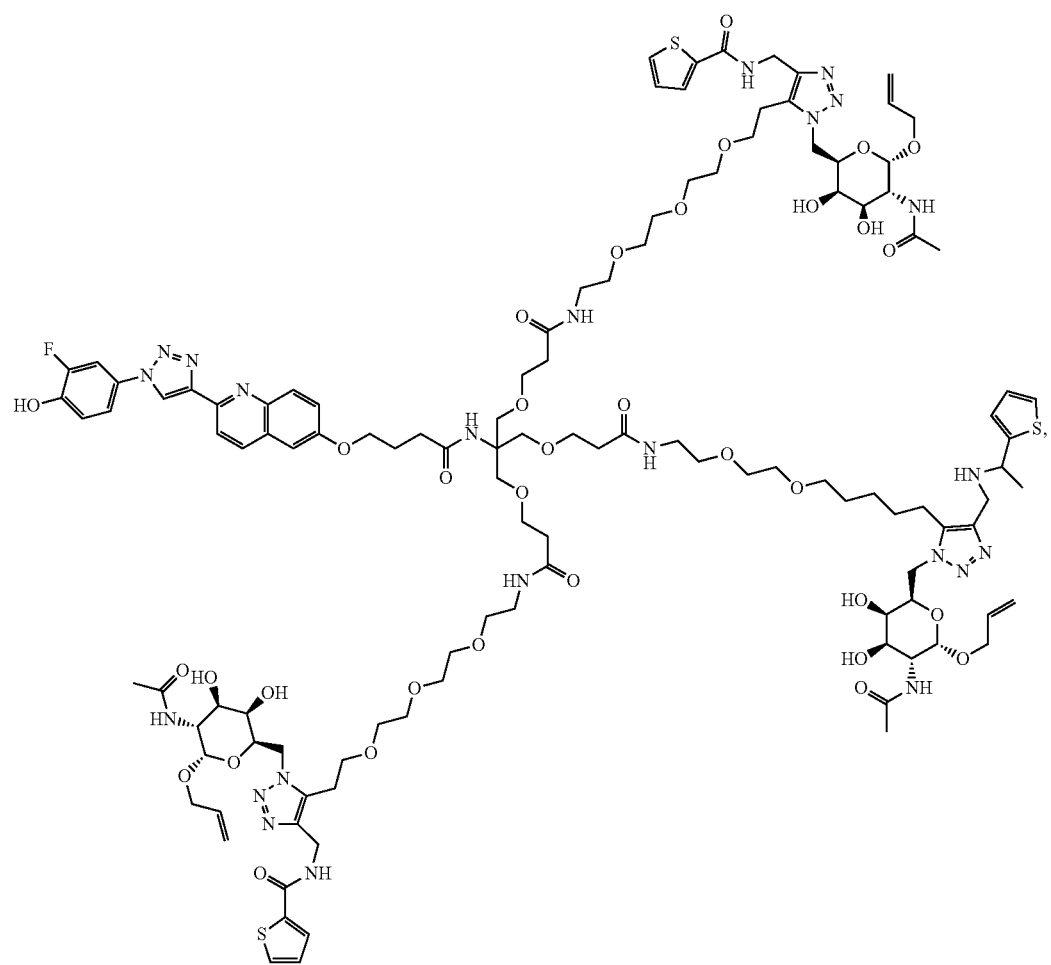 [SMILES: C=CCO[C@H]1O[C@H](Cn2nnc(CNC(=O)c3cccs3)c2CCOCCOCCOCCNC(=O)CCOCC(COCCC(=O)NCCOCCOCCCCCc2c(CNC(C)c3cccs3)nnn2C[C@H]2O[C@H](OCC=C)[C@H](NC(C)=O)[C@@H](O)[C@H]2O)(COCCC(=O)NCCOCCOCCOCCc2c(CNC(=O)c3cccs3)nnn2C[C@H]2O[C@H](OCC=C)[C@H](NC(C)=O)[C@@H](O)[C@H]2O)NC(=O)CCCOc2ccc3nc(-c4cn(-c5ccc(O)c(F)c5)nn4)ccc3c2)[C@H](O)[C@H](O)[C@H]1NC(C)=O]

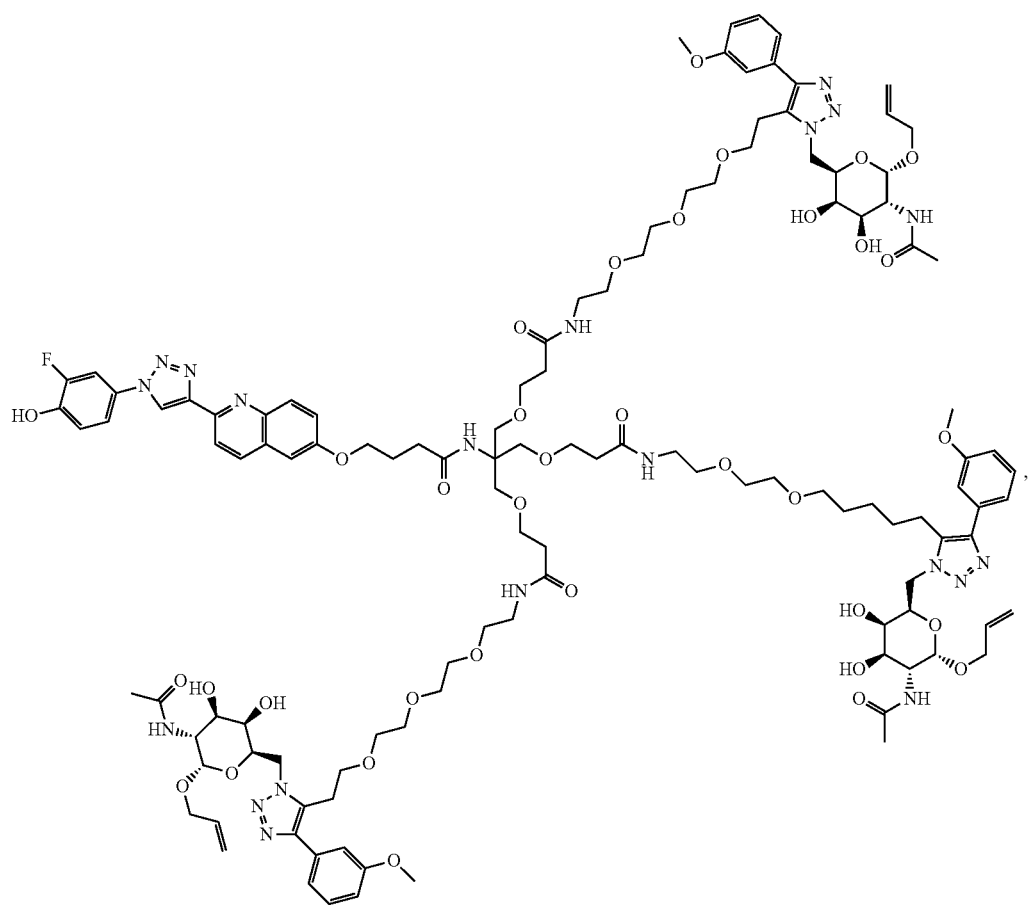 [SMILES: C=CCO[C@H]1O[C@H](Cn2nnc(-c3cccc(OC)c3)c2CCCCCOCCOCCNC(=O)CCOCC(COCCC(=O)NCCOCCOCCOCCc2c(-c3cccc(OC)c3)nnn2C[C@H]2O[C@H](OCC=C)[C@H](NC(C)=O)[C@@H](O)[C@H]2O)(COCCC(=O)NCCOCCOCCOCCc2c(-c3cccc(OC)c3)nnn2C[C@H]2O[C@H](OCC=C)[C@H](NC(C)=O)[C@@H](O)[C@H]2O)NC(=O)CCCOc2ccc3nc(-c4cn(-c5ccc(O)c(F)c5)nn4)ccc3c2)[C@H](O)[C@H](O)[C@H]1NC(C)=O]

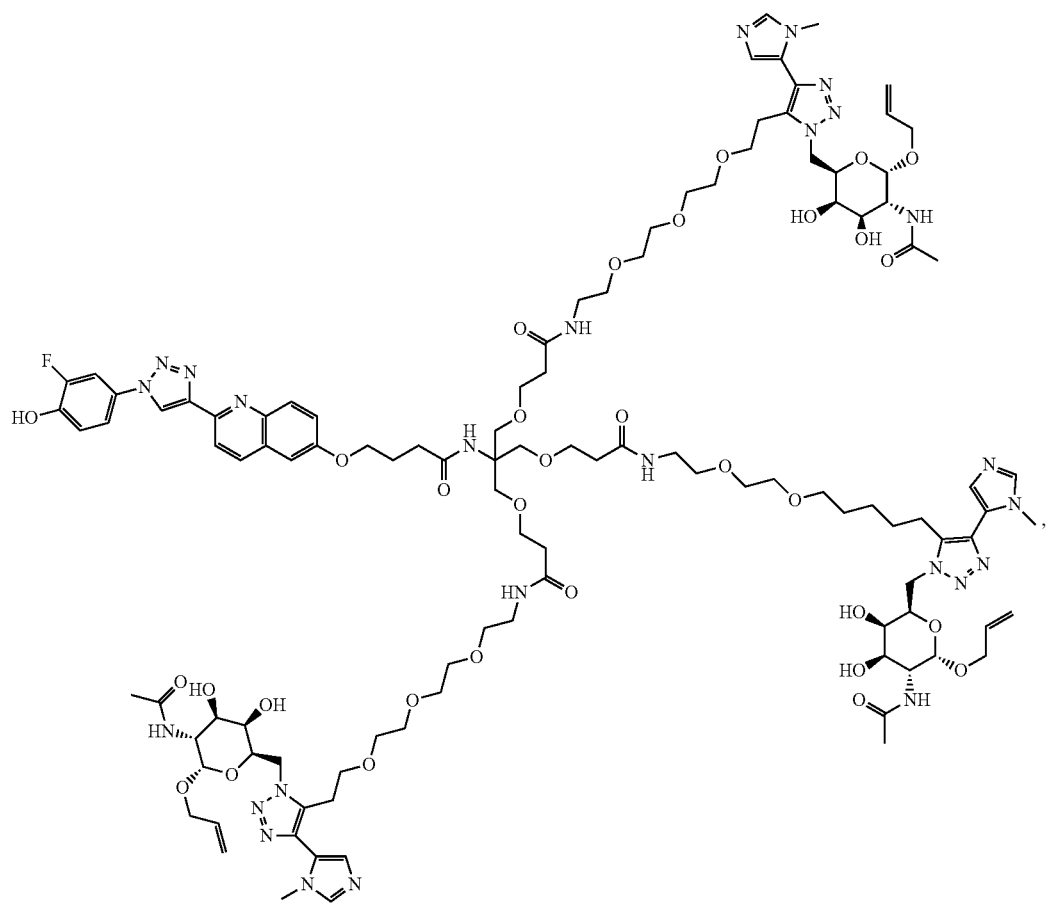 [SMILES: C=CCO[C@H]1O[C@H](Cn2nnc(-c3cncn3C)c2CCCCCOCCOCCNC(=O)CCOCC(COCCC(=O)NCCOCCOCCOCCc2c(-c3cncn3C)nnn2C[C@H]2O[C@H](OCC=C)[C@H](NC(C)=O)[C@@H](O)[C@H]2O)(COCCC(=O)NCCOCCOCCOCCc2c(-c3cncn3C)nnn2C[C@H]2O[C@H](OCC=C)[C@H](NC(C)=O)[C@@H](O)[C@H]2O)NC(=O)CCCOc2ccc3nc(-c4cn(-c5ccc(O)c(F)c5)nn4)ccc3c2)[C@H](O)[C@H](O)[C@H]1NC(C)=O]

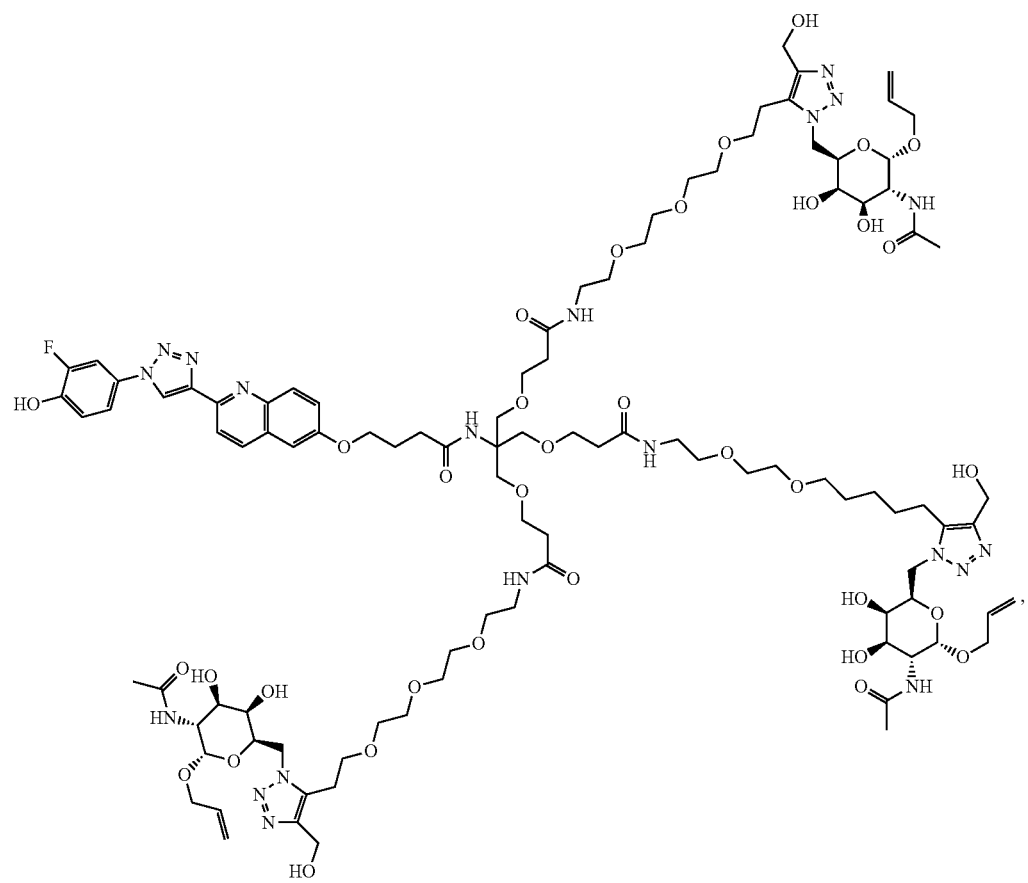 [SMILES: C=CCO[C@H]1O[C@H](Cn2nnc(CO)c2CCCCCOCCOCCNC(=O)CCOCC(COCCC(=O)NCCOCCOCCOCCc2c(CO)nnn2C[C@H]2O[C@H](OCC=C)[C@H](NC(C)=O)[C@@H](O)[C@H]2O)(COCCC(=O)NCCOCCOCCOCCc2c(CO)nnn2C[C@H]2O[C@H](OCC=C)[C@H](NC(C)=O)[C@@H](O)[C@H]2O)NC(=O)CCCOc2ccc3nc(-c4cn(-c5ccc(O)c(F)c5)nn4)ccc3c2)[C@H](O)[C@H](O)[C@H]1NC(C)=O]

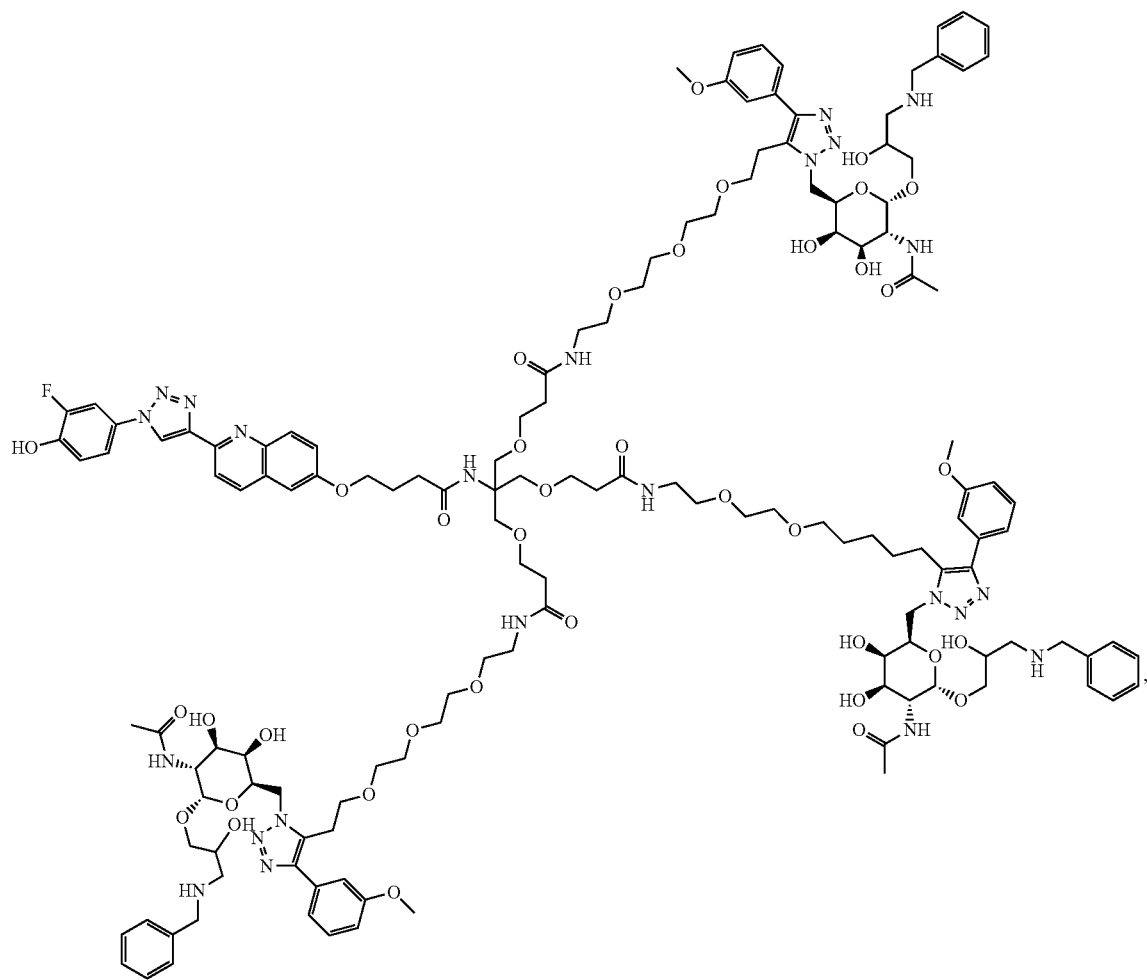 [SMILES: COc1cccc(-c2nnn(C[C@H]3O[C@H](OCC(O)CNCc4ccccc4)[C@H](NC(C)=O)[C@@H](O)[C@H]3O)c2CCCCCOCCOCCNC(=O)CCOCC(COCCC(=O)NCCOCCOCCOCCc2c(-c3cccc(OC)c3)nnn2C[C@H]2O[C@H](OCC(O)CNCc3ccccc3)[C@H](NC(C)=O)[C@@H](O)[C@H]2O)(COCCC(=O)NCCOCCOCCOCCc2c(-c3cccc(OC)c3)nnn2C[C@H]2O[C@H](OCC(O)CNCc3ccccc3)[C@H](NC(C)=O)[C@@H](O)[C@H]2O)NC(=O)CCCOc2ccc3nc(-c4cn(-c5ccc(O)c(F)c5)nn4)ccc3c2)c1]

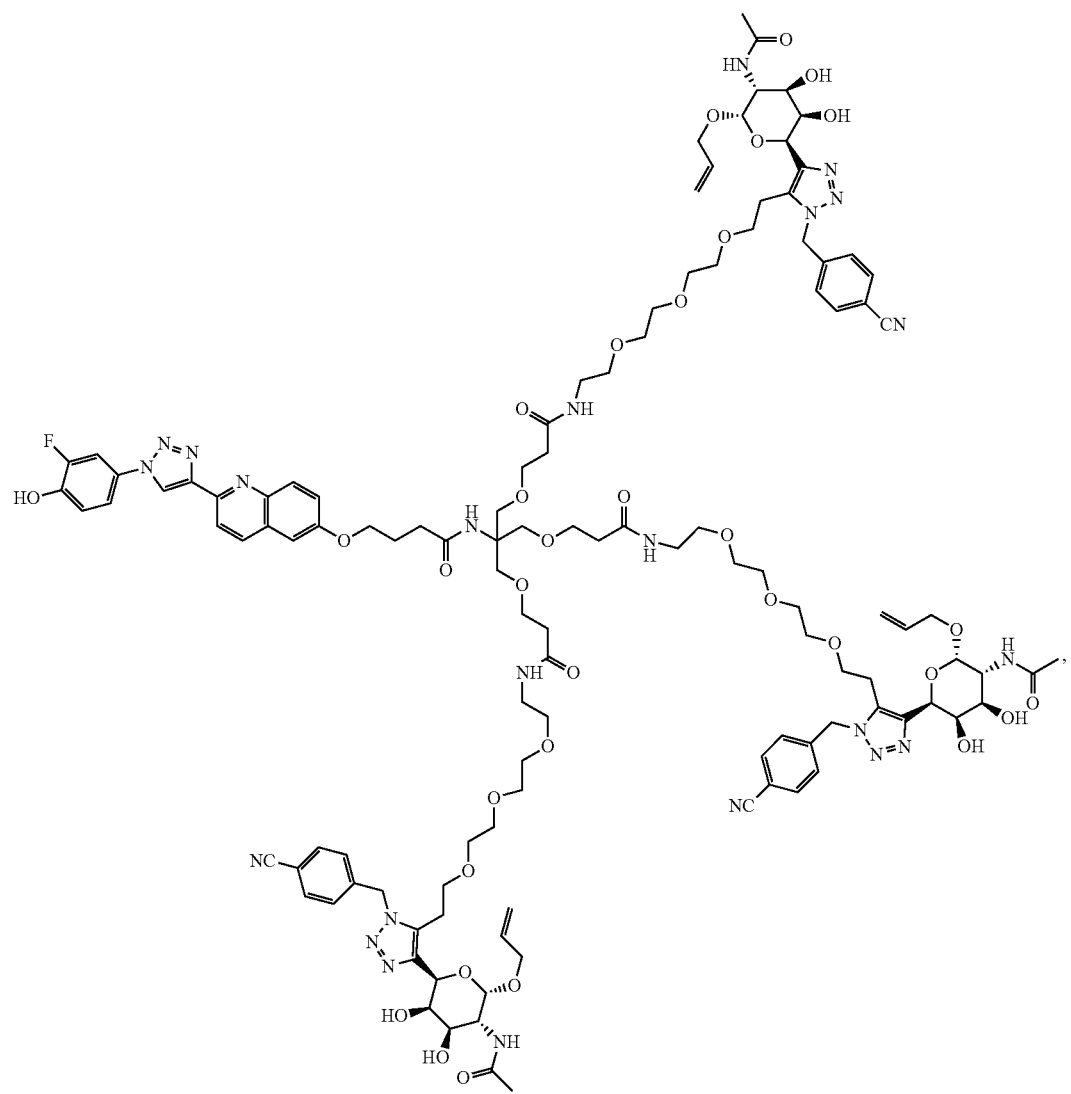 [SMILES: C=CCO[C@H]1O[C@H](c2nnn(Cc3ccc(C#N)cc3)c2CCOCCOCCOCCNC(=O)CCOCC(COCCC(=O)NCCOCCOCCOCCc2c([C@H]3O[C@H](OCC=C)[C@H](NC(C)=O)[C@@H](O)[C@H]3O)nnn2Cc2ccc(C#N)cc2)(COCCC(=O)NCCOCCOCCOCCc2c([C@H]3O[C@H](OCC=C)[C@H](NC(C)=O)[C@@H](O)[C@H]3O)nnn2Cc2ccc(C#N)cc2)NC(=O)CCCOc2ccc3nc(-c4cn(-c5ccc(O)c(F)c5)nn4)ccc3c2)[C@H](O)[C@H](O)[C@H]1NC(C)=O]

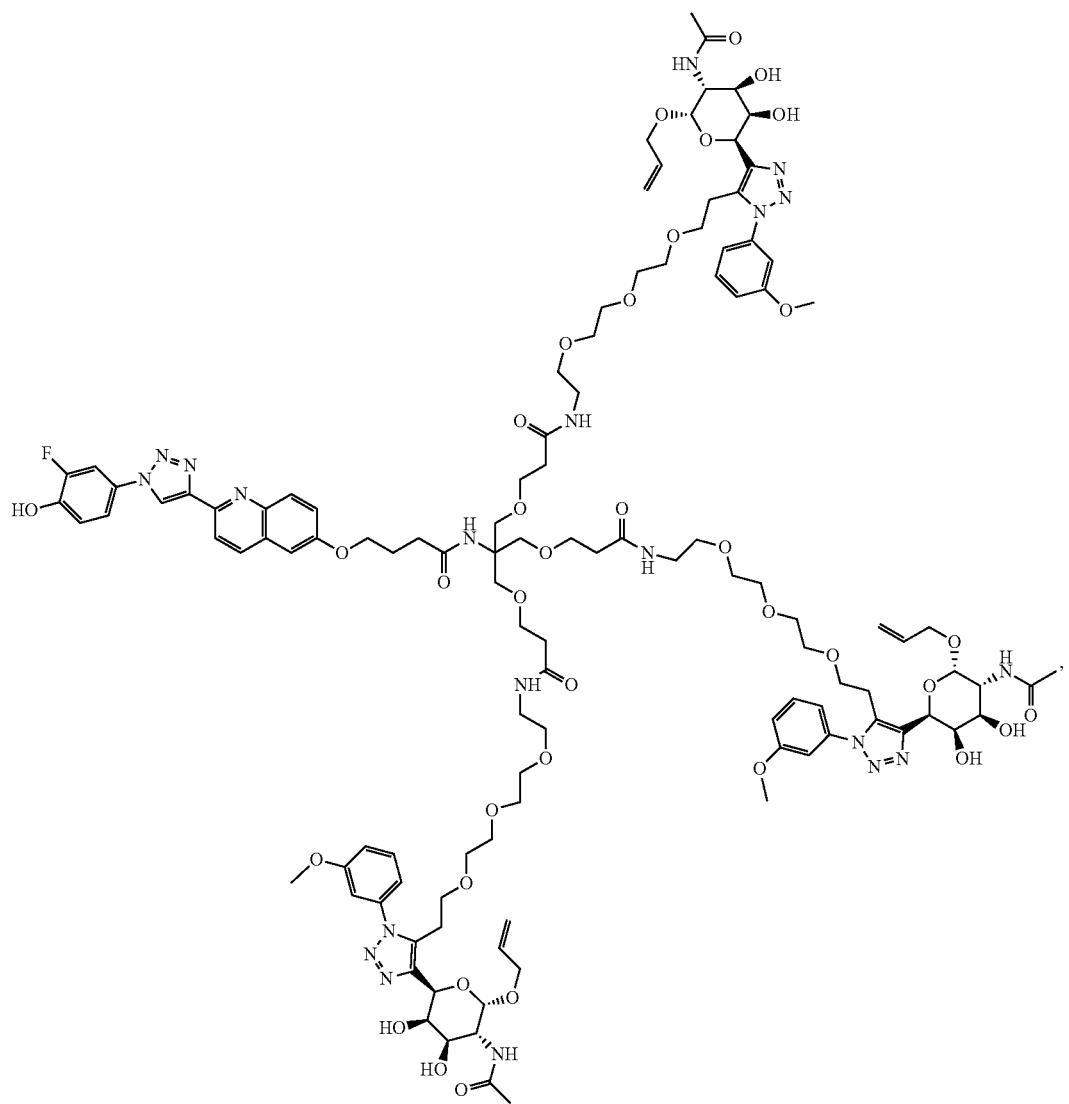 [SMILES: C=CCO[C@H]1O[C@H](c2nnn(-c3cccc(OC)c3)c2CCOCCOCCOCCNC(=O)CCOCC(COCCC(=O)NCCOCCOCCOCCc2c([C@H]3O[C@H](OCC=C)[C@H](NC(C)=O)[C@@H](O)[C@H]3O)nnn2-c2cccc(OC)c2)(COCCC(=O)NCCOCCOCCOCCc2c([C@H]3O[C@H](OCC=C)[C@H](NC(C)=O)[C@@H](O)[C@H]3O)nnn2-c2cccc(OC)c2)NC(=O)CCCOc2ccc3nc(-c4cn(-c5ccc(O)c(F)c5)nn4)ccc3c2)[C@H](O)[C@H](O)[C@H]1NC(C)=O]

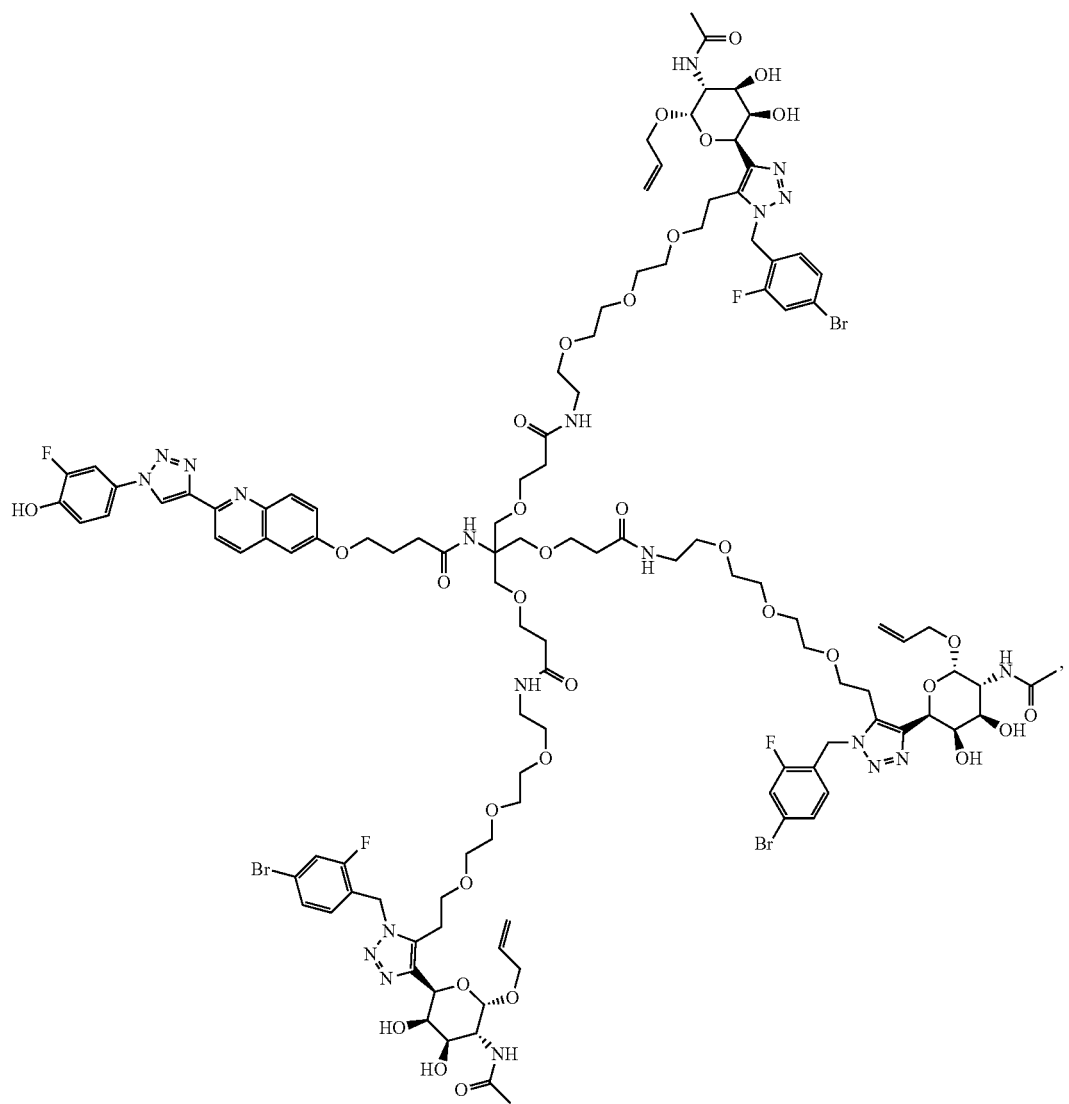 [SMILES: C=CCO[C@H]1O[C@H](c2nnn(Cc3ccc(Br)cc3F)c2CCOCCOCCOCCNC(=O)CCOCC(COCCC(=O)NCCOCCOCCOCCc2c([C@H]3O[C@H](OCC=C)[C@H](NC(C)=O)[C@@H](O)[C@H]3O)nnn2Cc2ccc(Br)cc2F)(COCCC(=O)NCCOCCOCCOCCc2c([C@H]3O[C@H](OCC=C)[C@H](NC(C)=O)[C@@H](O)[C@H]3O)nnn2Cc2ccc(Br)cc2F)NC(=O)CCCOc2ccc3nc(-c4cn(-c5ccc(O)c(F)c5)nn4)ccc3c2)[C@H](O)[C@H](O)[C@H]1NC(C)=O]

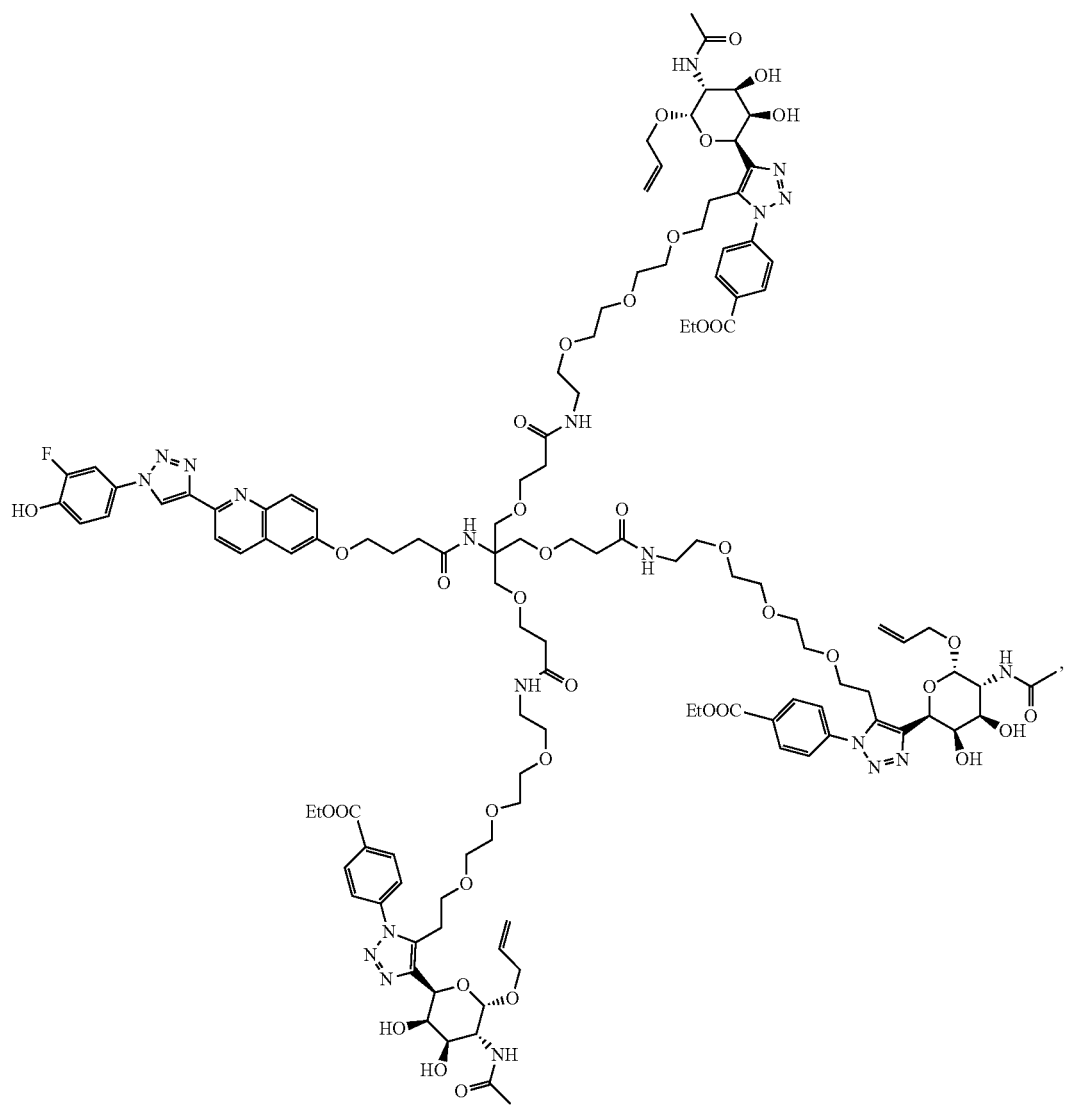 [SMILES: C=CCO[C@H]1O[C@H](c2nnn(-c3ccc(C(=O)OCC)cc3)c2CCOCCOCCOCCNC(=O)CCOCC(COCCC(=O)NCCOCCOCCOCCc2c([C@H]3O[C@H](OCC=C)[C@H](NC(C)=O)[C@@H](O)[C@H]3O)nnn2-c2ccc(C(=O)OCC)cc2)(COCCC(=O)NCCOCCOCCOCCc2c([C@H]3O[C@H](OCC=C)[C@H](NC(C)=O)[C@@H](O)[C@H]3O)nnn2-c2ccc(C(=O)OCC)cc2)NC(=O)CCCOc2ccc3nc(-c4cn(-c5ccc(O)c(F)c5)nn4)ccc3c2)[C@H](O)[C@H](O)[C@H]1NC(C)=O]

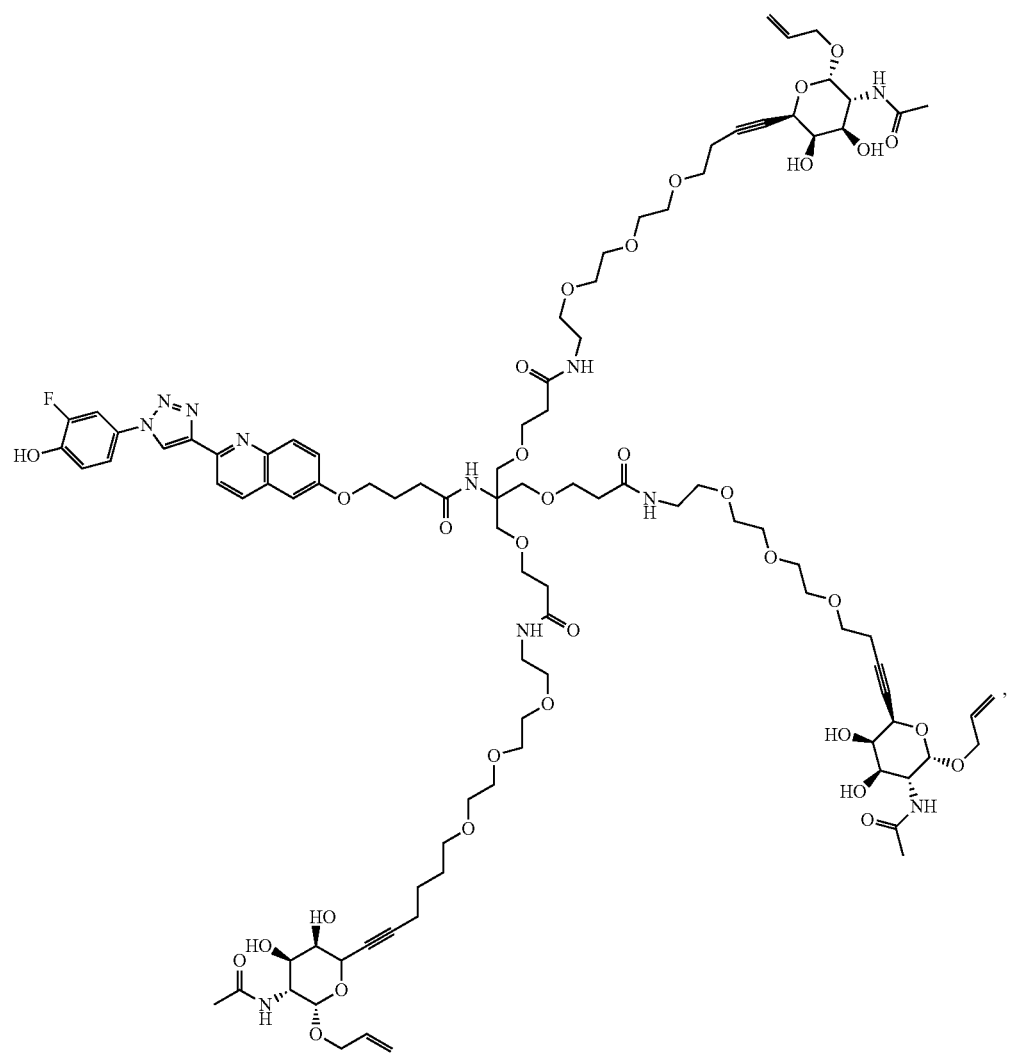 [SMILES: C=CCO[C@H]1OC(C#CCCCCOCCOCCOCCNC(=O)CCOCC(COCCC(=O)NCCOCCOCCOCCC#C[C@H]2O[C@H](OCC=C)[C@H](NC(C)=O)[C@@H](O)[C@H]2O)(COCCC(=O)NCCOCCOCCOCCC#C[C@H]2O[C@H](OCC=C)[C@H](NC(C)=O)[C@@H](O)[C@H]2O)NC(=O)CCCOc2ccc3nc(-c4cn(-c5ccc(O)c(F)c5)nn4)ccc3c2)[C@H](O)[C@H](O)[C@H]1NC(C)=O]

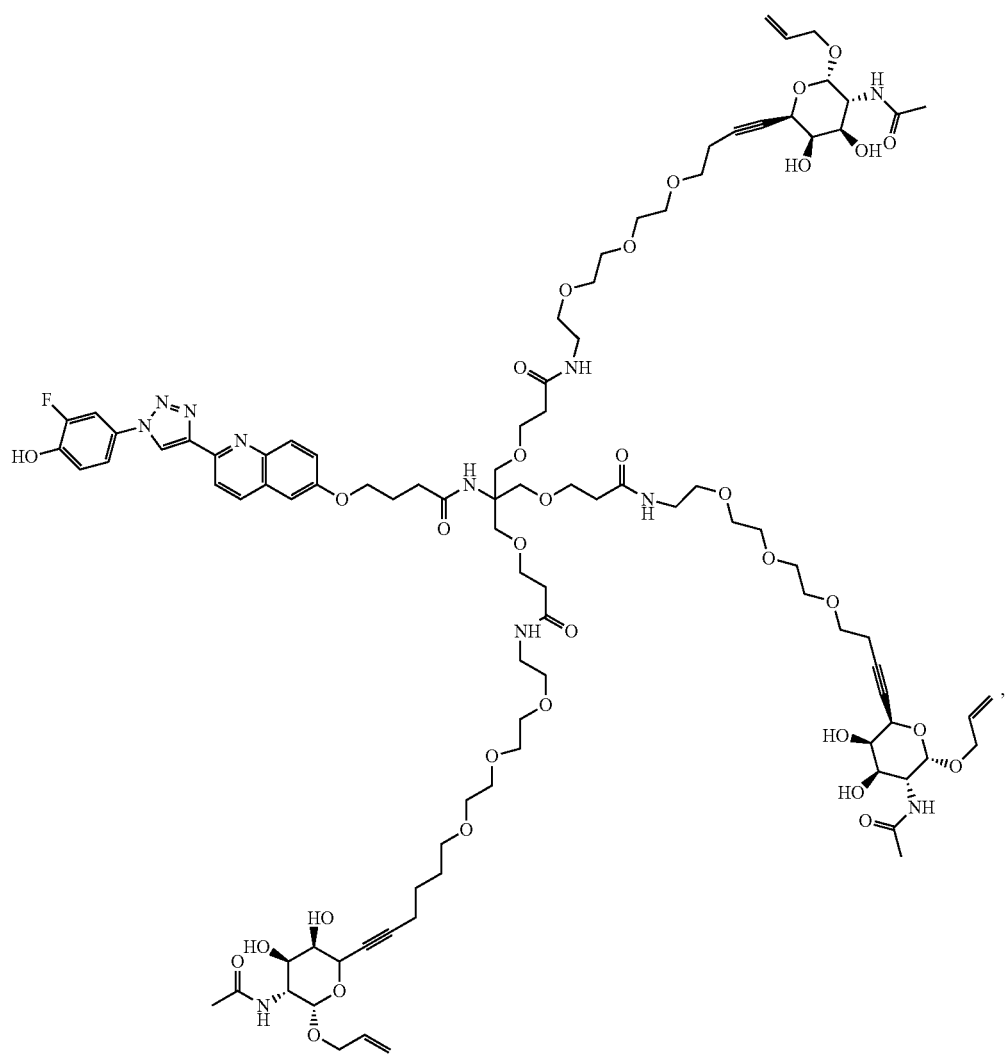 [SMILES: C=CCO[C@H]1OC(C#CCCCCOCCOCCOCCNC(=O)CCOCC(COCCC(=O)NCCOCCOCCOCCC#C[C@H]2O[C@H](OCC=C)[C@H](NC(C)=O)[C@@H](O)[C@H]2O)(COCCC(=O)NCCOCCOCCOCCC#C[C@H]2O[C@H](OCC=C)[C@H](NC(C)=O)[C@@H](O)[C@H]2O)NC(=O)CCCOc2ccc3nc(-c4cn(-c5ccc(O)c(F)c5)nn4)ccc3c2)[C@H](O)[C@H](O)[C@H]1NC(C)=O]

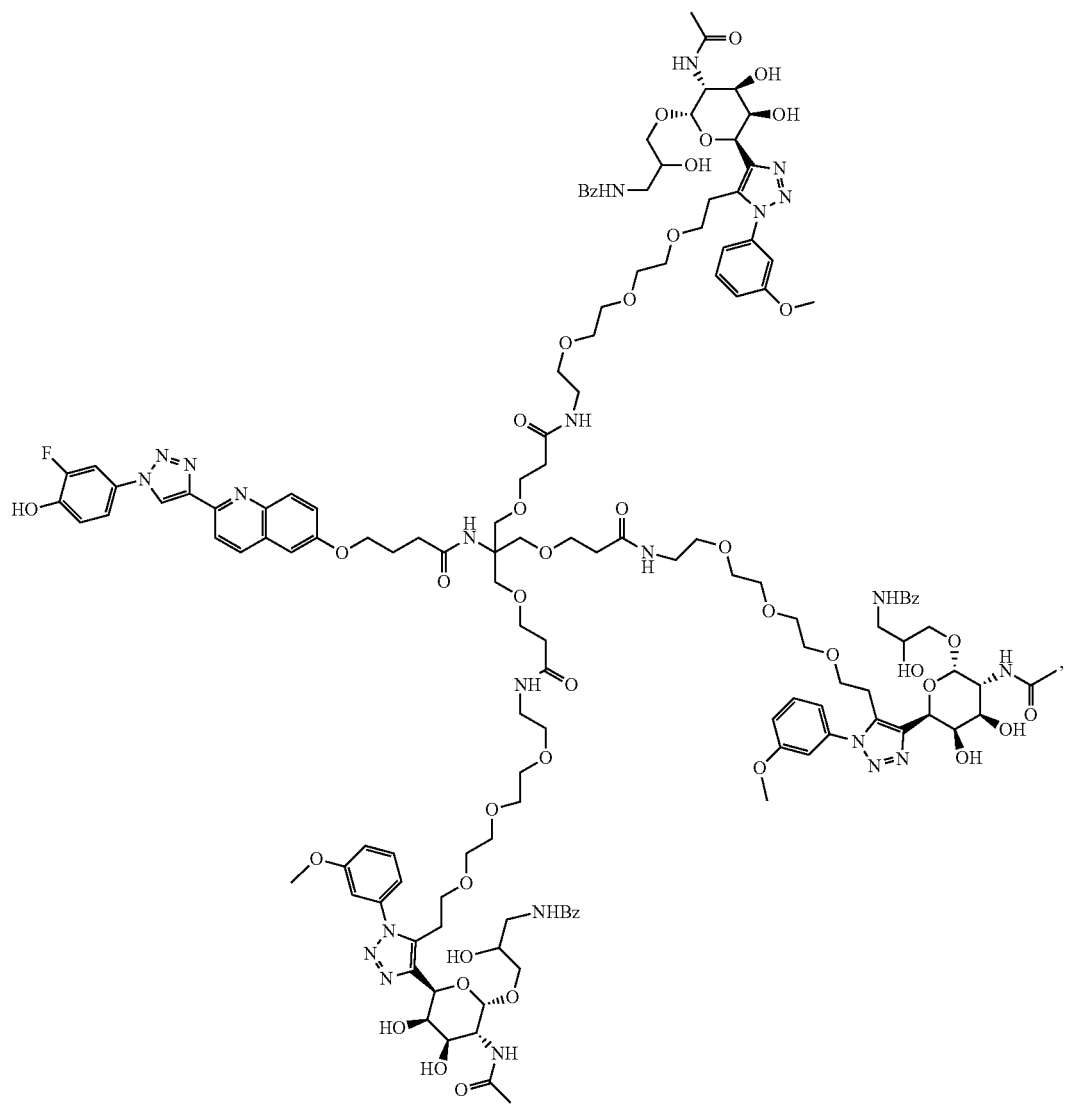

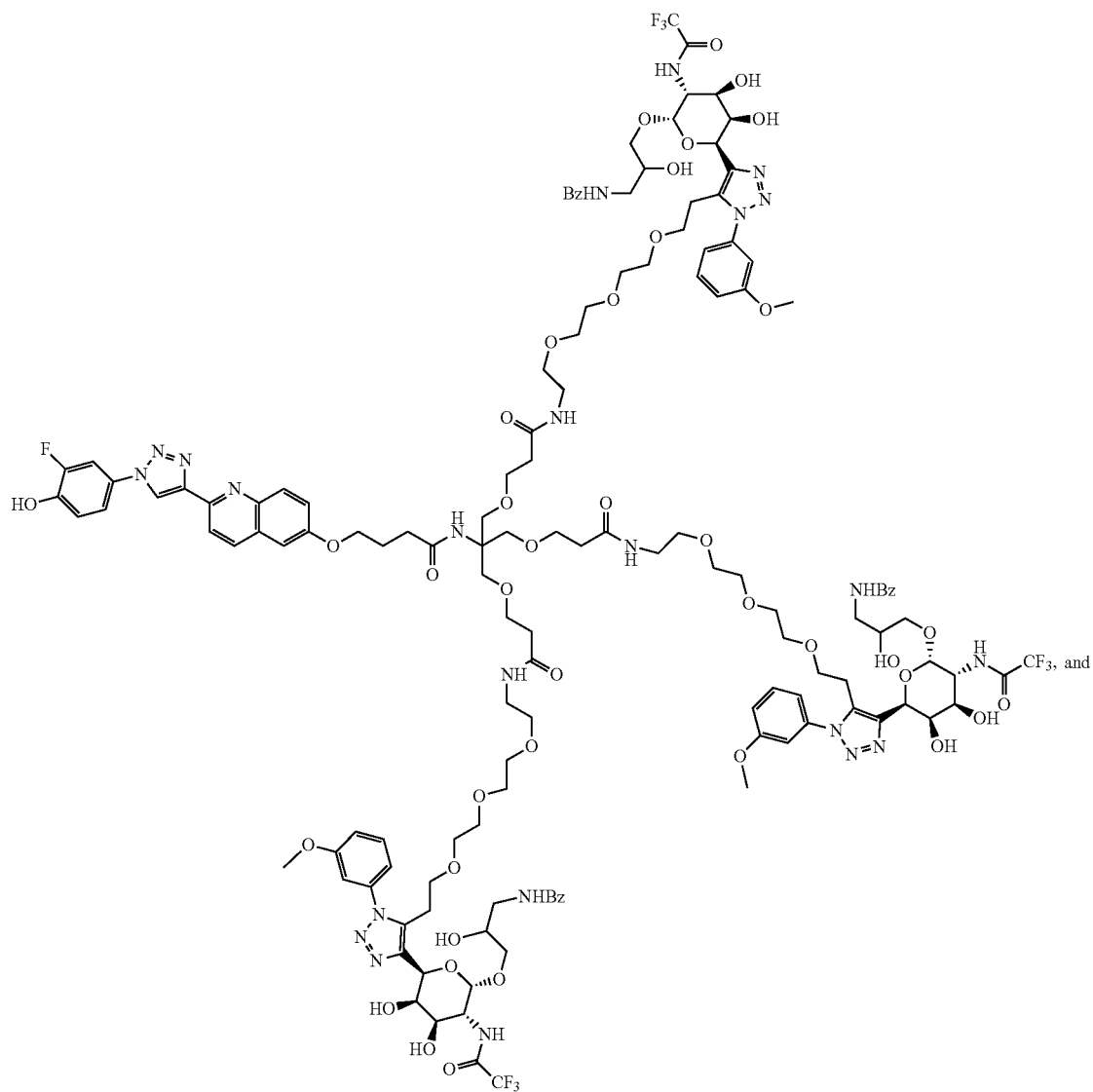

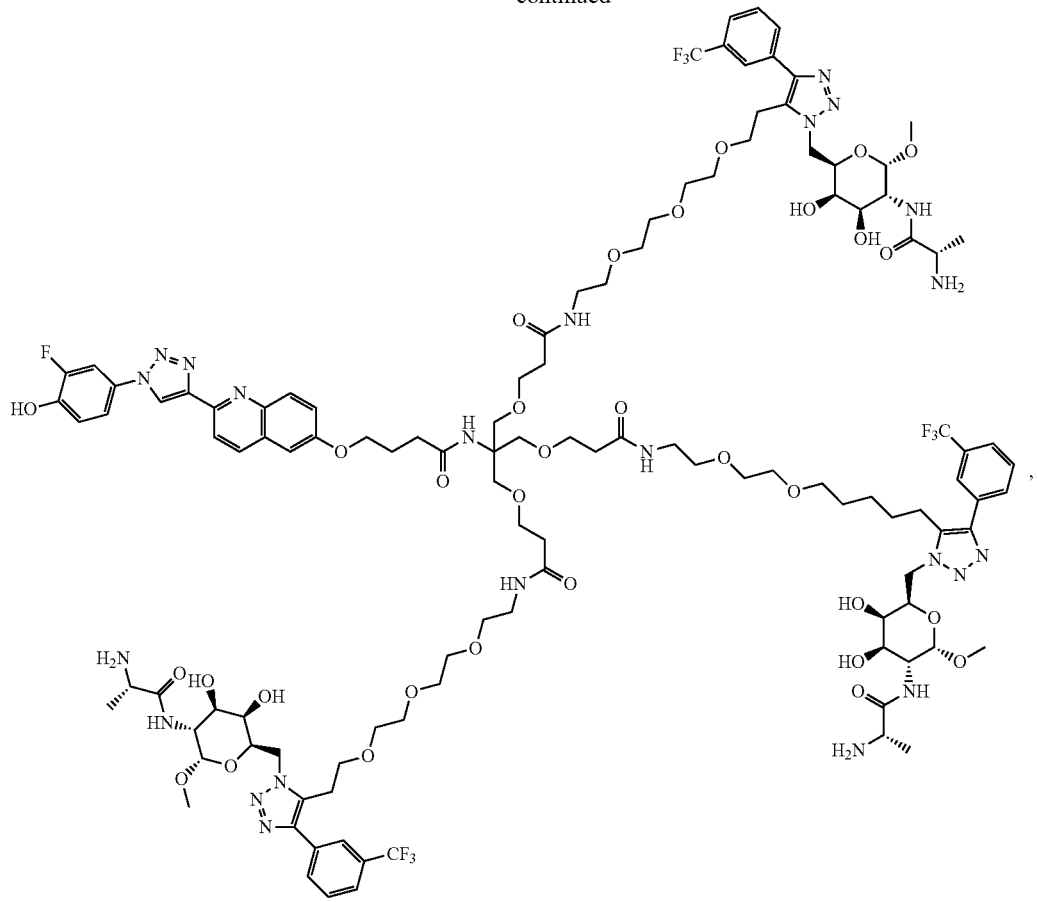 [SMILES: CO[C@H]1O[C@H](CN2NNC(c3cccc(C(F)(F)F)c3)=C2CCCCCOCCOCCNC(=O)CCOCC(COCCC(=O)NCCOCCOCCOCCc2c(-c3cccc(C(F)(F)F)c3)nnn2C[C@H]2O[C@H](OC)[C@H](NC(=O)[C@H](C)N)[C@@H](O)[C@H]2O)(COCCC(=O)NCCOCCOCCOCCc2c(-c3cccc(C(F)(F)F)c3)nnn2C[C@H]2O[C@H](OC)[C@H](NC(=O)[C@H](C)N)[C@@H](O)[C@H]2O)NC(=O)CCCOc2ccc3nc(-c4cn(-c5ccc(O)c(F)c5)nn4)ccc3c2)[C@H](O)[C@H](O)[C@H]1NC(=O)[C@H](C)N]

or a salt, stereoisomer, or solvate thereof.

14. A pharmaceutical composition comprising an effective amount of a compound of claim 1 in combination with a pharmaceutically acceptable carrier, additive, or excipient, optionally further comprising an additional bioactive agent effective to treat cancer, autoimmune disease, inflammatory disease, or a disease or disorder associated with upregulation of IgG in the patient or subject.

15. The composition of claim 14, wherein the additional bioactive agent to treat cancer is selected from the group consisting of: everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an EGFR TK inhibitor, an aurora kinase inhibitor, a PIK-1 modulator, a Bcl-2 inhibitor, an HDAC inhbitor, a c-MET inhibitor, a PARP inhibitor, a Cdk inhibitor, an EGFR TK inhibitor, an IGFR-TK inhibitor, an anti-HGF antibody, a PI3 kinase inhibitors, an AKT inhibitor, a JAK/STAT inhibitor, a checkpoint-1 or 2 inhibitor, a focal adhesion kinase inhibitor, a Map kinase kinase (mek) inhibitor, a VEGF trap antibody, pemetrexed, erlotinib, dasatanib, nilotinib, decatanib, panitumumab, amrubicin, oregovomab, Lep-etu, nolatrexed, azd2171, batabulin, ofatumumab (Arzerra), zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL 13-PE38QQR, INO 1001, IPdR₁ KRX-0402, lucanthone, LY 317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxonibicin, irinotecan, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES (diethylstilbestrol), estradiol, estrogen, conjugated estrogen, bevacizumab, IMC-1C11, CH IR-258,); 3-[5-(methylsulfonylpiperadinemethyl)-indolylj-quinolone, vatalanib, AG-013736, AVE-0005, the acetate salt of [D-Ser(But) 6,Azgly 10] (pyro-Glu-His-Trp-Ser-Tyr-D-Ser(Bu t)-Leu-Arg-Pro-Azgly-$NH_2$ acetate [$C_{59}H_{84}N_{18}Oi_4$-$(C_2H_4O_2)$x where x=1 to 2.4], goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, lonafarnib, BMS-214662, tipifarnib; amifostine, NVP-LAQ824, suberoyl analide hydroxamic acid, valproic acid, trichostatin A, FK-228, SUI11248, sorafenib, KRN951, aminoglutethimide, arnsacrine, anagrelide, L-asparaginase, *Bacillus* Calmette-Guerin (BCG) vaccine, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gemcitabine, gleevac, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deoxyuridine, cytosine arabinoside, 6-mercaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, S16668, EMD121974, interleukin-12, iM862, angiostatin, vitaxin, droloxifene, idoxyfene, spironolactone, finasteride, cimitidine, trastuzumab, denileukin diftitox,gefitinib, bortezimib, paclitaxel, irinotecan, topotecan, doxorubicin, docetaxel, vinorelbine, bevacizumab, erbitux, cremophor-free paclitaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonists, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa and darbepoetin alfa, vemurafenib, a PD-L1 inhibitor, a PD-1 inhibitor, and a CTLA-4 inhibitor.

16. A method of removing excess circulating IgG in a patient or subject, or treating a disease state or condition which is associated with the upregulation of IgG in a patient or subject, the method comprising administering to the patient or subject an effective amount of a compound of claim 1.

17. The method of claim 16, wherein the disease state or condition is cancer, an autoimmune disease, or an inflammatory disease.

18. A method of treating cancer, an autoimmune disease, or an inflammatory disease in a subject or patient, the method comprising administering to the subject or patient a therapeutically effective amount of a composition of claim 14.

* * * * *